(12) United States Patent
Hershberger

(10) Patent No.: US 12,257,307 B2
(45) Date of Patent: Mar. 25, 2025

(54) β-LACTAM-CANNABINOID CONJUGATE MOLECULES

(71) Applicant: Diverse Biotech, Inc., Orlando, FL (US)

(72) Inventor: Paul Hershberger, Orlando, FL (US)

(73) Assignee: Diverse Biotech, Inc., Miami, FL (US)

( * ) Notice: Subject to any disclaimer, the term of this patent is extended or adjusted under 35 U.S.C. 154(b) by 728 days.

(21) Appl. No.: 17/622,319

(22) PCT Filed: Jun. 24, 2020

(86) PCT No.: PCT/US2020/039354
§ 371 (c)(1),
(2) Date: Dec. 23, 2021

(87) PCT Pub. No.: WO2020/263975
PCT Pub. Date: Dec. 30, 2020

(65) Prior Publication Data
US 2022/0257778 A1    Aug. 18, 2022

Related U.S. Application Data

(60) Provisional application No. 62/960,064, filed on Jan. 12, 2020, provisional application No. 62/899,657, filed on Sep. 12, 2019, provisional application No. 62/865,687, filed on Jun. 24, 2019.

(51) Int. Cl.
| | | |
|---|---|---|
| A61K 47/55 | (2017.01) |
| A61K 45/06 | (2006.01) |
| A61K 47/54 | (2017.01) |
| C07D 463/18 | (2006.01) |
| C07D 477/14 | (2006.01) |
| C07D 499/883 | (2006.01) |
| C07D 501/46 | (2006.01) |

(52) U.S. Cl.
CPC ............ A61K 47/552 (2017.08); A61K 45/06 (2013.01); A61K 47/545 (2017.08); C07D 463/18 (2013.01); C07D 477/14 (2013.01); C07D 499/883 (2013.01); C07D 501/46 (2013.01)

(58) Field of Classification Search
CPC .... A61K 47/552; A61K 47/545; A61K 45/06; C07D 463/18; C07D 477/14; C07D 499/883; C07D 501/46
See application file for complete search history.

(56) References Cited

U.S. PATENT DOCUMENTS

| | | |
|---|---|---|
| 3,639,427 A | 2/1972 | Razdan et al. |
| 4,036,857 A | 7/1977 | Razdan et al. |
| 4,051,152 A | 9/1977 | Razdan et al. |
| 4,133,819 A | 1/1979 | Johnson |
| 4,285,941 A | 8/1981 | Machida et al. |
| 4,327,028 A | 4/1982 | Kaplan |
| 5,180,719 A | 1/1993 | White et al. |
| 5,273,973 A | 12/1993 | White et al. |
| 5,434,147 A | 7/1995 | White et al. |
| 6,627,625 B1 | 9/2003 | Koppel |
| 6,726,911 B1 * | 4/2004 | Julich ................. A61K 8/9794 424/195.15 |
| 8,445,476 B2 | 5/2013 | Wagman et al. |
| 8,829,043 B2 | 9/2014 | Riggs-Sauthier et al. |
| 9,155,797 B2 | 10/2015 | Riggs-Sauthier et al. |
| 9,345,691 B2 | 5/2016 | Cohen et al. |
| 9,580,400 B2 | 2/2017 | Makriyannis et al. |
| 2003/0096844 A1 | 5/2003 | Kozlowski et al. |
| 2004/0132707 A1 | 7/2004 | Heinisch et al. |
| 2004/0157262 A1 | 8/2004 | Kohl et al. |
| 2004/0214838 A1 | 10/2004 | Carpino et al. |
| 2005/0014786 A1 | 1/2005 | Sun et al. |
| 2006/0160787 A1 | 7/2006 | Dou et al. |
| 2007/0060561 A1 | 3/2007 | Corey et al. |
| 2007/0238717 A1 | 10/2007 | Rothstein et al. |
| 2010/0016274 A1 | 1/2010 | Koppel et al. |
| 2011/0039808 A1 | 2/2011 | Desreumaux et al. |
| 2011/0144165 A1 | 6/2011 | Nelson et al. |
| 2011/0224186 A1 | 9/2011 | Wagman et al. |
| 2012/0022063 A1 | 1/2012 | Riggs-Sauthier et al. |
| 2013/0281424 A1 | 10/2013 | Miller et al. |
| 2014/0234282 A1 | 8/2014 | Cohen et al. |
| 2014/0302121 A1 | 10/2014 | Bevier |
| 2014/0329895 A1 | 11/2014 | Riggs-Sauthier et al. |
| 2017/0166587 A1 | 6/2017 | Maiti et al. |

(Continued)

FOREIGN PATENT DOCUMENTS

| | | | |
|---|---|---|---|
| EP | 363223 | A2 | 4/1990 |
| EP | 366189 | A2 | 5/1990 |
| EP | 3651760 | A1 | 5/2020 |
| EP | 3484469 | A4 | 7/2020 |
| EP | 3846616 | A1 | 7/2021 |

(Continued)

OTHER PUBLICATIONS

Search Report for EP20831227.2 dated Mar. 7, 2023, 7 pages.
Appendino et al., "Antibacterial Cannabinoids from *Cannabis sativa*: A Structure-Activity Study," J. Nat. Prod. 71, 1427-30, 2008.
Brenneisen, "Chemistry and Analysis of Phytocannabinoids and Other Cannabis Constituents," Chapter 2 in Forensic Science and Medicine: Marijuana and the Cannabinoids, ElSohly, ed., Humana Press Inc., Totowa, New Jersey, 17-49.
Diarra et al., "Species Selectivity of New Siderophore-Drug Conjugates that Use Specific Iron Uptake for Entry into Bacteria," Antimicrobial Agents and Chemotherapy 40, 2610-17, 1996.
Domalaon et al., "Antibiotic Hybrids: the Next Generation of Agents and Adjuvants against Gram-Negative Pathogens:" Clin. Microbiol. Rev. 31, e00077-17, 2018, 45 pages.

(Continued)

Primary Examiner — Jeffrey S Lundgren
Assistant Examiner — W. Justin Youngblood
(74) Attorney, Agent, or Firm — Banner & Witcoff, Ltd.

(57) ABSTRACT

This disclosure provides multifunctional conjugate molecules in which at least one β-lactam antibiotic is covalently attached to a cannabinoid by means of a linker. The disclosed conjugate molecules are designed to deliver therapeutic benefits as intact molecules, with release of the cannabinoid upon binding of the β-lactam antibiotic to its target conveying further therapeutic benefits, and can be used to treat bacterial infections and other disorders.

18 Claims, No Drawings

(56) References Cited

U.S. PATENT DOCUMENTS

| | | |
|---|---|---|
| 2017/0298399 A1 | 10/2017 | Peet et al. |
| 2018/0264122 A1 | 9/2018 | Zipp et al. |
| 2020/0376156 A1 | 12/2020 | Palaio |
| 2021/0077455 A1 | 3/2021 | Whalley et al. |
| 2021/0093652 A1 | 4/2021 | Brener et al. |
| 2021/0315837 A1 | 10/2021 | Murphy et al. |
| 2021/0379010 A1 | 12/2021 | Steinberg et al. |

FOREIGN PATENT DOCUMENTS

| | | |
|---|---|---|
| EP | 3873449 A1 | 9/2021 |
| WO | 199315084 A1 | 8/1993 |
| WO | 2008034032 A2 | 3/2008 |
| WO | 2008097546 A2 | 8/2008 |
| WO | 2009099670 A2 | 8/2009 |
| WO | 2014134127 A1 | 9/2014 |
| WO | 2017181118 A1 | 10/2017 |
| WO | 2018011813 A1 | 1/2018 |
| WO | 2020089902 A1 | 5/2020 |
| WO | 2021076197 A1 | 4/2021 |
| WO | 2021102515 A1 | 6/2021 |

OTHER PUBLICATIONS

Fernandes et al., "ß-Lactams: chemical structure, mode of action and mechanisms of resistance," Rev. Med. Microbiol. 24, Jul. 17, 2013.

Hanessian & Wang, "Design and synthesis of a cephalosporin-carboplatinum prodrug activatable by a ?-lactamase," Can. J. Chem. 71, 896-906, 1993.

Hernandez-Cervantes et al., "Immunoregulatory Role of Cannabinoids during Infectious Disease," Neuroimmunomodulation 24, 183-99, 2017.

Hershberger & Demuth, "Concept, Design, and Preclinical Evaluation of Quinolonyl Lactam Antibacterials," Chapter 13 in Resolving the Antibiotic Paradox, Rosen & Mobasher, eds., Plenum Publishers, New York, 1998, pp. 239-267.

Kirkby et al., "Aztreonam (for inhalation solution) for the treatment of chronic lung infections in patients with cystic fibrosis: an evidence-based review," Core Evidence 6, 59-66, 2011.

Morales et al., "An Overview on Medicinal Chemistry of Synthetic and Natural Derivatives of Cannabidiol," Frontiers in Pharmacology, Aug. 2017, 18 pages.

Papp-Wallace et al., "Carbapenems: Past, Present, and Future," Antimicrogial Agents and Chemotherapy 55, 4943-60, 2011.

Shevyrin & Morzherin, "Cannabinoids: structures, effects, and classification," Russian Chemical Bulletin, International Edition, 64, 1249-66, 2015.

Urits et al., "An Update of Current Cannabis-Based Pharmaceuticals in Pain Medicine," Pain Ther. 8, 41-51, 2019.

West et al., "Purification Efficacy of Synthetic Cannabinoid Conjugates Using High-Pressure Liquid Chromatography," US Army Research Lab ARL-TR-7570, Jan. 2016, 28 pages.

International Search Report and Written Opinion for PCT/US2020/039354, dated Oct. 6, 2020, 7 pages.

* cited by examiner

β-LACTAM-CANNABINOID CONJUGATE MOLECULES

Each reference cited in this disclosure is incorporated by reference herein in its entirety.

TECHNICAL FIELD

This disclosure relates generally to multifunctional therapeutics.

DETAILED DESCRIPTION

This disclosure describes multifunctional conjugate molecules comprising a β-lactam antibiotic component and a cannabinoid component covalently attached by a linker:

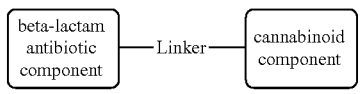

In contrast to traditional prodrugs, embodiments of the disclosed conjugate molecules are designed to deliver more than one therapeutic benefit via more than one mechanism of action; this is achieved when the covalent binding of the β-lactam antibiotic component to its target enables the release of the cannabinoid at or near the site of the β-lactam's therapeutic action, where the released cannabinoid can then effect a second therapeutic benefit. That is, these conjugate molecules are designed to deliver the therapeutic benefits of each of their components. In other embodiments, the therapeutic agent component and the cannabinoid component are released to provide their respective therapeutic benefits via functionality of the linker.

For example, the formation of reactive oxygen species (ROS) is a by-product of the normal process of respiration in an oxygen-rich environment (Storz & Imlay, Curr. Opin. Microbiol. 2, 188-94, 1999). There is significant evidence in the literature for the role endogenous ROS plays in mutagenesis, as well as its contribution to the mutational burden experienced by microbes during periods of oxidative stress (reviewed in Dwyer et al., Curr. Opin. Microbiol. 12, 482-89, 2009). In fact, bacteria have evolved several enzymatic mechanisms to combat ROS toxicity (Imlay, Ann. Rev. Biochem. 77, 755-76, 2008).

ROS are generated intracellularly and include superoxide ($O_2.^-$), hydrogen peroxide ($H_2O_2$), and highly-destructive hydroxyl radicals (OH·). The species $O_2.^-$ and $H_2O_2$ can be enzymatically eradicated by the activity of superoxide dismutases and catalases/peroxidases, respectively.

Excess intracellular levels of ROS cause damage to proteins, nucleic acids, lipids, membranes, and organelles, which can lead to activation of cell death processes such as apoptosis. Apoptosis is a tightly regulated and highly conserved process of cell death during which a cell undergoes self-destruction (Kerr et al., Br. J. Cancer 26, 239-57, 1972). Apoptosis can be triggered by a variety of extrinsic and intrinsic signals, including ROS (reviewed in Redza-Dutordoir & Averill-Bates, Biochem. Biophys. Acta 1863, 2977-92, 2016). Exposure to xenobiotics such as antibiotics and chemotherapeutic drugs can also trigger apoptosis, and is often mediated by ROS.

All classes of bactericidal antibiotics, regardless of their specific target, promote the generation of lethal hydroxyl radicals in both Gram-negative and Gram-positive bacteria (Kohanski et al., Cell 130, 797-810, 2007).

Cannabinoids, too, have demonstrated their ability to promote ROS production. Cannabidiol (CBD) is a non-toxic and non-psychoactive cannabinoid that has been shown to have anti-tumor activity in multiple cancer types (Massi et al., J. Pharmacol. Exp. Ther. 308, 838-45, e-pub 2003). CBD has been reported to inhibit human GBM viability in culture, an effect that was reversed in the presence of the ROS scavenger α-tocopherol/vitamin E (Velasco et al., 2012).

CBD-dependent production of ROS has been shown to accompany a reduction in glutathione (Massi et al., Cell. Mol. Sci. 63, 2057-66, 2006), an important anti-oxidant that prevents damage to cellular components by ROS. The source of CBD-dependent stress in part originated in the mitochondria and led to activation of multiple caspases involved in intrinsic and extrinsic pathways of apoptosis.

Cannabigerol (CBG) is another non-psychotropic cannabinoid that interacts with specific targets involved in carcinogenesis and has shown potent anti-tumor activity (Guindon & Hohmann, Br. J. Pharmacol. 163, 1447-63, 2011). Mechanistically, CBG, similar to CBD, appears to influence the inflammatory microenvironment (Mantovani et al., Nature 454, 436-44, 2008; Solinas et al., Cancer Metastasis Rev. 29, 243-48, 2010) and exert pro-apoptotic effects by selectively increasing ROS production (Borrelli et al., Carcinogenesis 35, 2787-97, 2014). Using cannabidiol as an example of the cannabinoid and cephalosporin as an example of a β-lactam antibiotic, this approach is illustrated in the schematic below, in which the conjugate molecule contains a cephalosporin component and a cannabidiol component and in which the antibiotic's target is a penicillin binding protein (PBP):

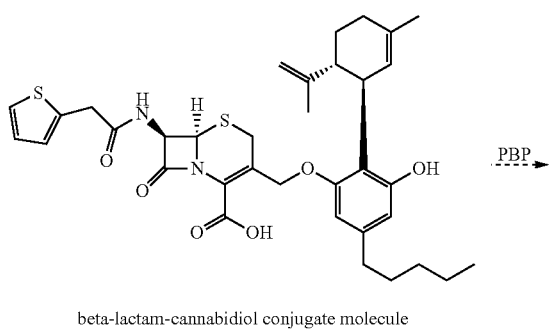

beta-lactam-cannabidiol conjugate molecule

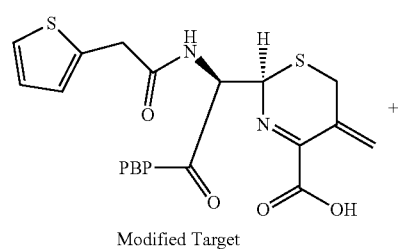

Modified Target

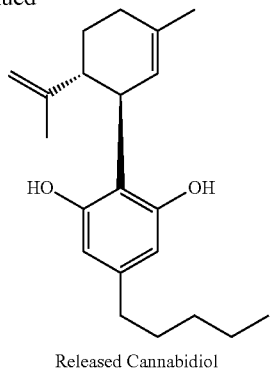

Released Cannabidiol

Conjugate Molecules

In some embodiments, conjugate molecules comprise a β-lactam antibiotic component and a cannabinoid component attached by means of a linker which is covalently attached at one end to the β-lactam antibiotic component and at the other end to a hydroxy group of the cannabinoid component. In some embodiments, the hydroxy group is an "aromatic hydroxy group;" i.e., a hydroxy group bonded directly to an aromatic hydrocarbon. In some embodiments, the hydroxy group is an "aliphatic hydroxy group;" i.e., a hydroxy group bound to a carbon that is not part of an aromatic ring.

In some embodiments, conjugate molecules contain only one β-lactam antibiotic component. In other embodiments, when the cannabinoid component has two or more hydroxy groups, conjugate molecules can contain two or more β-lactam antibiotic components, each attached to one of the two or more hydroxy groups by means of a linker. In such embodiments, the two or more linkers can be the same or different. Independently, the two or more β-lactam antibiotic components can be the same or different. Also independently, the two or more hydroxy groups can be aliphatic or the two hydroxy groups can be aromatic, or, for example, a first hydroxy group can be aliphatic and a second hydroxy group can be aromatic.

Conjugate molecules can have one or more centers of asymmetry and can therefore be prepared either as a mixture of isomers (e.g., a racemic or diasteromeric mixture) or in an enantiomerically or diastereomerically pure form. Such forms include, but are not limited to, diastereomers, enantiomers, and atropisomers. Conjugate molecules can also include alkenes and can therefore be prepared either as a mixture of double bond isomers or independently as either an E or Z isomer. Isotopic variants of conjugate molecules can also be prepared.

Conjugate molecules can form salts. "Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19.

Definitions

The following definitions apply to the descriptions of the "Therapeutic Agent Component(s)" and "Linkers" in the sections below and to the descriptions of "Group One Substituents" and "Group Two Substituents."

"C1-C3 linear or branched alkyl" means "methyl, ethyl, propyl, and isopropyl."

"C1-C8 linear or branched alkyl" means "methyl, ethyl, C3, C4, C5, C6, C7, and C8 linear alkyl and C3, C4, C5, C6, C7, and C8 branched alkyl."

"C1-C3 linear or branched heteroalkyl" means "a linear or branched heteroalkyl containing 1, 2, or 3 carbon atoms."

"C1-C8 linear or branched heteroalkyl" means "each of a C1, C2, C3, C4, C5, C6, C7, and C8 linear heteroalkyl and C1, C2, C3, C4, C5, C6, C7, and C8 branched heteroalkyl."

"C1-C6 linear or branched alkoxyl" means "a linear or branched alkoxyl containing 1, 2, 3, 4, 5, or C carbon atoms."

"C1-C6 linear or branched alkylamino" means "a linear or branched alkylamino containing 1, 2, 3, 4, 5, or 6 carbon atoms."

"C1-C6 linear or branched dialkylamino" means "each linear or branched dialkylamino in which each alkyl independently contains 1, 2, 3, 4, 5, or 6 carbon atoms."

"6-10-membered aromatic" means "each of a 6-, 7-, 8-, 9-, and 10-membered aromatic."

"5- to 10-membered heteroaromatic" means "each of a 6-, 7-, 8-, 9-, and 10-membered heteroaromatic."

"3- to 9-membered cycloheteroalkyl" means "each of a 3-, 4-, 5-, 6-, 7-, 8-, and 9-membered cycloheteroalkyl.

"C3-C6 cycloalkyl" means "C3, C4, C5, and C6 cycloalkyl."

"Halide" means "Cl, Br, and I."

"Group One Substituents" is a group of substituents consisting of:
(a) —OH;
(b) —NH2;
(c) =O;
(d) =S;
(e) =NR7, where R7 is H or is C1-C3 linear or branched alkyl or C1-C3 linear or branched heteroalkyl comprising an O, N, or S atom;
(f) —C(O)OR4, wherein R4 is H or C1-C3 linear or branched alkyl;
(g) —C(O)NR5R6, wherein R5 and R6 independently are H or C1-C6 linear or branched alkyl;
(h) halide;
(i) C1-C6 linear or branched alkoxyl;
(j) C1-C6 linear or branched alkylamino;
(k) C1-C6 linear or branched dialkylamino;
(l) 6- to 10-membered aromatic, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and (v) C1-C6 linear or branched heteroalkyl containing 1, 2, or 3 atoms independently selected from O, N, and S and optionally substituted with
  (1) 1, 2, 3, 4, 5, 6, 7, 8, or 9 fluorine atoms; and/or
  (2) 1, 2, or 3 substituents independently selected from the Group Two Substituents;
(m) 5- to 10-membered heteroaromatic, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and
  (v) C1-C6 linear or branched heteroalkyl containing 1, 2, or 3 atoms independently selected from O, N, and S and optionally substituted with
    (1) 1, 2, 3, 4, 5, 6, 7, 8, or 9 fluorine atoms; and/or
    (2) 1, 2, or 3 substituents independently selected from the Group Two Substituents;
(n) 3- to 9-membered cycloheteroalkyl having 1, 2, or 3 heteroatoms independently selected from O, N, and S, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and
  (v) C1-C6 linear or branched heteroalkyl containing 1, 2, or 3 atoms independently selected from O, N, and S and optionally substituted with
    (1) 1, 2, 3, 4, 5, 6, 7, 8, or 9 fluorine atoms; and/or
    (2) 1, 2, or 3 substituents independently selected from the Group Two Substituents; and
(o) C3-C6 cycloalkyl, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and
  (v) C1-C6 linear or branched heteroalkyl containing 1, 2, or 3 atoms independently selected from O, N, and S and optionally substituted with
    (1) 1, 2, 3, 4, 5, 6, 7, 8, or 9 fluorine atoms; and/or
    (2) 1, 2, or 3 substituents independently selected from the Group Two Substituents.

"Group Two Substituents" is a group of substituents consisting of:
(a) —OH;
(b) —NH2;
(c) =O;
(d) =S;
(e) =NR7, where R7 is H or is C1-C3 linear or branched alkyl or C1-C3 linear or branched heteroalkyl comprising an O, N, or S atom;
(f) —C(O)OR4, wherein R4 is H or C1-C3 linear or branched alkyl;
(g) —C(O)NR5R6, wherein R5 and R6 independently are H or C1-C6 linear or branched alkyl;
(h) halide;
(i) cyano;
(j) trifluoromethyl;
(k) C1-C6 linear or branched alkoxyl;
(l) C1-C6 linear or branched alkylamino;
(m) C1-C6 linear or branched dialkylamino;
(n) 6- to 10-membered aromatic; and
(o) 5- to 10-membered heteroaromatic comprising 1, 2, 3, 4, 5, or 6 heteroatoms independently selected from O, N, and S.

β-Lactam Antibiotic Component(s)

A "β-lactam antibiotic" as used in this disclosure is molecule that contains a 4-membered lactam ring (β-lactam) and that has antibacterial activity. A "β-lactam antibiotic component" as used in this disclosure is that portion of the β-lactam antibiotic that is present in the conjugate molecule and covalently attached to the linker. A number of β-lactam antibiotics can be used to provide the β-lactam antibiotic component of a conjugate molecule.

Cephems and Carbacephems

In some embodiments, the β-lactam antibiotic component is a cephem component. As used in this disclosure, a "cephem component" is a cephem in which the substituent ordinarily present at the 3 position of the molecule is not present, as illustrated below:

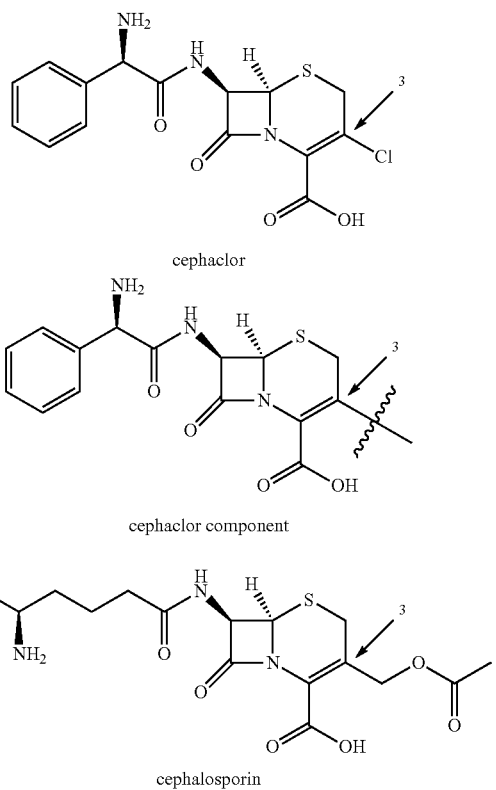

cephaclor cephaclor component cephalosporin

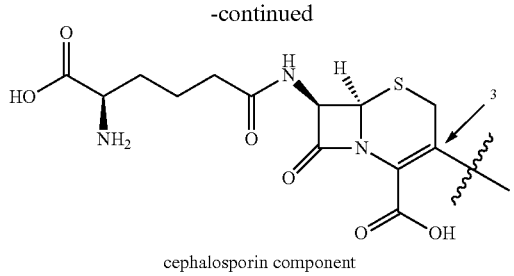

cephalosporin component

A cephem component can be provided by any of a variety of cephems including, but not limited to, cefazolin, cephalexin, cefadroxil, cefapirin, cefazedone, cefazaflur, cefradine, cefroxadine, ceftezole, cefaloglycin, cephacetrile, cefalonium, cefaloridine, cefalotin, cefatrizine, cefaclor, cefotetan, cephamycin, cefoxitin, cefprozil, cefuorixime, cefuroxime axetil, cefamandole, cefminox, cefonicid, ceforanide, cefotiam, cefbuperazone, cefuzonam, cefmetazole, cefixime, ceftriazxone, ceftazidime, cefoperazone, cefdinir, cefcapene, cefdaloxime, ceftizoxime, cefminoxime, cefotaxime, cefpiramide, cefpodoxime, ceftibuten, cefditoren, cefetamet, cefodizime, cefpimizole, cefsulodin, cefteram ceftiolene, flomoxef, latamoxef, cefepime, cefozopran, cefpirome, cefquinome, ceftaroline fosamil, ceftolozane, ceftobiprole, ceftiofur, cefquinome, and cefovecin. See also, for example, U.S. Pat. Nos. 9,751,894; 7,696,354; 6,150,351.

In some embodiments, the β-lactam antibiotic component is a carbacephem component. As used in this disclosure, a "carbacephem component" is a carbacephem in which the substituent ordinarily present at the 3 position of the molecule is not present, as illustrated below:

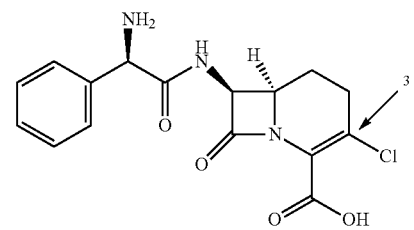

loracarbef

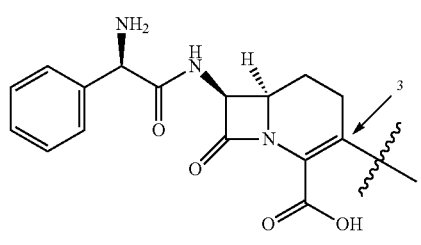

loracarbef component

Carbacephems include, but are not limited to, loracarbef. See also, for example, U.S. Pat. Nos. 8,445,476, 4,980,348.

In some embodiments the β-lactam antibiotic component falls within structural Formula (A):

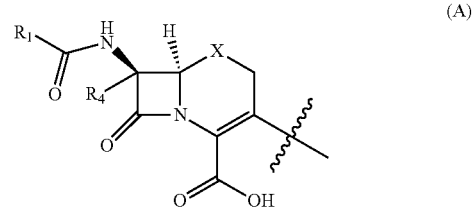

(A)

in which X is S, C, or O; $R_1$ is a side chain of a cephem or a side chain of a carbacephem; and $R_4$ is H or —$OCH_3$. Cephem side chains include, for example:

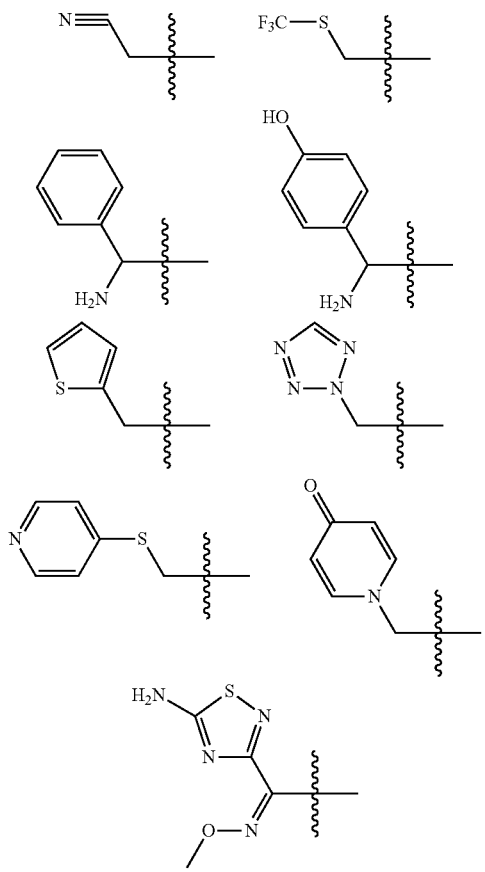

Carbacephem side chains include, for example,

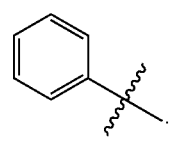 [SMILES: *c1ccccc1]

Penems and Carbapenems

In some embodiments, the β-lactam antibiotic component is a penem component. As used in this disclosure, a "penem component" is a penem in which the substituent ordinarily present at the 3 position of the molecule is not present, as illustrated below:

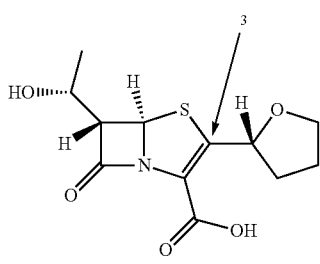

faropenem

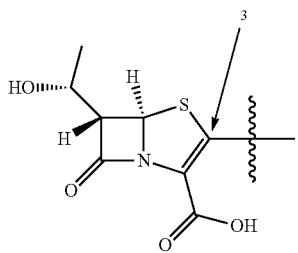

faropenem component

Penems include, but are not limited to, faropenem and ritipenem. See also U.S. Pat. Nos. 6,271,222; 5,757,583.

In other embodiments, the β-lactam antibiotic component is a carbapenem component. As used in this disclosure, a "carbapenem component" is a carbapenem in which the substituent ordinarily present at the 3 position of the molecule is not present, as illustrated below:

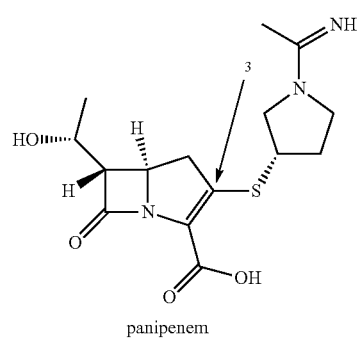

panipenem

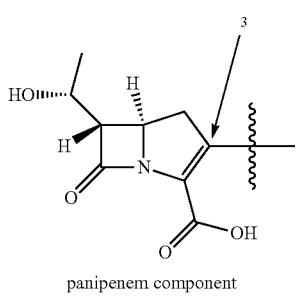

panipenem component

Carbapenems include, but are not limited to, ertapenem, doripenem, imipenem, meropenem, biapenem, and panipenem. See also U.S. Pat. Nos. 9,937,151; 8,318,716.

In some embodiments the β-lactam antibiotic component falls within structural Formula (B):

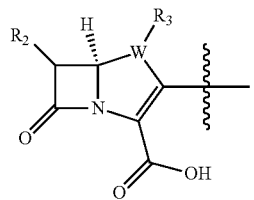

(B)

in which W is S or C; $R_2$ is a side chain of a penem or a side chain of a carbapenem; and, when W is C, $R_3$ is H, —$CH_3$, or phenyl, wherein the phenyl is optionally substituted with 1-4 groups selected from the group consisting of halide, trifluoromethyl, C1-C6 linear or branched alkyl optionally substituted with up to nine fluorine atoms, and C1-C6 linear or branched heteroalkyl optionally substituted with up to 9 fluorine atoms.

In some embodiments, the side chain of the penem or carbapenem is

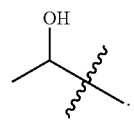

In some embodiments, $R_3$ is β-methyl.

Monobactams

In some embodiments, the β-lactam antibiotic component is a monobactam component. As used in this disclosure, "monobactam component" is a monobactam in which the substituent ordinarily present at the 2 position of the molecule is not present, as illustrated by the example below.

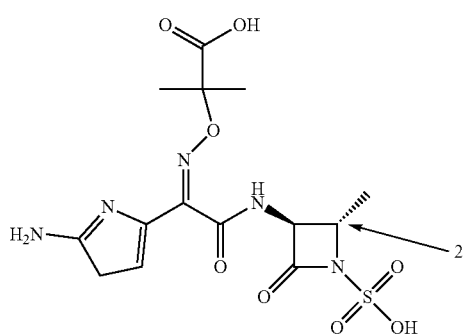

aztreonam

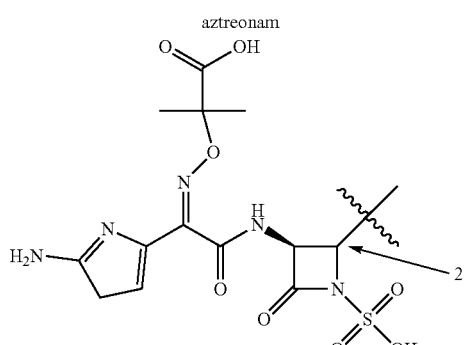

aztreonam component

Monobactams include, but are not limited to, aztreonam, tigemonam, carumonam, and nocardicin A. See also, for example, U.S. Pat. No. 9,174,978.

In some embodiments the β-lactam antibiotic component falls within structural Formula (C):

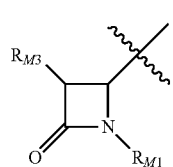
(C)

in which $R_{M3}$ is a position 3 monobactam substituent, and $R_{M1}$ is a position 1 monobactam substituent.

Examples of $R_{M3}$ include

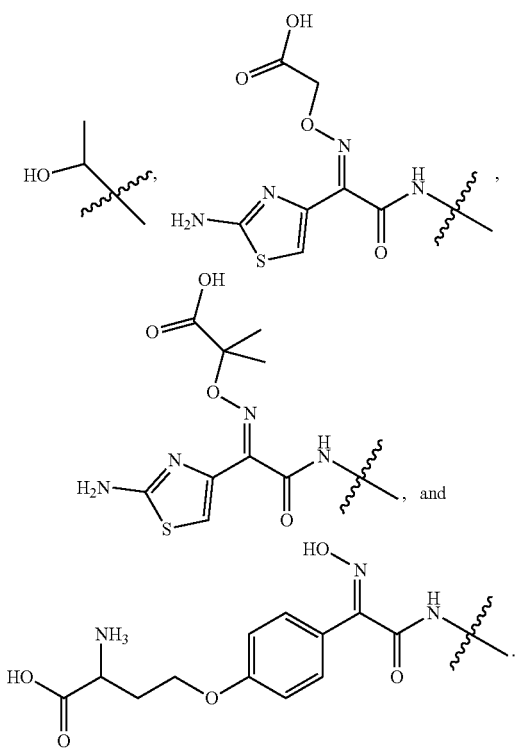

Examples of $R_{M1}$ include

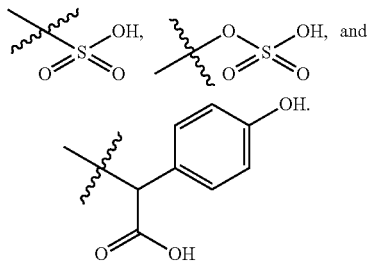

Linkers

Linkers used to connect a β-lactam antibiotic component and a cannabinoid component are typically two to 10 atoms in length and are functionalized to facilitate release of the cannabinoid when the β-lactam antibiotic engages its biological target. When a β-lactam antibiotic component is provided by a cephem, carbacephem, penem, or carbapenem, the linker is covalently attached to the 3 position of the β-lactam antibiotic component; e.g.:

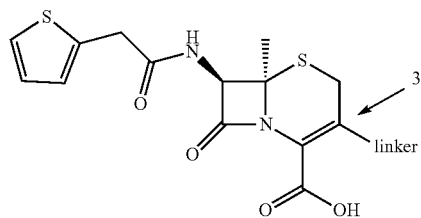

When a β-lactam antibiotic component is provided by a monobactam, the linker is covalently attached to the 2 position of the monobactam component; e.g.:

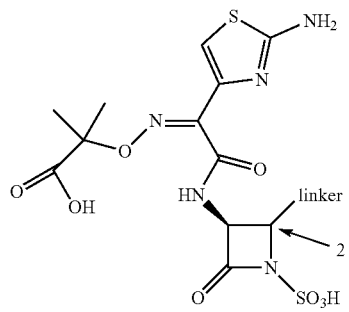

A variety of linkers can be used in the conjugate molecules, including ethers, acetals, alkenes, propenyl amines, carbamates, carbonates, xanthates, aminals, propenyl carbamates, propenyl thiocarbamates, propenyl carbonates, propenyl thiocarbonates, S-alkyl thiocarbonates, thiocarbamates, thiocarbonates, and thiohemiacetal ethers.

When a β-lactam antibiotic component is provided by a cephem, carbacephem, penem, or carbapenem, the linker can be selected from the group of linkers shown below ("Group AB Linkers"):

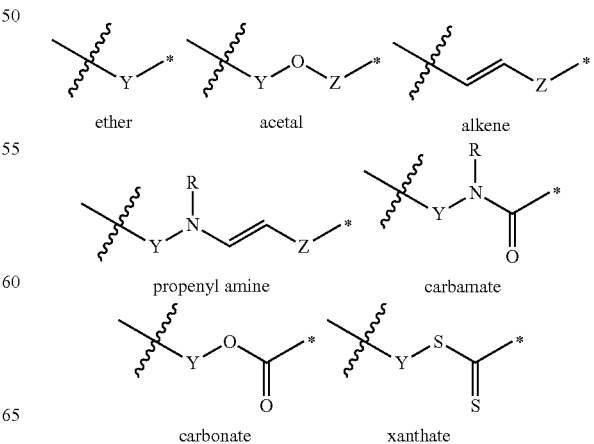

-continued

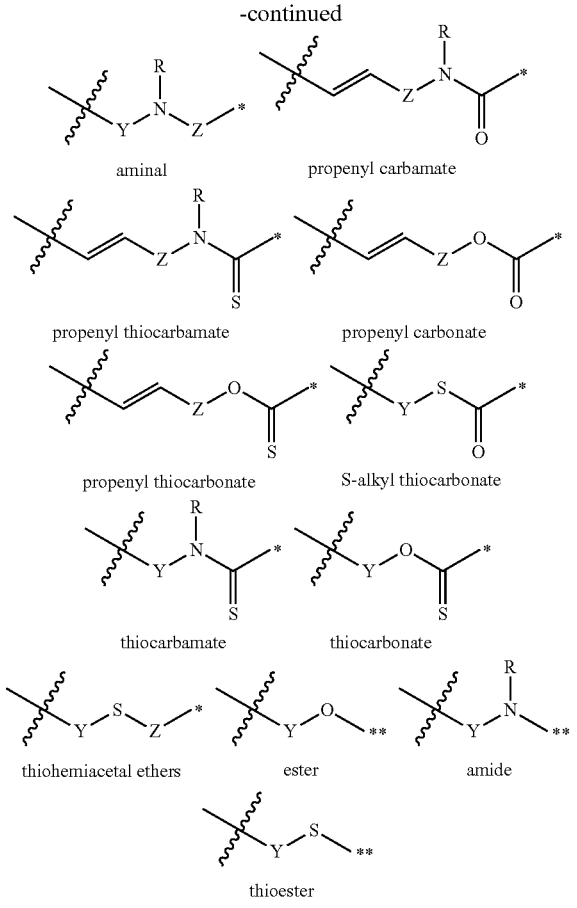

aminal
propenyl carbamate
propenyl thiocarbamate
propenyl carbonate
propenyl thiocarbonate
S-alkyl thiocarbonate
thiocarbamate
thiocarbonate
thiohemiacetal ethers
ester
amide
thioester wherein * indicates a site of covalent attachment to the oxygen atom from the OH of a cannabinoid component, ** in cases such as ester, amide, and thioester indicates the site of covalent attachment to the carbon atom of a carbonyl component of a carboxylic acid—bearing cannabinoid component, and ⟿ marks a bond by which the linker is covalently attached to the β-lactam antibiotic component and wherein Y is absent or is —CH$_2$, —CHCH$_3$, or —CH-phenyl;

Z is CR$_1$R$_2$; and

R, R$_1$ and R$_2$ independently are selected from the group consisting of:

(a) H;
(b) C1-C8 linear or branched alkyl, optionally substituted with
  (1) 1, 2, 3, 4, 5, 6, 7, 8, or 9 fluorine atoms; and/or
  (2) 1, 2, or 3 substituents independently selected from the Group One Substituents;
(c) C1-C8 linear or branched heteroalkyl containing 1, 2, or 3 heteroatoms independently selected from O, N, and S and optionally substituted with
  (1) 1, 2, 3, 4, 5, 6, 7, 8, or 9 fluorine atoms; and/or
  (2) 1, 2, or 3 substituents independently selected from the Group One Substituents;
(d) phenyl, optionally substituted with 1, 2, or 3 substituents independently selected from the group consisting of:
  (1) C1-C6 linear or branched alkyl, optionally substituted with
    (i) 1, 2, 3, 4, 5, or 6 fluorine atoms; and/or
    (ii) 1 or 2 substituents independently selected from the Group Two Substituents; and
  (2) C1-C6 linear or branched heteroalkyl containing 1 or 2 heteroatoms independently selected from O, N, and S and optionally substituted with
    (i) 1, 2, 3, 4, 5, or 6 fluorine atoms; and/or
    (ii) 1 or 2 substituents independently selected from the Group One Substituents;
(e) a 6- to 10-membered aromatic, optionally substituted with 1, 2, 3, or 4 substituents independently selected from the group consisting of:
  (1) phenyl;
  (2) halide;
  (3) cyano;
  (4) C1-C6 linear or branched alkyl, optionally substituted with
    (i) 1, 2, 3, 4, 5, 6, 7, 8, or 9 fluorine atoms; and/or
    (ii) 1, 2, or 3 substituents independently selected from the Group Two Substituents, and
  (5) C1-C6 linear or branched heteroalkyl containing 1, 2, or 3 atoms independently selected from O, N, and S and optionally substituted with
    (i) 1, 2, 3, 4, 5, 6, 7, 8, or 9 fluorine atoms; and/or
    (ii) 1, 2, or 3 substituents independently selected from the Group Two Substituents;
(f) 5- to 10-membered heteroaromatic comprising 1, 2, 3, 4, 5, or 6 heteroatoms independently selected from O, N, and S and optionally substituted with 1, 2, 3, or 4 substituents independently selected from
  (1) phenyl;
  (2) halide;
  (3) cyano;
  (4) trifluoromethyl;
  (5) C1-C6 linear or branched alkyl optionally substituted with
    (i) 1, 2, 3, 4, 5, 6, 7, 8, or 9 fluorine atoms; and/or
    (ii) 1, 2, or 3 substituents independently selected from the Group Two Substituents; and
  (6) C1-C6 linear or branched heteroalkyl containing 1, 2, or 3 atoms independently selected from O, N, and S and optionally substituted with
    (i) 1, 2, 3, 4, 5, 6, 7, 8, or 9 fluorine atoms; and/or
    (ii) 1, 2, or 3 substituents independently selected from the Group Two Substituents;
(g)

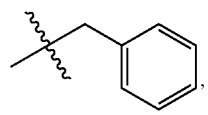

optionally substituted with 1, 2, or 3 substituents independently selected from the group consisting of:
  (1) C1-C6 linear or branched alkyl, optionally substituted with
    (i) 1, 2, 3, 4, 5, or 6 fluorine atoms; and/or
    (ii) 1, 2, or 3 substituents independently selected from the Group Two Substituents;
(h) 3- to 9-membered cycloheteroalkyl having 1, 2, or 3 heteroatoms independently selected from O, N, and S and optionally substituted with 1, 2, or 3 substituents independently selected from the group consisting of:

(1) C1-C6 linear or branched alkyl, optionally substituted with
  (i) 1, 2, 3, 4, 5, 6, 7, 8, or 9 fluorine atoms; and/or
  (ii) 1, 2, or 3 substituents independently selected from the Group Two Substituents,
(2) C1-C6 linear or branched heteroalkyl, optionally substituted with
  (i) 1, 2, 3, 4, 5, 6, 7, 8, or 9 fluorine atoms and/or
  (ii) 1, 2, or 3 substituents independently selected from the Group Two Substituents,
(3) phenyl, optionally substituted with 1, 2, or 3 substituents independently selected from the Group Two Substituents, and
(4) 5- to 10-membered heteroaromatic, optionally substituted with 1, 2, or 3 substituents independently selected from the Group Two Substituents; and
(i) C3-C6 cycloalkyl, optionally substituted with 1, 2, or 3 substituents independently selected from:
  (1) C1-C6 linear or branched alkyl, optionally substituted with
    (i) 1, 2, 3, 4, 5, 6, 7, 8, or 9 fluorine atoms; and/or
    (ii) 1, 2, or 3 substituents independently selected from the Group Two Substituents,
  (2) C1-C6 linear or branched heteroalkyl, optionally substituted with
    (i) 1, 2, 3, 4, 5, 6, 7, 8, or 9 fluorine atoms; and/or
    (ii) 1, 2, or 3 substituents independently selected from the Group Two Substituents,
  (3) phenyl, optionally substituted with 1, 2, or 3 substituents independently selected from Group Two Substituents; and
  (4) 5- to 10-membered heteroaromatic, optionally substituted with 1, 2, or 3 substituents independently selected from the Group Two Substituents;
OR $R_1$ and $R_2$, together with the atom to which they are attached, form a 3- to 9-membered cycloheteroalkyl having 1, 2, 3, or 4 heteroatoms independently selected from O, S, and N, wherein the cycloheteroalkyl optionally is substituted with 1, 2, or 3 substituents independently selected from, C1-C6 linear or branched alkyl optionally substituted with 1, 2, 3, 4, 5, 6, 7, 8, or 9 fluorine atoms, C1-C6 linear or branched heteroalkyl optionally substituted with 1, 2, 3, 4, 5, 6, 7, 8, or 9 fluorine atoms, phenyl optionally substituted with 1, 2, or 3 substituents independently selected from Group Two Substituents, or 5- to 10-membered heteroaromatic optionally substituted with 1, 2, or 3 independently selected from Group Two Substituents When a β-lactam antibiotic component is provided by a monobactam, the linker by which the β-lactam antibiotic component is covalently attached to the cannabinoid component can be selected from the group of linkers shown below ("Group C Linkers"):

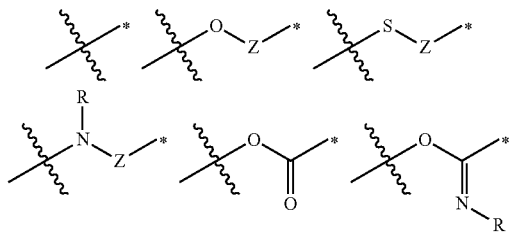

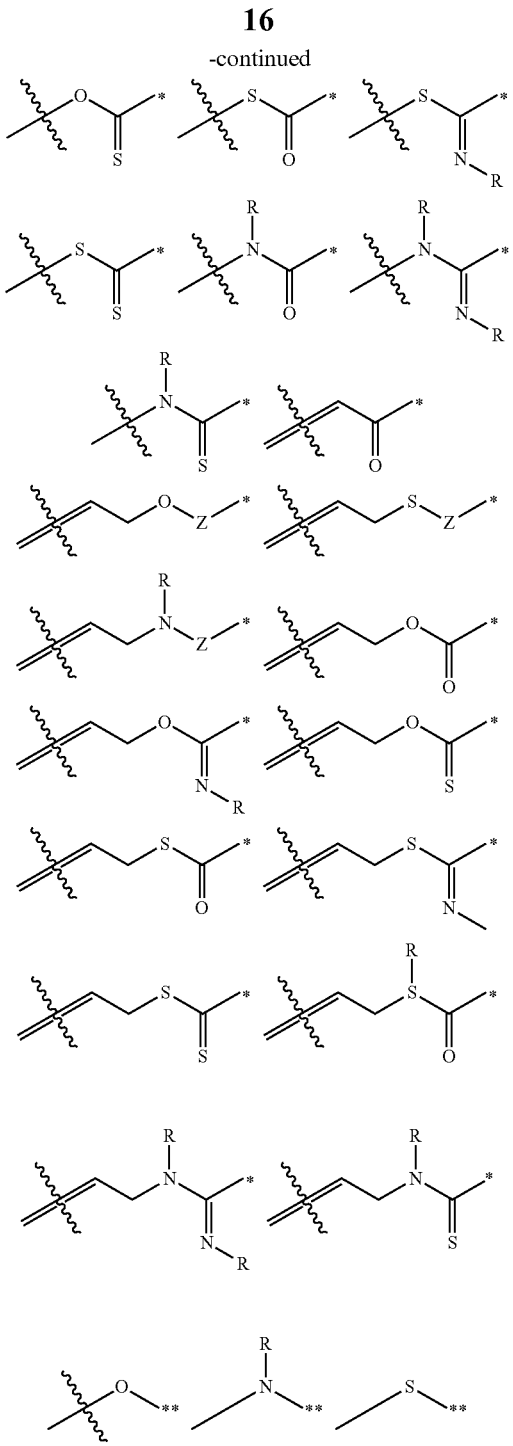

in which *, **, Z, and R are as defined for Group AB linkers.

Cannabinoid Component

A "cannabinoid component" as used in this disclosure is that portion of the cannabinoid that is present in the conjugate molecule and covalently attached to the linker, as shown in the examples below.

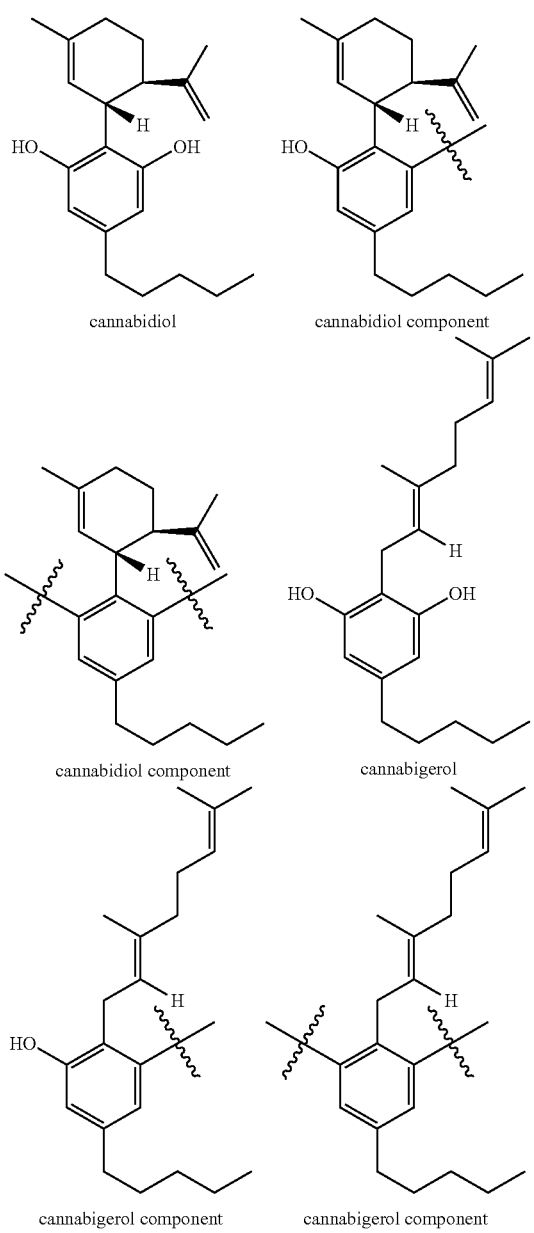

The cannabinoid component can be provided by any cannabinoid that contains a hydroxy group to which the linker can be attached. The cannabinoid can be a naturally occurring molecule, either isolated or synthesized, or a modified version of a naturally occurring molecule. See, for example, Morales et al., Frontiers in Pharmacology June 2017 review, 1-18.

Examples of cannabinoids include, but are not limited to, cannabigerols, cannabichromenes, cannabidiols, tetrahydrocannabinols, cannabicyclols, cannabielsoins, cannabinols, cannabinodiols, cannabitriols, dehydrocannabifurans, cannabifurans, cannabichromanons, and cannabiripsols.

Examples of cannabigerols include cannabigerolic acid (CBGA), cannabigerolic acid monomethylether (CBGAM), cannabigerol (CBG), cannabigerol monomethyleither (CBGM), cannabigerovarinic acid (CBGVA), and cannabigerovarin (CBGV).

Examples of cannabichromenes include cannabichromenic acid (CBC), cannabichromene (CBC), cannabichromevarinic acid (CBCVA), and cannabichromevarin (CBCV).

Examples of cannabidiols include cannabidiolic acid (CBDA), cannabidiol (CBD), cannabidiol monomethylether (CBDM), cannabidiol-$C_4$ (CBD-$C_4$), cannabidivarinic acid (CBDVA), cannabidivarin (CBDV), and cannabidiorcol (CBD-$C_1$).

Examples of tetrahydrocannabinols include Δ-9-tetrahydrocannabinolic acid A (THCA-A), Δ-9-tetrahydrocannabinolic acid B (THCA-B), Δ-9-tetrahydrocannabinol (THC), Δ-9-tetrahydrocannabinolic acid-C4 (THCA-C4), Δ-9-tetrahydrocannabinol-C4 (THC-C4), Δ-9-tetrahydrocannabivarinic acid (THCVA), Δ-9-tetrahydrocannabivarin (THCV), Δ-9-tetrahydrocannabiorcolic acid (THCA-$C_1$), Δ-9-tetrahydrocannabiorcol (THC-$C_1$), Δ-7-cis-tetrahydrocannabivarin, Δ-8-tetrahydrocannabinolic acid ($Δ^8$-THCA), and Δ-8-tetrahydrocannabinol ($Δ^8$-THC).

Examples of cannabicyclols include cannabicyclolic acid (CBLA), cannabicyclol (CBL), and cannabicyclovarin (CBLV).

Examples of cannabielsoins include cannabielsoic acid A (CBEA-A), cannabielsoic acid B (CBEA-B), and cannabielsoin (CBE).

Examples of cannabinols and cannabinodiols include cannabinolic acid (CBNA), cannabinol (CBN), cannabinol-$C_4$ (CBN-$C_4$), cannabivarin (CBV), cannabinol-$C_2$ (CBN-$C_2$), cannabiorcol (CBN-$C_1$), cannabinodiol (CBND), and cannabinodivarin (CBVD).

Examples of cannabitriols include cannabitriol (CBT), 10-ethoxy-9-hydroxy-Δ-6a-tetrahydrocannabinol, cannabitriolvarin (CBTV), and ethoxy-cannabitriolvarin (CBTVE).

Cannabifurans include dehydrocannabifuran (DCBF) and cannabifuran (CBF).

Examples of other cannabinoids include cannabichromanon (CBCN), 10-oxo-Δ-6a-tetrahydrocannabinol (OTHC), cannabiripsol (CBR), and trihydroxy-Δ-9-tetrahydrocannabinol (triOH-THC).

In some embodiments, the cannabinoid component is provided by cannabidiol.

Conjugate Molecules Comprising Two β-Lactam Antibiotic Components

In some embodiments, in which the cannabinoid component has two hydroxy groups, a second β-lactam antibiotic component can be covalently attached to the second hydroxy group by means of a second linker such that the conjugate molecule contains a first β-lactam antibiotic component and a second β-lactam antibiotic component covalently attached to the cannabinoid component by means of a first linker and a second linker, respectively.

In some embodiments, the first β-lactam antibiotic component is a cephem component. In some embodiments, the first β-lactam antibiotic component is a carbacephem component. In some embodiments, the first β-lactam component is a penem component. In some embodiments, the first β-lactam component is a carbapenem component. In some embodiments, the first β-lactam component is a monobactam component. In any of these embodiments, the second β-lactam antibiotic component can be carbapenem component, a cephem component, a carbacephem component, or a monobactam component. That is, the two β-lactam antibiotic components can be the same or different, in any combination.

The first and second linkers, too, can be the same or different. In some embodiments, the first and second linkers independently are selected from Group AB linkers. In some embodiments, the first and second linkers independently are selected from Group C linkers. In some embodiments, the first linker is selected from Group AB linkers and the second linker is selected from Group C linkers.

Examples of Conjugate Molecules

Examples of conjugate molecules comprising cephem, carbacephem, penem, carbapenem, and beta-methyl carbapenem components are shown below. For simplicity, the illustrated cannabinoid component is a cannabidiol component covalently linked to a single β-lactam antibiotic. In each case, $R_{3A}$ is

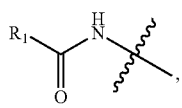

in which $R_1$ is as defined above; and $R_{3B}$ is $R_2$ as defined above.

Conjugate Molecules with Ether Linkages

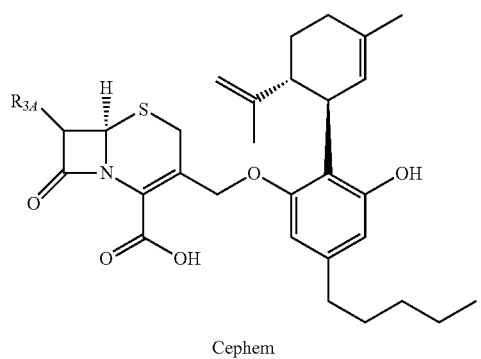

Cephem

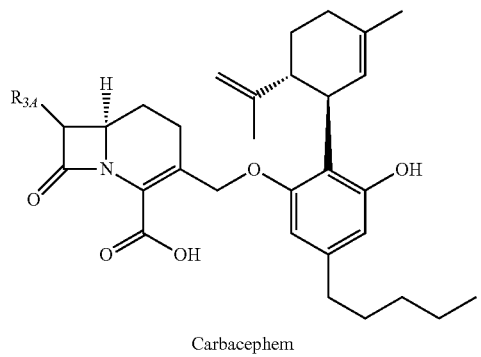

Carbacephem

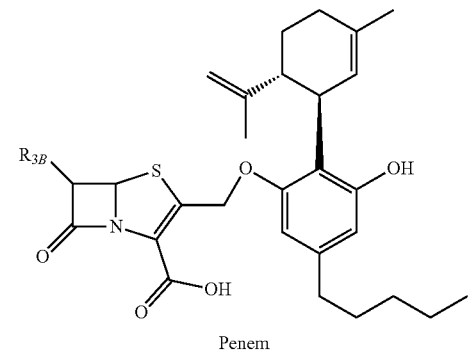

Penem

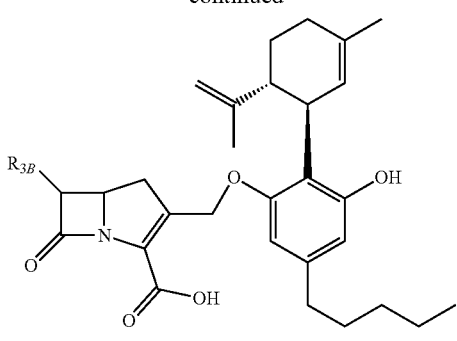

Carbapenem

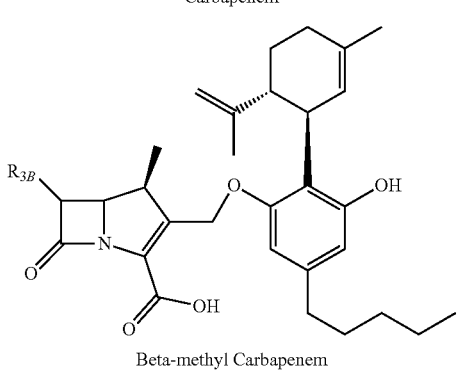

Beta-methyl Carbapenem

Conjugate Molecules with Acetal Linkages

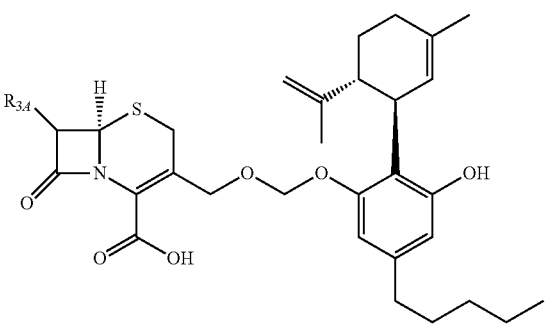

Cephem

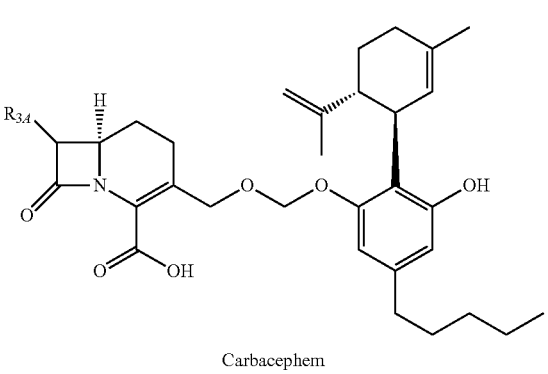

Carbacephem

22
Conjugate Molecules with Alkene Linkages
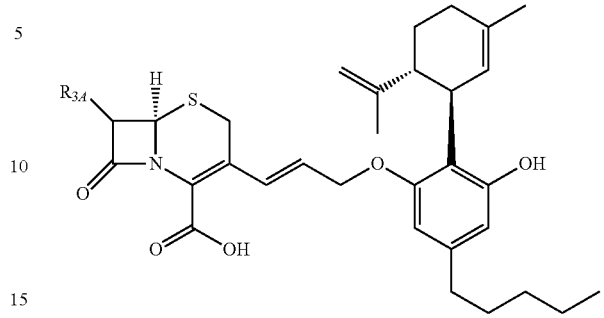
Cephem
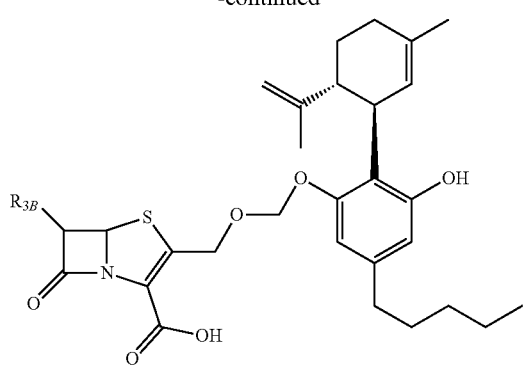
Penem
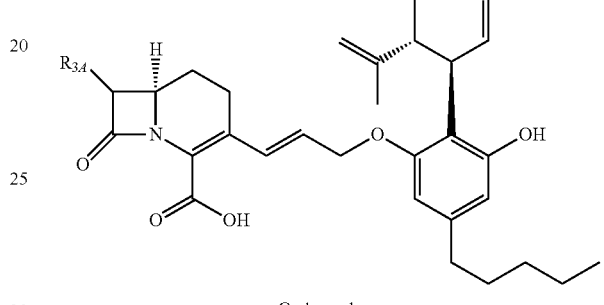
Carbacephem
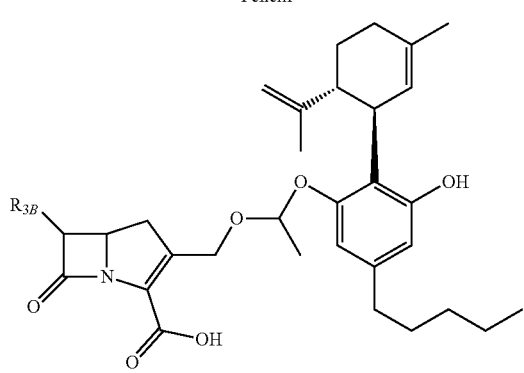
Penem
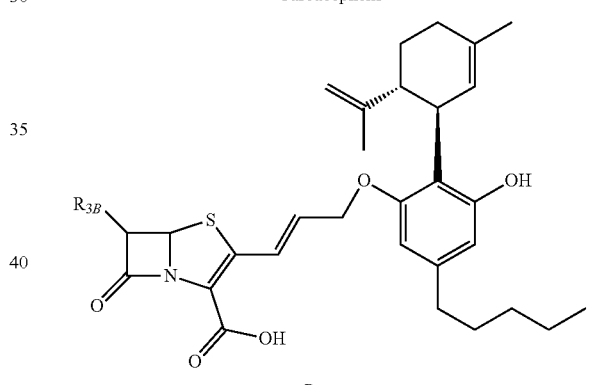
Penem
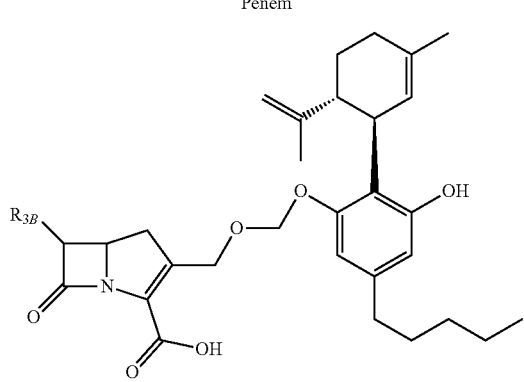
Carbapenem
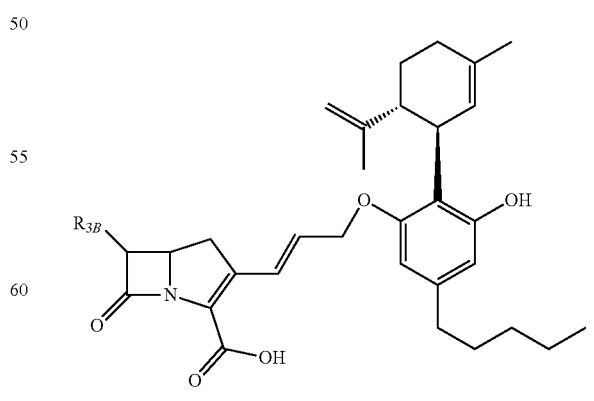
Carbapenem
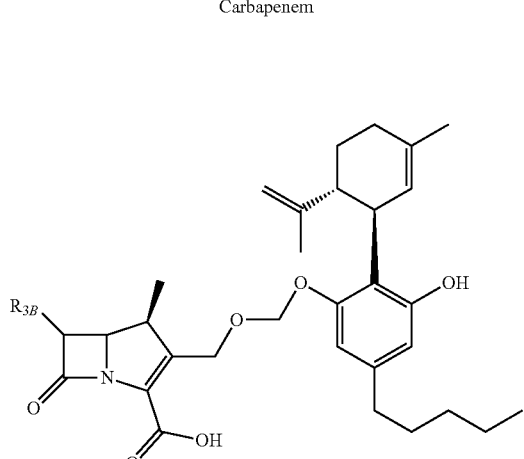
Beta-methyl Carbapenem -continued
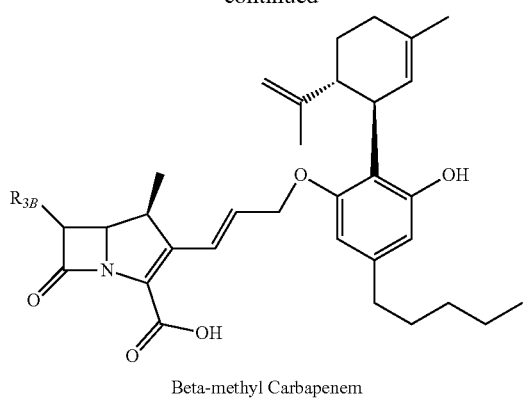
Beta-methyl Carbapenem
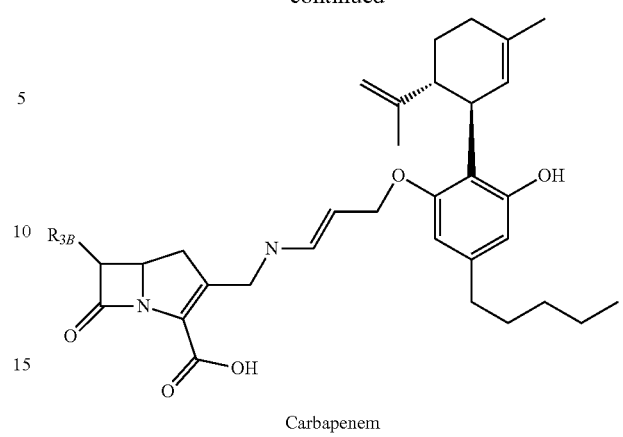
Carbapenem
Conjugate Molecules with Propenyl Amine Linkages
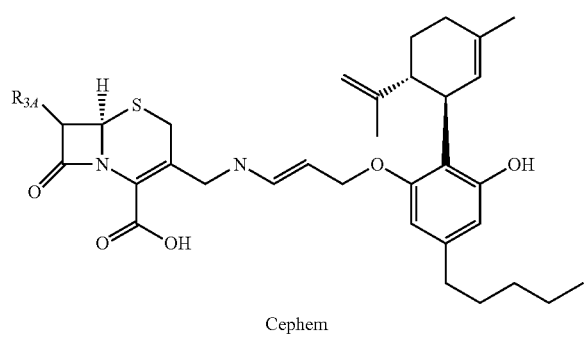
Cephem
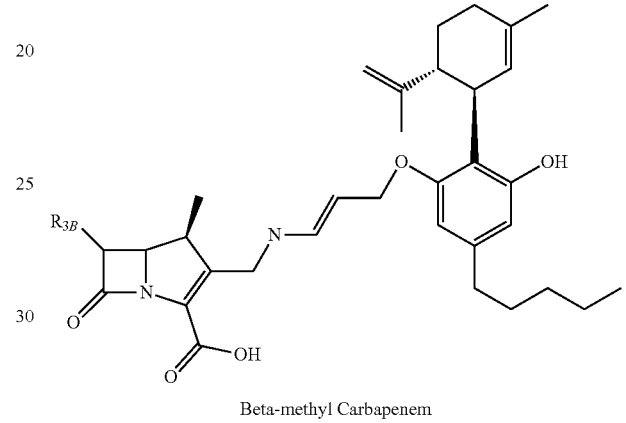
Beta-methyl Carbapenem
Conjugate Molecules with Carbamate Linkages
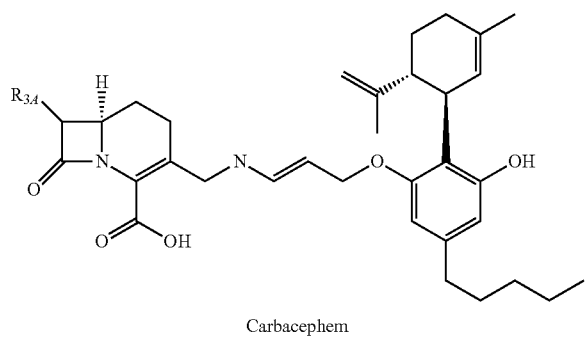
Carbacephem
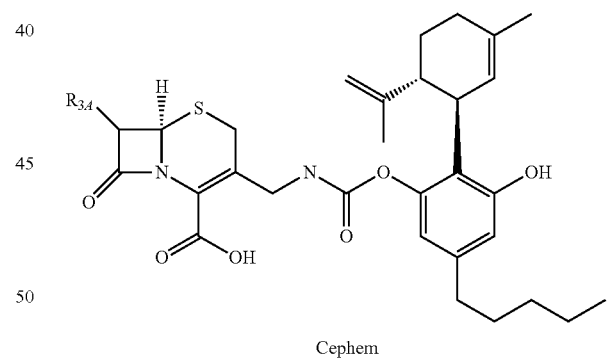
Cephem
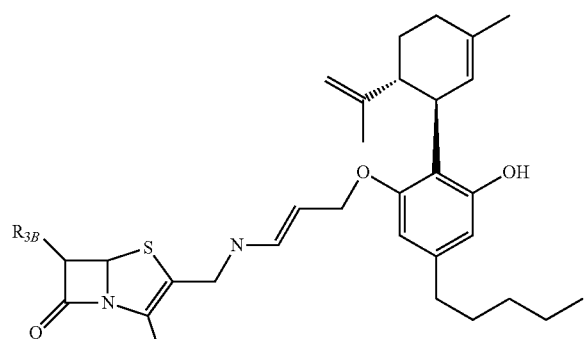
Penem
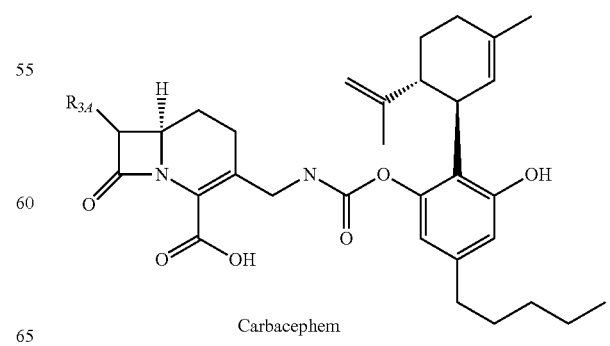
Carbacephem -continued
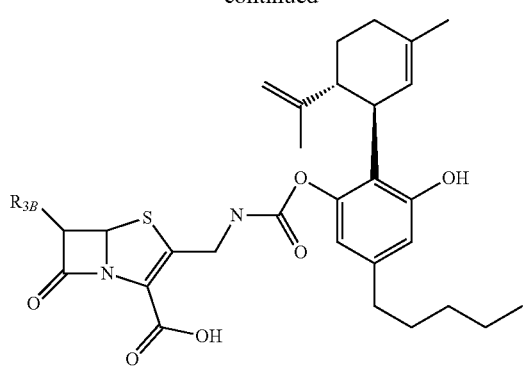
Penem
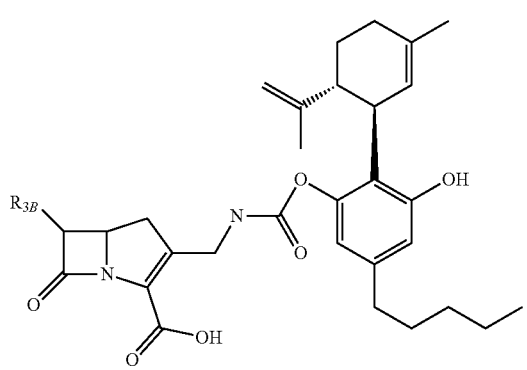
Carbapenem
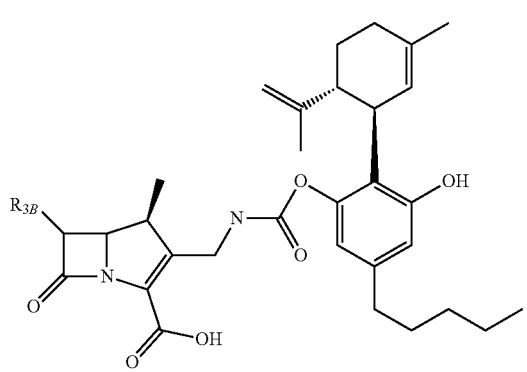
Beta-methyl Carbapenem
Conjugate Molecules with Carbonate Linkages
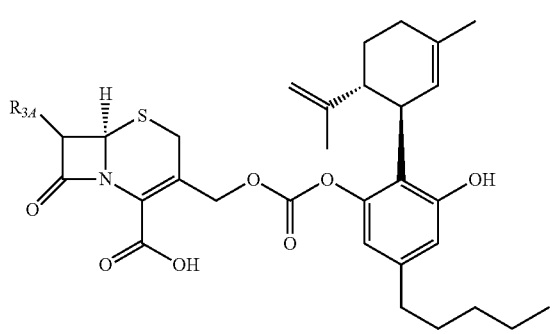
Cephem
-continued
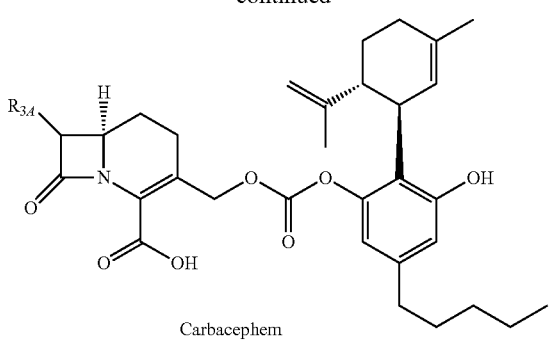
Carbacephem
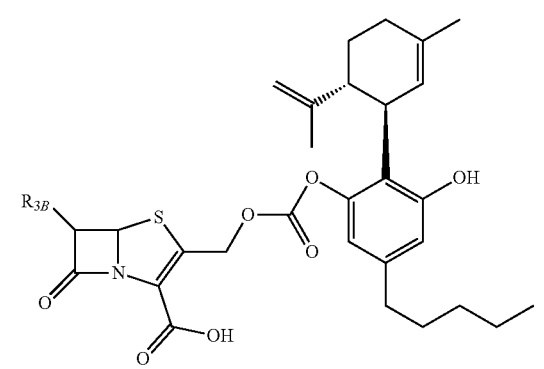
Penem
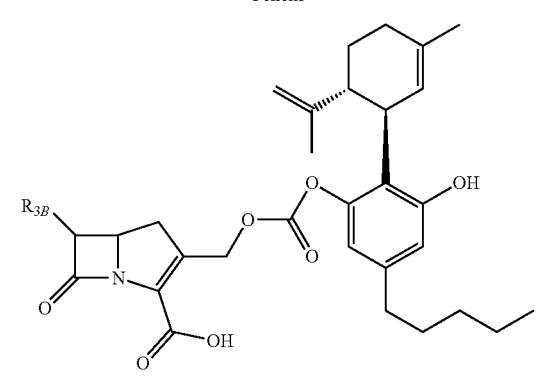
Carbapenem
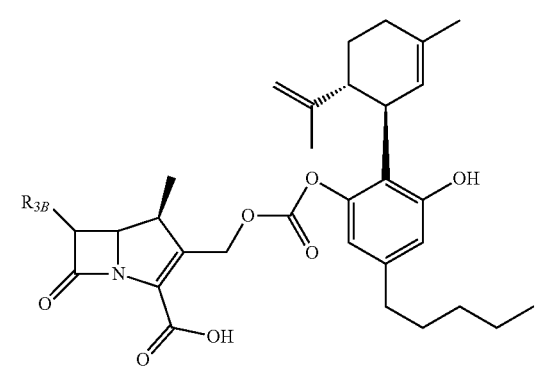
Beta-methyl Carbapenem Conjugate Molecules with Xanthate Linkages
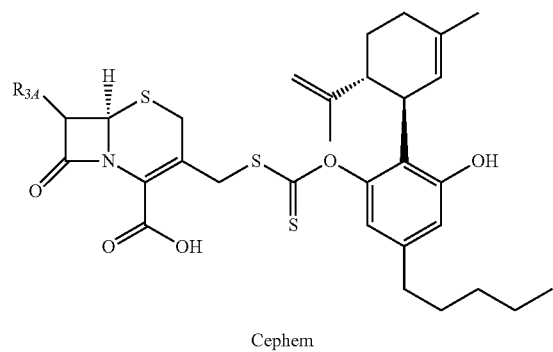
Cephem
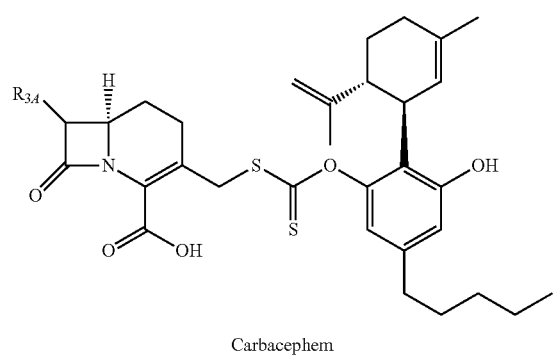
Carbacephem
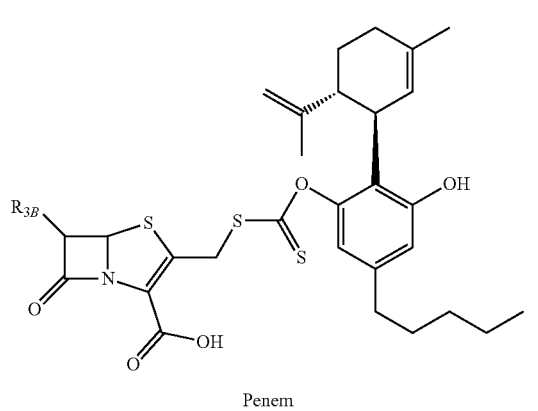
Penem
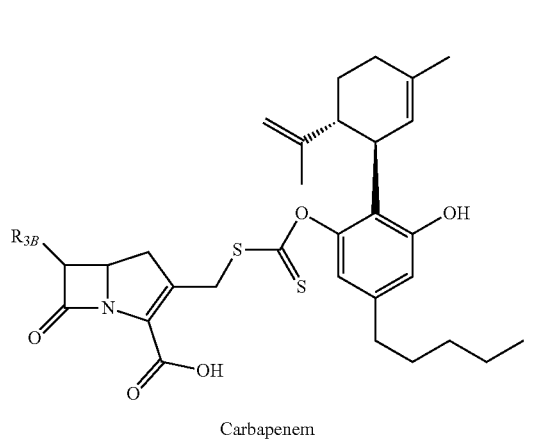
Carbapenem
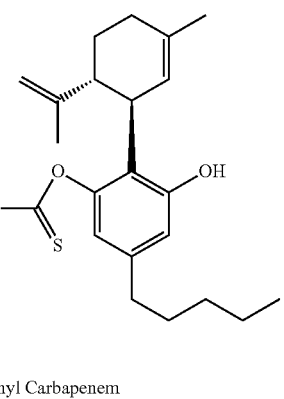
Beta-methyl Carbapenem
Conjugate Molecules with Aminal Linkages
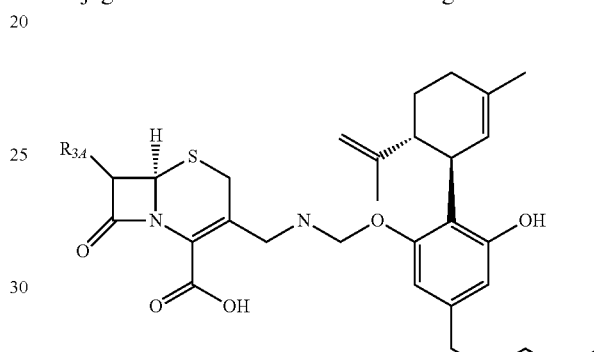
Cephem
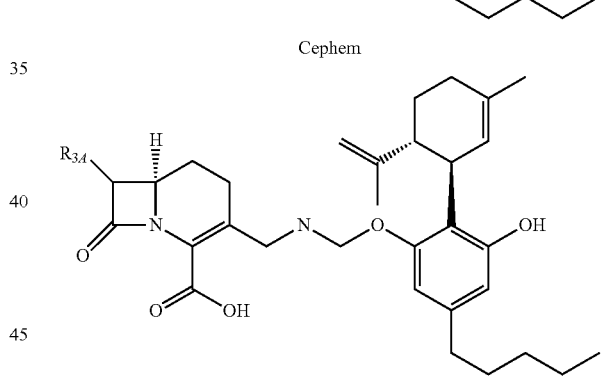
Carbacephem
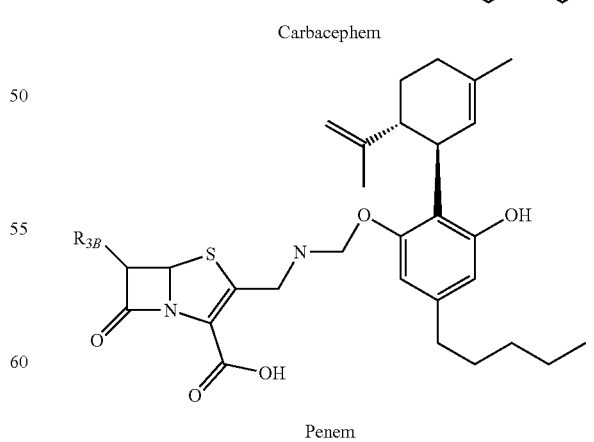
Penem

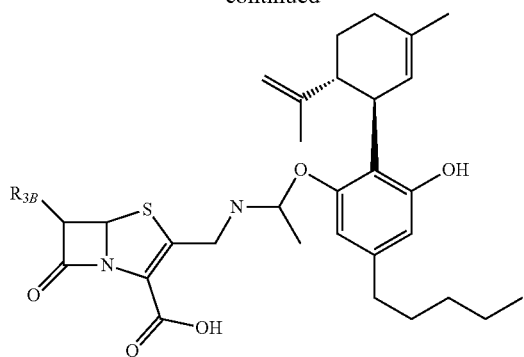
Penem
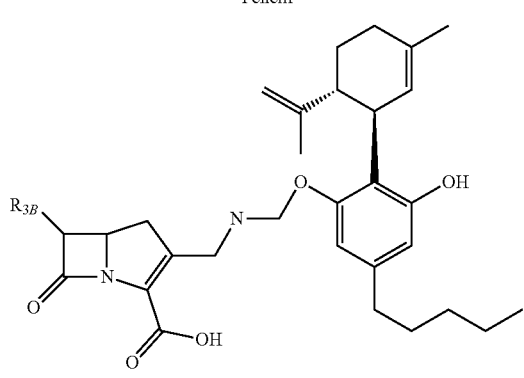
Carbapenem
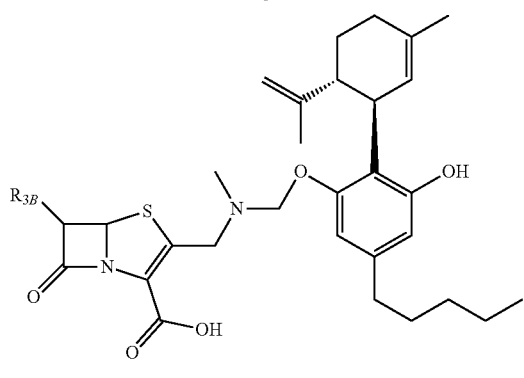
Penem
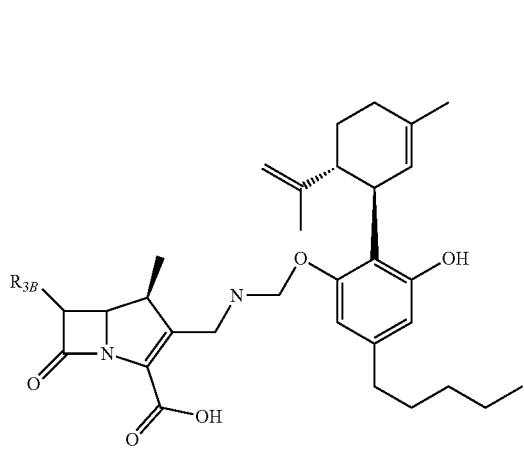
Beta-methyl Carbapenem
Conjugate Molecules with Propenyl Carbamate Linkages
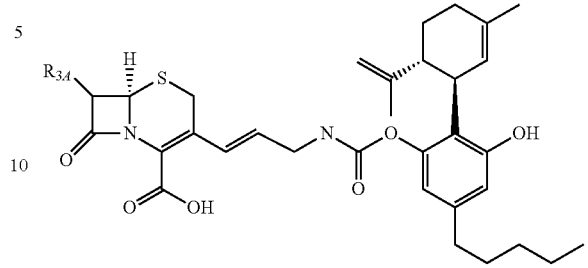
Cephem
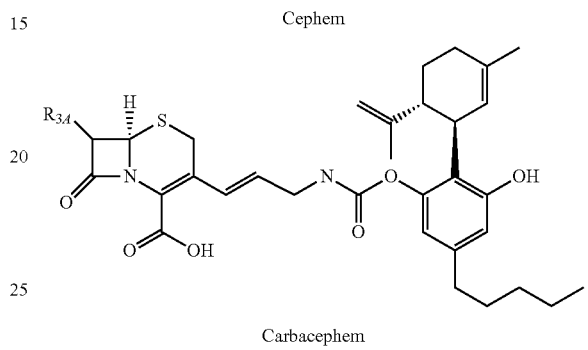
Carbacephem
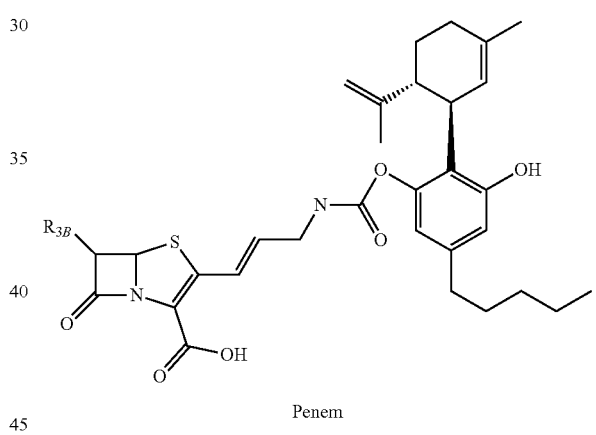
Penem
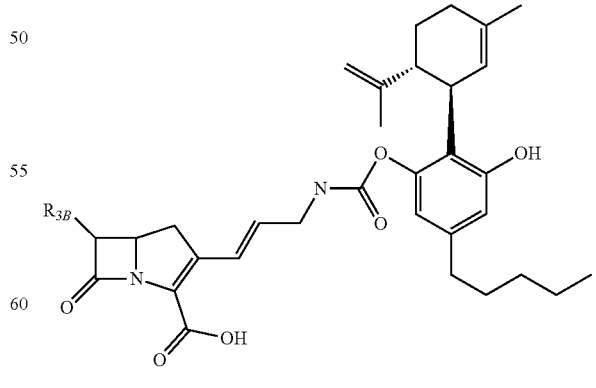
Carbapenem -continued
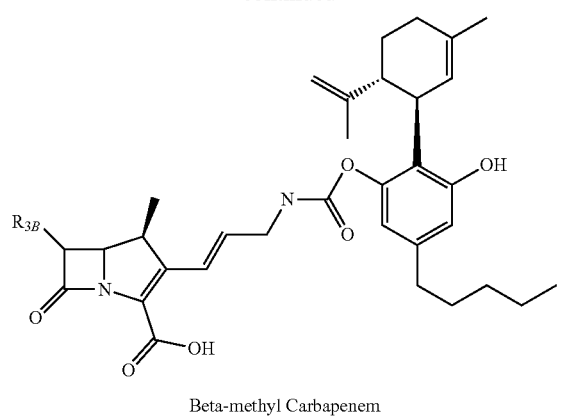
Beta-methyl Carbapenem
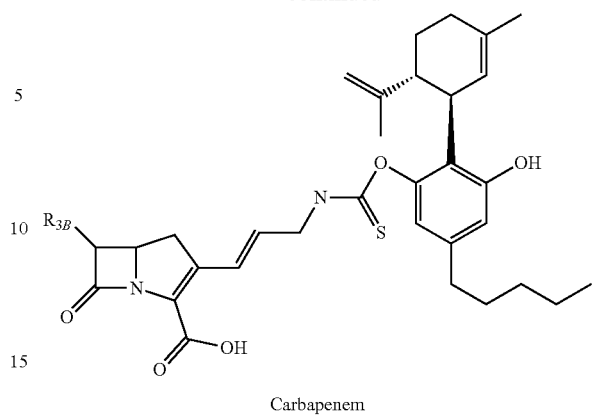
Carbapenem
Conjugate Molecules with Propenyl Thiocarbamate Linkages
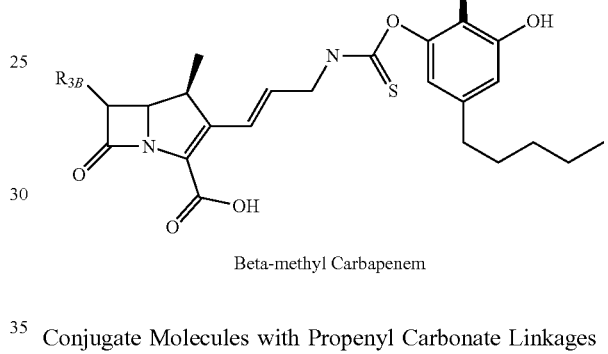
Beta-methyl Carbapenem
Conjugate Molecules with Propenyl Carbonate Linkages
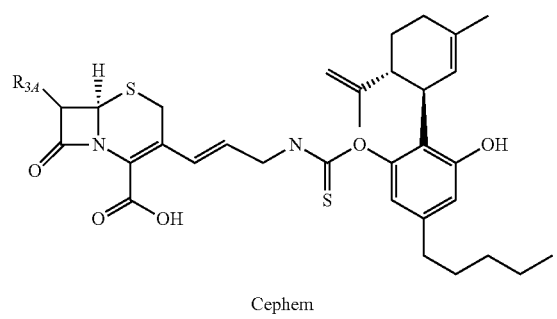
Cephem
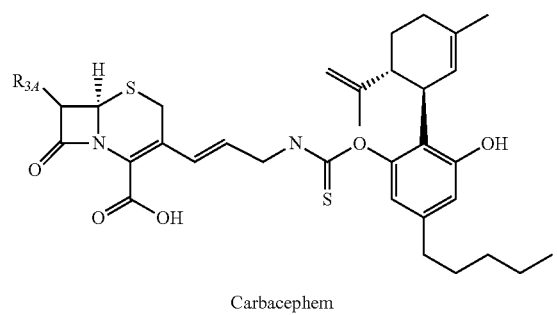
Carbacephem
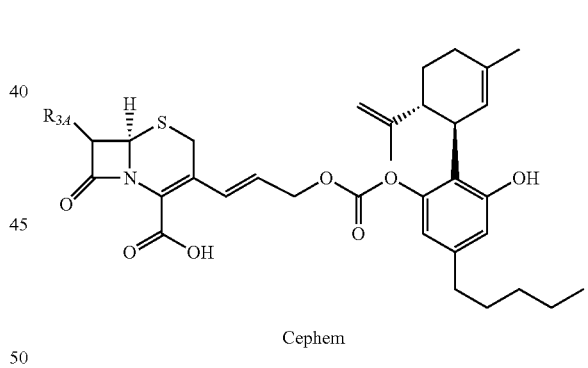
Cephem
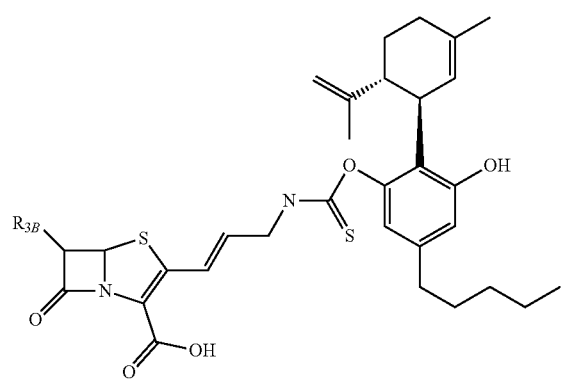
Penem
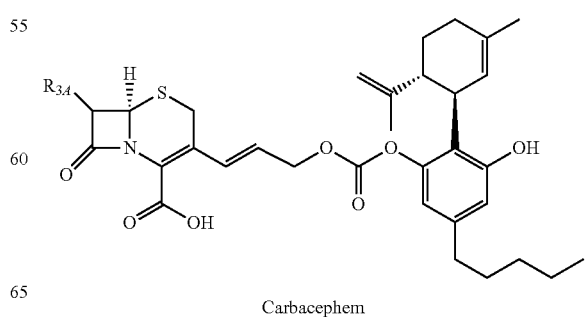
Carbacephem -continued
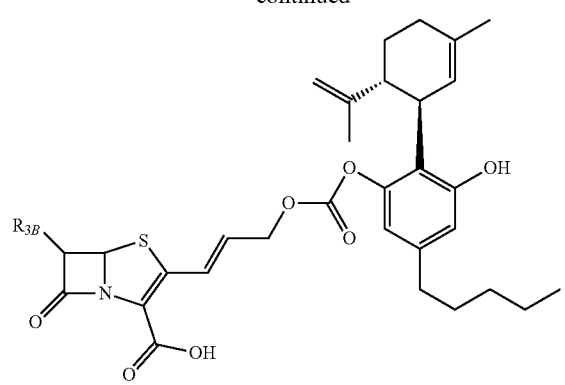
Penem
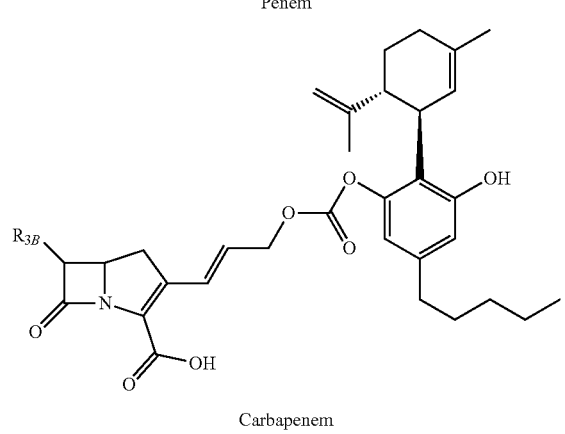
Carbapenem
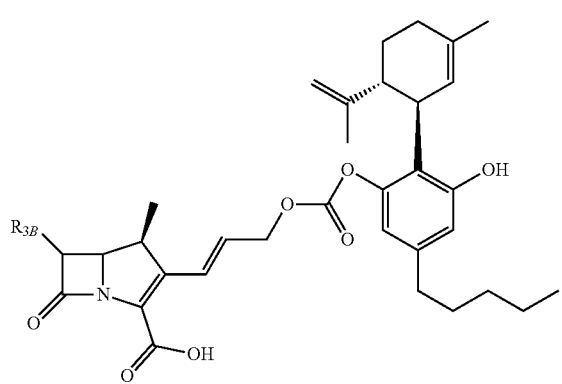
Beta-methyl Carbapenem
Conjugate Molecules with Propenyl Thiocarbonate Linkages
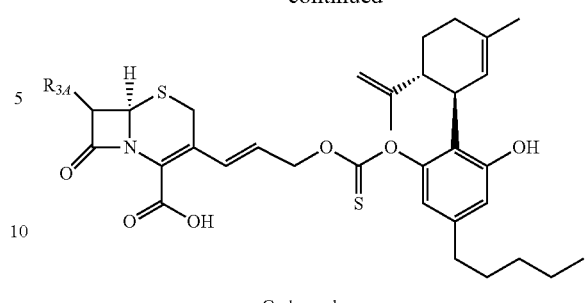
Carbacephem
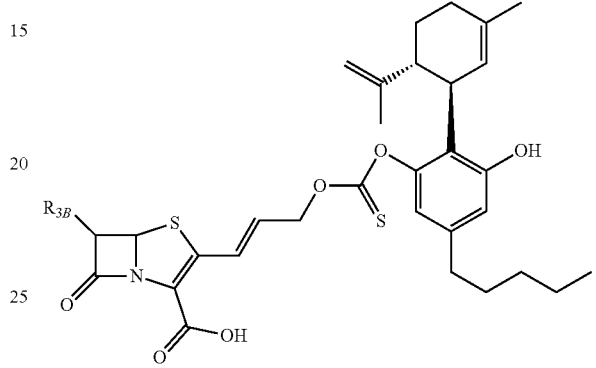
Penem
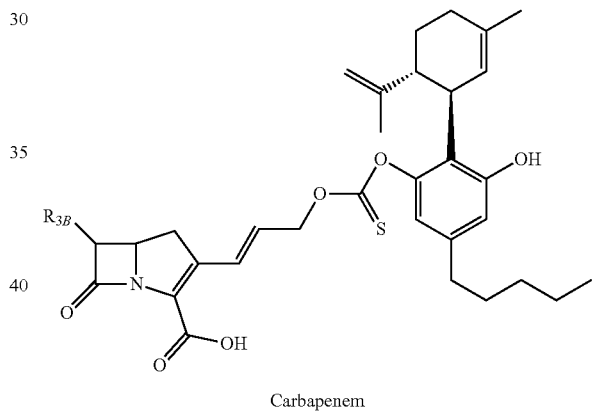
Carbapenem
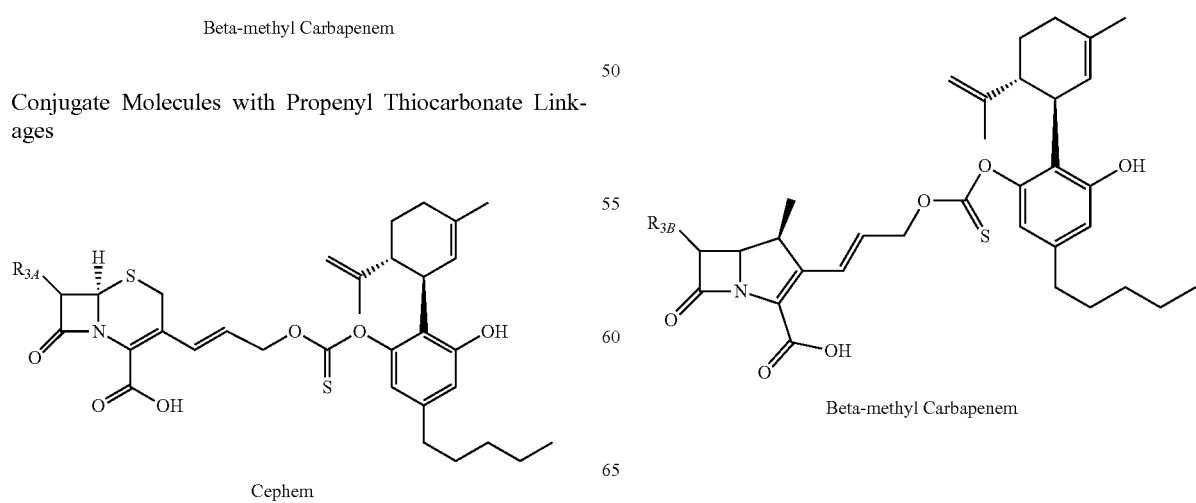
Cephem
Beta-methyl Carbapenem

Conjugate Molecules with Thiocarbamate Linkages
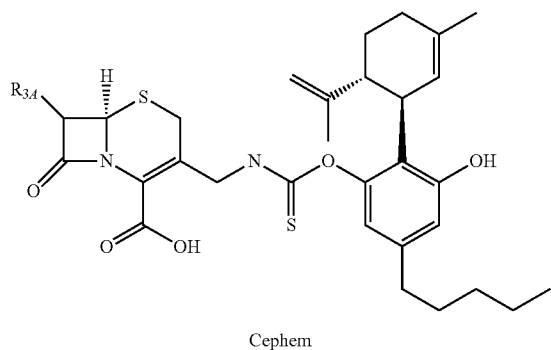
Cephem
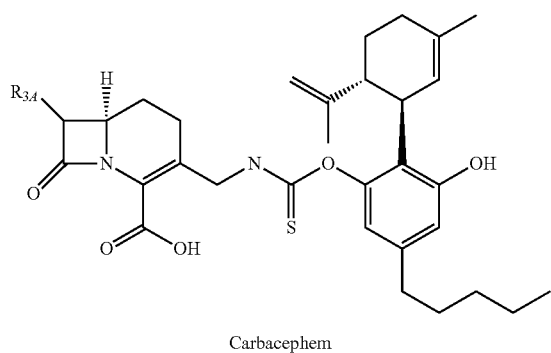
Carbacephem
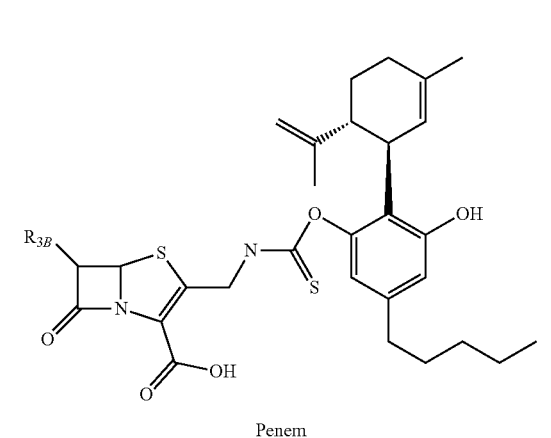
Penem
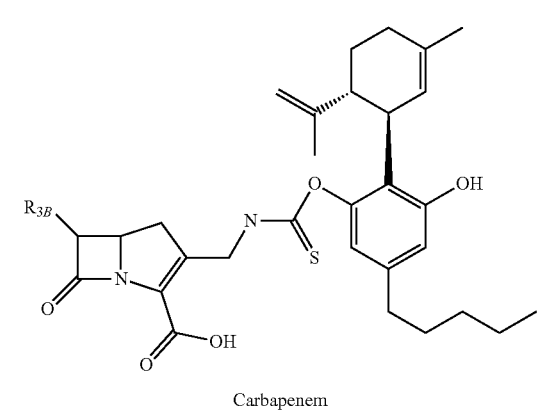
Carbapenem
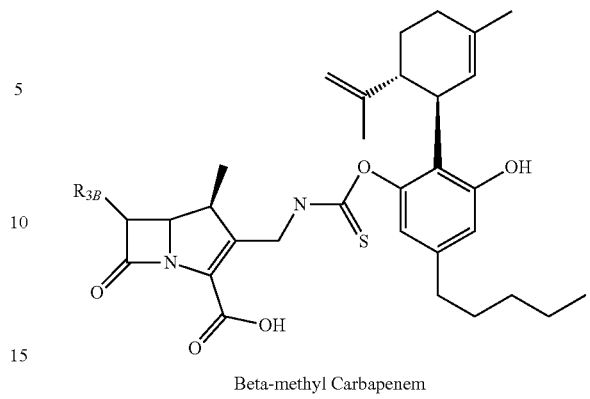
Beta-methyl Carbapenem
Conjugate Molecules with S-Alkylthiocarbonate Linkages
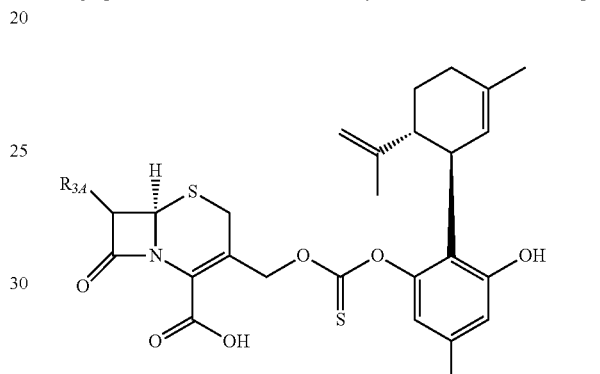
Cephem
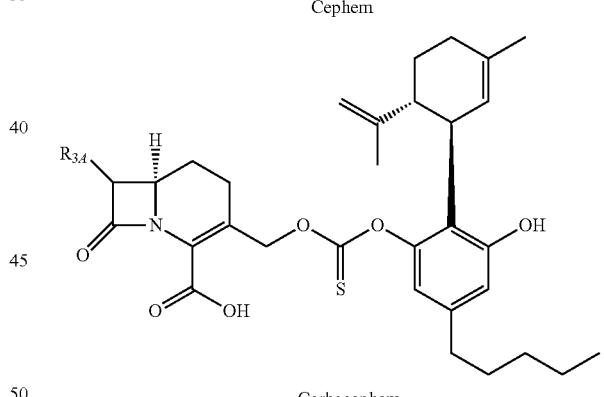
Carbacephem
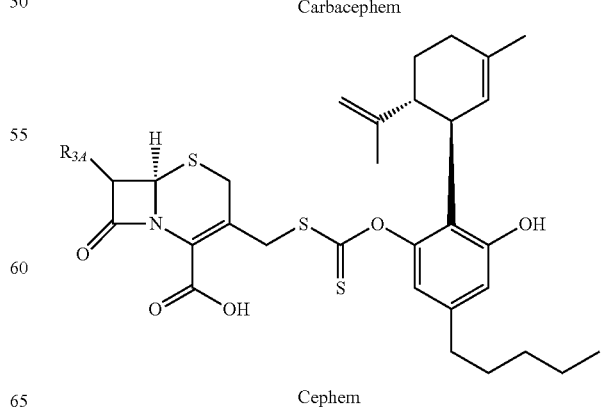
Cephem

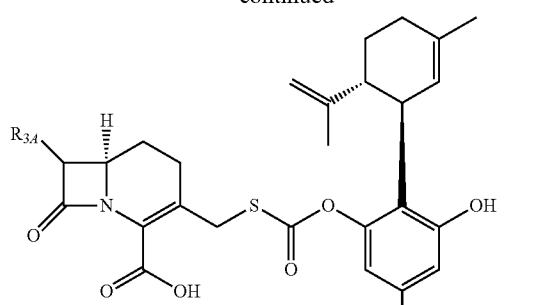
Carbacephem
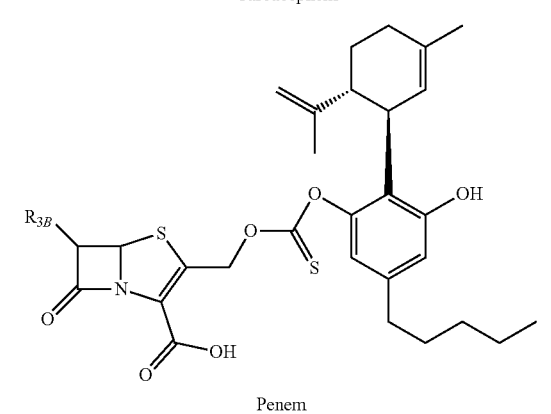
Penem
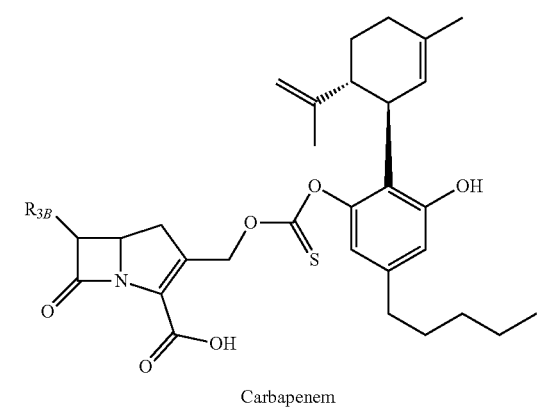
Carbapenem
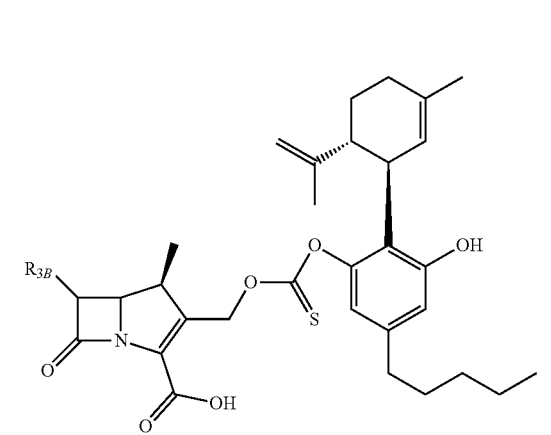
Beta-methyl Carbapenem
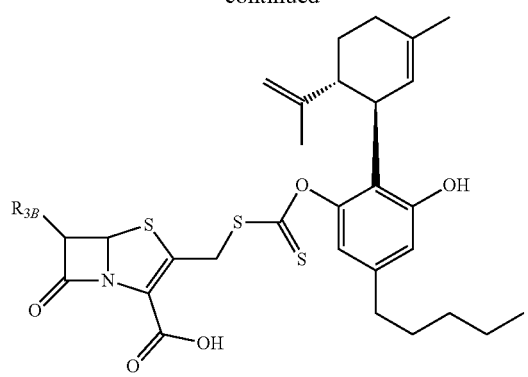
Penem
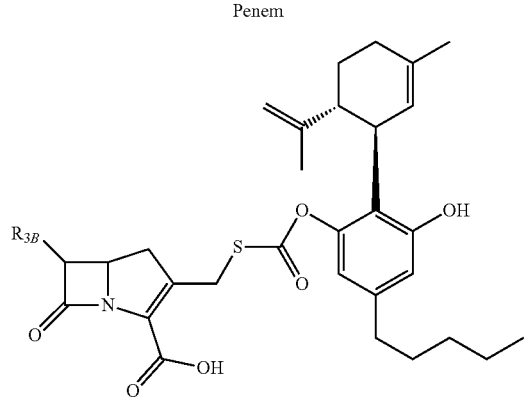
Carbapenem
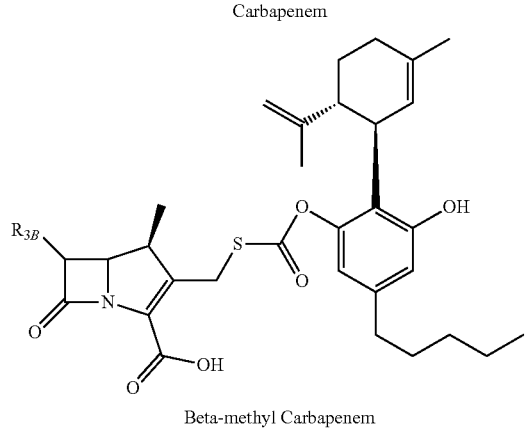
Beta-methyl Carbapenem
Conjugate Molecules with Thiohemiacetal Linkages
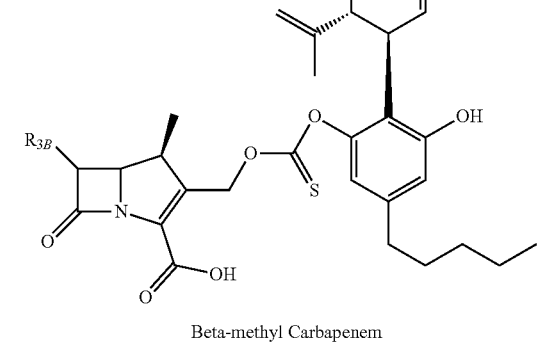
Cephem

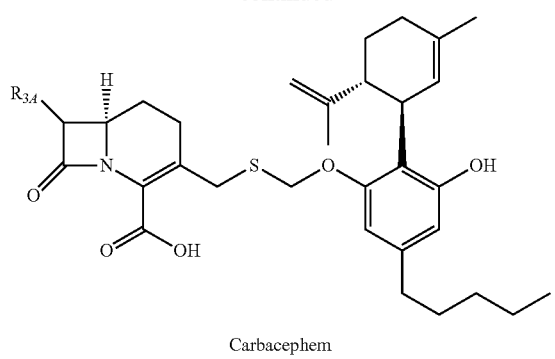
Carbacephem
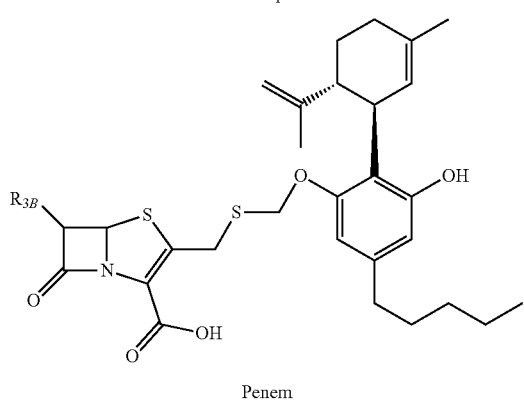
Penem
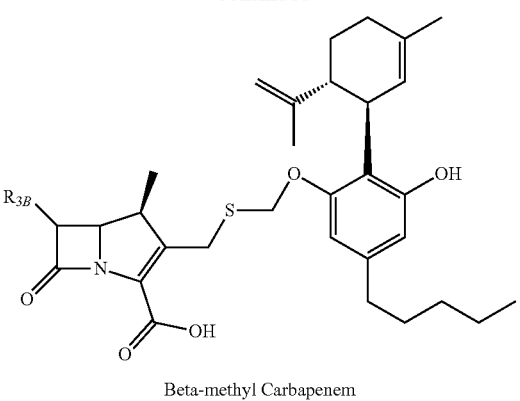
Beta-methyl Carbapenem
Examples of conjugate molecules comprising a monobactam component are shown below. For simplicity, the cannabinoid component is a cannabidiol component covalently linked to a single aztreonam component.
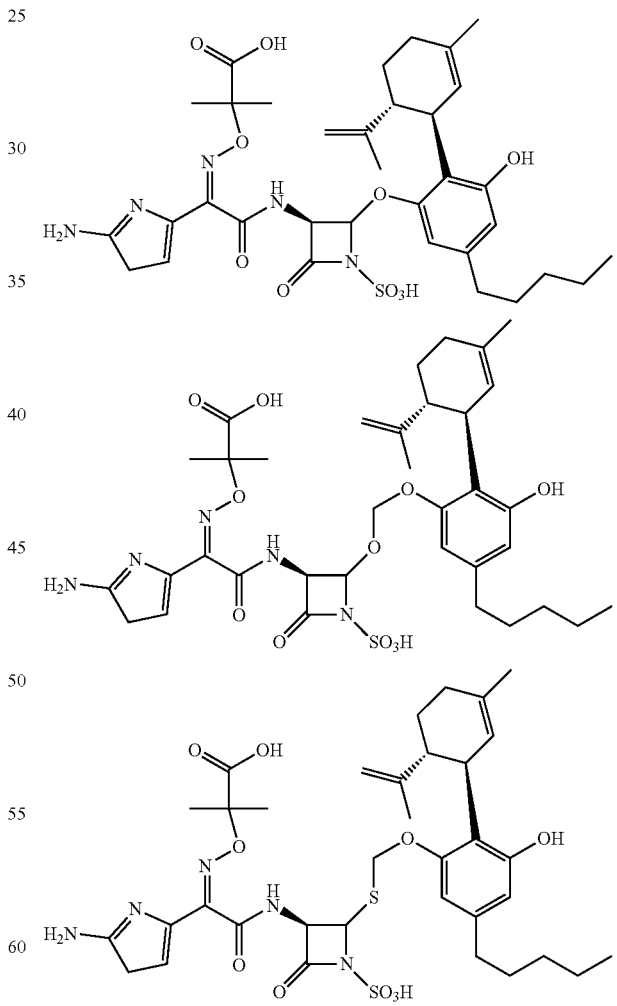
Penem
Carbapenem

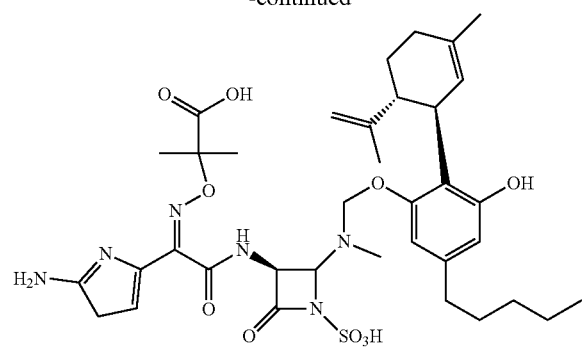
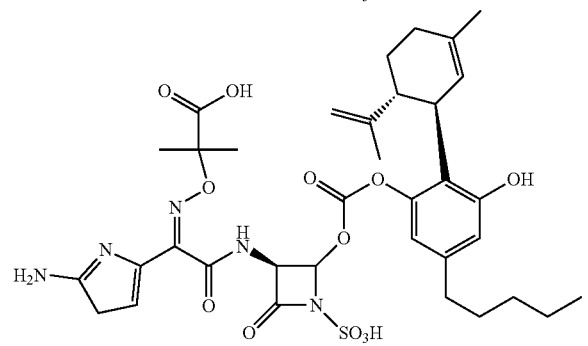
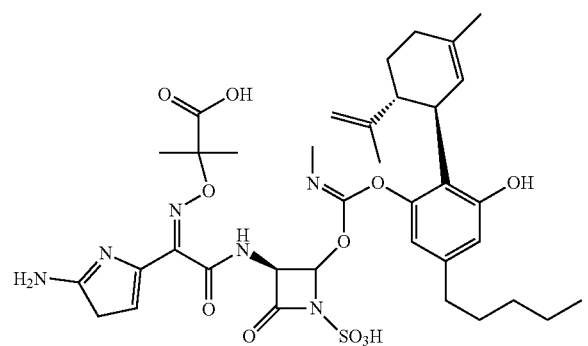
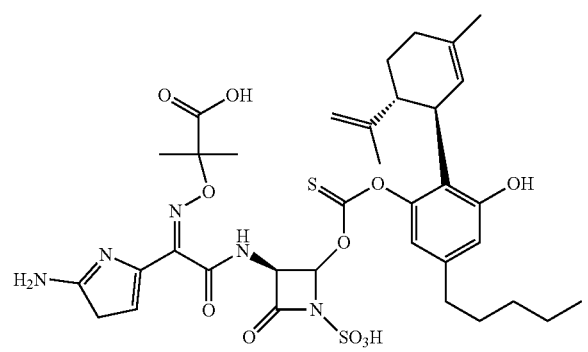
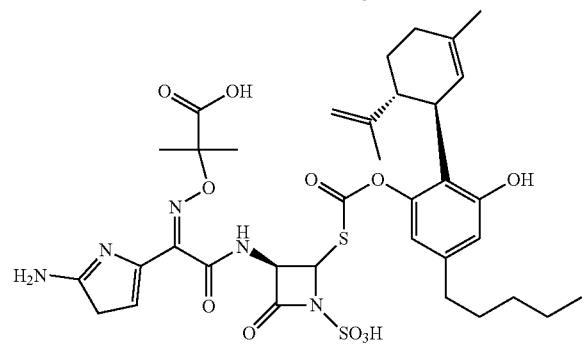
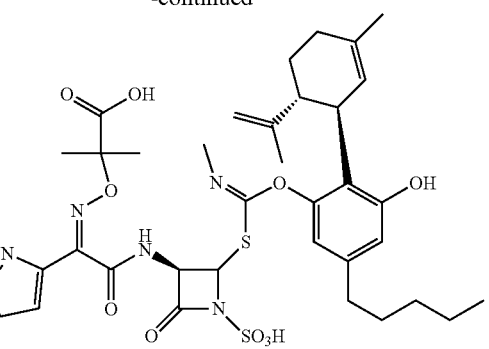
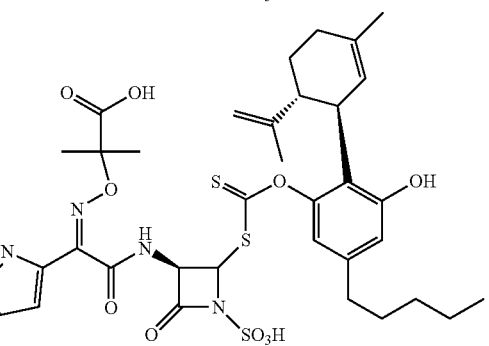
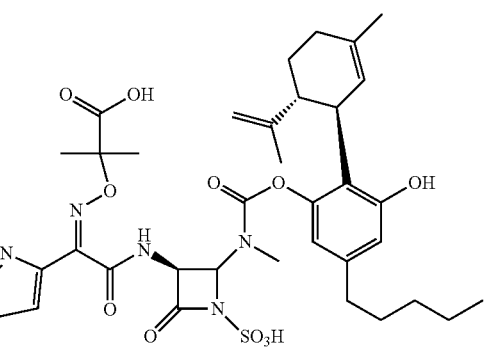
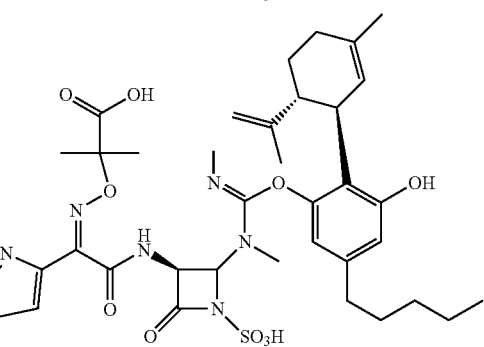
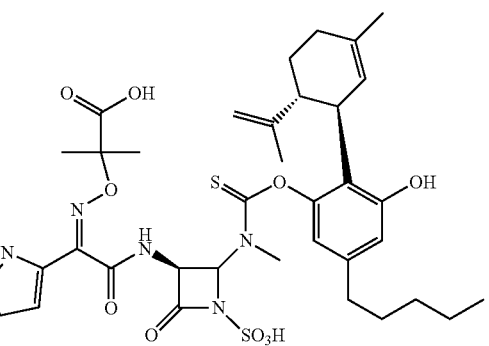

43
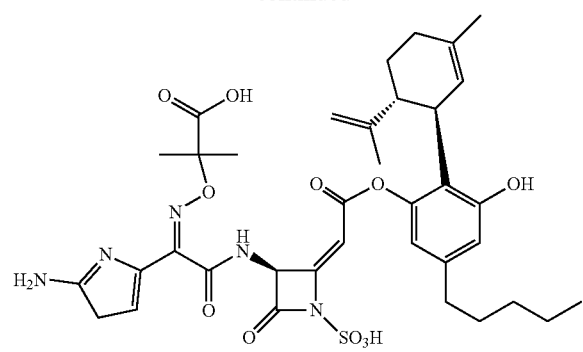
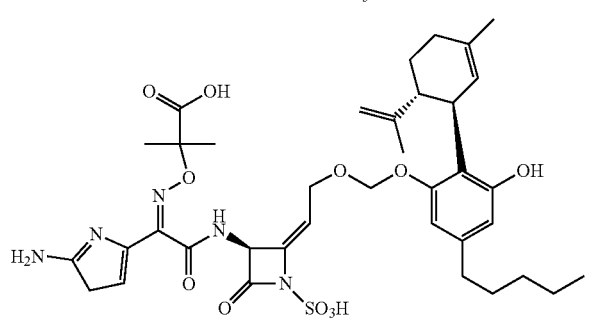
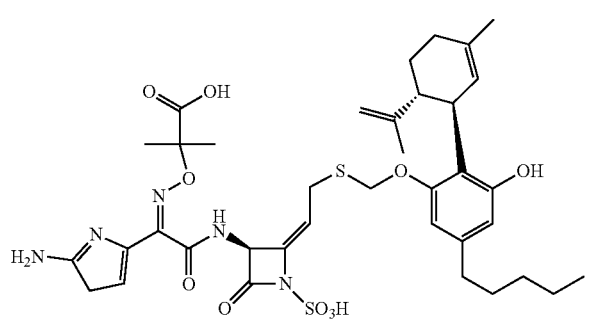
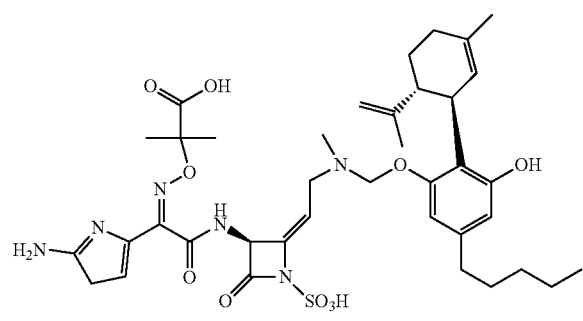
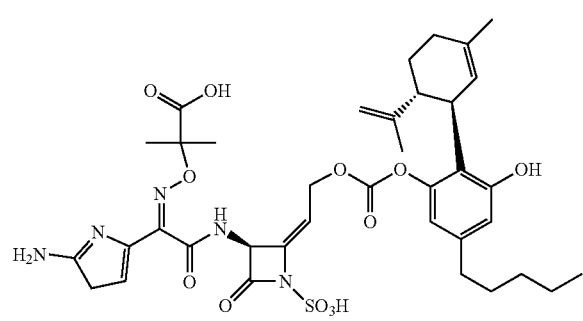
44
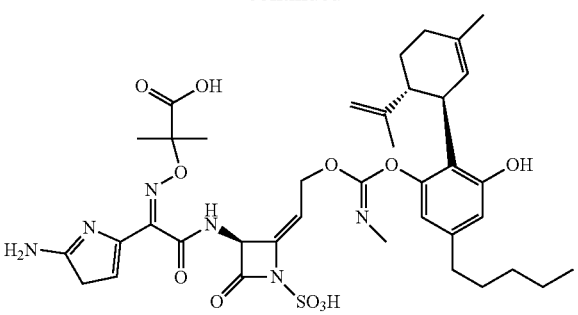
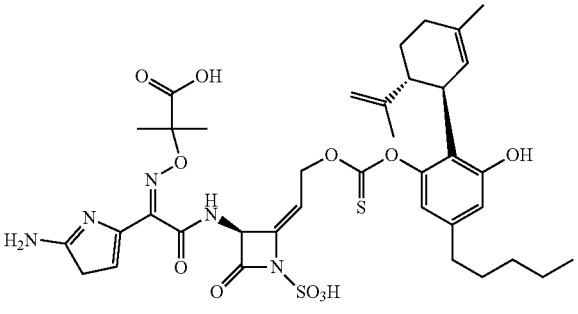
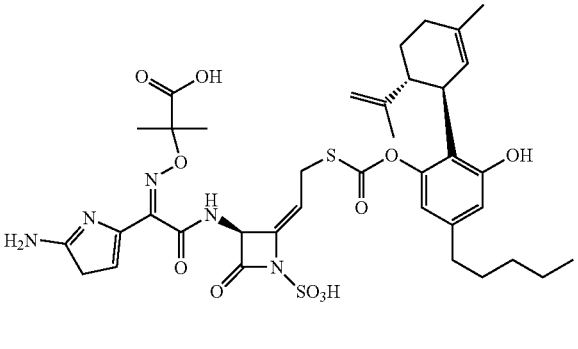
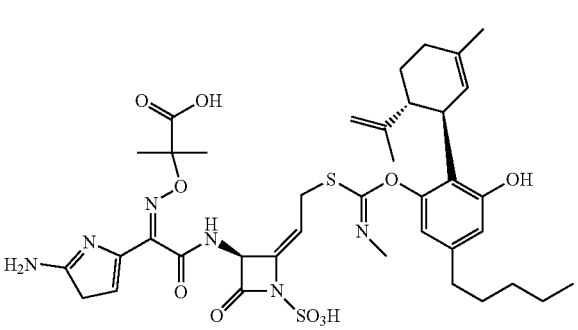
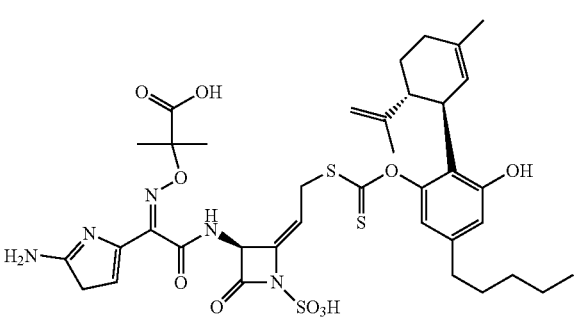

-continued

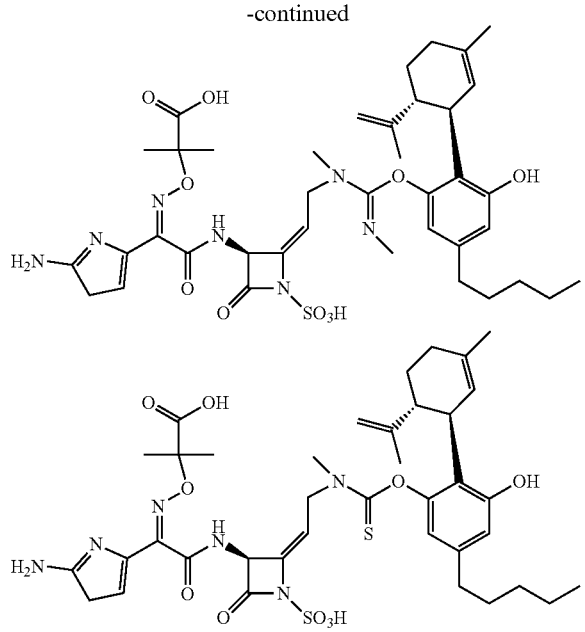

Pharmaceutical Compositions, Routes of Administration, and Dosages

One or more conjugate molecules, which can be the same or different, can be provided in a pharmaceutical composition together with a pharmaceutically acceptable vehicle. The "pharmaceutically acceptable vehicle" can comprise one or more substances which do not affect the biological activities of the conjugate molecules and, when administered to a patient, do not cause an adverse reaction. Excipients, such as calcium carbonate, calcium phosphate, various sugars and types of starch, cellulose derivatives, and gelatin can be included. Pharmaceutically acceptable vehicles for liquid compositions include, but are not limited to, water, saline, polyalkylene glycols (e.g., polyethylene glycol), vegetable oils, and hydrogenated naphthalenes. Controlled release, for example, can be achieved using biocompatible, biodegradable polymers of lactide or copolymers of lactide/glycolide or polyoxyethylene/polyoxypropylene.

Methods of preparing pharmaceutical compositions are well known. Pharmaceutical compositions can be prepared as solids, semi-solids, or liquid forms, such as tablets, capsules, powders, granules, ointments, solutions, suspensions, emulsions, suppositories, injections, inhalants, gels, microspheres, aerosols, and mists. Liquid pharmaceutical compositions can be lyophilized. Lyophilized compositions can be provided in a kit with a suitable liquid, typically water for injection (WFI) for use in reconstituting the composition.

Typical administration routes include, but are not limited to, oral, topical, transdermal, inhalation, parenteral, sublingual, buccal, rectal, vaginal, and intranasal.

The dose of a pharmaceutical composition can be based on the doses typically used for the particular antibiotic(s) which provide the β-lactam antibiotic component(s) of a conjugate molecule. These doses are well known in the art.

In some embodiments, one or more conjugate molecules are co-administered with an inhibitor of β-lactamase (e.g., clavulanic acid, sulbactam, tazobactam). "Co-administration" includes administration together with, before, or after administration of a β-lactamase inhibitor.

Therapeutic Methods

The disclosed conjugate molecules have a variety of therapeutic uses depending on which β-lactam antibiotic component(s) are included in a conjugate molecule. "Treat" as used in this disclosure means reducing or inhibiting the progression of one or more symptoms of the disorder or disease for which the conjugate molecule is administered, such as inflammation or pain.

For example, in addition to treating bacterial infections (including chronic lung infections in cystic fibrosis; e.g., Kirkby et al., Core Evidence 6, 59-66, 2011), β-lactam antibiotics have been proposed for the treatment of type I diabetes (e.g., US 2014/0234282, US 2007/0060561); treatment of cancer (e.g., US 2006/0160787,); as neuroprotective compounds (e.g., US 2007/0238717); and as proteasome inhibitors, for treatment of, e.g., Alzheimer's disease, cachexia and muscle-wasting diseases, allergies, and inflammation (in connection with rheumatoid arthritis, scleroderma, rheumatic fever, inflammatory bowel disease, myasthenia gravis, multiple sclerosis, Guillain-Barre syndrome, conjunctiva of the eye, systemic lupus erythematosus, encephalitis, Adult Respiratory Distress Syndrome, psoriasis, emphysema, and muscular dystrophy (e.g., US 2007/0060561).

The disclosed conjugate molecules can be used to treat these and other disorders in the same way the β-lactam antibiotic components of the molecules are used, and these methods are well known. An advantage of conjugate molecules, however, is that the cannabinoid can be delivered directly to the site of infection where it can provide further therapeutic benefits. The therapeutic benefits and potential benefits of cannabinoids are well known. For example, see Dzierzanowski, Cancers 11, 129-41, 2019 (oncology and palliative care); Urits et al., Pain Ther. 8, 41-51, 2019 (pain); Hillen et al., Ther. Adv. Drug Safety 10, 1-23 2019 (neuropsychiatric symptoms in dementia)

In addition, C. sativa extracts have microbicidal activity in vitro against gram-positive bacteria (e.g., Bacillus subtilis, Bacillus pumilus, Stephlococcus aureus, Micrococcus flavus, Clostridium sporogens, Enterococcus faecium, and Streptococcus salivarius); gram-negative bacteria (e.g., Proteus vulgaris, Bordetella bronchioseptica, Pectobacterium carotovorum, and Pseudomonas savastonoi); and fungi (e.g., Aspergillus niger). See Elphick, Gene 399, 65-71, 2007; Wasim et al., J. Pharm. Sci. 8, 29-38, 1995; Nissen et al., Fitoterapia 81, 413-19, 2010; and Hernandez-Cervantes et al., Neuroimmunomodulation 24, 183-99, 2017. See also Appendino et al., J. Nat. Prod. 71, 1427-30, 2008.

EXAMPLES

The following synthetic methods are general. They can be used to make these examples or related conjugate molecules using alternative building blocks, intermediates, or reagents. Alternative reagent systems and conditions to achieve desired transformations can be used. Alternative protecting group strategies can be used. Standard purification techniques can be used at any stage of a synthesis.

Example 1. Ether-Linked Conjugate Molecules

Cephem Conjugate Molecules

Cephem ether linked conjugate molecules are synthesized according to the following Scheme. The CAS numbers for the two key building blocks is shown. Reaction conditions follow standard conditions for amine acylation in the first step to attach the cephem side chain, for alkylation of a phenol group of CBD in the second step with optional use of a catalyst or enhancer such as NaI, followed by standard removal of the p-methoxybenzyl protecting group in the third step to furnish the product.

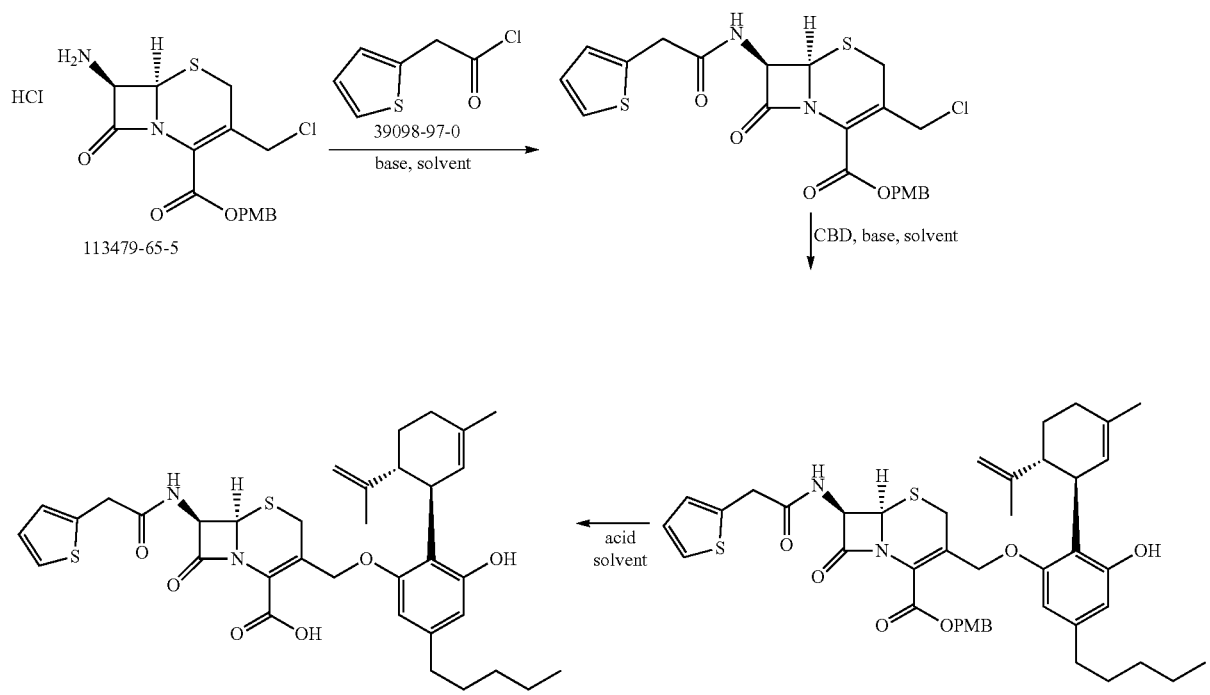

Carbacephem Conjugate Molecules

Carbacephem ether linked conjugate molecules are synthesized according to the following Scheme. The general starting material [177472-75-2] was reported in racemic form as [54296-34-3] (Journal of the American Chemical Society (1974), 96(24), 7584) and is elaborated to the iodide intermediate after installing a side chain of choice using a previously reported process (WO 96/04247). Alkylation of CBD with the iodide followed by deprotection, both steps under standard conditions, provides the desired product.

Penem Conjugate Molecules

Penem ether linked conjugate molecules are synthesized according to the following Scheme. The starting material [145354-22-9], prepared as reported (Journal of Organic Chemistry, 58(1), 272-4; 1993), is reacted with CBD under standard alkylating conditions. The silyl ether TBS protecting group is then removed followed by deallylation under known conditions to give the desired product.

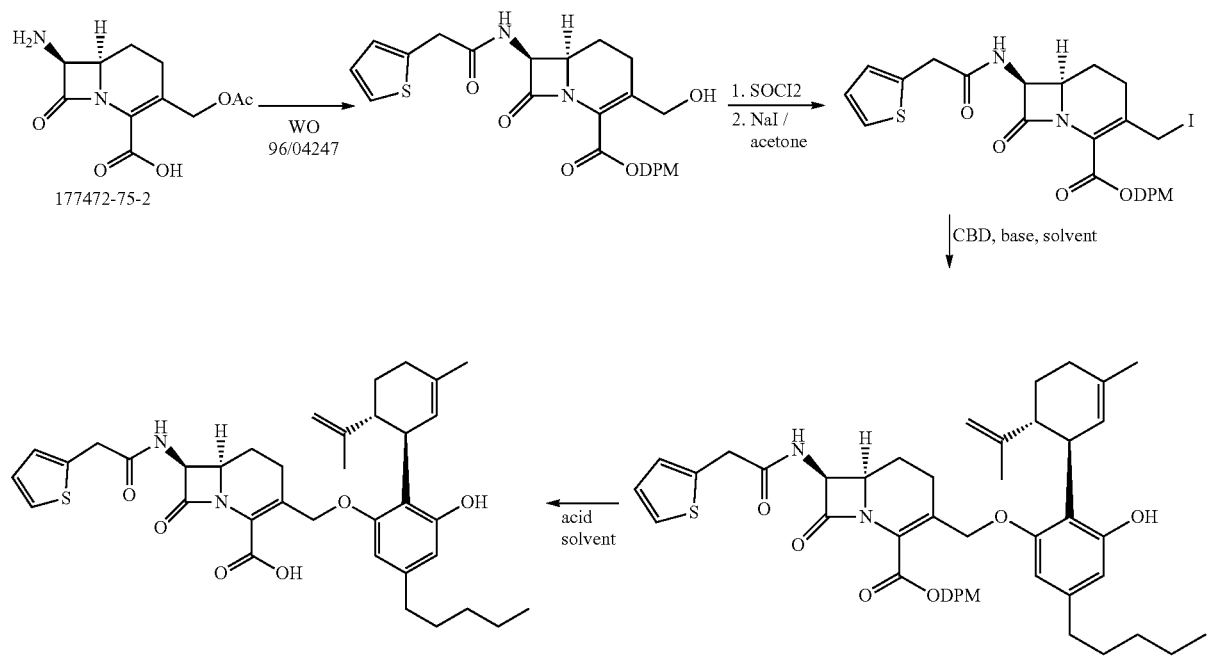

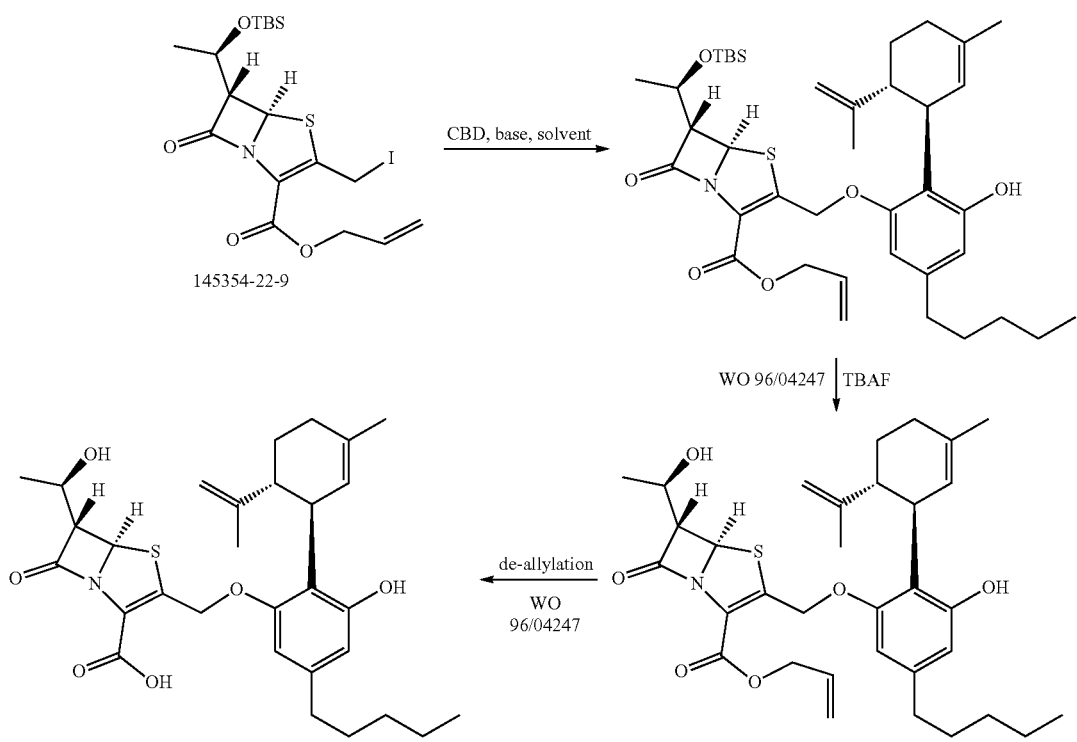

Carbapenem Conjugate Molecules

Carbapenem ether linked conjugate molecules are synthesized according to the following Scheme. The starting material [136324-03-3] is reacted with CBD under standard alkylating conditions. The silyl ether TES protecting group is then removed followed by removal of the p-methoxybenzyl ester protecting group under known conditions to give the desired product.

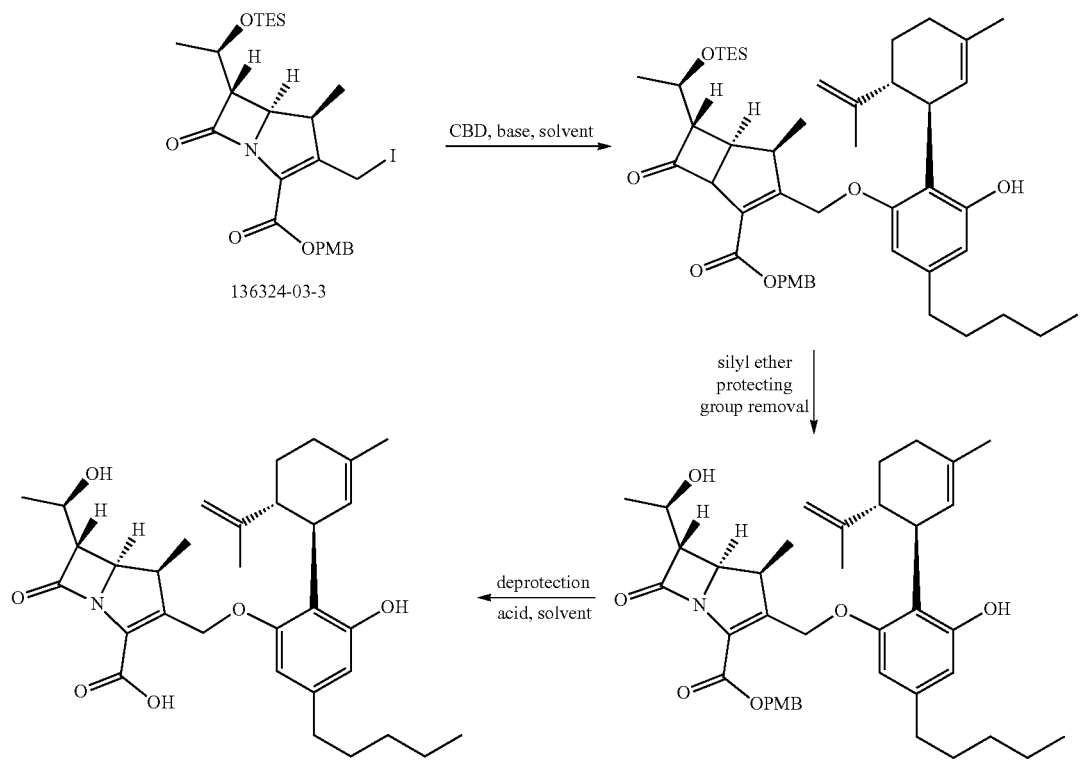

Example 2. Carbonate-Linked Conjugate Molecules

Cephem Conjugate Molecules

Cephem carbonate linked conjugate molecules are synthesized according to the following Scheme. The starting material is acylated with a side chain of choice and then the acid is protected as described previously (WO 96/04247). The resulting alcohol is then treated with phosgene and the adduct reacted with CBD in the presence of base to form the carbonate-linked intermediate, which is then deprotected with acid to deliver the desired product.

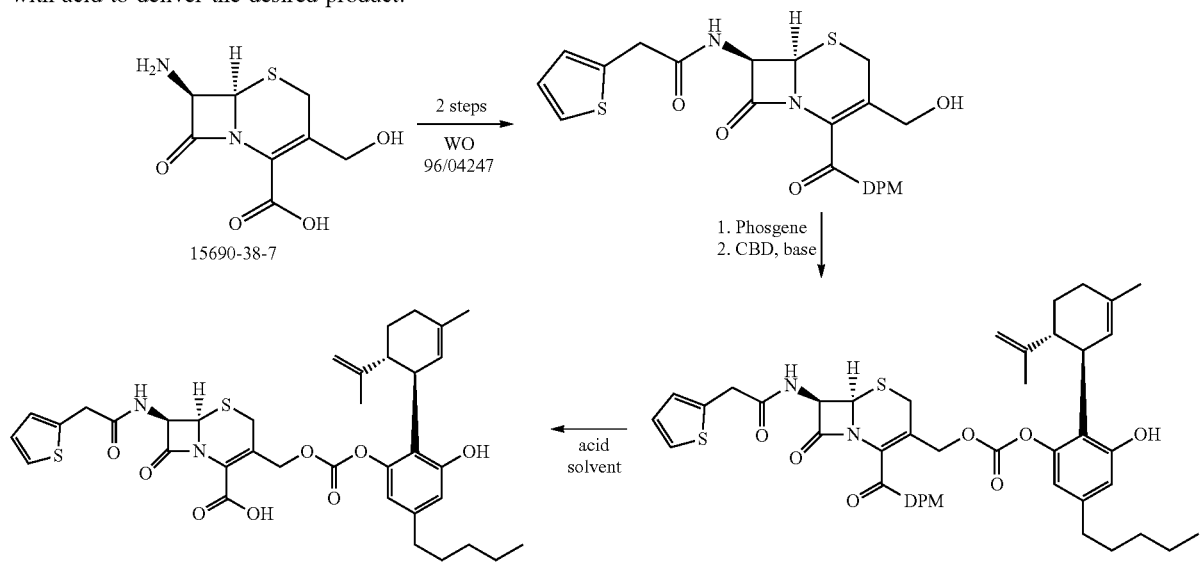

Carbacephem Conjugate Molecules

Carbacephem carbonate linked conjugate molecules are synthesized according to the following Scheme. The starting material is acylated with a side chain of choice and then the acid is protected as described previously (WO 96/04247). The resulting alcohol is then treated with phosgene and the adduct reacted with CBD in the presence of base to form the carbonate-linked intermediate, which is then deprotected with acid to deliver the desired product.

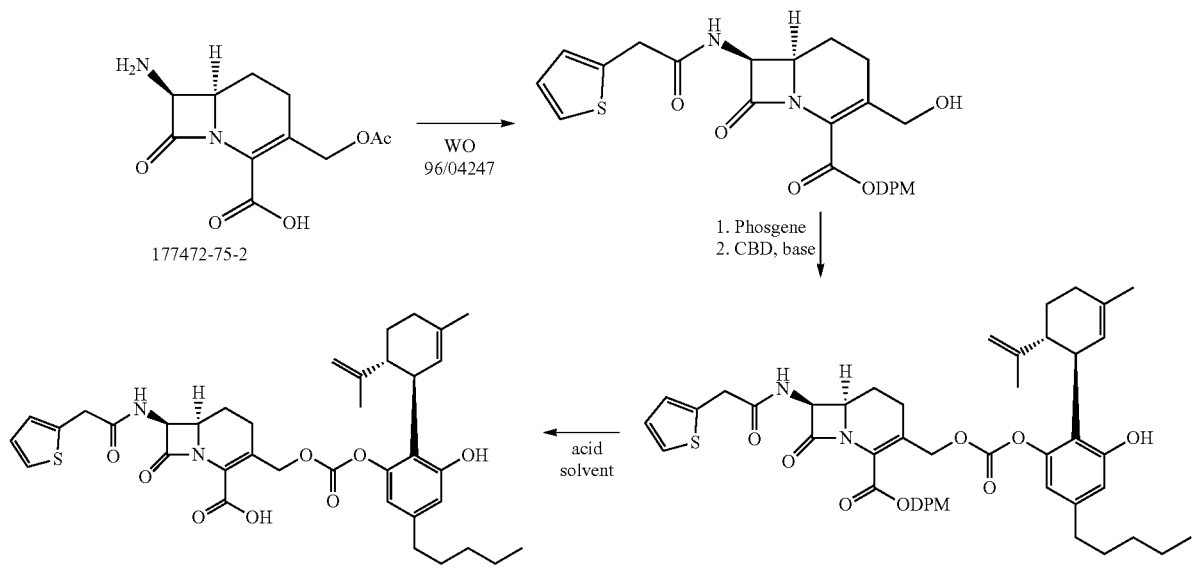

Penem Conjugate Molecules

Penem carbonate linked conjugate molecules are synthesized according to the following Scheme. The starting material [88585-78-8], prepared as reported (U.S. Pat. No. 4,631,150), is reacted with phosgene and the intermediate reacted with CBD under standard basic conditions. The silyl ether TBS protecting group is then removed followed by deallylation under known conditions to give the desired product.

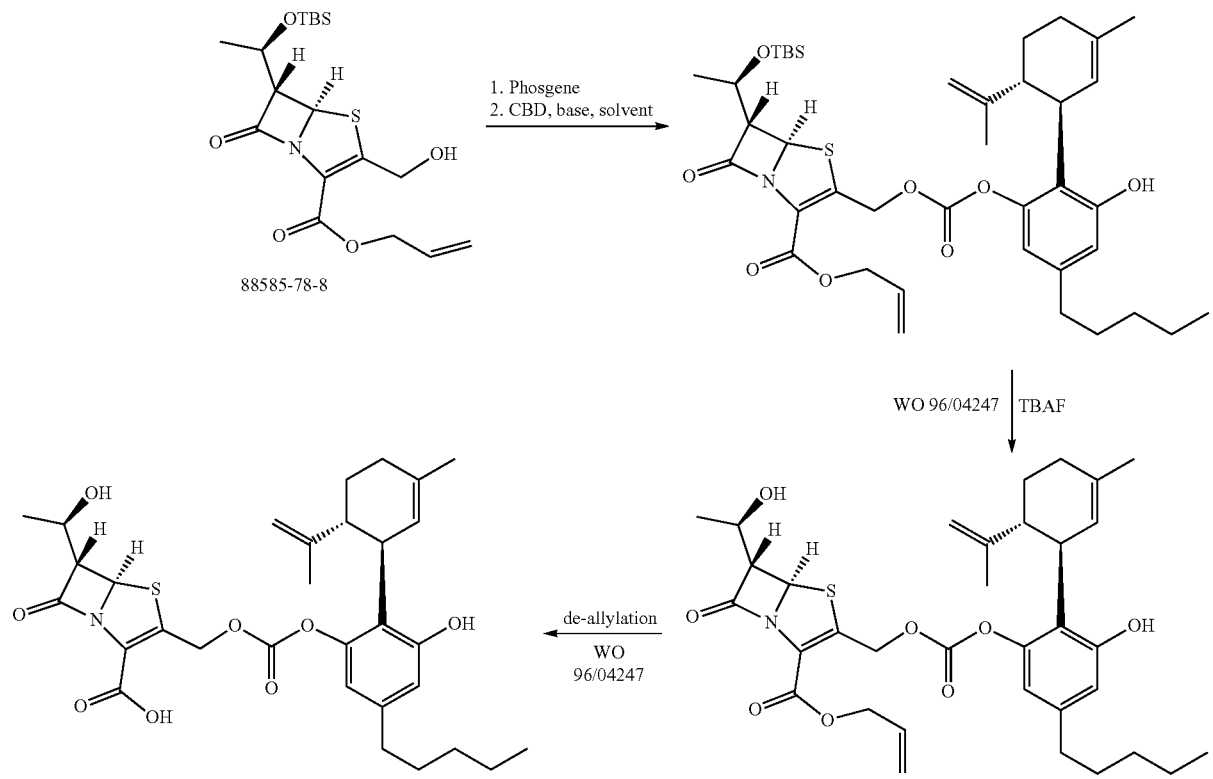 [SMILES: C=CCOC(=O)C1=C(CO)S[C@@H]2[C@@H]([C@@H](C)O[Si](C)(C)C(C)(C)C)C(=O)N12 ; C=CCOC(=O)C1=C(COC(=O)Oc2cc(CCCCC)cc(O)c2[C@@H]2C=C(C)CC[C@H]2C(=C)C)S[C@@H]2[C@@H]([C@@H](C)O[Si](C)(C)C(C)(C)C)C(=O)N12 ; "TBAF" ; C=C(C)[C@@H]1CCC(C)=C[C@H]1c1c(O)cc(CCCCC)cc1OC(=O)OCC1=C(C(=O)O)N2C(=O)[C@H]([C@@H](C)O)[C@H]2S1 ; C=CCOC(=O)C1=C(COC(=O)Oc2cc(CCCCC)cc(O)c2[C@@H]2C=C(C)CC[C@H]2C(=C)C)S[C@@H]2[C@@H]([C@@H](C)O)C(=O)N12]

Carbapenem Conjugate Molecules

Carbapenem carbonate linked conjugate molecules are synthesized according to the following Scheme. The starting material [118990-99-1], prepared as reported (Journal of Antibiotics (1988), 41(6), 780-7), is reacted with phosgene and the intermediate reacted with CBD under standard basic conditions. Deallylation under known conditions gives the desired product.

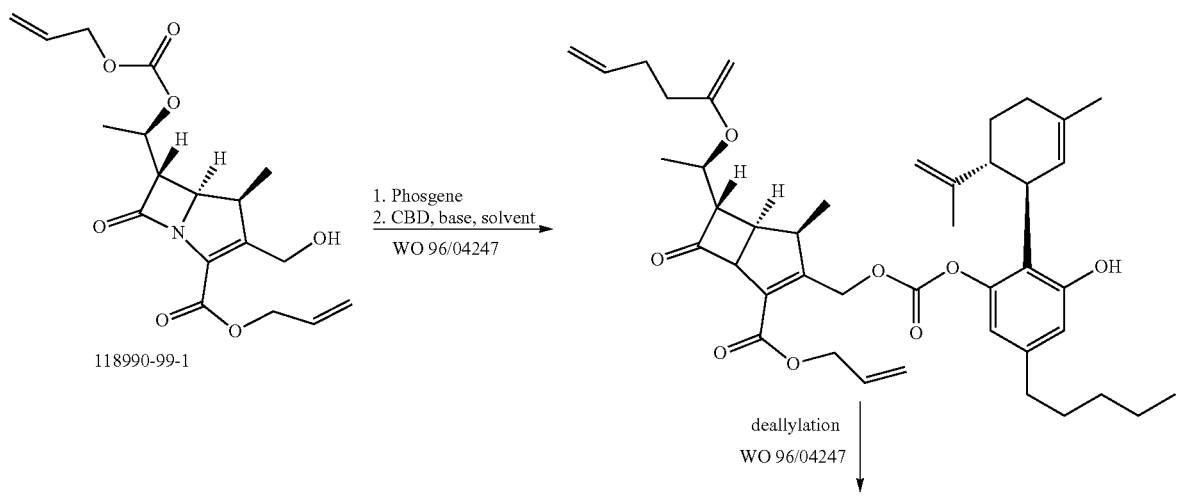

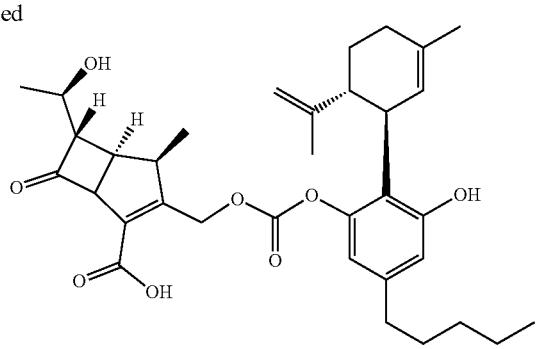

Example 3. Thiocarbonate-Linked Conjugate Molecules

Cephem Conjugate Molecules

Cephem thiocarbonate linked conjugate molecules are synthesized according to the following Scheme. The starting material is acylated with a side chain of choice and then the acid is protected as described previously (WO 96/04247). The resulting alcohol is then treated with thiophosgene and the adduct reacted with CBD in the presence of base to form the thiocarbonate product which is then deprotected with acid to deliver the desired product.

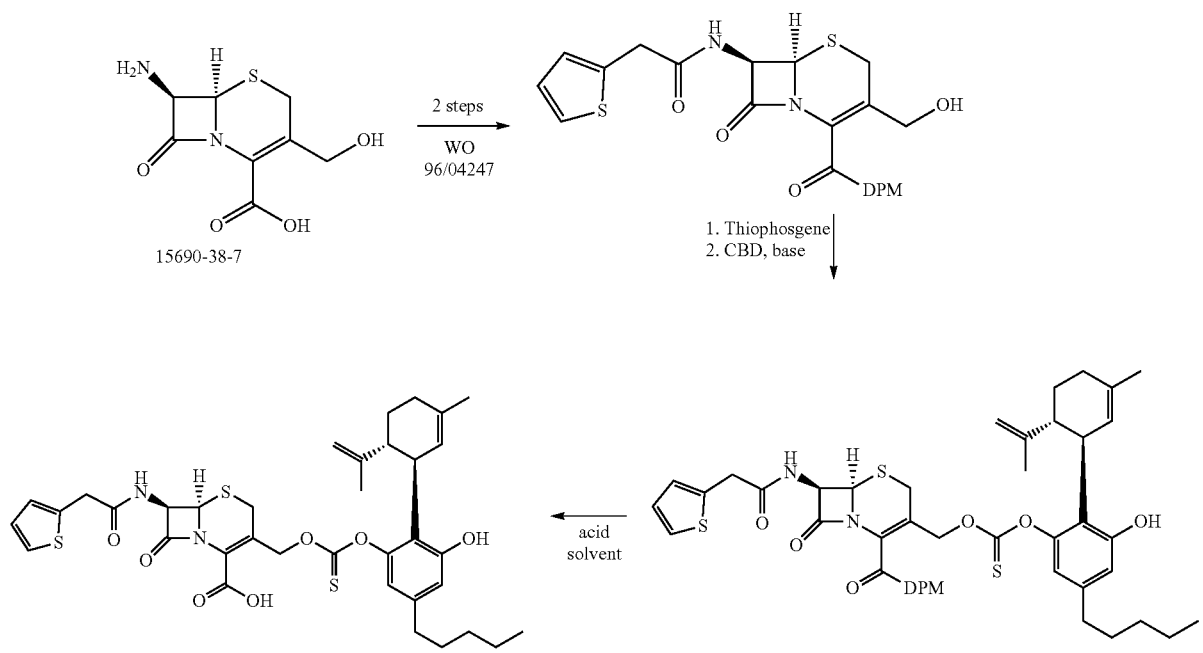

Carbacephem Conjugate Molecules

Carbacephem thiocarbonate linked conjugate molecules are synthesized according to the following Scheme. The starting material is acylated with a side chain of choice and then the acid is protected as described previously (WO 96/04247). The resulting alcohol is then treated with thiophosgene and the adduct reacted with CBD in the presence of base to form the thiocarbonate product which is then deprotected with acid to deliver the desired product.

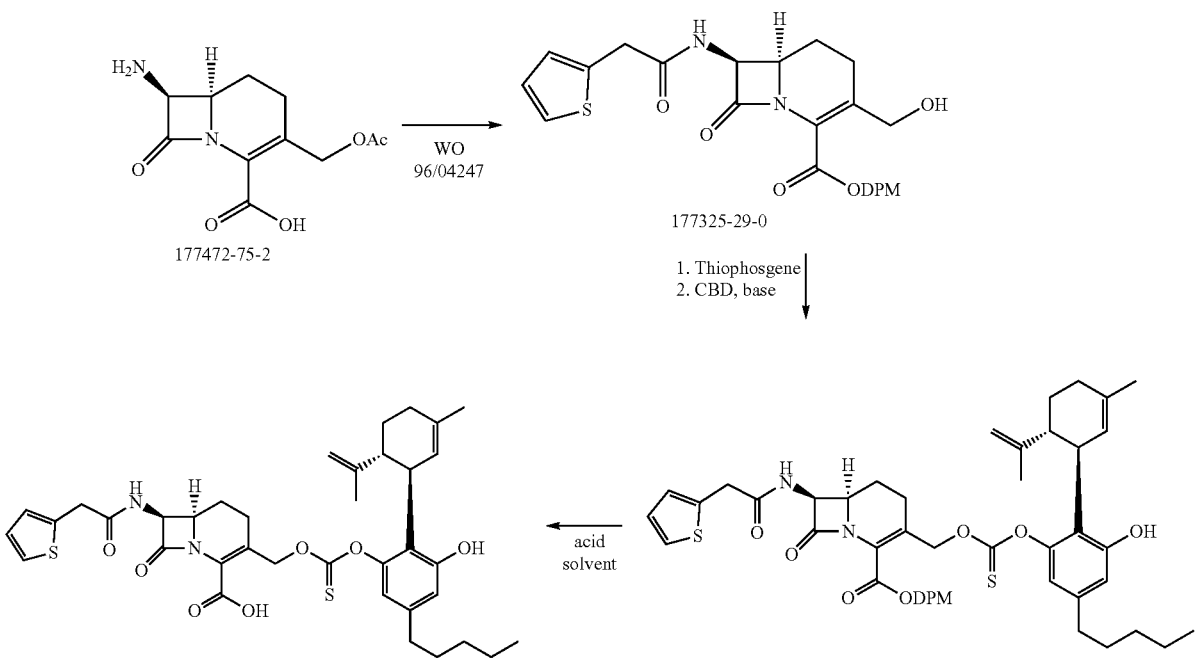

Penem Conjugate Molecules

Penem thiocarbonate linked conjugate molecules are synthesized according to the following Scheme. The starting material [88585-78-8], prepared as reported (U.S. Pat. No. 4,631,150), is reacted with thiophosgene and the intermediate reacted with CBD under standard basic conditions. The silyl ether TBS protecting group is then removed followed by deallylation under known conditions to give the desired product.

Carbapenem Conjugate Molecules

Carbapenem thiocarbonate linked conjugate molecules are synthesized according to the following Scheme. The starting material [118990-99-1], prepared as reported (Journal of Antibiotics (1988), 41(6), 780-7), is reacted with thiophosgene and the intermediate reacted with CBD under standard basic conditions. Deallylation under known conditions gives the desired product.

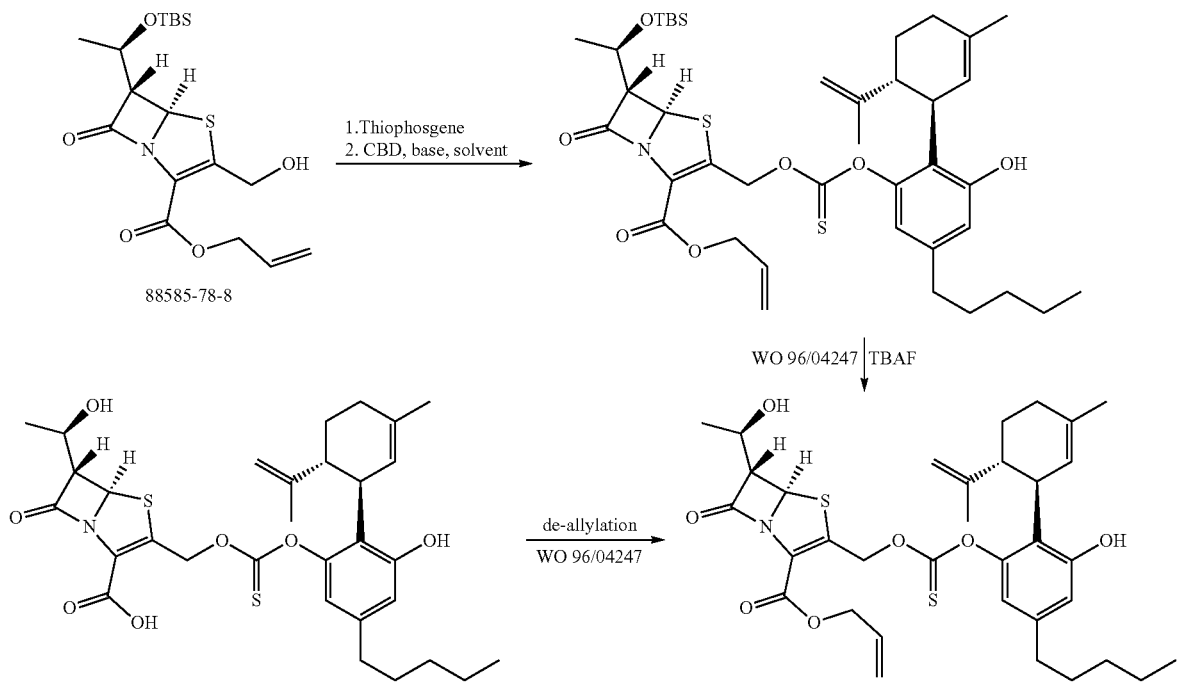

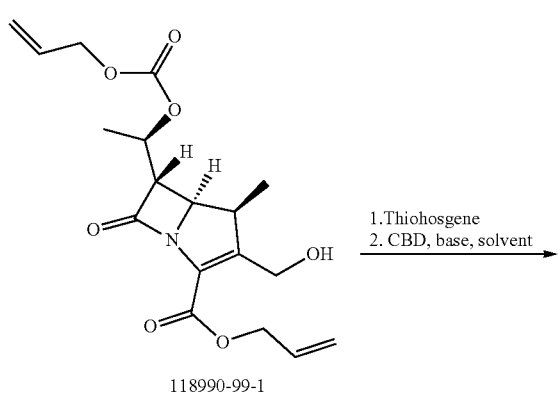

118990-99-1

1. Thiohosgene
2. CBD, base, solvent

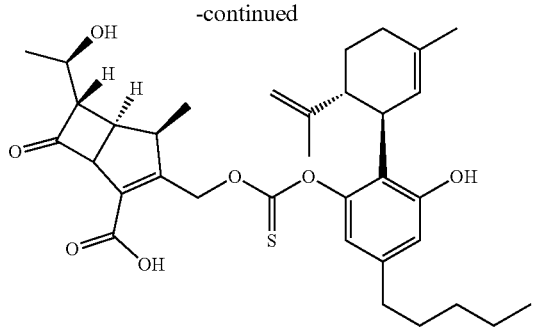

-continued

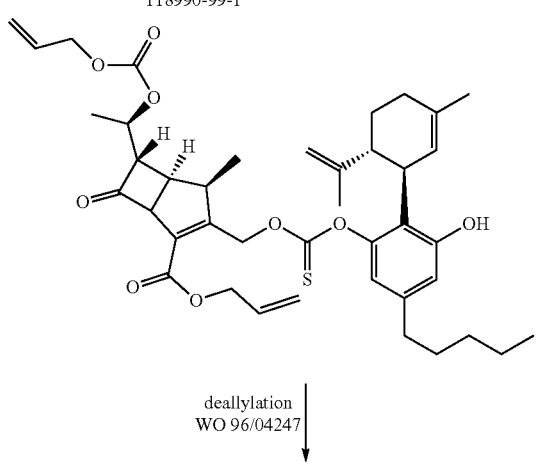

deallylation
WO 96/04247

Example 4. Carbamate-Linked Conjugate Molecules

Cephem Conjugate Molecules

Cephem carbamate linked conjugate molecules are synthesized according to the following Scheme. The starting material [6187-87-7] is acylated with a side chain of choice. The acetate group is then converted to the iodide with TMS-I as has been reported for similar molecules (WO 96/04247). The iodide is then converted to the azide which is then reduced to the amine, both steps under standard conditions. Reaction of the amine with phosgene followed by addition of the cannabinoid CBD forms the carbamate linkage. Deprotection of the t-butyl ester under standard conditions gives the desired product.

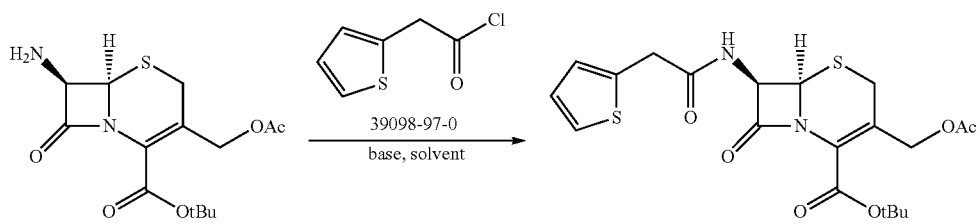

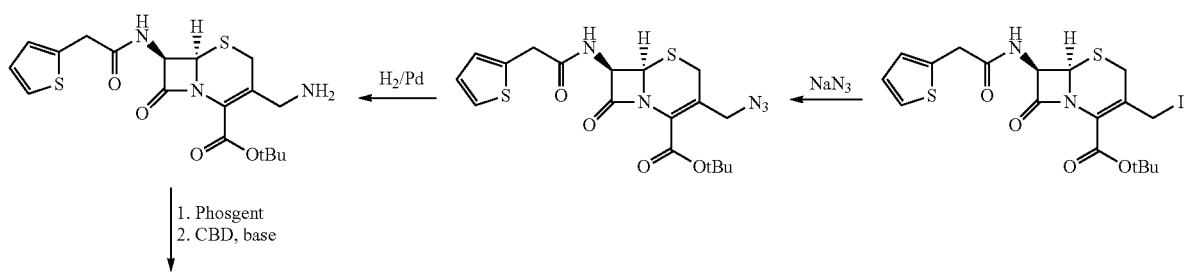

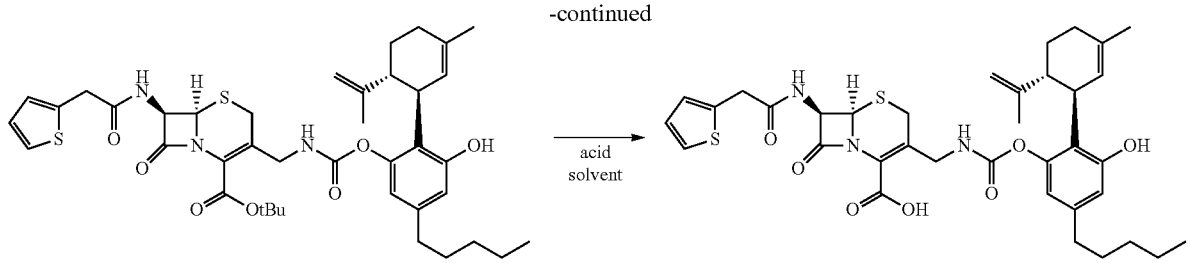

Carbacephem Conjugate Molecules

Carbacephem carbamate linked conjugate molecules are synthesized according to the following Scheme. The starting material [177472-75-2] has been previously described (WO 96/04247; Journal of the American Chemical Society (1974), 96(24), 7584). It is converted to the t-butyl ester under established isobutylene conditions, and then is acylated with a side chain of choice. The acetate group is then converted to the iodide with TMS-I as has been reported for similar molecules (WO 96/04247). The iodide is then converted to the azide which is then reduced to the amine, both steps under standard conditions. Reaction of the amine with phosgene followed by addition of the cannabinoid CBD forms the carbamate linkage. Deprotection of the t-butyl ester under standard conditions gives the desired product.

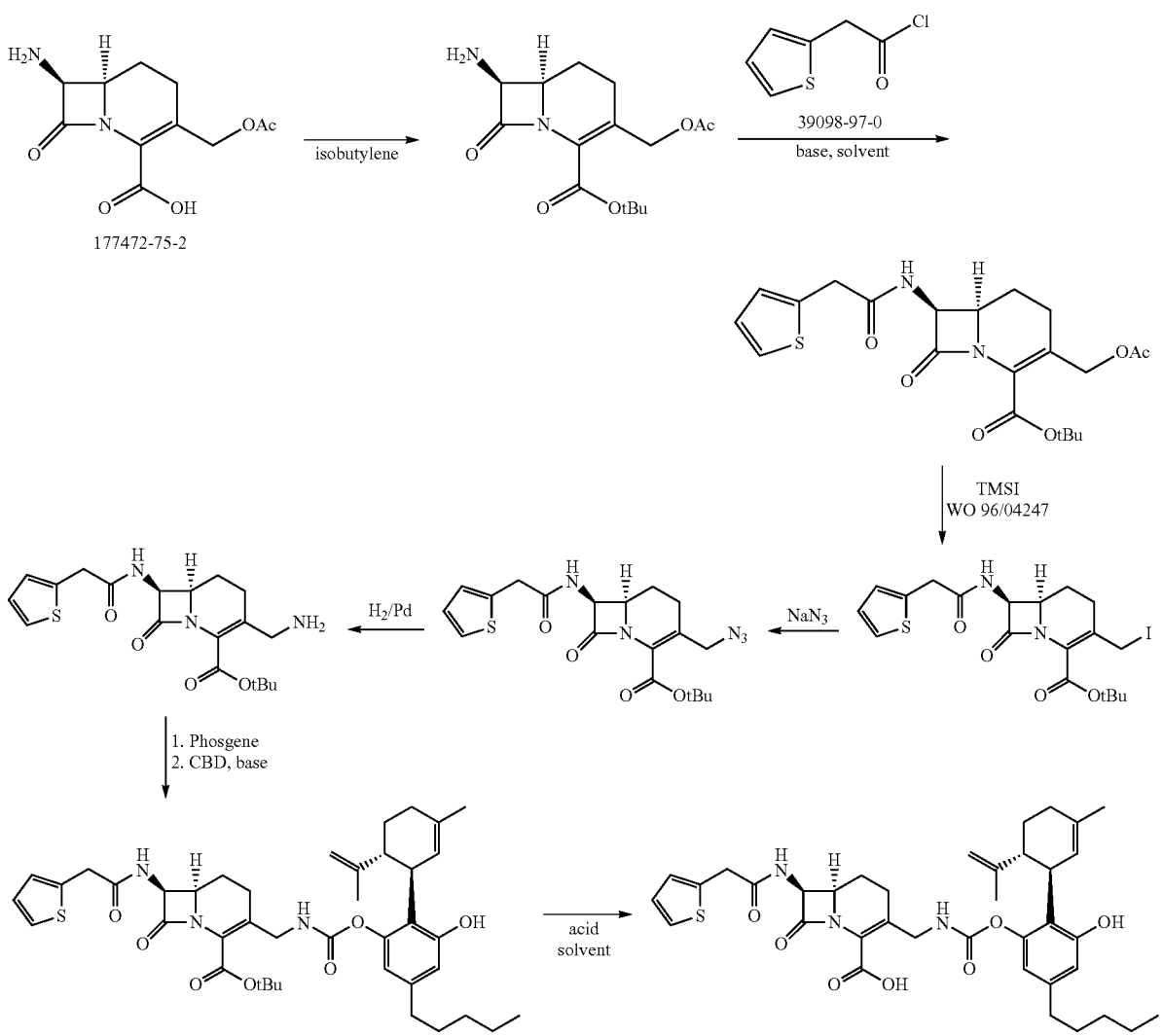

Penem Conjugate Molecules

Penem carbamate linked conjugate molecules are synthesized according to the following Scheme. The starting material [83572-65-0] has been previously described (Journal of Antibiotics (1982), 35(9), 1248-51). It is converted to the t-butyl ester under established isobutylene conditions, and then the hydroxy group is protected as the TBDMS ether. The acetate group is then converted to the iodide with TMS-I as has been reported for similar molecules (WO 96/04247). The iodide is then converted to the azide which is then reduced to the amine, both steps under standard conditions. Reaction of the amine with phosgene followed by addition of the cannabinoid CBD forms the carbamate linkage. Removal of the TBDMS ether and t-butyl ester protecting groups under standard conditions gives the desired product.

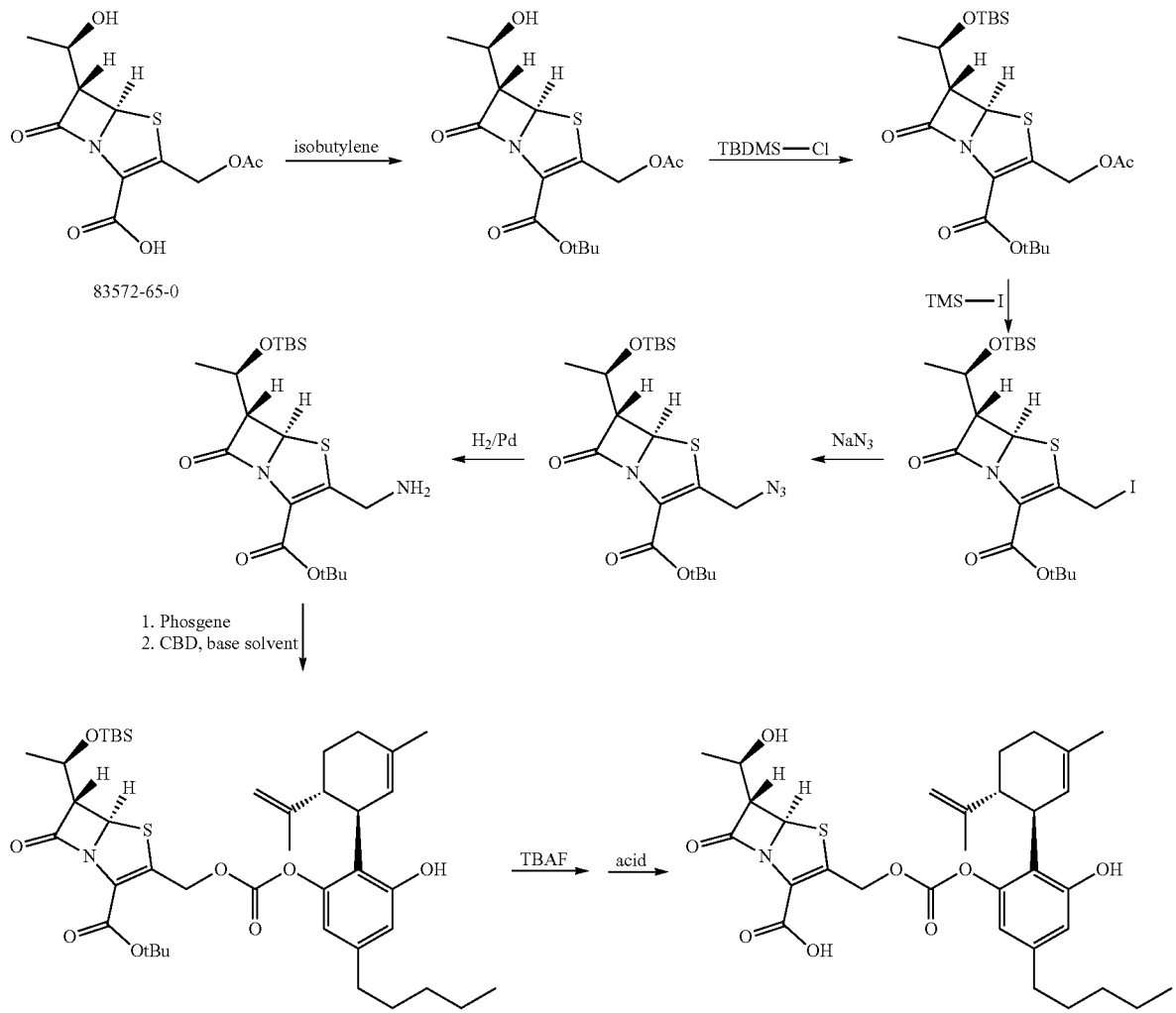

Carbapenem Conjugate Molecules

Carbapenem carbamate linked conjugate molecules are synthesized according to the following Scheme. The starting material [112064-40-1] has been previously described (Journal of Antibiotics (1988), 41(6), 780-7). It is converted to the t-butyl ester under established isobutylene conditions, and then the hydroxy group is protected as the TBDMS ether. The acetate group is then converted to the iodide with TMS-I as has been reported for similar molecules (WO 96/04247). The iodide is then converted to the azide which is then reduced to the amine, both steps under standard conditions. Reaction of the amine with phosgene followed by addition of the cannabinoid CBD forms the carbamate linkage. Removal of the TBDMS ether and t-butyl ester protecting groups under standard conditions gives the desired product.

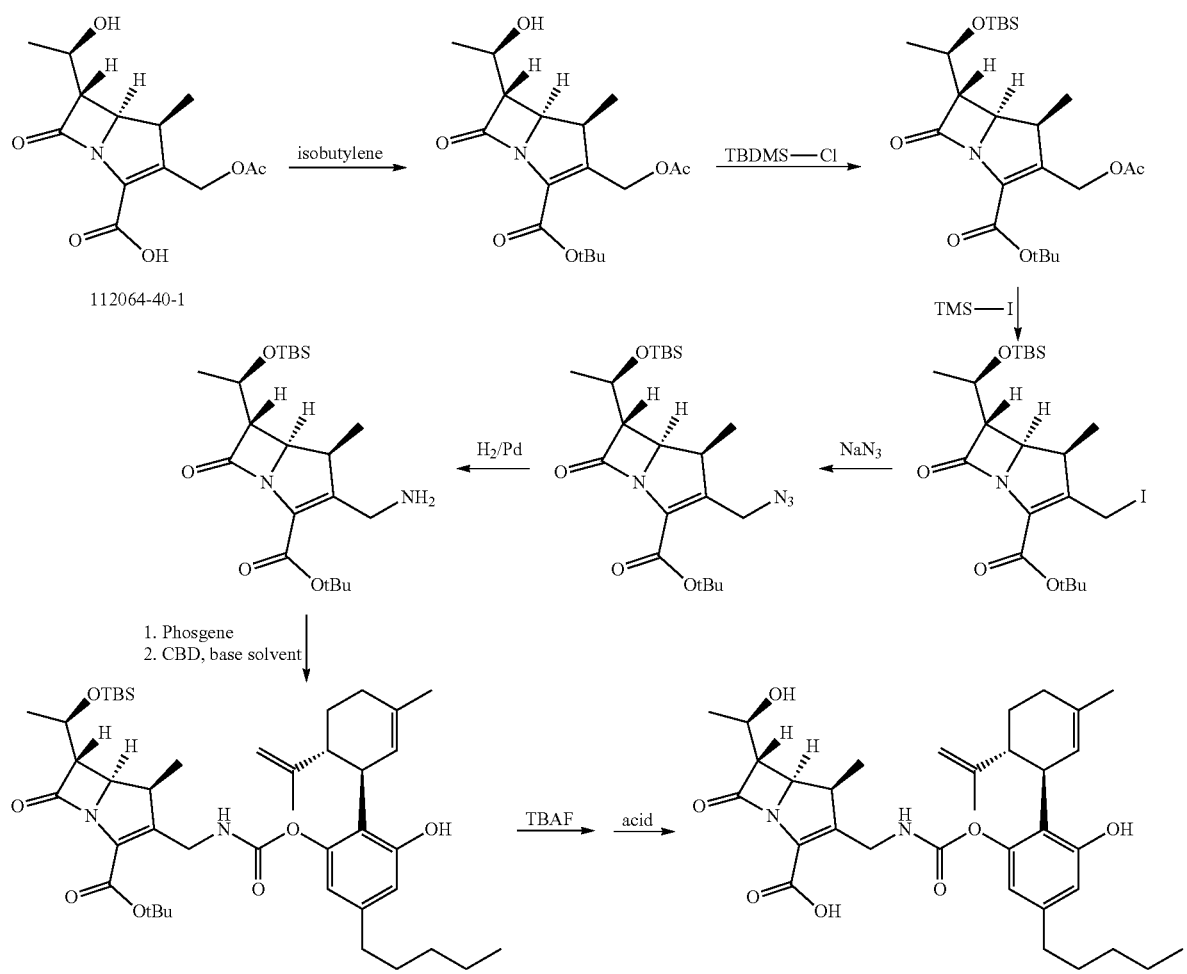

112064-40-1

Example 5. Thiocarbamate-Linked Conjugate Molecules

Cephem Conjugate Molecules

Cephem thiocarbamate linked conjugate molecules are synthesized according to the following Scheme. The starting material [6187-87-7] is acylated with a side chain of choice. The acetate group is then converted to the iodide with TMS-I as has been reported for similar molecules (WO 96/04247). The iodide is then converted to the azide which is then reduced to the amine, both steps under standard conditions. Reaction of the amine with thiophosgene followed by addition of the cannabinoid CBD forms the thiocarbamate linkage. Deprotection of the t-butyl ester under standard conditions gives the desired product.

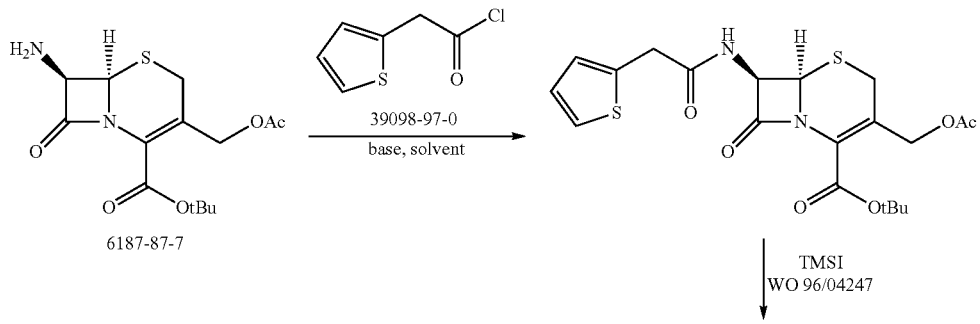

6187-87-7

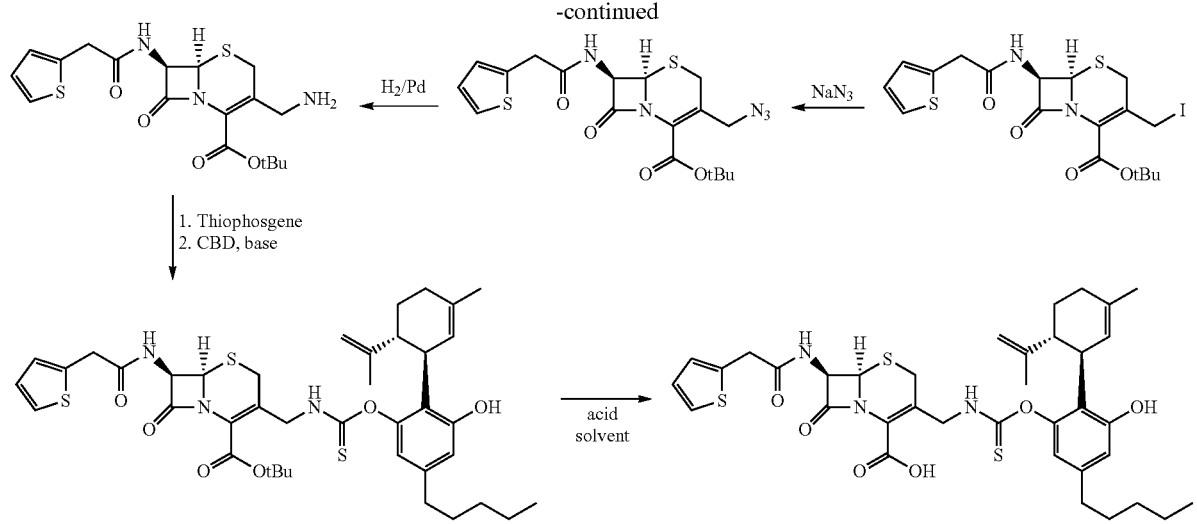

Carbacephem Conjugate Molecules

Carbacephem thiocarbamate linked conjugate molecules are synthesized according to the following Scheme. The starting material [177472-75-2] has been previously described (WO 96/04247; Journal of the American Chemical Society (1974), 96(24), 7584). It is converted to the t-butyl ester under established isobutylene conditions, and then is acylated with a side chain of choice. The acetate group is then converted to the iodide with TMS-I as has been reported for similar molecules (WO 96/04247). The iodide is then converted to the azide which is then reduced to the amine, both steps under standard conditions. Reaction of the amine with thiophosgene followed by addition of the cannabinoid CBD forms the thiocarbamate linkage. Deprotection of the t-butyl ester under standard conditions gives the desired product.

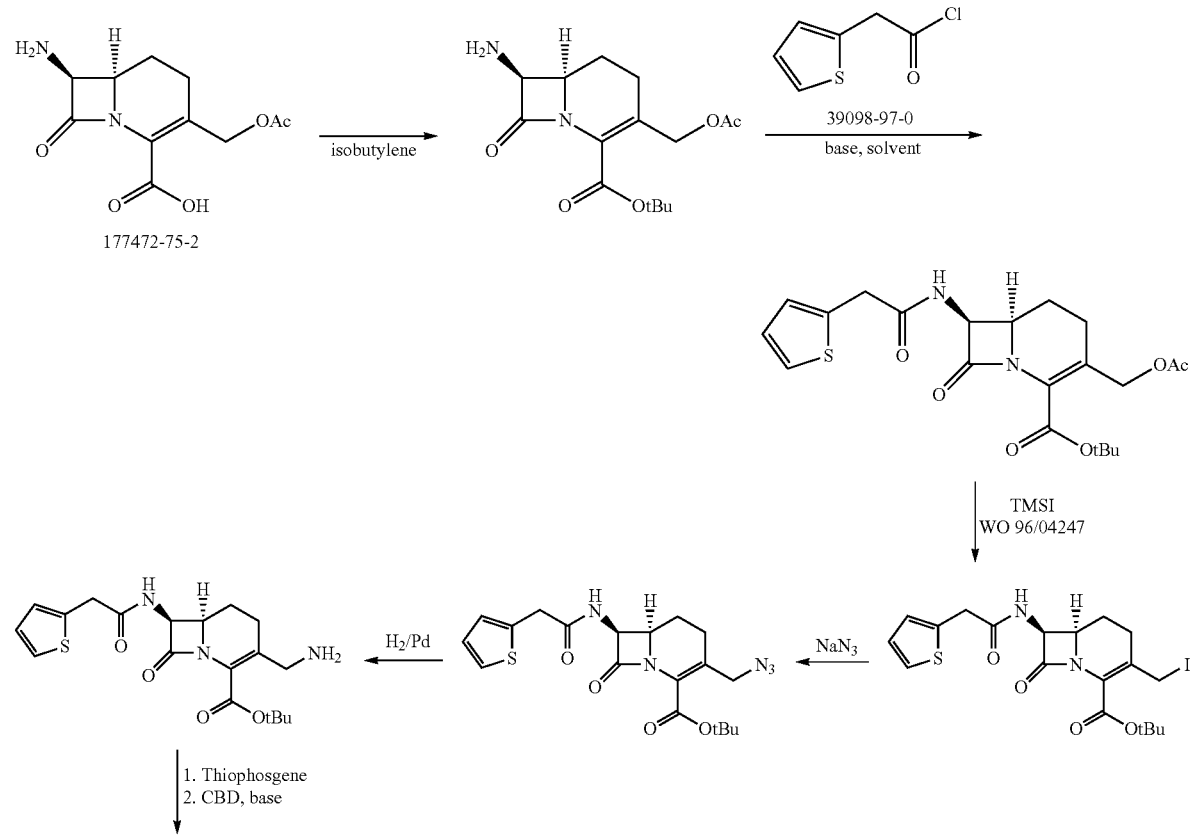

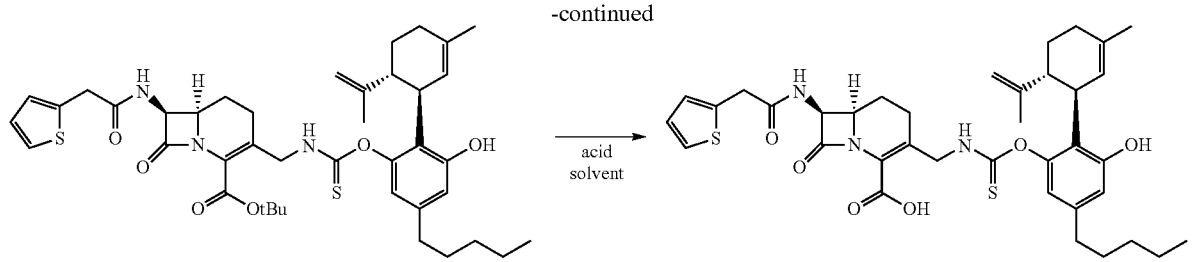

Penem Conjugate Molecules

Penem thiocarbamate linked conjugate molecules are synthesized according to the following Scheme. The starting material [83572-65-0] has been previously described (Journal of Antibiotics (1982), 35(9), 1248-51). It is converted to the t-butyl ester under established isobutylene conditions, and then the hydroxy group is protected as the TBDMS ether. The acetate group is then converted to the iodide with TMS-I as has been reported for similar molecules (WO 96/04247). The iodide is then converted to the azide which is then reduced to the amine, both steps under standard conditions. Reaction of the amine with thiophosgene followed by addition of the cannabinoid CBD forms the thiocarbamate linkage. Removal of the TBDMS ether and t-butyl ester protecting groups under standard conditions gives the desired product.

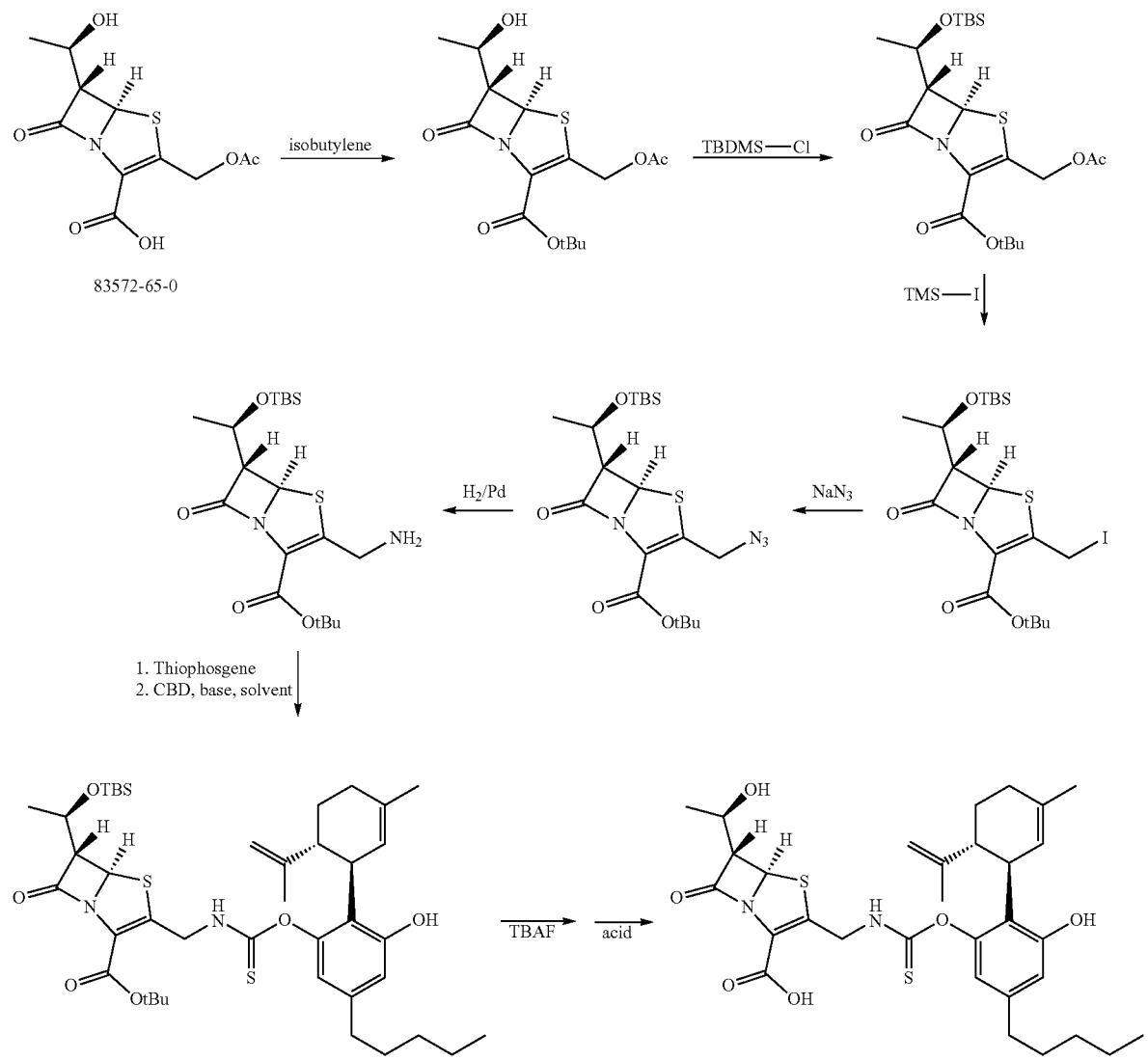

Carbapenem Conjugate Molecules

Carbapenem thiocarbamate linked conjugate molecules are synthesized according to the following Scheme. The starting material [112064-40-1] has been previously described (Journal of Antibiotics (1988), 41(6), 780-7). It is converted to the t-butyl ester under established isobutylene conditions, and then the hydroxy group is protected as the TBDMS ether. The acetate group is then converted to the iodide with TMS-I as has been reported for similar molecules (WO 96/04247). The iodide is then converted to the azide which is then reduced to the amine, both steps under standard conditions. Reaction of the amine with thiophosgene followed by addition of the cannabinoid CBD forms the thiocarbamate linkage. Removal of the TBDMS ether and t-butyl ester protecting groups under standard conditions gives the desired product.

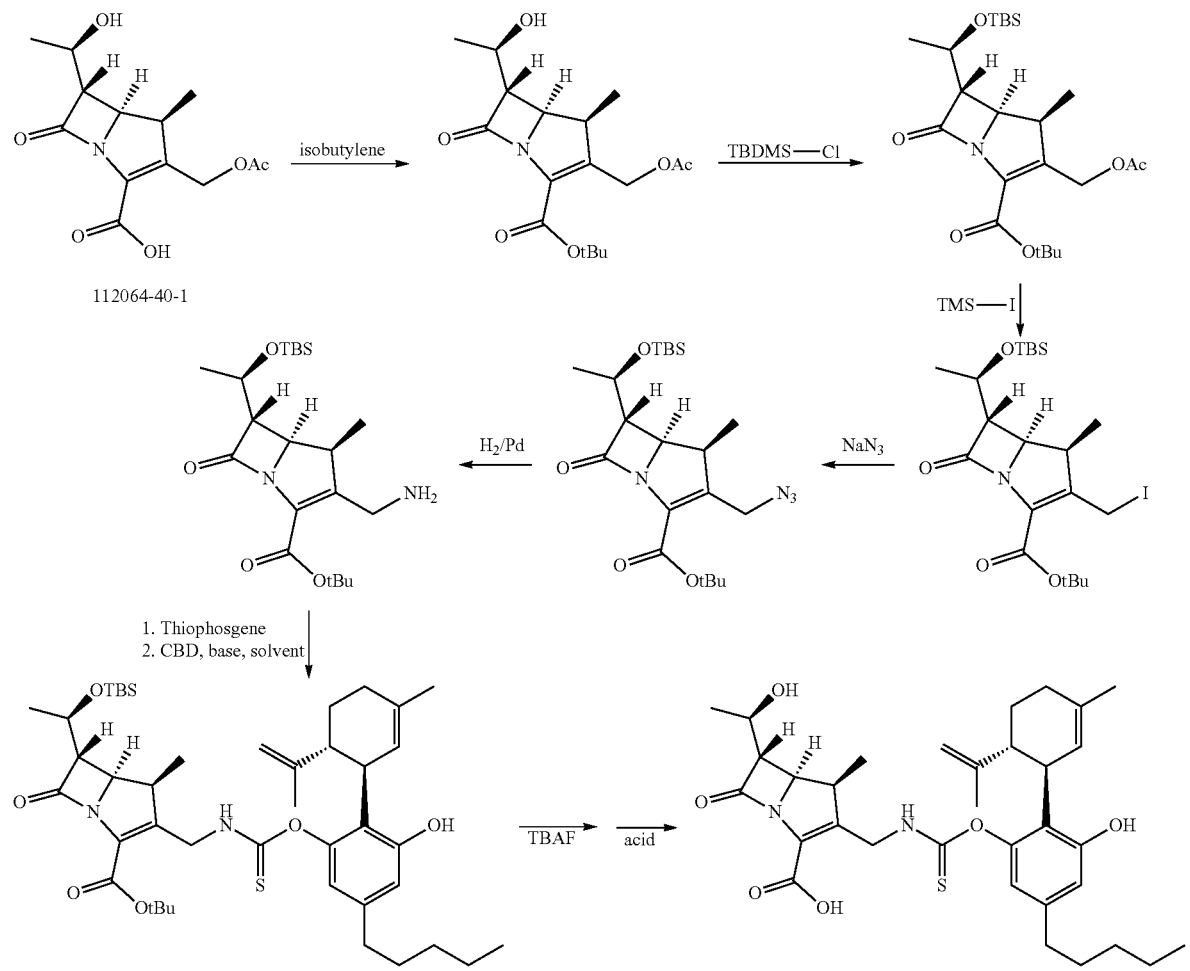

Example 6. Propenylamine-Linked Conjugate Molecules

Cephem Conjugate Molecules

Cephem propenylamine linked conjugate molecules are synthesized according to the following Scheme. The starting material [6187-87-7] is acylated with a side chain of choice. The acetate group is then converted to the iodide with TMS-I as has been reported for similar molecules (WO 96/04247). The iodide is then converted to the azide which is then reduced to the amine, both steps under standard conditions. Condensation of the amine with a 3-halopropanal (3-bromo, 65032-54-4) produces the bromopropenyl intermediate which is then used to alkylate the cannabinoid (CBD) under standard basic conditions. Removal of the t-butyl ester protecting group under acidic conditions generates the desired product.

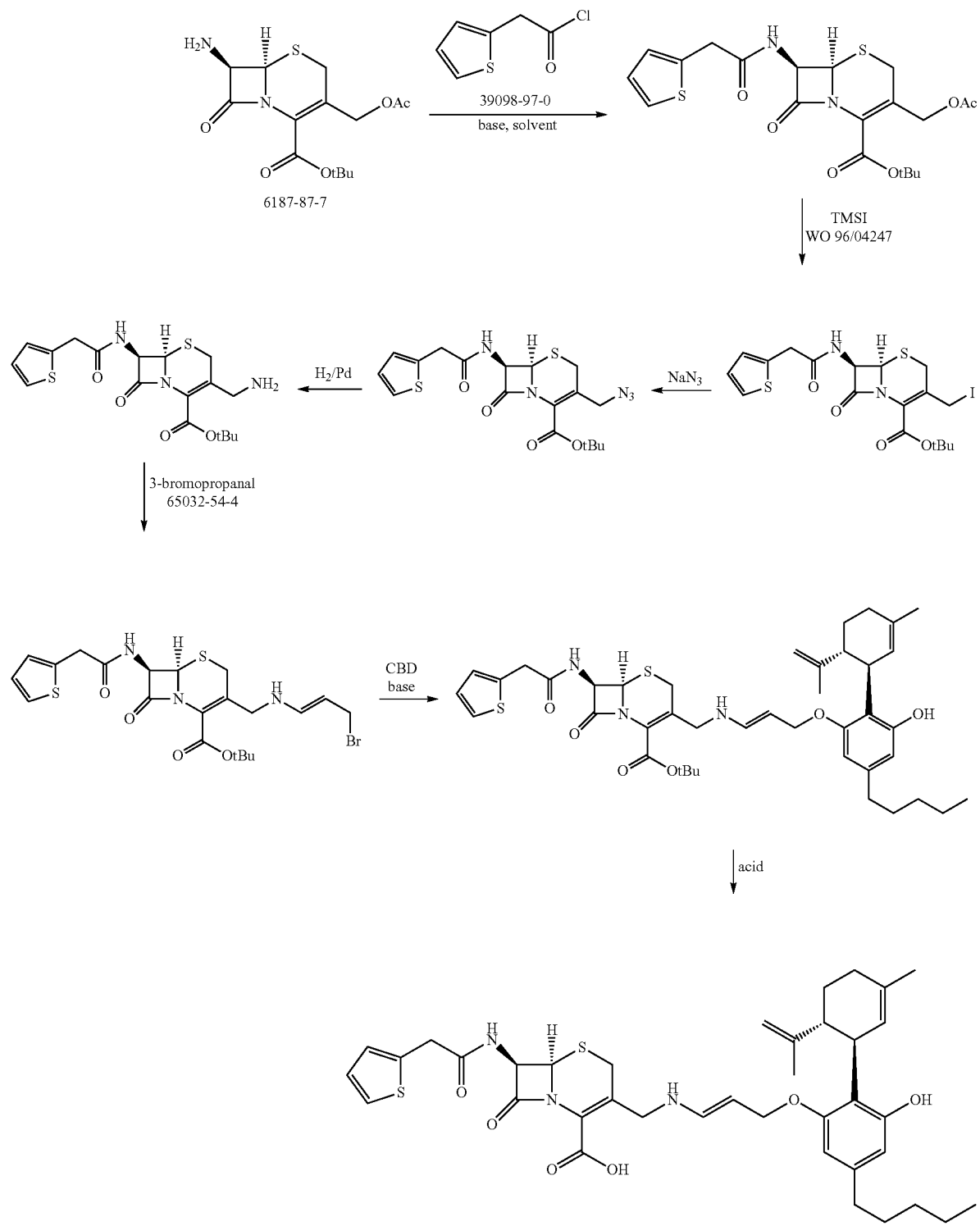

Carbacephem Conjugate Molecules

Carbacephem propenylamine linked conjugate molecules are synthesized according to the following Scheme. The starting material [177472-75-2] is protected as the t-butyl ester under standard isobutylene conditions and then is acylated with a side chain of choice. The acetate group is then converted to the iodide with TMS-I as has been reported for similar molecules (WO 96/04247). The iodide is then converted to the azide which is then reduced to the amine, both steps under standard conditions. Condensation of the amine with a 3-halopropanal (3-bromo, 65032-54-4) produces the bromopropenyl intermediate which is then used to alkylate the cannabinoid (CBD) under standard basic conditions. Removal of the t-butyl ester protecting group under acidic conditions generates the desired product.

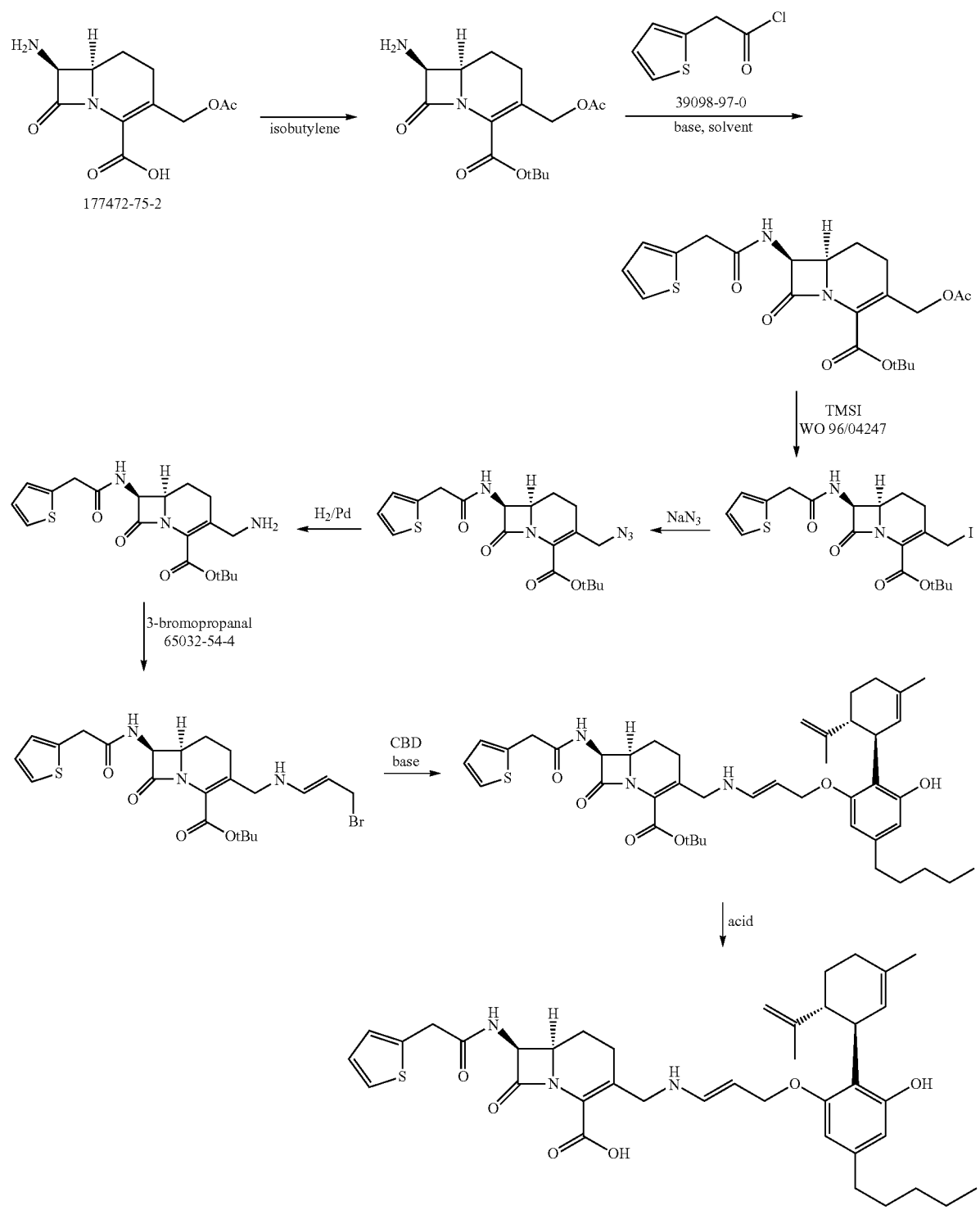

Penem Conjugate Molecules

Penem propenylamine linked conjugate molecules are synthesized according to the following Scheme. The starting material [83572-65-0] is protected as the t-butyl ester under standard isobutylene conditions and then the secondary alcohol is protected as the TBDMS ether. The acetate group is then converted to the iodide with TMS-I as has been reported for similar molecules (WO 96/04247). The iodide is then converted to the azide which is then reduced to the amine, both steps under standard conditions. Condensation of the amine with a 3-halopropanal (3-bromo, 65032-54-4) produces the bromopropenyl intermediate which is then used to alkylate the cannabinoid (CBD) under standard basic conditions. Removal of the TBDMS ether and t-butyl ester protecting groups under standard conditions gives the desired product.

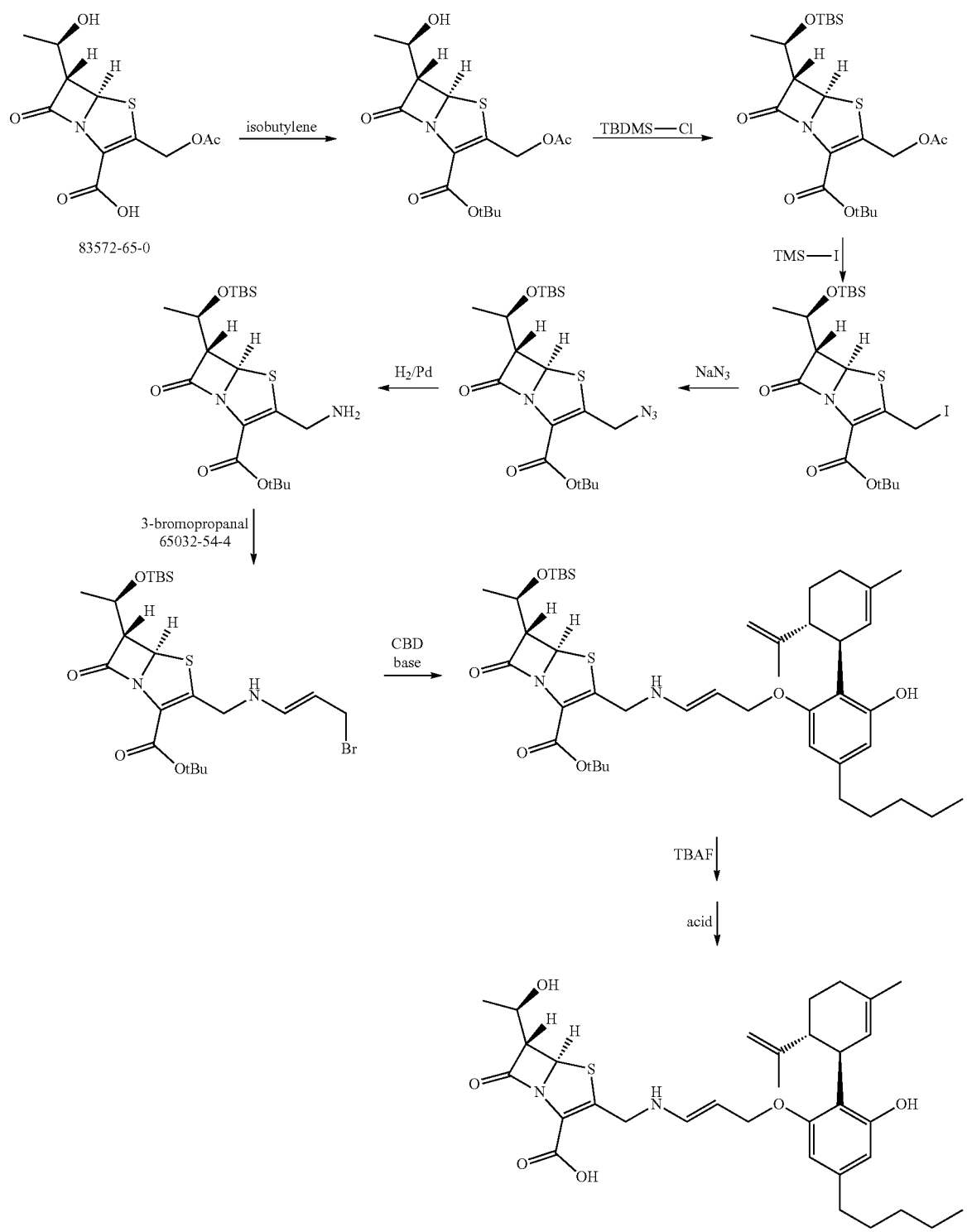

Carbapenem Conjugate Molecules

Carbapenem propenylamine linked conjugate molecules are synthesized according to the following Scheme. The starting material [112064-40-1] is protected as the t-butyl ester under standard isobutylene conditions and then the secondary alcohol is protected as the TBDMS ether. The acetate group is then converted to the iodide with TMS-I as has been reported for similar molecules (WO 96/04247). The iodide is then converted to the azide which is then reduced to the amine, both steps under standard conditions. Condensation of the amine with a 3-halopropanal (3-bromo, 65032-54-4) produces the bromopropenyl intermediate which is then used to alkylate the cannabinoid (CBD) under standard basic conditions. Removal of the TBDMS ether and t-butyl ester protecting groups under standard conditions gives the desired product.

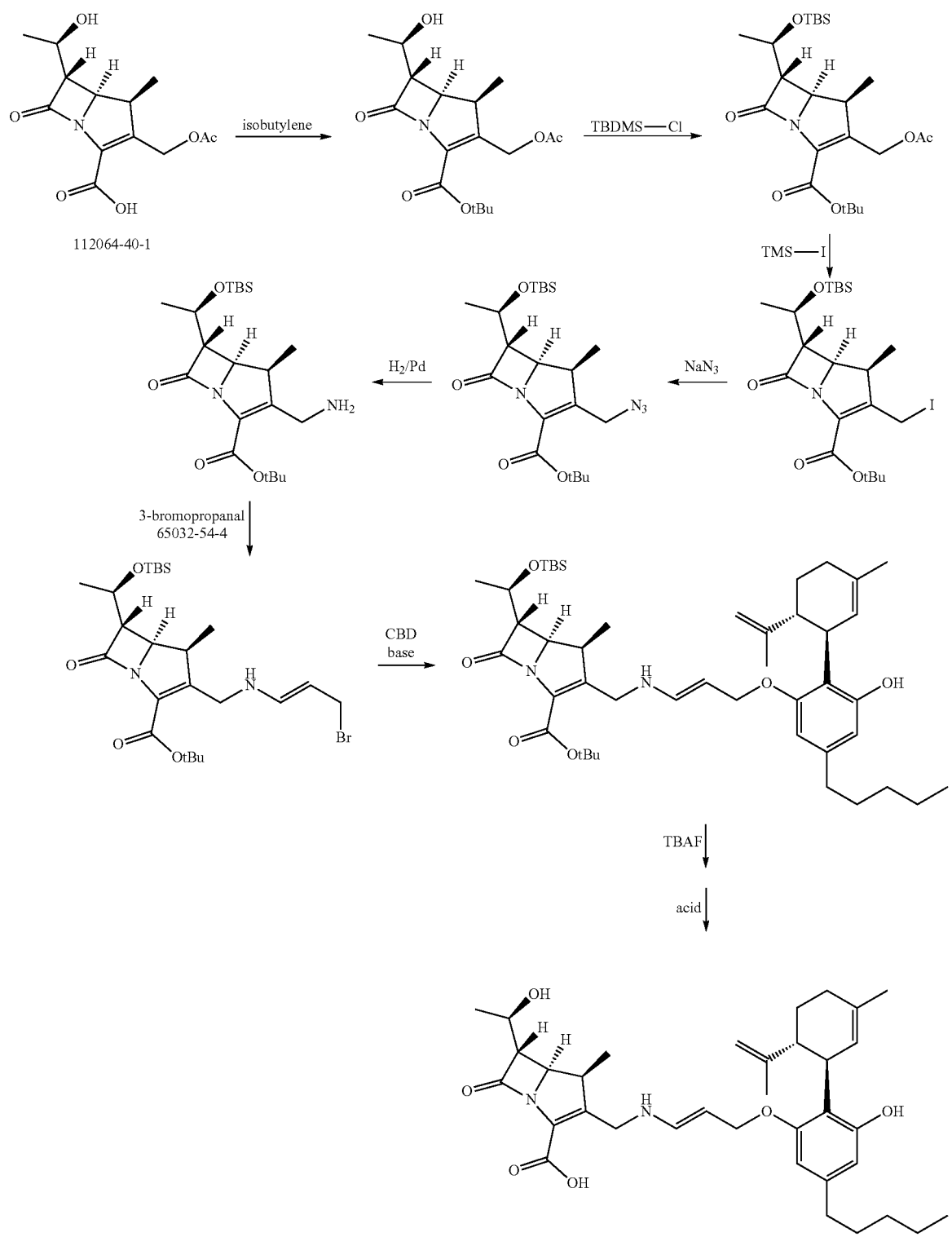

Example 7. Alkene-Linked Conjugate Molecules

Cephem Conjugate Molecules

Cephem alkene linked conjugate molecules are synthesized according to the following Scheme. The starting material [130516-07-3] has been reported previously (Journal of Organic Chemistry (1993), 58(8), 2296-2301). It is reacted with the organostannane under conditions described for related molecules (WO 99/62906) to give the allylic alcohol intermediate. The alcohol is then activated as the mesylate and reacted with the cannabinoid (CBD) under basic conditions to produce the alkene linked intermediate. Removal of the DPM protecting group under standard conditions gives the desired product.

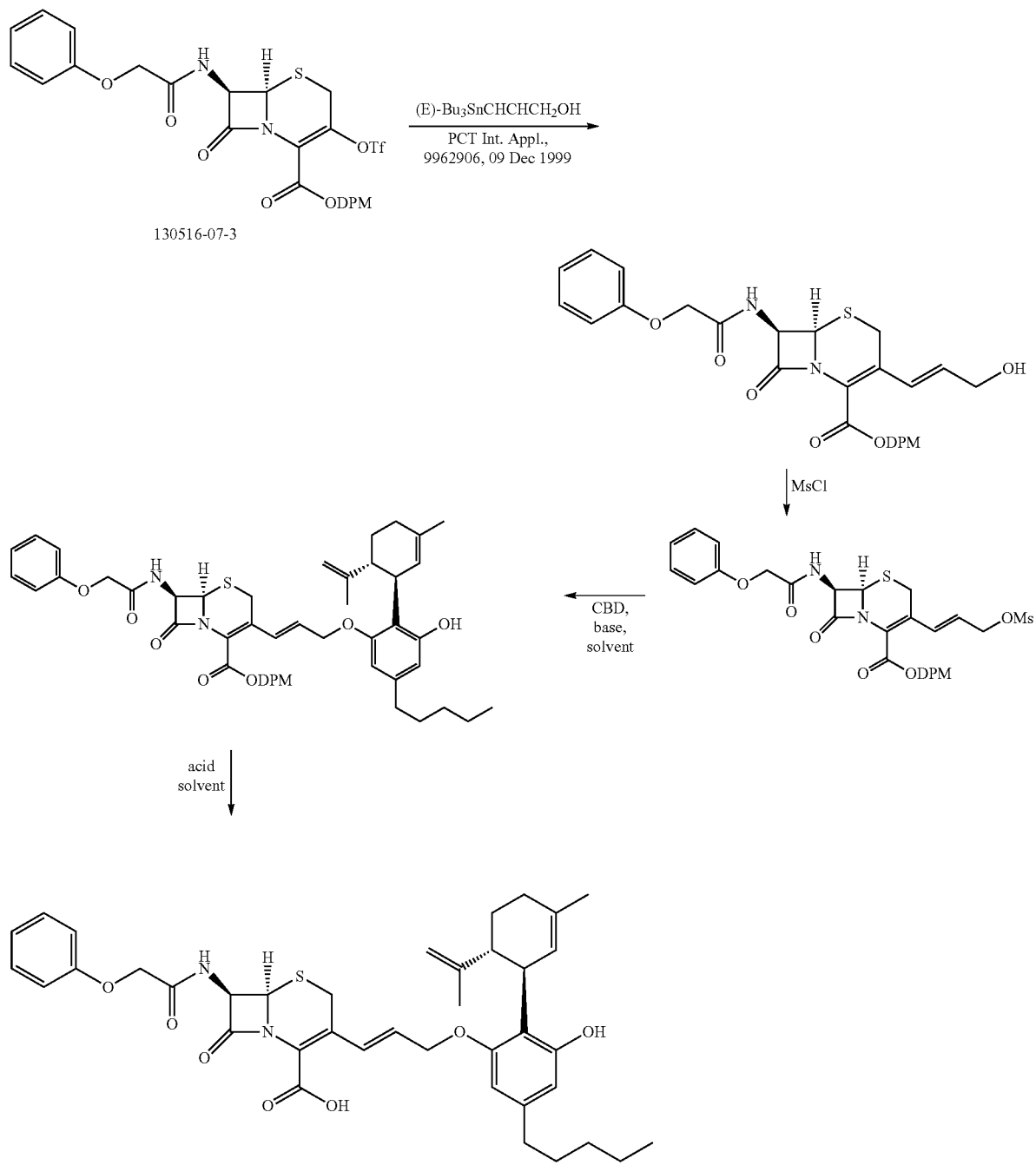

Carbacephem Conjugate Molecules

Carbacephem alkene linked conjugate molecules are synthesized according to the following Scheme. The starting material [123078-32-0] has been reported previously (Journal of Organic Chemistry, 54(24), 5828-30; 1989). It is reacted with the organostannane under conditions described for related molecules (WO 99/62906) to give the allylic alcohol intermediate. The alcohol is then activated as the mesylate and reacted with the cannabinoid (CBD) under basic conditions to produce the alkene linked intermediate. Removal of the DPM protecting group under standard conditions gives the desired product.

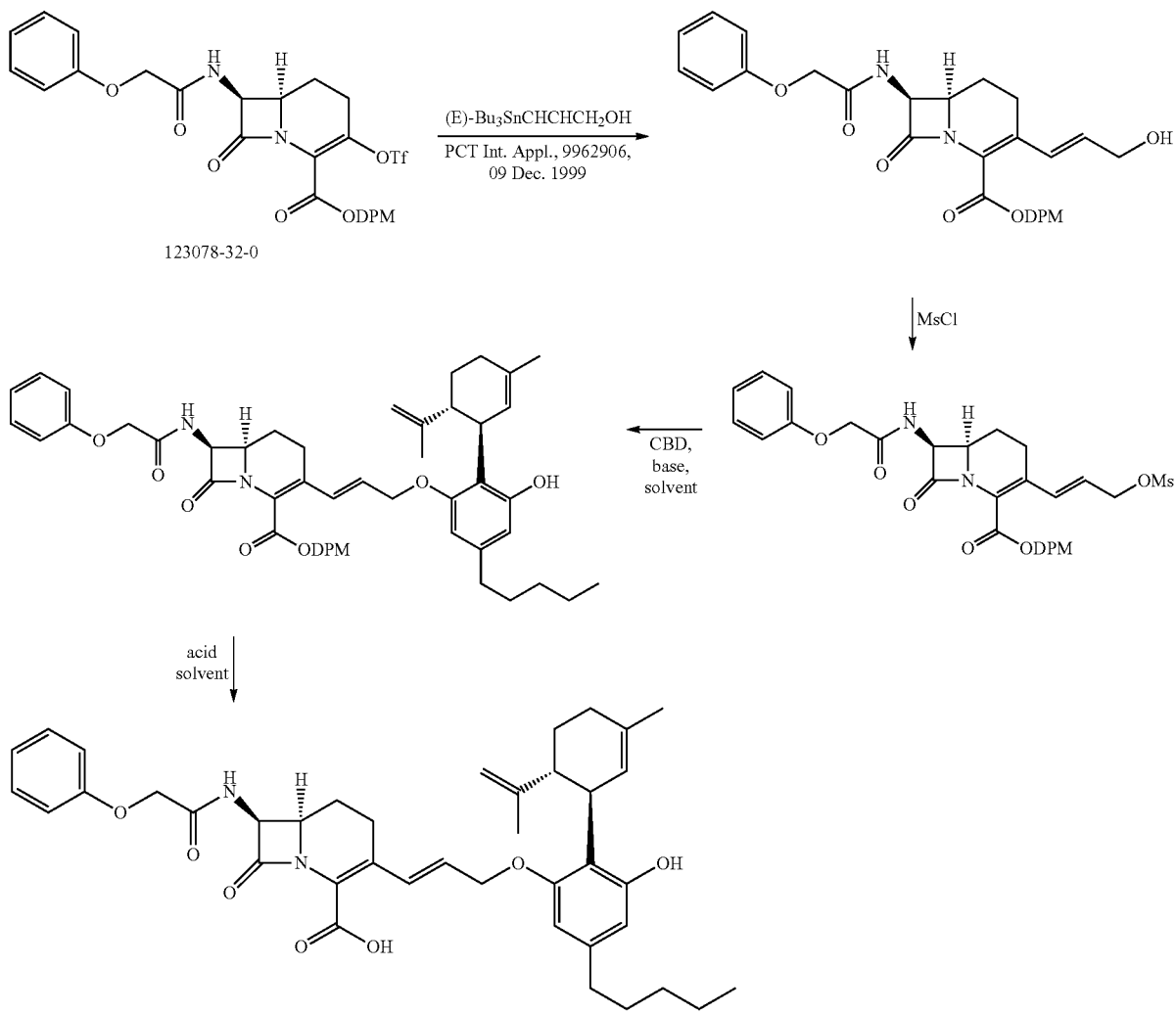

Penem Conjugate Molecules

Penem alkene linked conjugate molecules are synthesized according to the following Scheme. The starting material [127941-62-2] has been previously reported (U.S. Pat. No. 4,895,940). It is converted to the allylic alcohol intermediate as previously described for similar molecules (WO 99/62906). The alcohol is then activated as the mesylate and reacted with the cannabinoid (CBD) under basic conditions to produce the alkene linked intermediate. Removal of the TBDMS ether and trimethylsilylethyl ester protecting groups is achieved under standard conditions of excess TBAF to give the desired product.

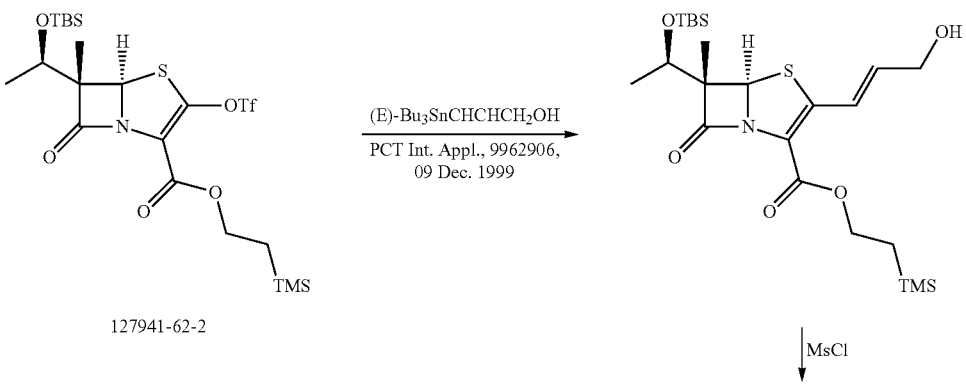

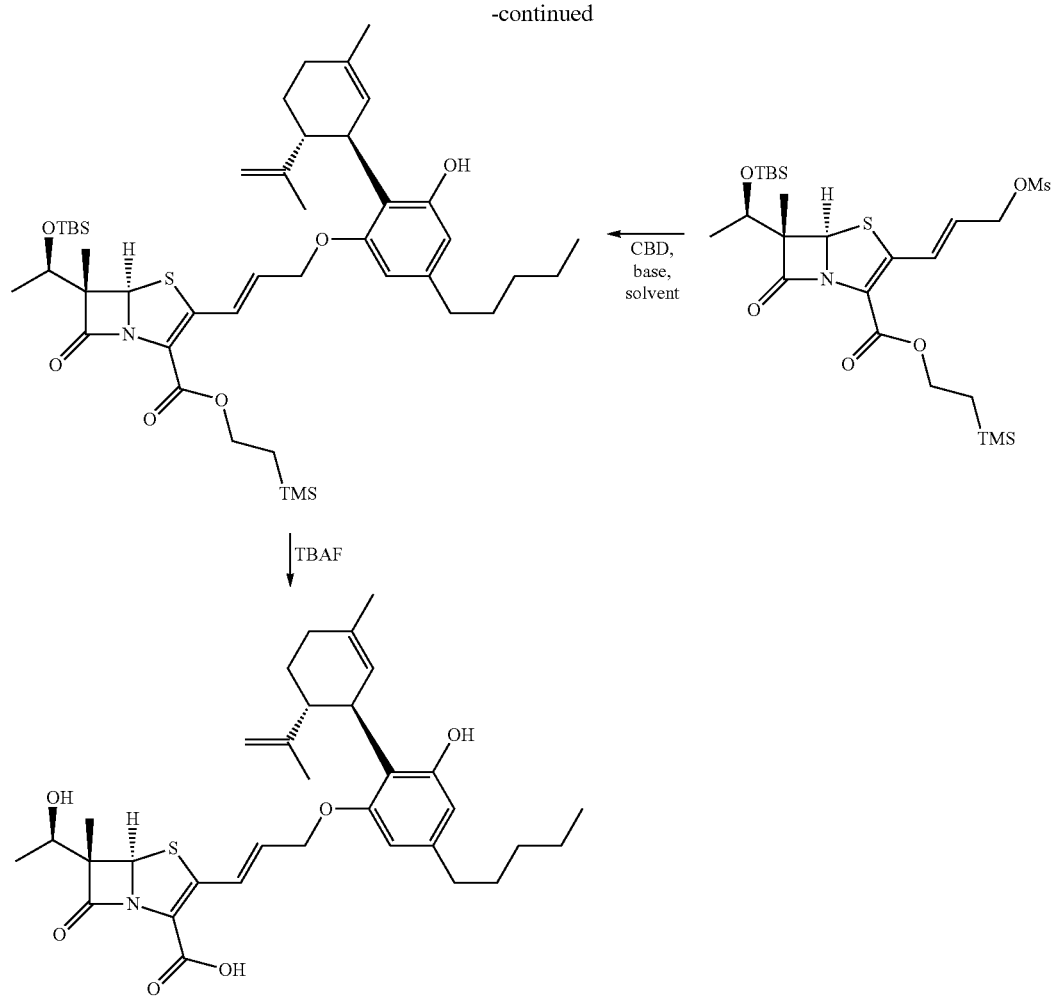

Carbapenem Conjugate Molecules

Carbapenem alkene linked conjugate molecules are synthesized according to the following Scheme. The starting material [165817-82-3] along with its conversion to the allylic alcohol intermediate has been described previously (WO 99/62906). The alcohol is then activated as the mesylate and reacted with the cannabinoid (CBD) under basic conditions to produce the alkene linked intermediate. Removal of the TES ether and PNB ester groups under standard conditions produces the desired product.

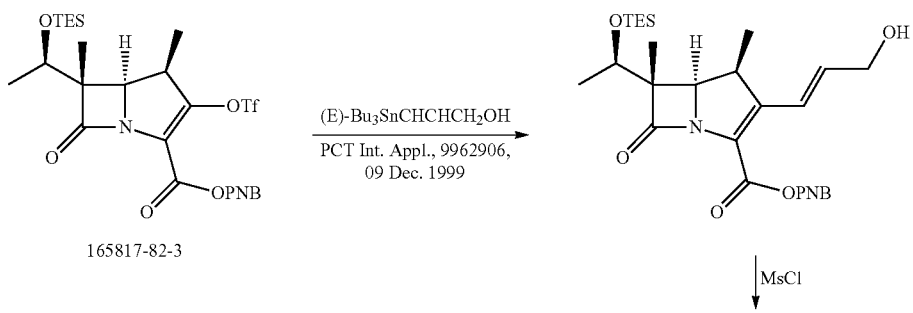

-continued

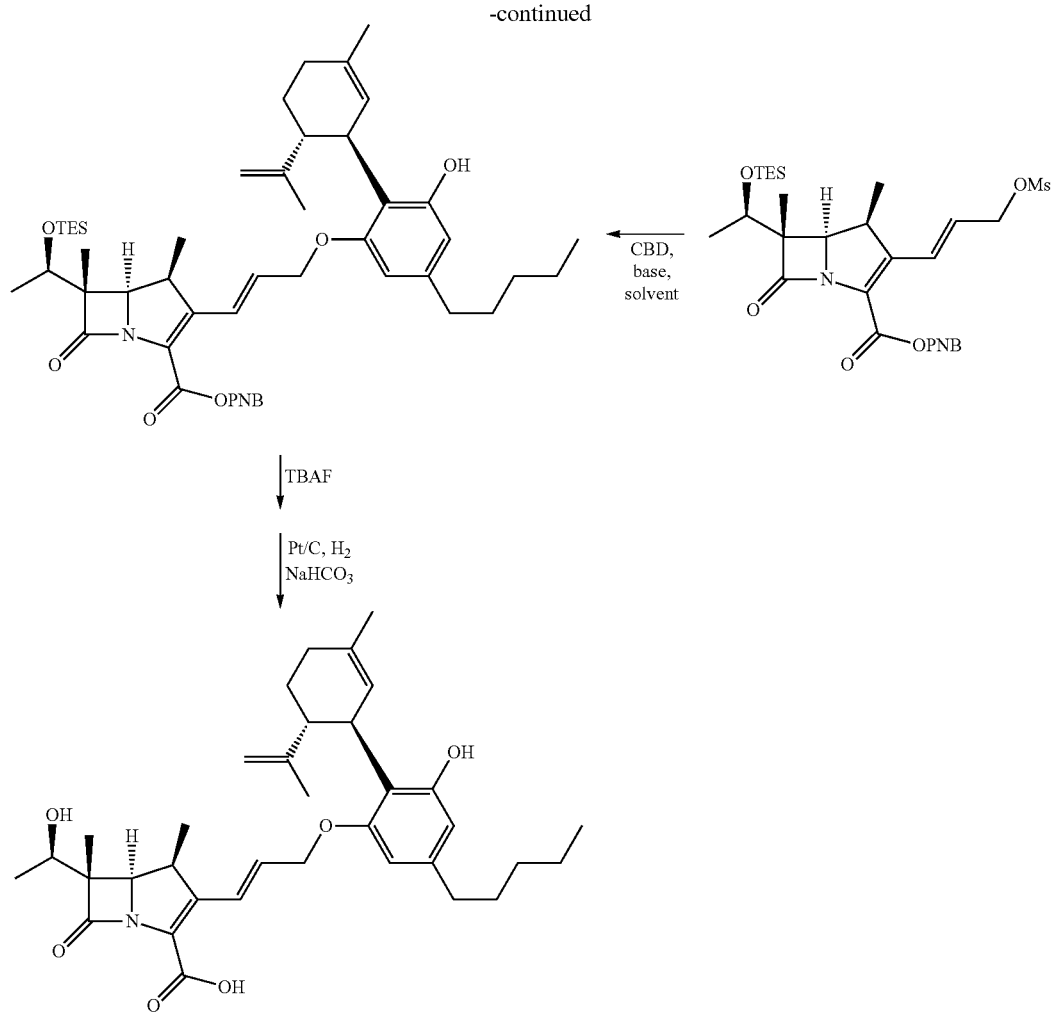

Example 8. Propenyl Carbonate-Linked Conjugate Molecules

Cephem Conjugate Molecules

Cephem propenyl carbonate linked conjugate molecules are synthesized according to the following Scheme. The starting material [130516-07-3] has been reported previously (Journal of Organic Chemistry (1993), 58(8), 2296-2301). It is converted to the allylic alcohol intermediate as previously described for similar molecules (WO 99/62906). This alcohol is reacted with phosgene and the resulting intermediate reacted with the cannabinoid (CBD) under basic conditions to form the carbonate group. Removal of the DPM ester protecting group under standard acidic conditions produces the desired product.

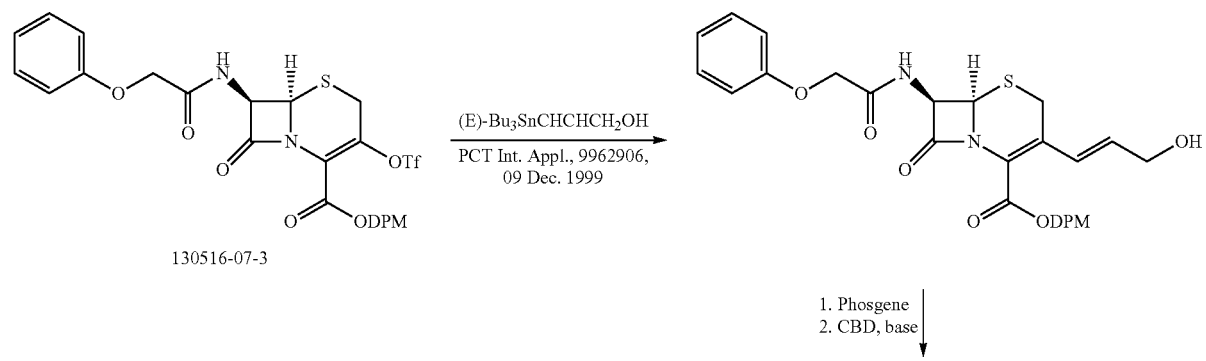

-continued

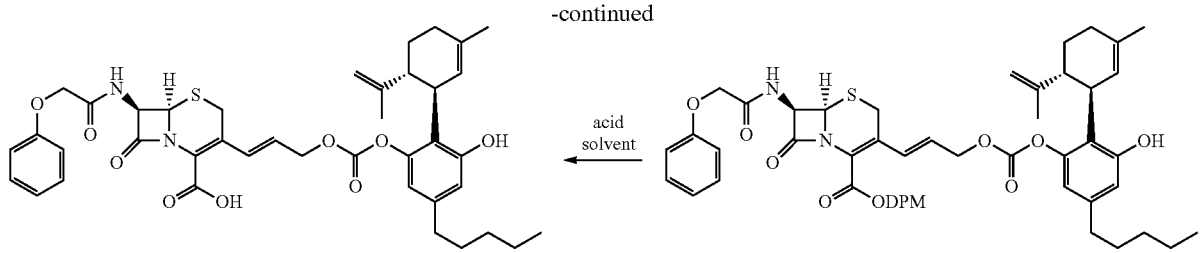

Carbacephem Conjugate Molecules

Carbacephem propenyl carbonate linked conjugate molecules are synthesized according to the following Scheme. The starting material [123078-32-0] has been reported previously (Journal of Organic Chemistry (1993), 58(8), 2296-2301). It is converted to the allylic alcohol intermediate as previously described for similar molecules (WO 99/62906). This alcohol is reacted with phosgene and the resulting intermediate reacted with the cannabinoid (CBD) under basic conditions to form the carbonate group. Removal of the DPM ester protecting group under standard acidic conditions produces the desired product.

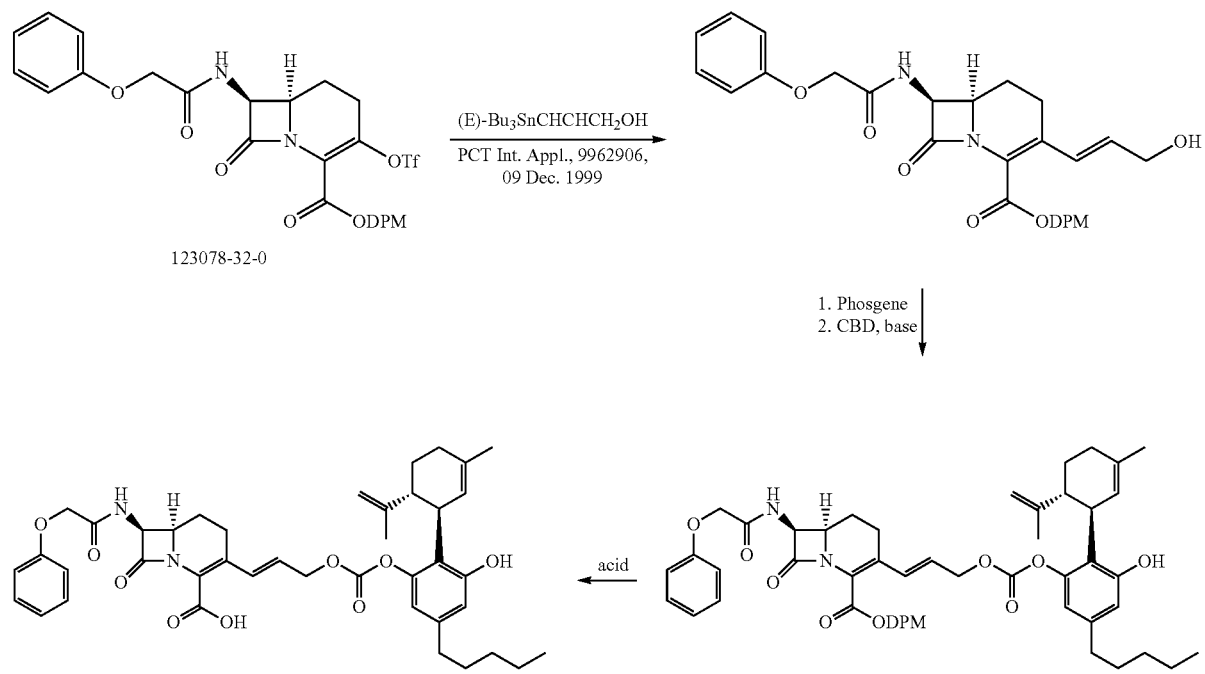

Penem Conjugate Molecules

Penem propenyl carbonate linked conjugate molecules are synthesized according to the following Scheme. The starting material [127941-62-2] has been previously reported (U.S. Pat. No. 4,895,940). It is converted to the allylic alcohol intermediate as previously described for similar molecules (WO 99/62906). The alcohol is then reacted with phosgene and the resulting intermediate reacted with the cannabinoid (CBD) under basic conditions to form the carbonate group. Removal of the TBDMS ether and trimethylsilylethyl ester protecting groups is achieved under standard conditions of excess TBAF to give the desired product.

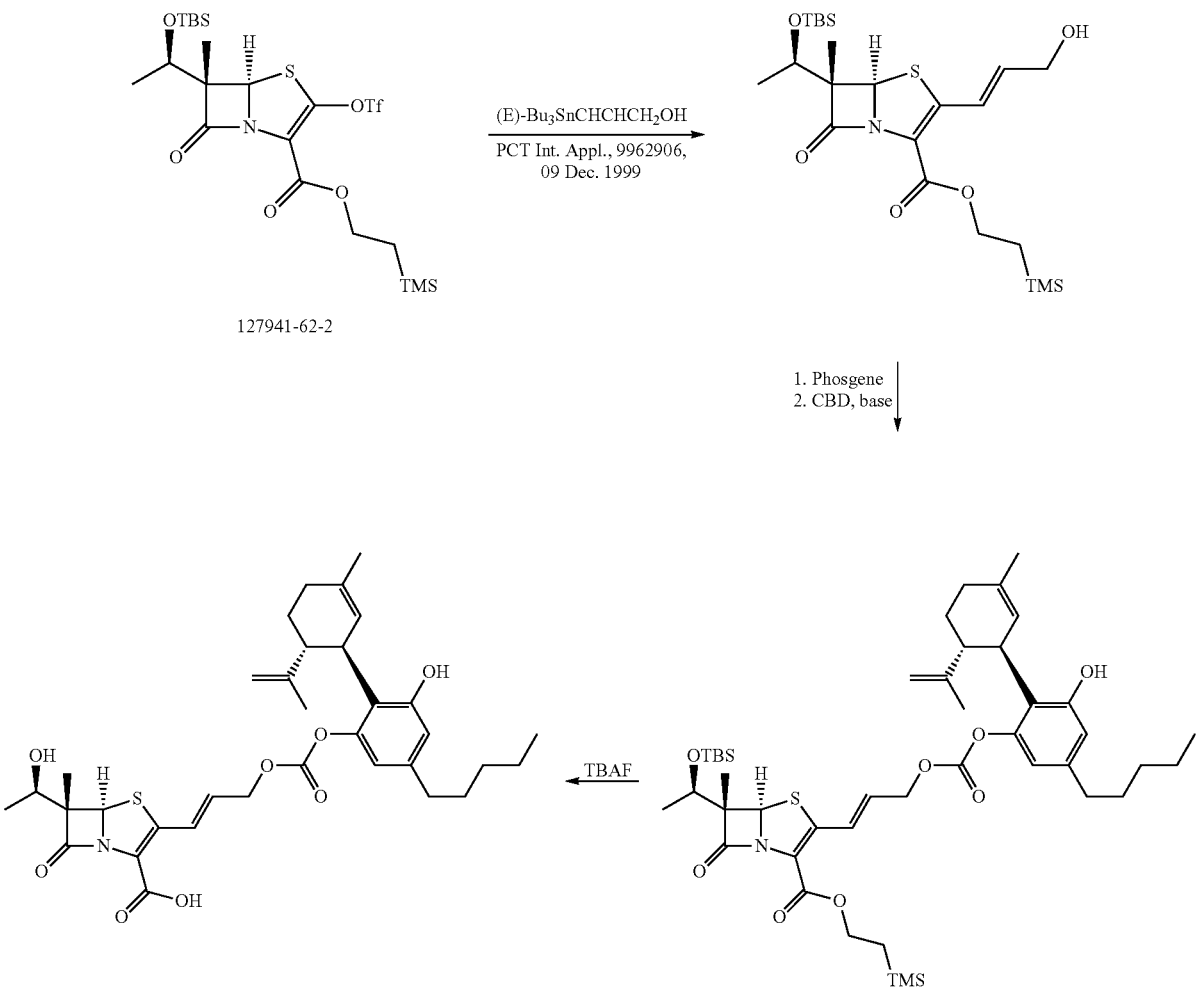

Carbapenem Conjugate Molecules

Carbapenem propenyl carbonate linked conjugate molecules are synthesized according to the following Scheme. The starting material [165817-82-3] along with its conversion to the allylic alcohol intermediate has been described previously (WO 99/62906). The alcohol is then reacted with phosgene and the resulting intermediate reacted with the cannabinoid (CBD) under basic conditions to form the carbonate group. Removal of the TES ether and PNB ester groups under standard conditions produces the desired product.

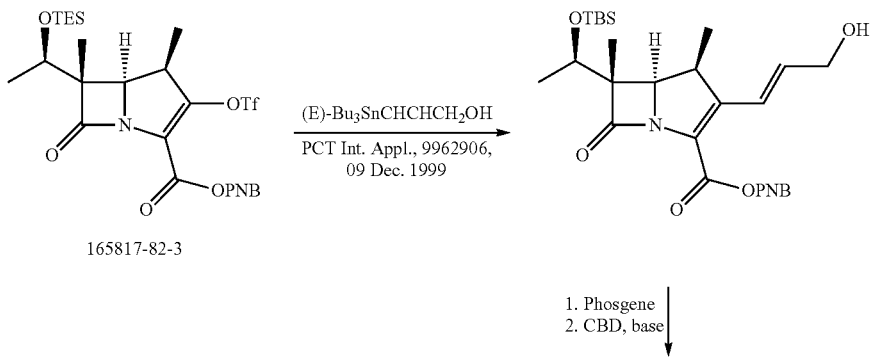

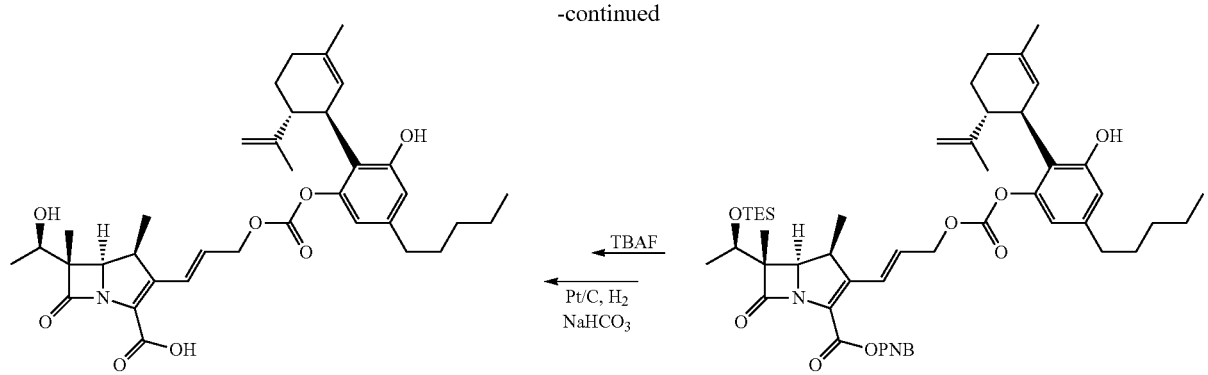

Example 9. Propenyl Thiocarbonate-Linked Conjugate Molecules

Cephem Conjugate Molecules

Cephem propenyl thiocarbonate linked conjugate molecules are synthesized according to the following Scheme. The starting material [130516-07-3] has been reported previously (Journal of Organic Chemistry (1993), 58(8), 2296-2301). It is converted to the allylic alcohol intermediate as previously described for similar molecules (WO 99/62906). This alcohol is reacted with thiophosgene and the resulting intermediate reacted with the cannabinoid (CBD) under basic conditions to form the thiocarbonate group. Removal of the DPM ester protecting group under standard acidic conditions produces the desired product.

Carbacephem Conjugate Molecules

Carbacephem propenyl thiocarbonate linked conjugate molecules are synthesized according to the following Scheme. The starting material [12078-32-0] has been reported previously (Journal of Organic Chemistry (1993), 58(8), 2296-2301). It is converted to the allylic alcohol intermediate as previously described for similar molecules (WO 99/62906). This alcohol is reacted with thiophosgene and the resulting intermediate reacted with the cannabinoid (CBD) under basic conditions to form the thiocarbonate group. Removal of the DPM ester protecting group under standard acidic conditions produces the desired product.

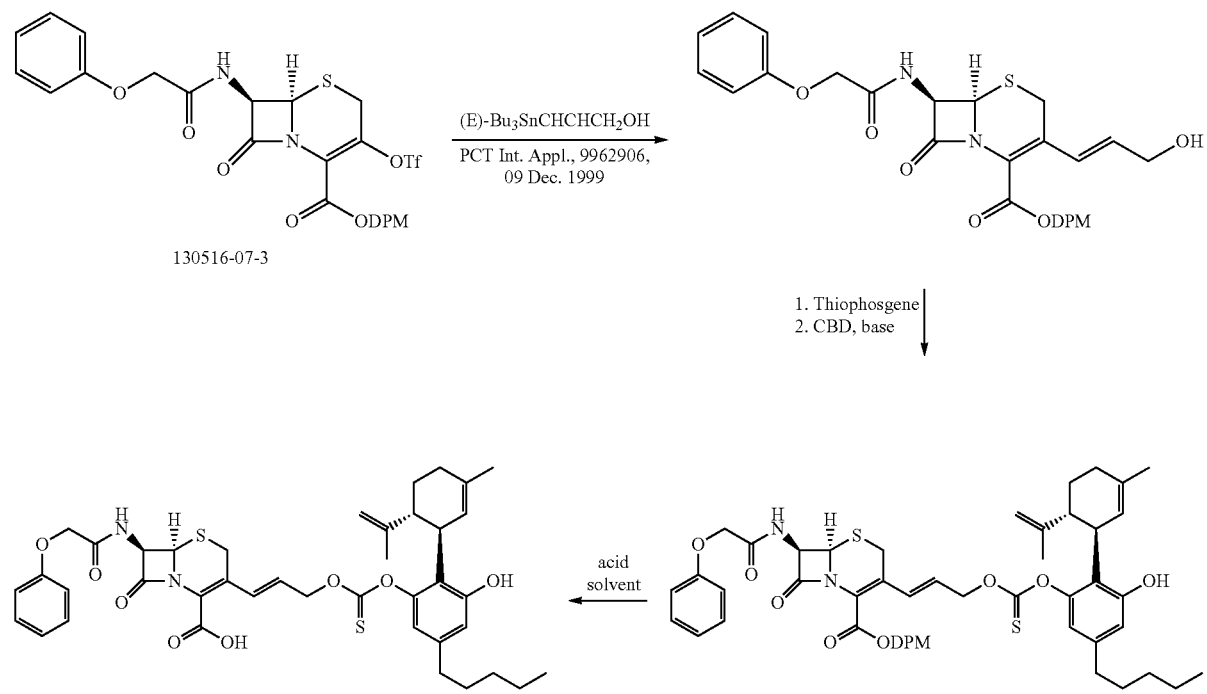

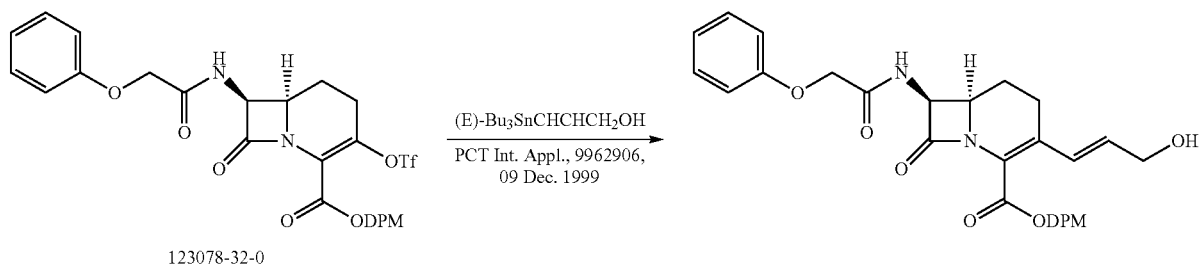

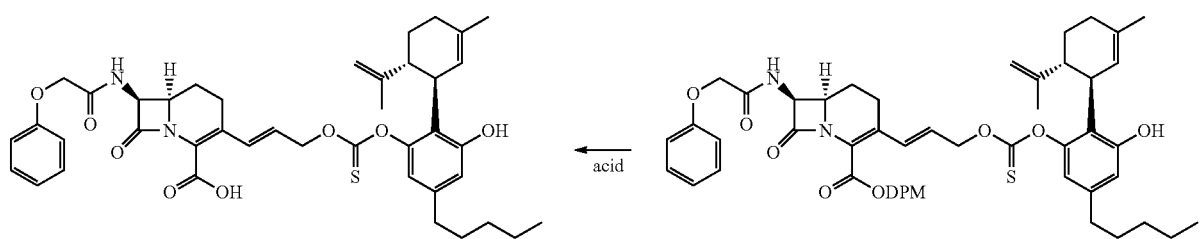

Penem Conjugate Molecules

Penem propenyl thiocarbonate linked conjugate molecules are synthesized according to the following Scheme. The starting material [127941-62-2] has been previously reported (U.S. Pat. No. 4,895,940). It is converted to the allylic alcohol intermediate as previously described for similar molecules (WO 99/62906). The alcohol is then reacted with thiophosgene and the resulting intermediate reacted with the cannabinoid (CBD) under basic conditions to form the thiocarbonate group. Removal of the TBDMS ether and trimethylsilylethyl ester protecting groups is achieved under standard conditions of excess TBAF to give the desired product.

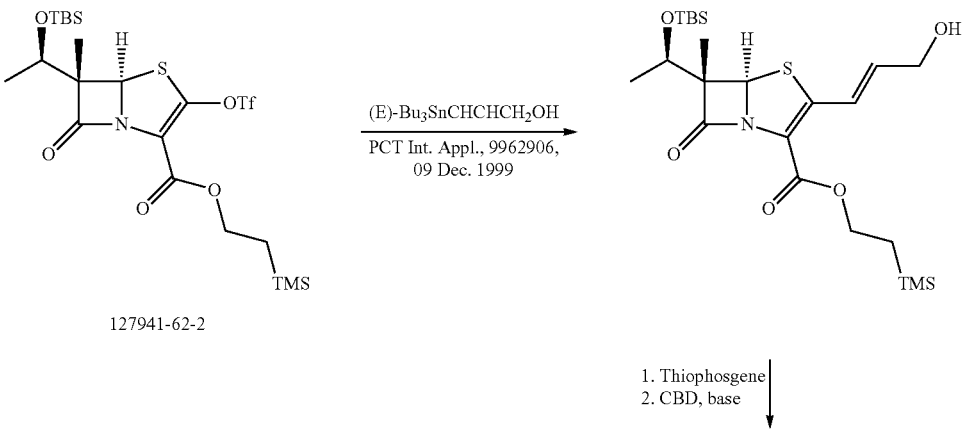

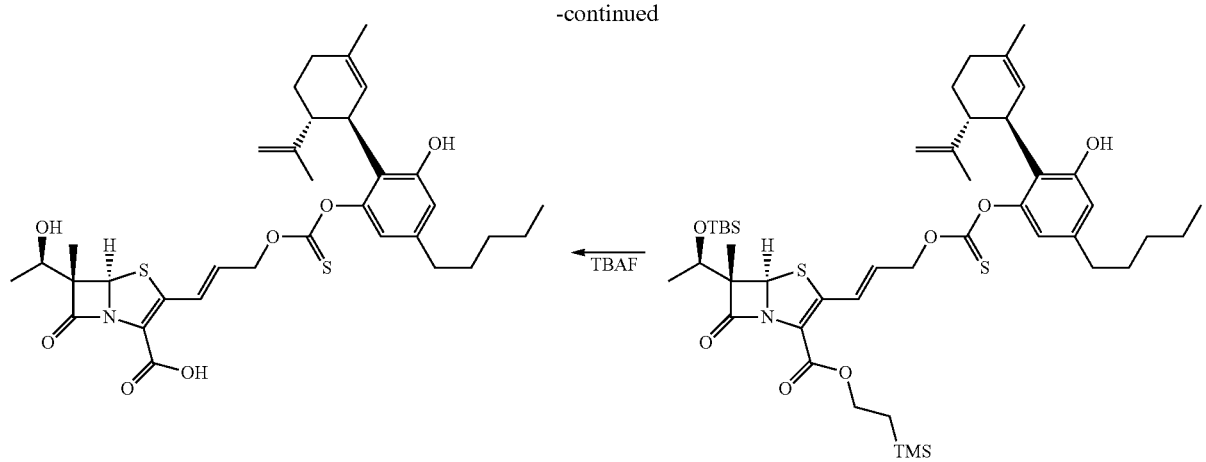

Carbapenem Conjugate Molecules

Carbapenem propenyl thiocarbonate linked conjugate molecules are synthesized according to the following Scheme. The starting material [165817-82-3] along with its conversion to the allylic alcohol intermediate has been described previously (WO 99/62906). The alcohol is then reacted with thiophosgene and the resulting intermediate reacted with the cannabinoid (CBD) under basic conditions to form the thiocarbonate group. Removal of the TES ether and PNB ester groups under standard conditions produces the desired product.

Example 10. Propenyl Carbamate-Linked Conjugate Molecules

Cephem Conjugate Molecules

Cephem propenyl carbamate linked conjugate molecules are synthesized according to the following Scheme. The starting material [57562-43-3] has been reported (CN 103588788 A 20140219). It is converted under standard conditions to the enol triflate, which is reacted with the BOC-protected aminoorganostannane [139111-44-7] (use in similar cephem triflate: Bioorganic & Medicinal Chemistry

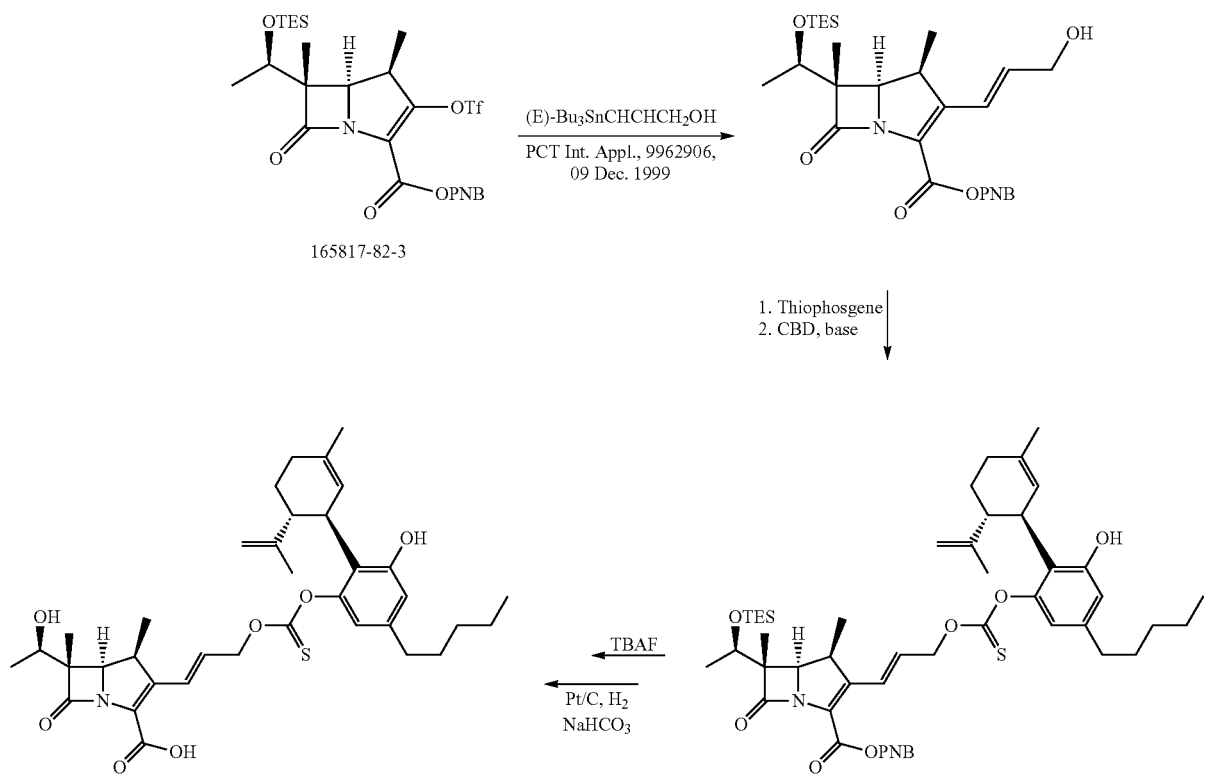

Letters (2010), 20(15), 4635-4638) followed by BOC removal under standard conditions to give the propenyl amine intermediate. This amine is reacted with phosgene and the resulting intermediate reacted with the cannabinoid (CBD) under basic conditions to form the carbamate group. Removal of the PNB ester group under standard conditions produces the desired product.

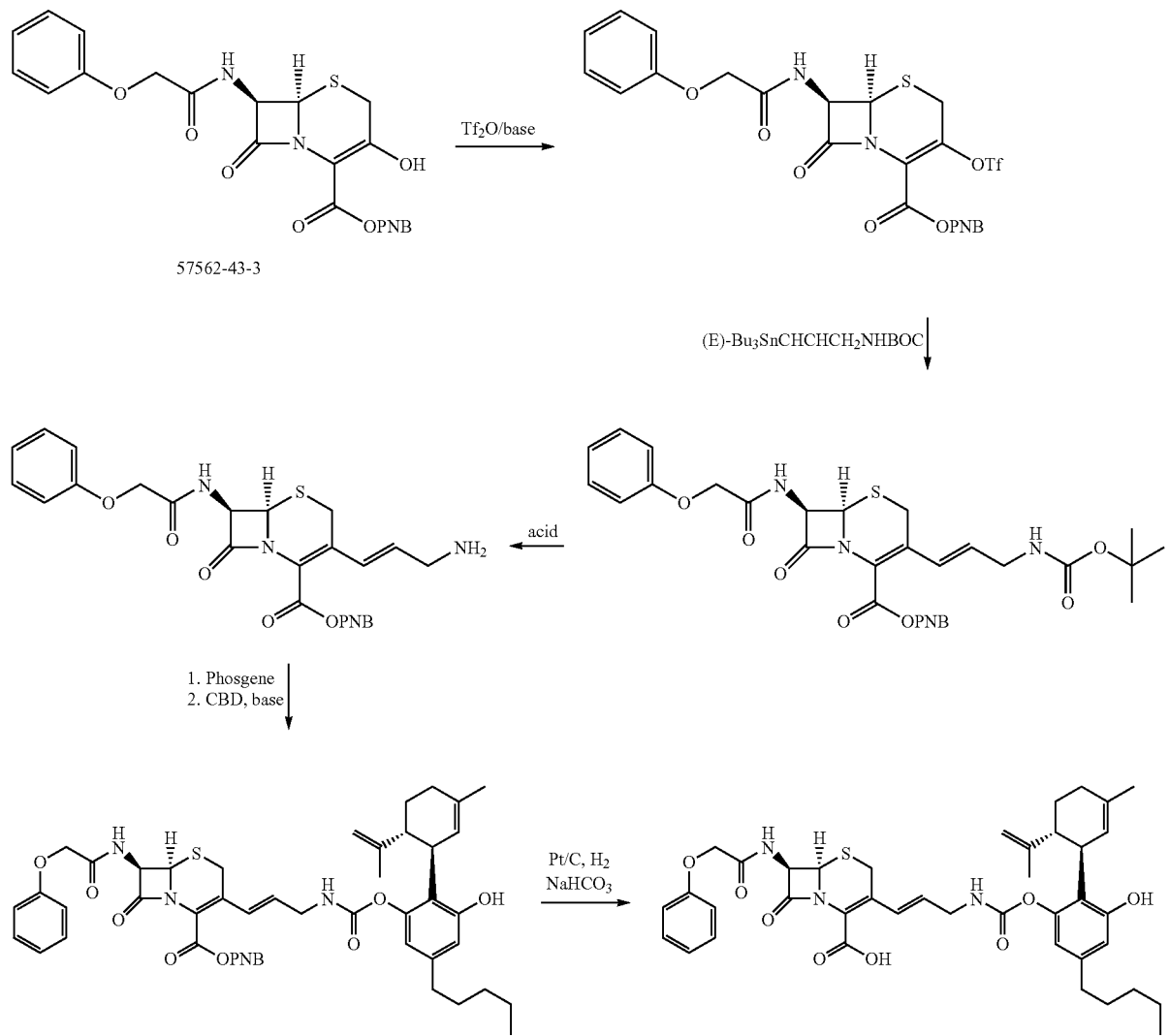

Carbacephem Conjugate Molecules

Carbacephem propenyl carbamate linked conjugate molecules are synthesized according to the following Scheme. The starting material [119892-46-5] (WO 2010/030810, and references cited therein) is converted under standard conditions to the enol triflate, which is reacted with the BOC-protected aminoorganostannane [139111-44-7] (use in similar cephem triflate: Bioorganic & Medicinal Chemistry Letters (2010), 20(15), 4635-4638) followed by BOC removal under standard conditions to give the propenyl amine intermediate. This amine is reacted with phosgene and the resulting intermediate reacted with the cannabinoid (CBD) under basic conditions to form the carbamate group. Removal of the PNB ester group under standard conditions produces the desired product.

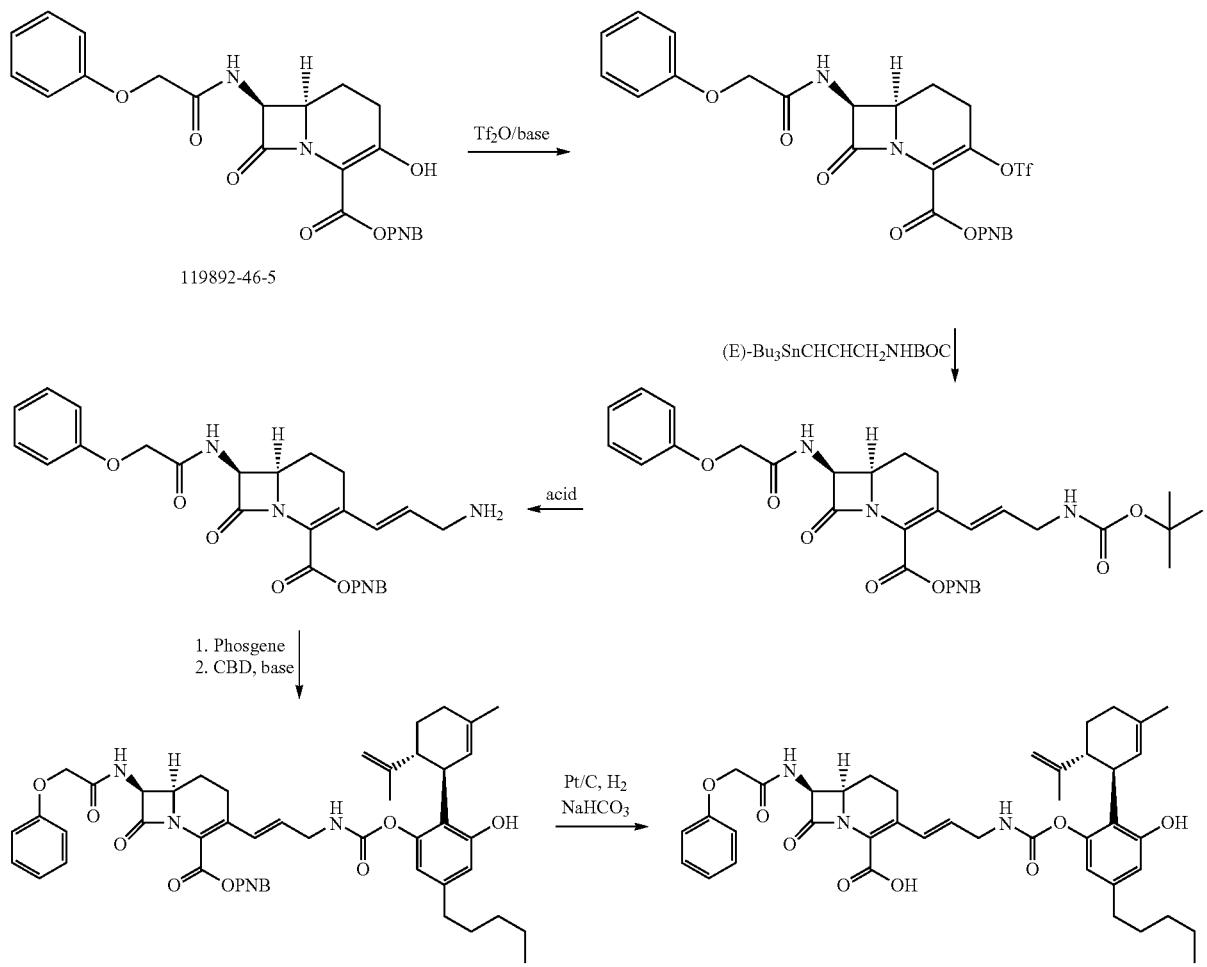

Penem Conjugate Molecules

Penem propenyl carbamate linked conjugate molecules are synthesized according to the following Scheme. The starting material [127941-62-2] has been previously reported (U.S. Pat. No. 4,895,940). Reaction with the BOC-protected aminoorganostannane [139111-44-7] (use in similar cephem triflate: Bioorganic & Medicinal Chemistry Letters (2010), 20(15), 4635-4638) followed by BOC removal under standard conditions gives the propenyl amine intermediate. This amine is reacted with phosgene and the resulting intermediate reacted with the cannabinoid (CBD) under basic conditions to form the carbamate group. Removal of the TES ether and trimethylsilylethyl ester groups under standard conditions produces the desired product.

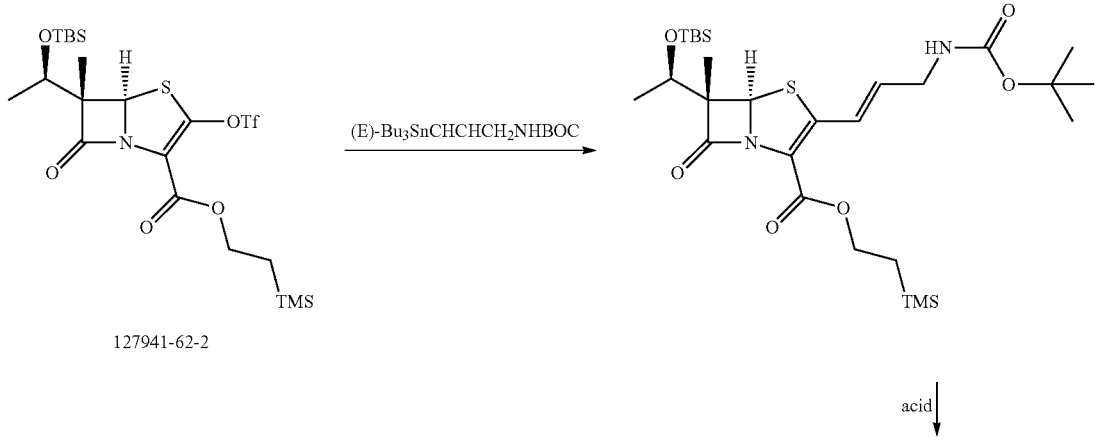

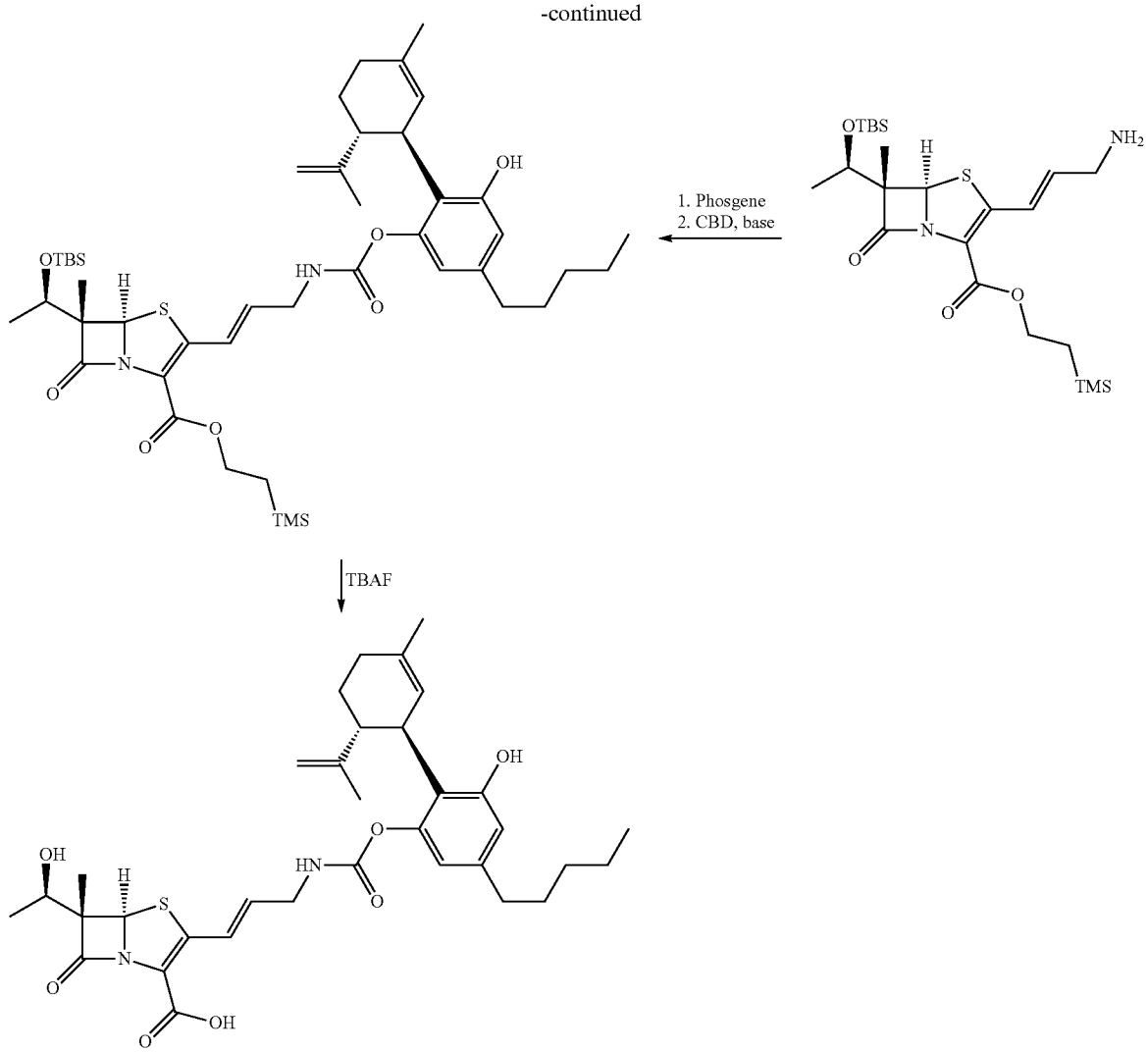

Carbapenem Conjugate Molecules

Carbapenem propenyl carbamate linked conjugate molecules are synthesized according to the following Scheme. The starting material [165817-82-3] has been described previously (WO 99/62906). Reaction with the BOC-protected aminoorganostannane [139111-44-7] (use in similar cephem triflate: Bioorganic & Medicinal Chemistry Letters (2010), 20(15), 4635-4638) followed by BOC removal under standard conditions gives the propenyl amine intermediate. This amine is reacted with phosgene and the resulting intermediate reacted with the cannabinoid (CBD) under basic conditions to form the carbamate group. Removal of the TES ether and PNB ester groups under standard conditions produces the desired product.

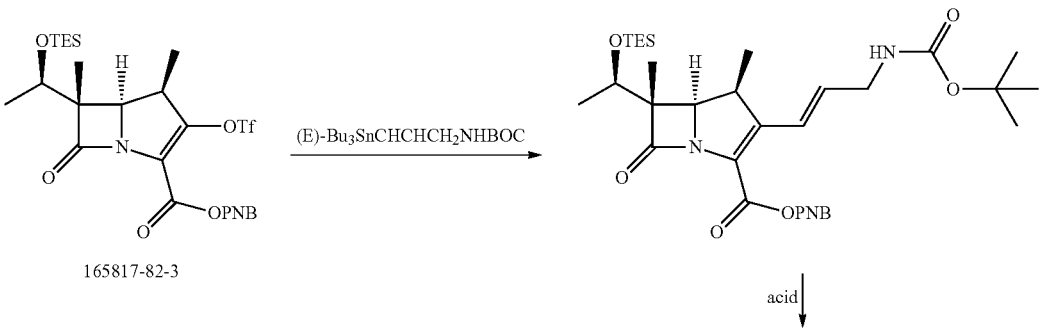

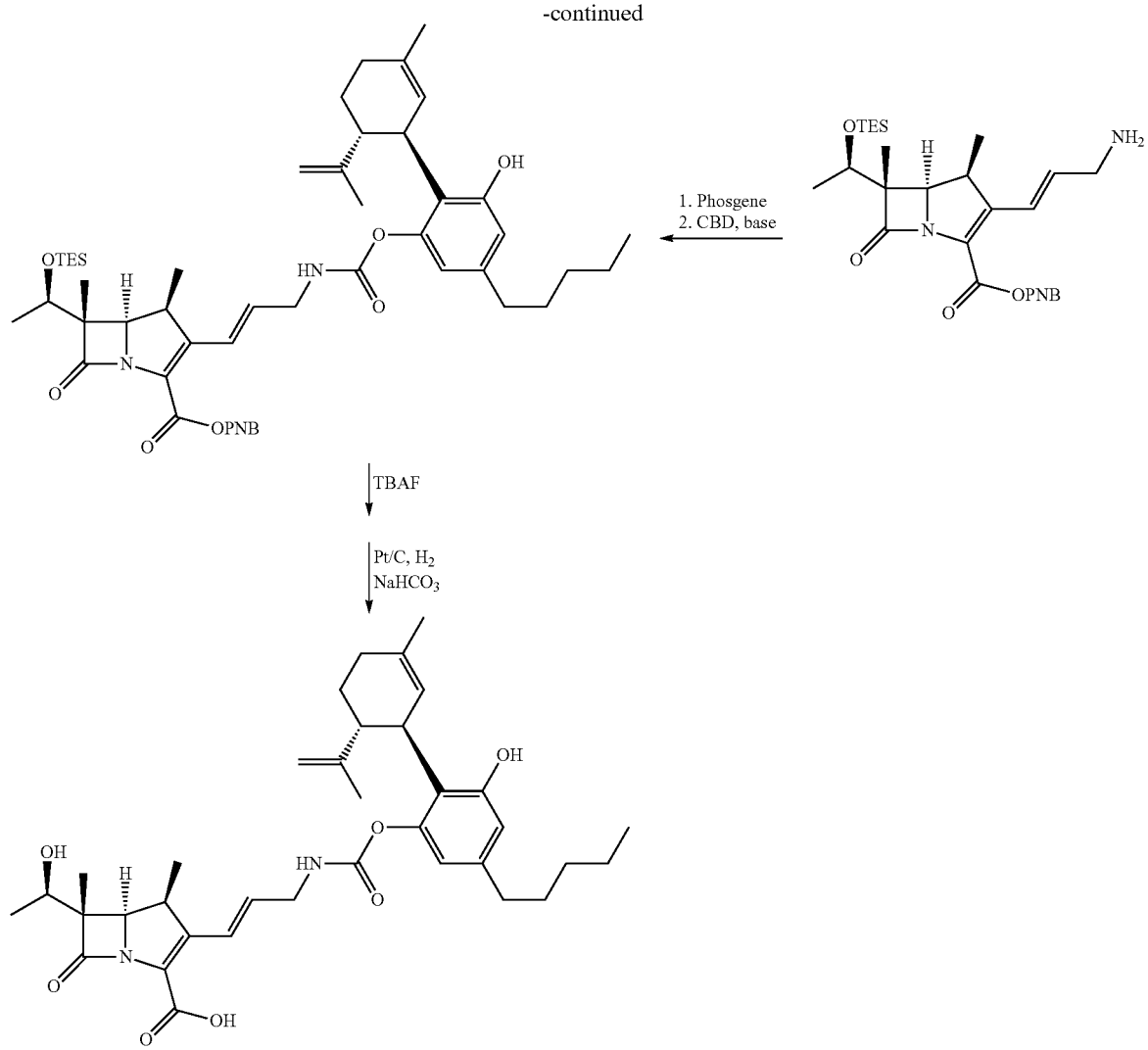

Example 11. Propenyl Thiocarbamate-Linked Conjugate Molecules

Cephem Conjugate Molecules

Cephem propenyl thiocarbamate linked conjugate molecules are synthesized according to the following Scheme. The starting material [57562-43-3] has been reported (CN 103588788 A 20140219). It is converted under standard conditions to the enol triflate, which is reacted with the BOC-protected aminoorganostannane [139111-44-7] (use in similar cephem triflate: Bioorganic & Medicinal Chemistry Letters (2010), 20(15), 4635-4638) followed by BOC removal under standard conditions to give the propenyl amine intermediate. This amine is reacted with thiophosgene and the resulting intermediate reacted with the cannabinoid (CBD) under basic conditions to form the thiocarbamate group. Removal of the PNB ester group under standard conditions produces the desired product.

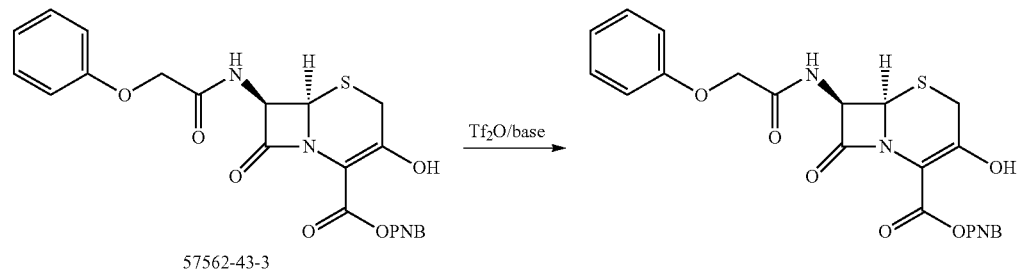

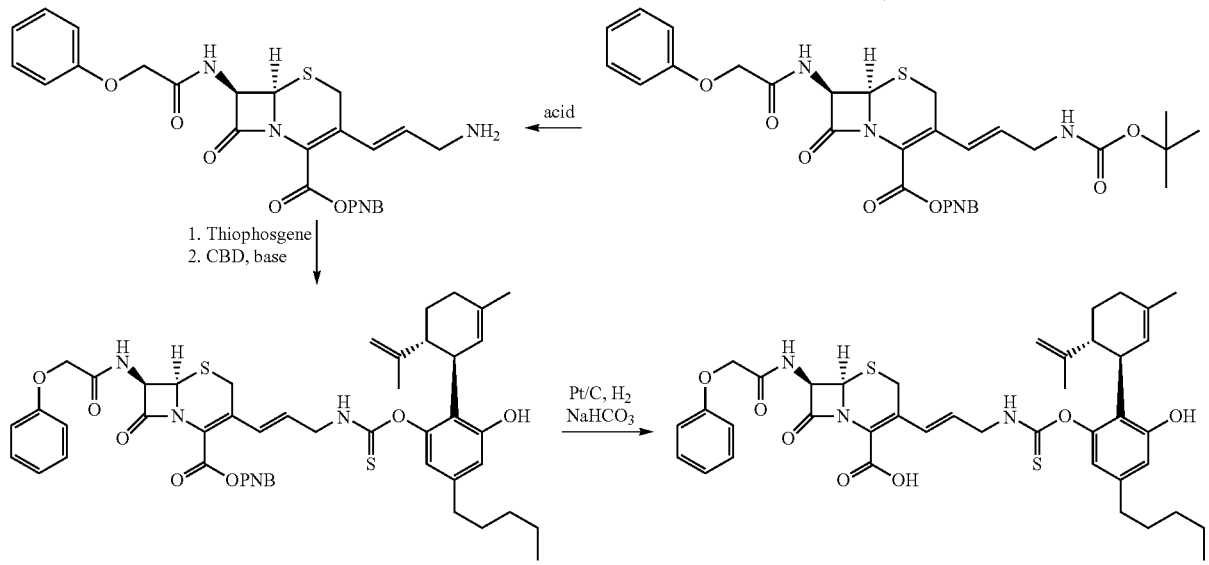

Carbacephem Conjugate Molecules

Carbacephem propenyl thiocarbamate linked conjugate molecules are synthesized according to the following Scheme. The starting material [119892-46-5] (WO 2010/030810, and references cited therein) is converted under standard conditions to the enol triflate, which is reacted with the BOC-protected aminoorganostannane [139111-44-7] (use in similar cephem triflate: Bioorganic & Medicinal Chemistry Letters (2010), 20(15), 4635-4638) followed by BOC removal under standard conditions to give the propenyl amine intermediate. This amine is reacted with thiophosgene and the resulting intermediate reacted with the cannabinoid (CBD) under basic conditions to form the thiocarbamate group. Removal of the PNB ester group under standard conditions produces the desired product.

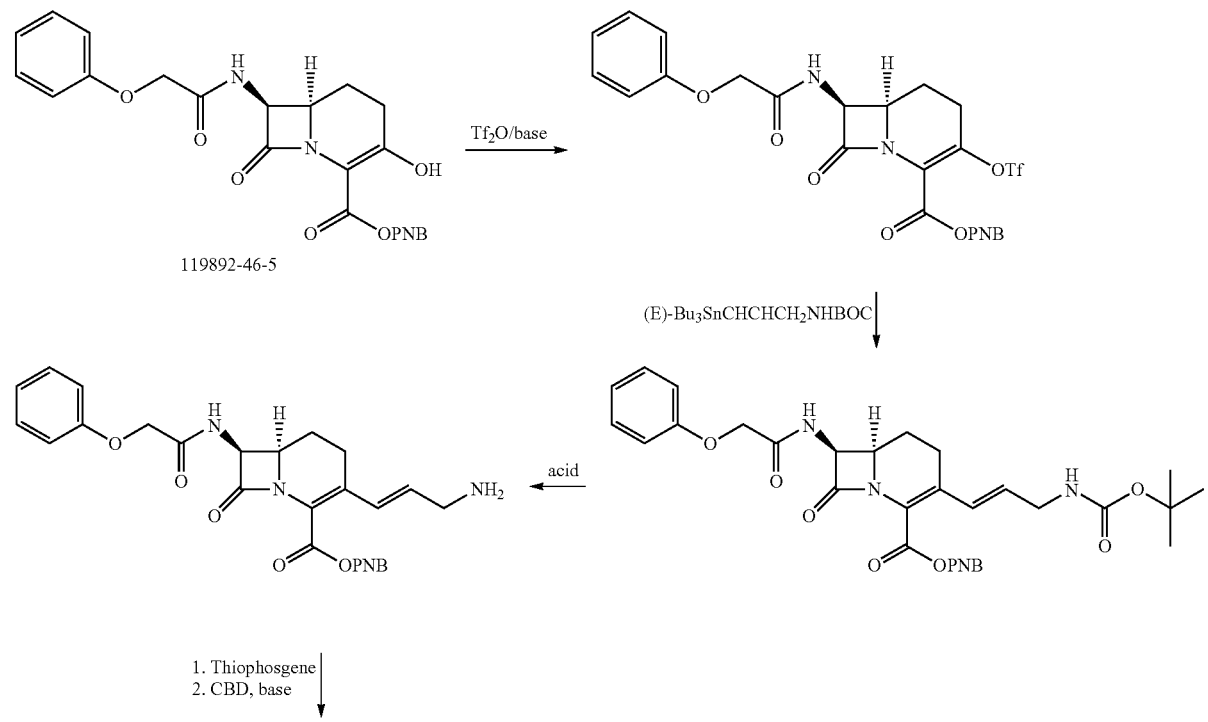

-continued

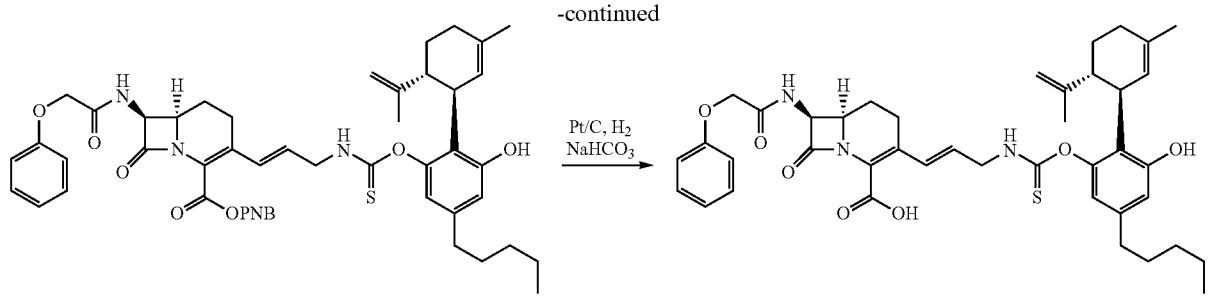

Penem Conjugate Molecules

Penem propenyl thiocarbamate linked conjugate molecules are synthesized according to the following Scheme. The starting material [127941-62-2] has been previously reported (U.S. Pat. No. 4,895,940). Reaction with the BOC-protected aminoorganostannane [139111-44-7] (use in similar cephem triflate: Bioorganic & Medicinal Chemistry Letters (2010), 20(15), 4635-4638) followed by BOC removal under standard conditions gives the propenyl amine intermediate. This amine is reacted with thiophosgene and the resulting intermediate reacted with the cannabinoid (CBD) under basic conditions to form the thiocarbamate group. Removal of the TES ether and trimethylsilylethyl ester groups under standard conditions produces the desired product.

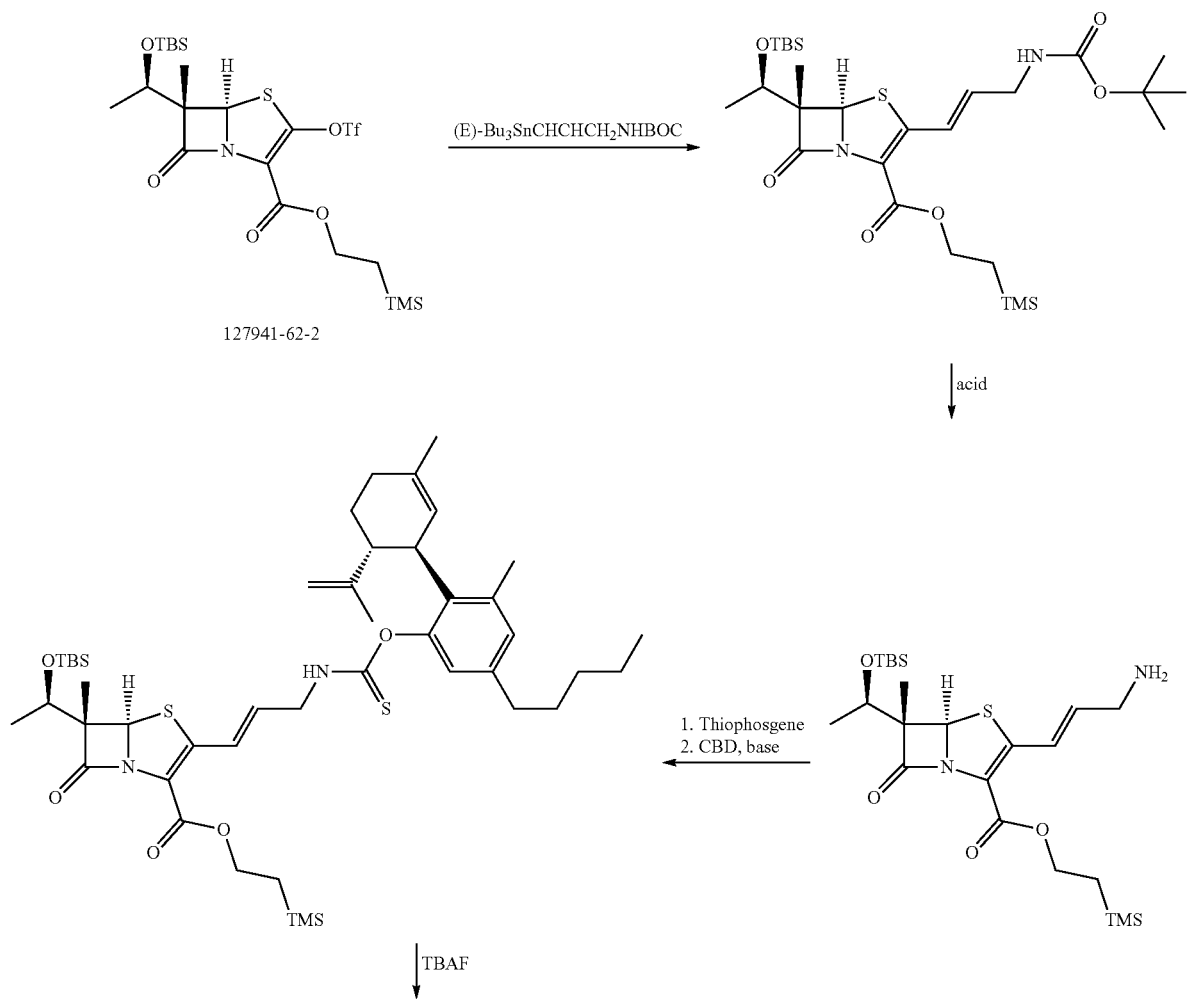

-continued

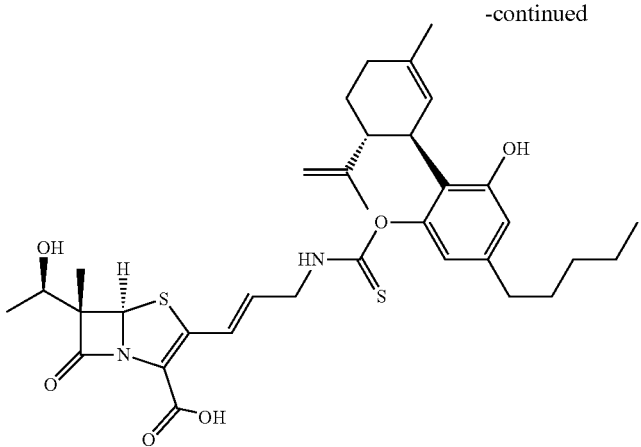

Carbapenem Conjugate Molecules

Carbapenem propenyl thiocarbamate linked conjugate molecules are synthesized according to the following Scheme. The starting material [165817-82-3] has been described previously (WO 99/62906). Reaction with the BOC-protected aminoorganostannane [139111-44-7] (use in similar cephem triflate: Bioorganic & Medicinal Chemistry Letters (2010), 20(15), 4635-4638) followed by BOC removal under standard conditions gives the propenyl amine intermediate. This amine is reacted with thiophosgene and the resulting intermediate reacted with the cannabinoid (CBD) under basic conditions to form the thiocarbamate group. Removal of the TES ether and PNB ester groups under standard conditions produces the desired product.

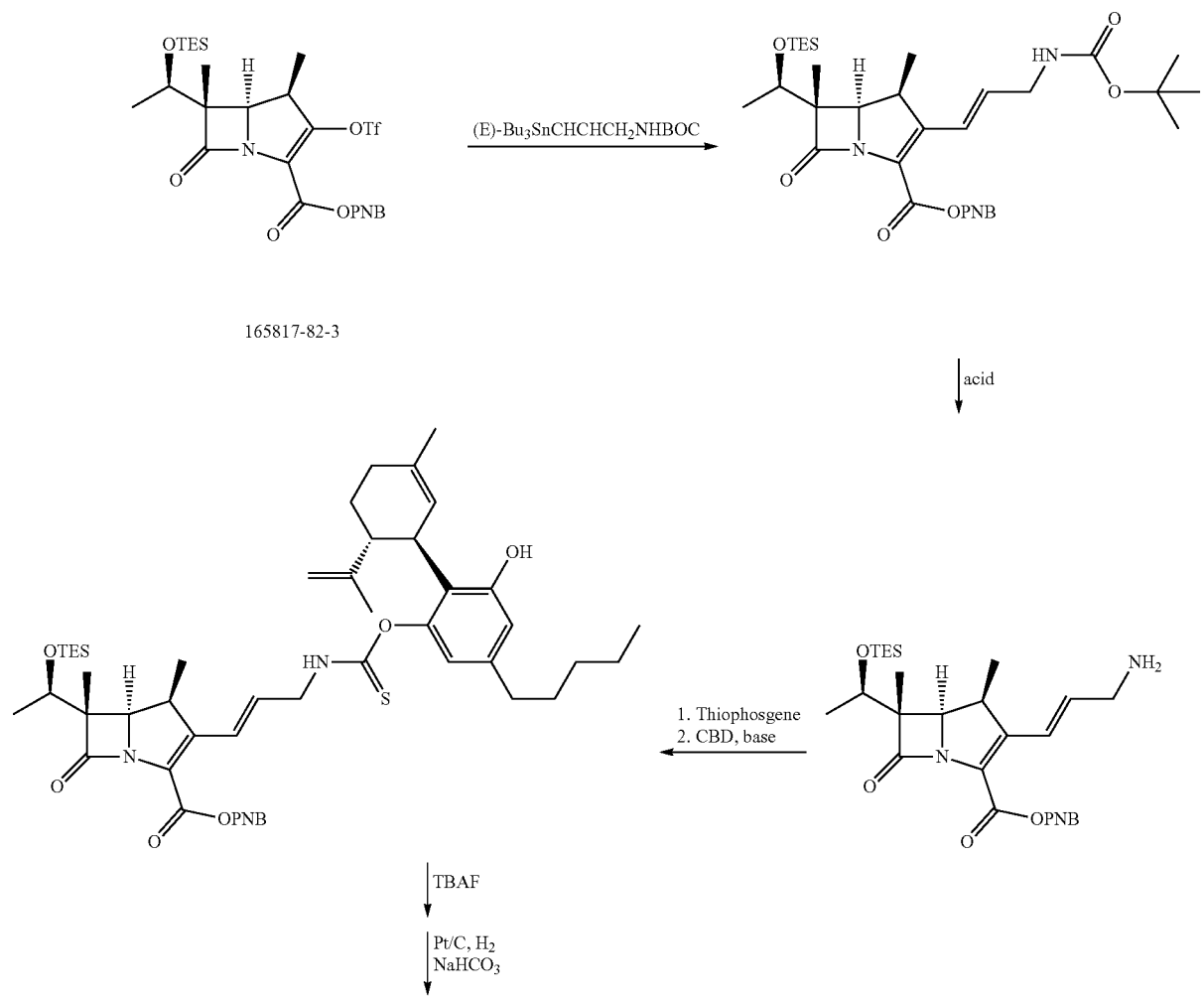

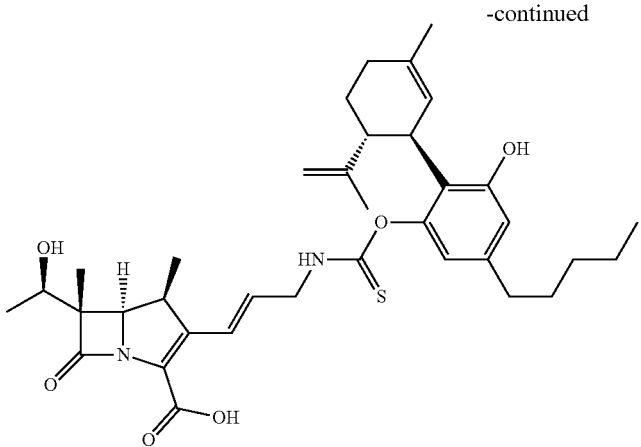

Example 12. S-Alkyl Thiocarbonate-Linked Conjugate Molecules

Cephem Conjugate Molecules

Cephem S-alkyl thiocarbonate linked conjugate molecules are synthesized according to the following Scheme. The starting material [61781-78-0] has been described previously (U.S. (1976), U.S. Pat. No. 3,979,384 A 19760907). Reaction with phosgene and the cannabinoid (CBD) under standard basic conditions to form the S-alkyl thiocarbonate linked intermediate. Removal of the diphenylmethyl ester protecting group gives the desired product.

Carbacephem Conjugate Molecules

Carbacephem S-alkyl thiocarbonate linked conjugate molecules are synthesized according to the following Scheme. The starting material [177325-29-0] is converted to the thiol intermediate using previously described (Faming Zhuanli Shenqing, 108623617, 9 Oct. 2018) conditions for a related system. The thiol intermediate is reacted with phosgene and the cannabinoid (CBD) under standard basic conditions to form the S-alkyl thiocarbonate linked intermediate. Removal of the diphenylmethyl ester protecting group gives the desired product.

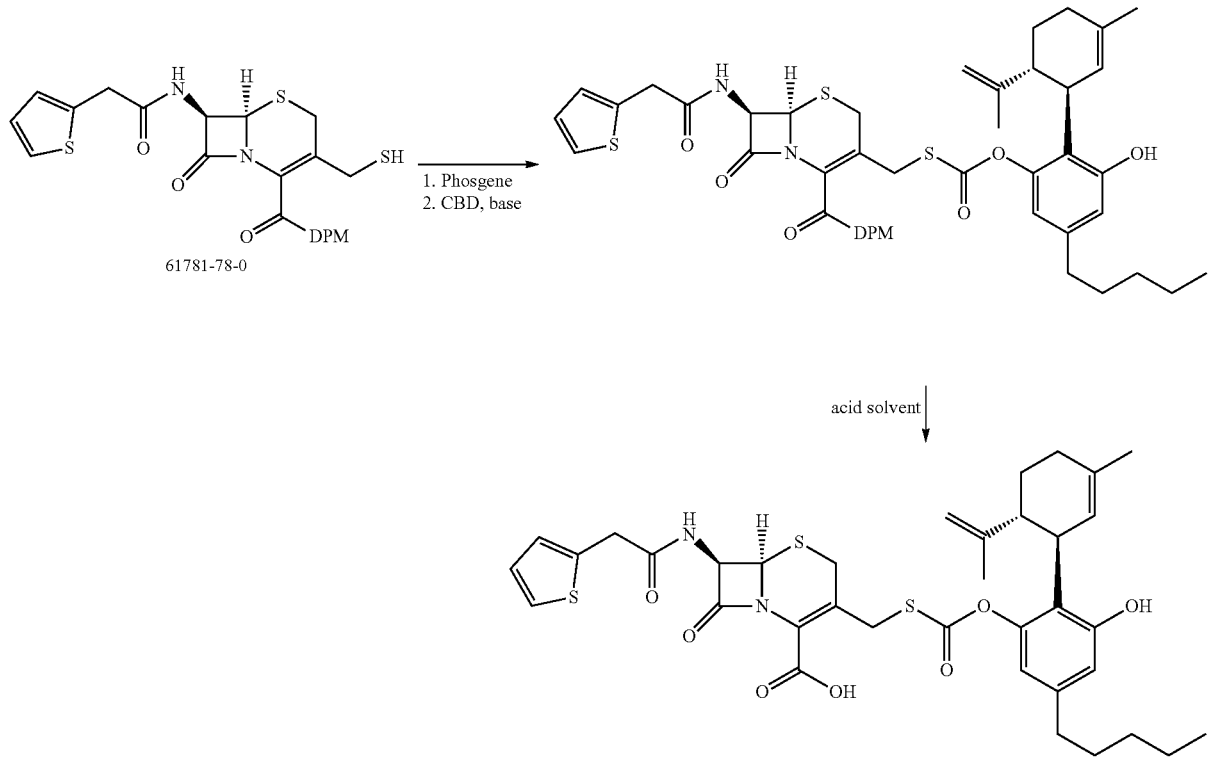

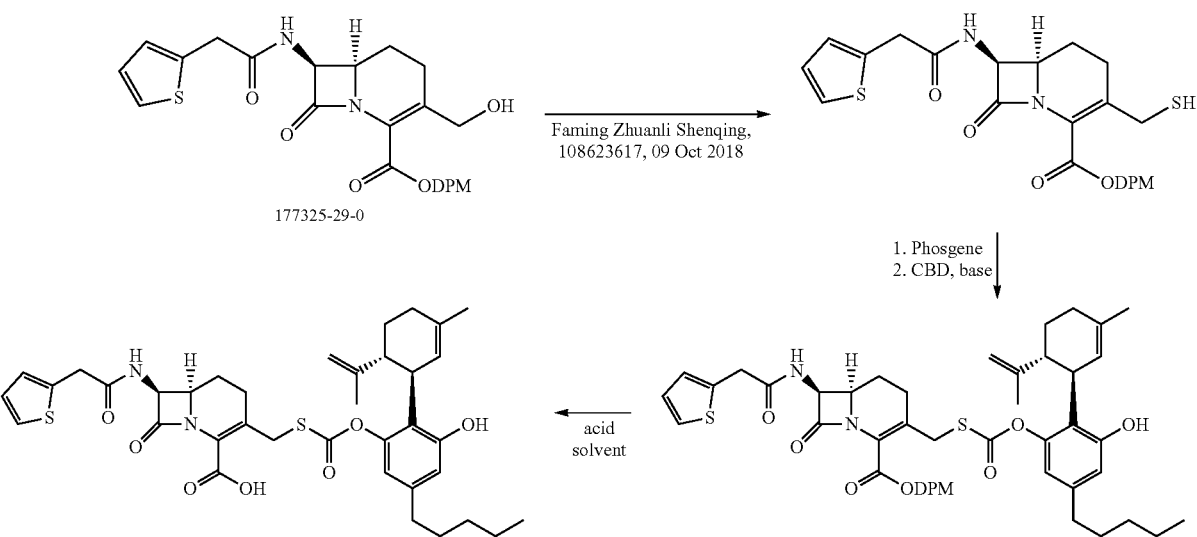

Penem Conjugate Molecules

Penem S-alkyl thiocarbonate linked conjugate molecules are synthesized according to the following Scheme. The starting material [88585-78-8] is converted to the thiol intermediate using previously described (Faming Zhuanli Shenqing, 108623617, 9 Oct. 2018) conditions for a related system. The thiol intermediate is reacted with phosgene and the cannabinoid (CBD) under standard basic conditions to form the S-alkyl thiocarbonate linked intermediate. Removal of the silyl ether and allyl ester protecting groups gives the desired product.

Carbapenem Conjugate Molecules

Carbapenem S-alkyl thiocarbonate linked conjugate molecules are synthesized according to the following Scheme. The starting material [118990-99-1] is converted to the thiol intermediate using previously described (Faming Zhuanli Shenqing, 108623617, 9 Oct. 2018) conditions for a related system. The thiol intermediate is reacted with phosgene and the cannabinoid (CBD) under standard basic conditions to form the S-alkyl thiocarbonate linked intermediate. Removal of the allyl protecting groups gives the desired product.

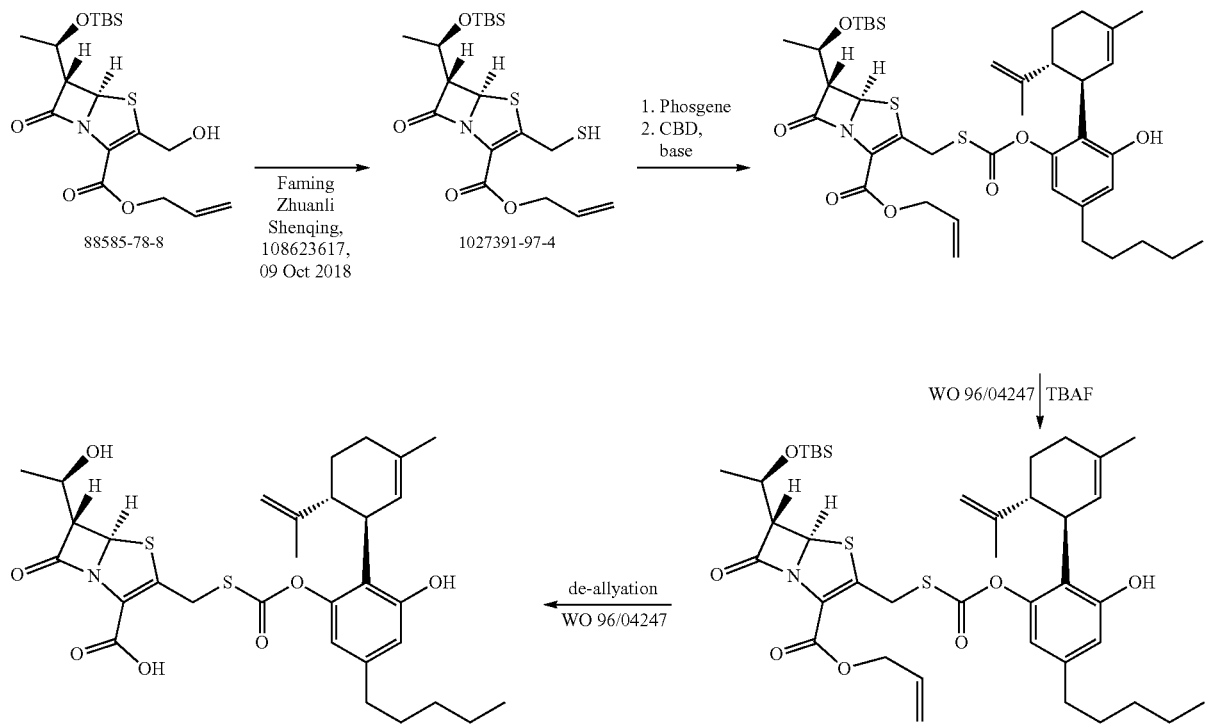

117 118

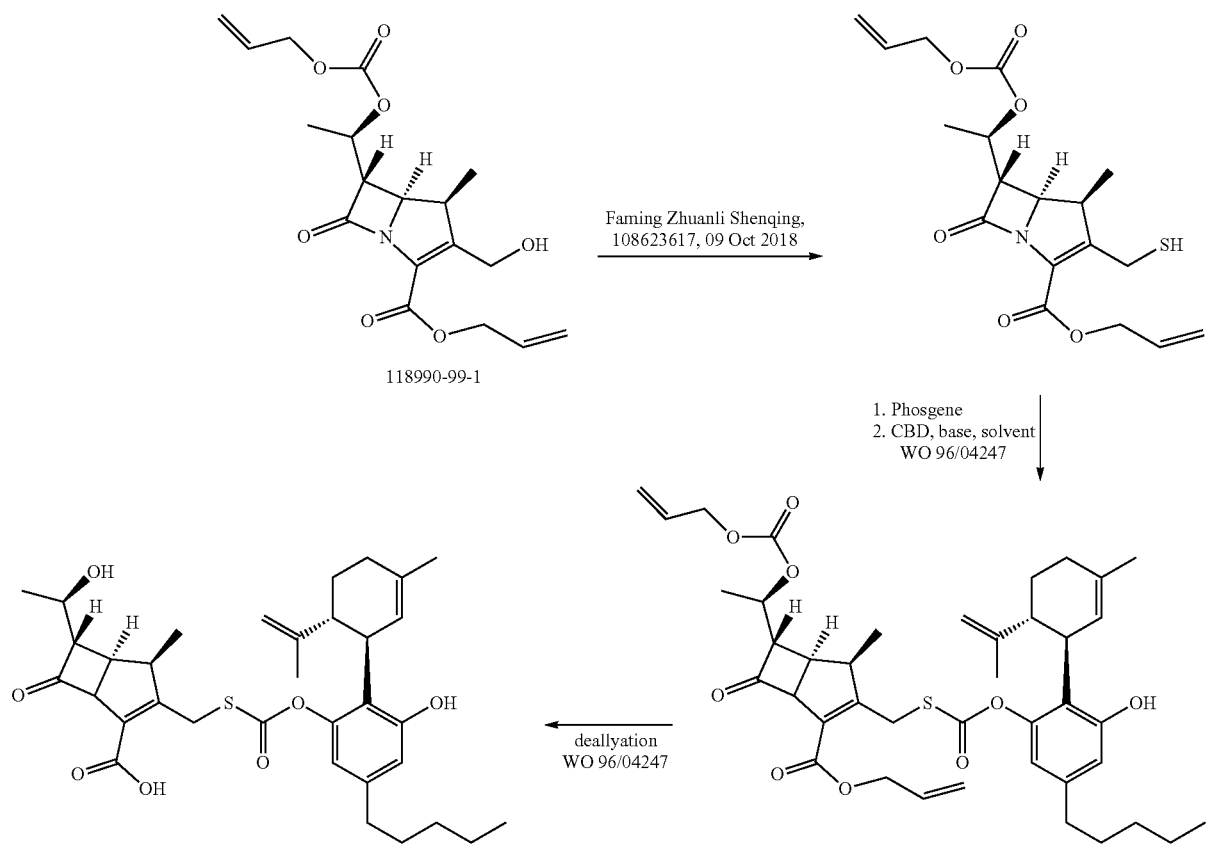

Example 13. Xanthate-Linked Conjugate Molecules

Cephem Conjugate Molecules

Cephem xanthate linked conjugate molecules are synthesized according to the following Scheme. The starting material [61781-78-0] has been described previously (U.S. (1976), U.S. Pat. No. 3,979,384 A 19760907). Reaction with thiophosgene and the cannabinoid (CBD) under standard basic conditions to form the xanthate linked intermediate. Removal of the diphenylmethyl ester protecting group gives the desired product.

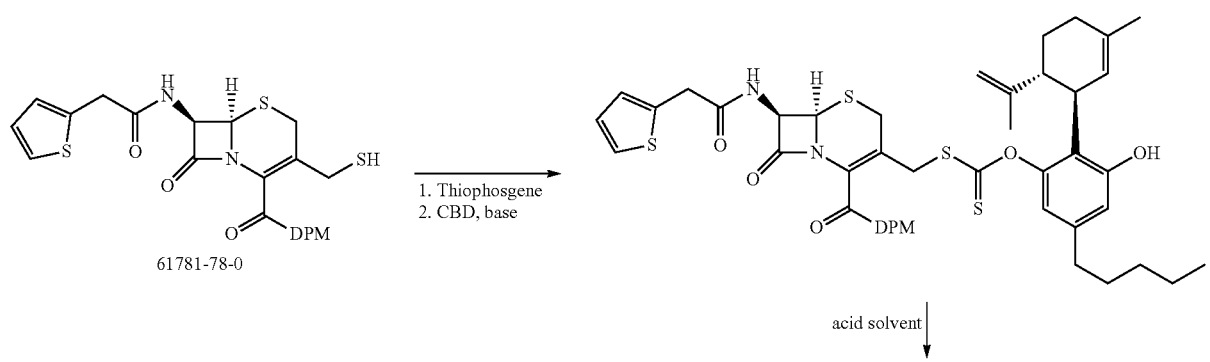

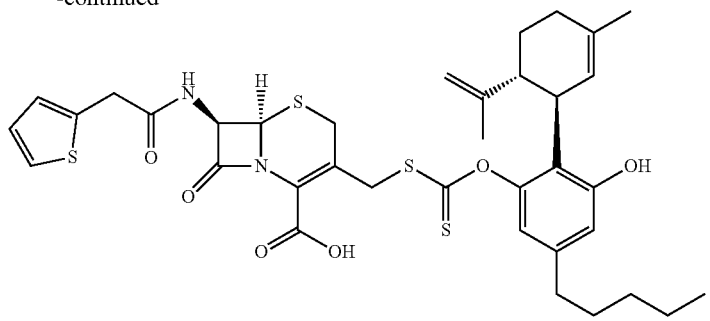

Carbacephem Conjugate Molecules

Carbacephem xanthate linked conjugate molecules are synthesized according to the following Scheme. The starting material [177325-29-0] is converted to the thiol intermediate using previously described (Faming Zhuanli Shenqing, 108623617, 9 Oct. 2018) conditions for a related system. The thiol intermediate is reacted with thiophosgene and the cannabinoid (CBD) under standard basic conditions to form the xanthate linked intermediate. Removal of the diphenylmethyl ester protecting group gives the desired product.

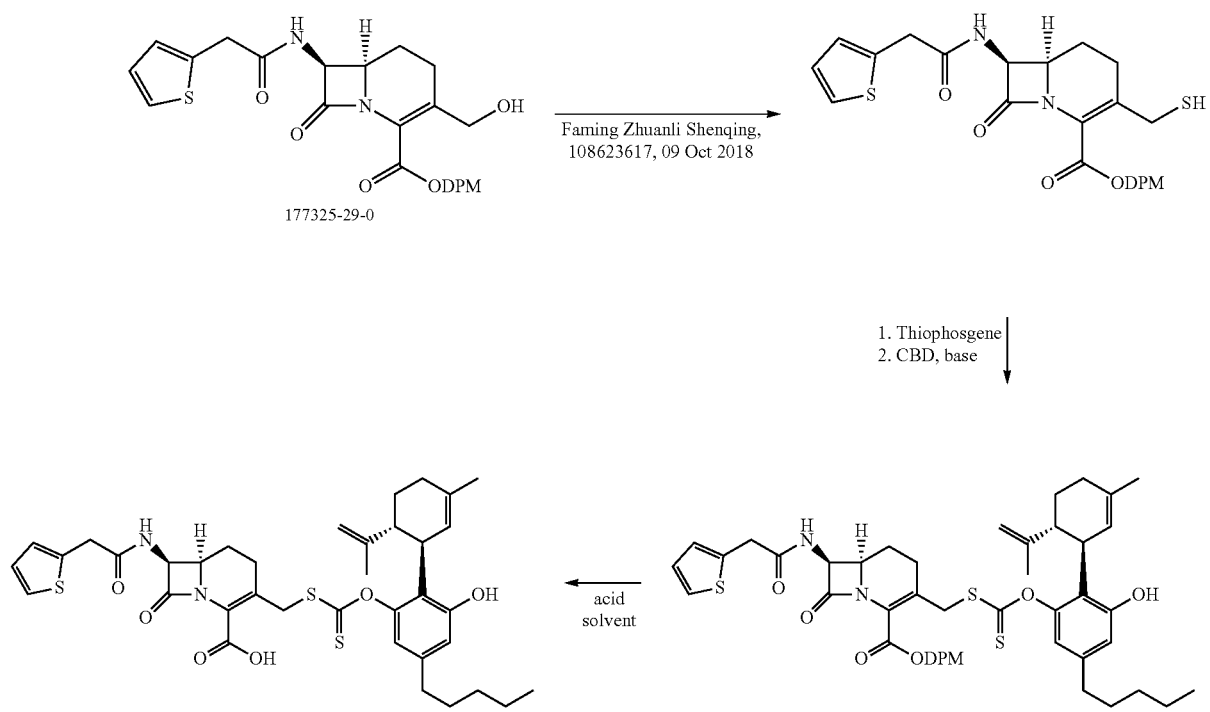

Penem Conjugate Molecules

Penem xanthate linked conjugate molecules are synthesized according to the following Scheme. The starting material [88585-78-8] is converted to the thiol intermediate using previously described (Faming Zhuanli Shenqing, 108623617, 9 Oct. 2018) conditions for a related system. The thiol intermediate is reacted with thiophosgene and the cannabinoid (CBD) under standard basic conditions to form the xanthate linked intermediate. Removal of the silyl ether and allyl ester protecting groups gives the desired product.

121

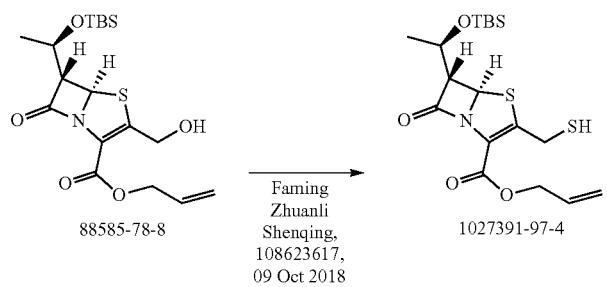

122

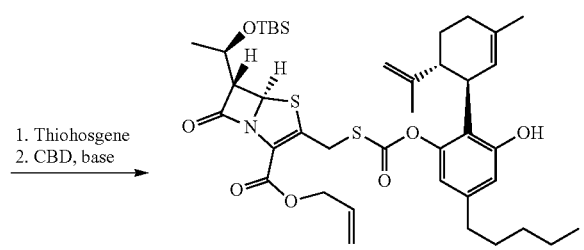

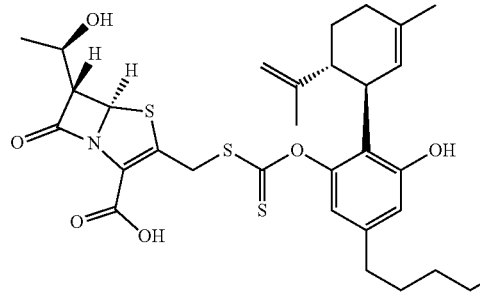

Carbapenem Conjugate Molecules

Carbapenem xanthate linked conjugate molecules are synthesized according to the following Scheme. The starting material [118990-99-1] is converted to the thiol intermediate using previously described (Faming Zhuanli Shenqing, 108623617, 9 Oct. 2018) conditions for a related system. The thiol intermediate is reacted with thiophosgene and the cannabinoid (CBD) under standard basic conditions to form the xanthate linked intermediate. Removal of the allyl protecting groups gives the desired product.

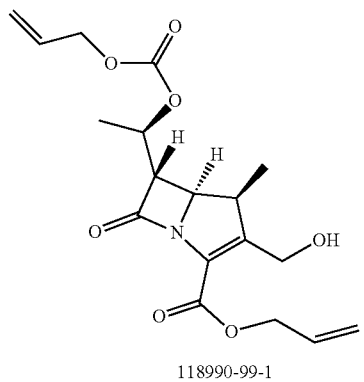

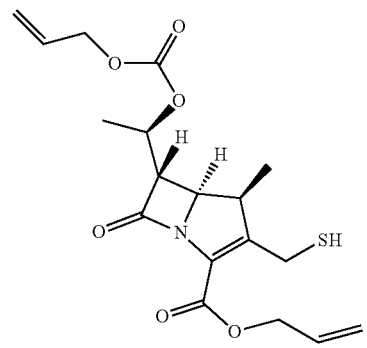

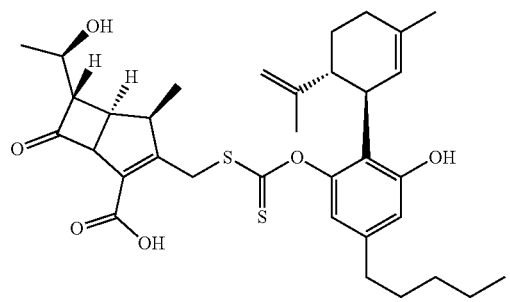
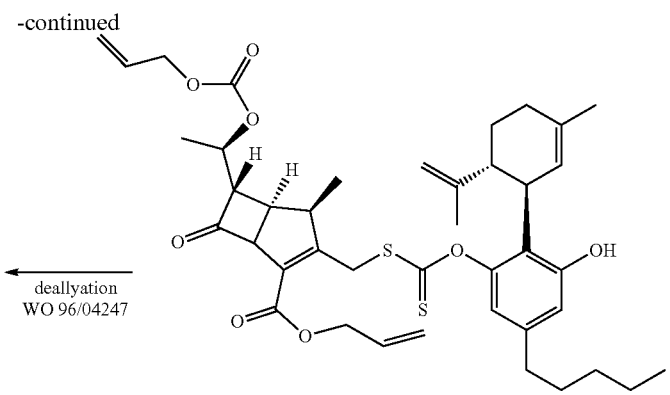

deallyation
WO 96/04247

Example 14. Acetal-Linked Conjugate Molecules

Cephem Conjugate Molecules

Cephem acetal linked conjugate molecules are synthesized according to the following Scheme. The starting material [15690-38-7] is converted to a hydroxymethyl intermediate containing a side chain and protecting ester of choice as described in the literature (WO 96/04247). A cannabinoid (CBD) is converted to the O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). The hydroxymethyl and 0-chloromethyl intermediates are reacted under previously reported conditions (Tetrahedron, 60(12), 2771-2784; 2004) to generate the acetal link. Removal of the diphenylmethyl ester protecting group gives the product.

Carbacephem Conjugate Molecules

Carbacephem acetal linked conjugate molecules are synthesized according to the following Scheme. The starting material [177472-75-2] is converted to a hydroxymethyl intermediate containing a side chain and protecting ester of choice as described in the literature (WO 96/04247). A cannabinoid (CBD) is converted to the O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). The hydroxymethyl and O-chloromethyl intermediates are reacted under previously reported conditions (Tetrahedron, 60(12), 2771-2784; 2004) to generate the acetal link. Removal of the diphenylmethyl ester protecting group gives the product.

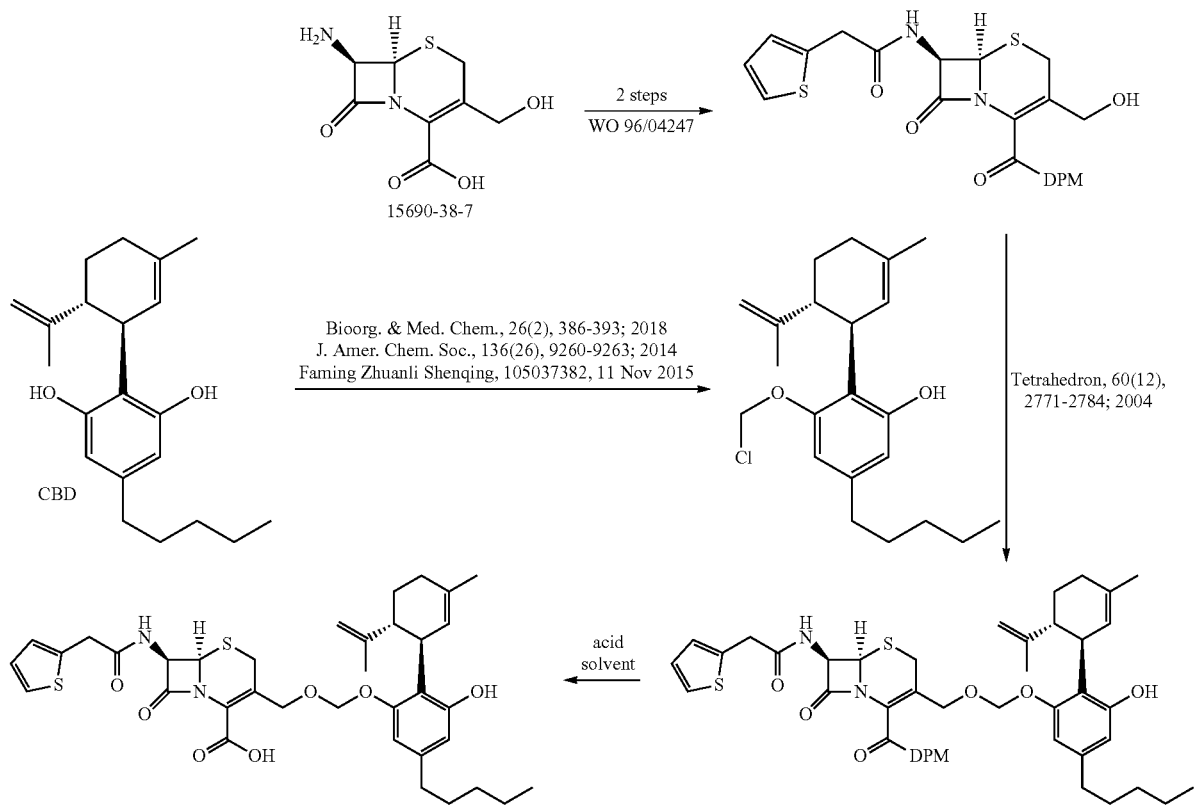

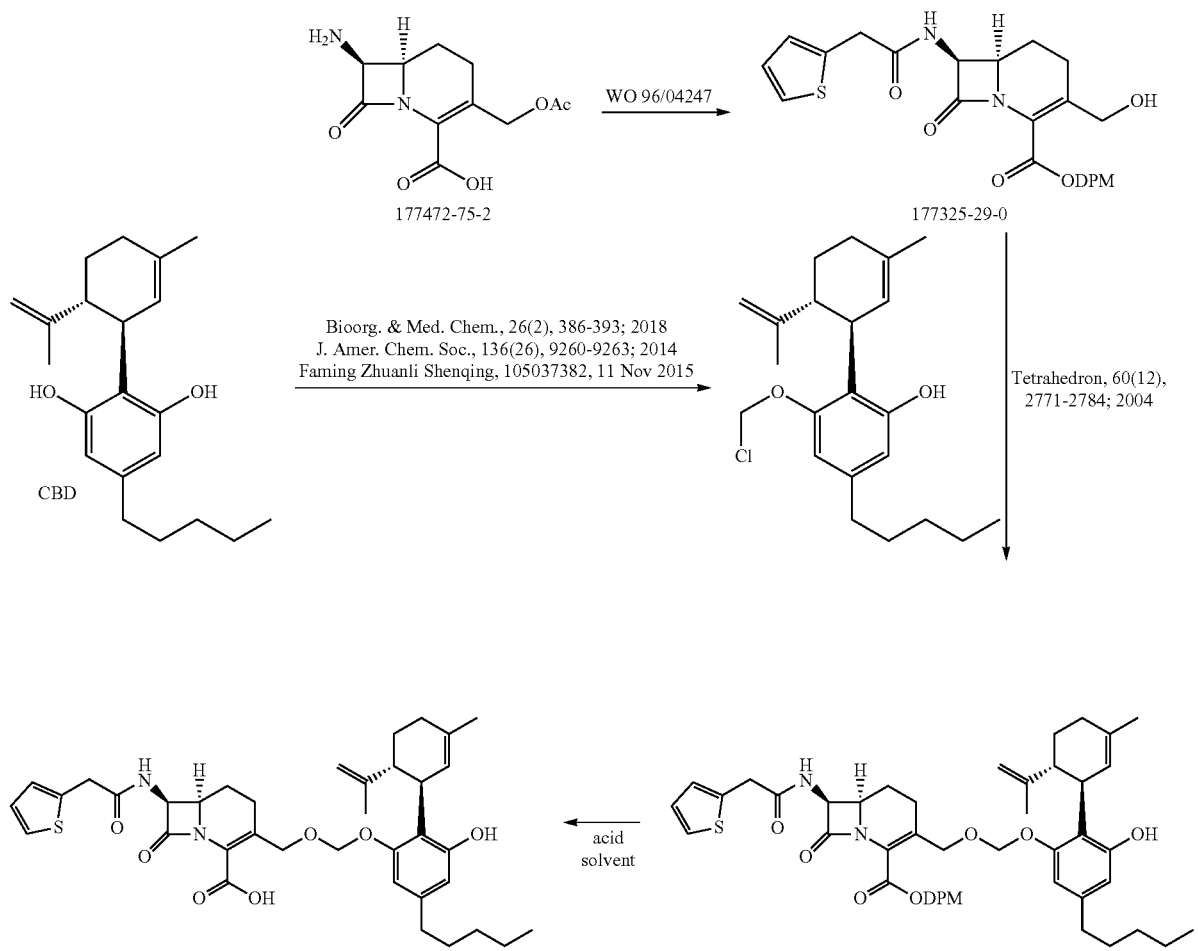

Penem Conjugate Molecules

Penem acetal linked conjugate molecules are synthesized according to the following Scheme. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted with a hydroxymethyl penem [88585-78-8] under reported conditions (Tetrahedron, 60(12), 2771-2784; 2004) to form the acetal link. Removal of the silyl ether and allyl ester protecting groups under standard conditions gives the product.

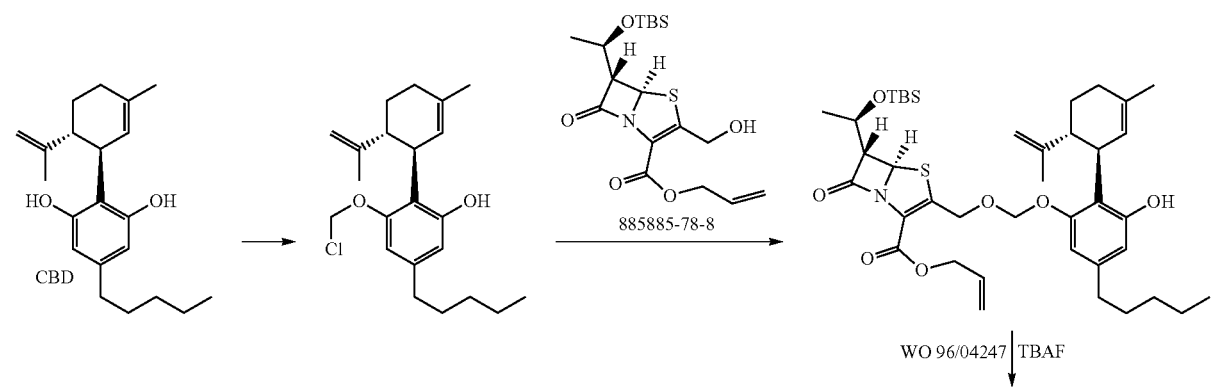

127

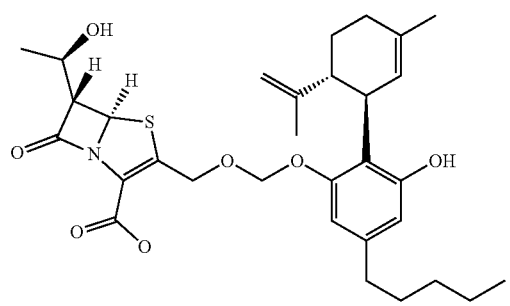

de-allyation
WO 96/04247

128

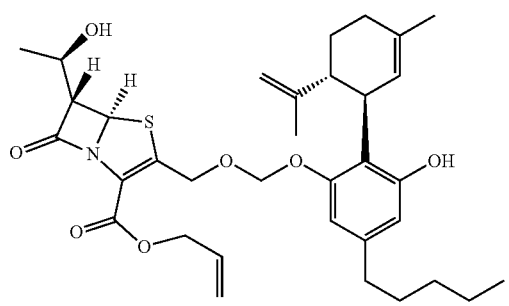

Carbapenem Conjugate Molecules

Carbapenem acetal linked conjugate molecules are synthesized according to the following Scheme. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted with a hydroxymethyl carbapenem [118990-99-1] under reported conditions (Tetrahedron, 60(12), 2771-2784; 2004) to form the acetal link. Removal of the allyl protecting groups under standard conditions gives the product.

Example 15. Aminal-Linked Conjugate Molecules

Cephem Conjugate Molecules

Cephem aminal linked conjugate molecules are synthesized according to the following Scheme. The aminomethyl cephem intermediate is synthesized according to the scheme shown above for cephem carbamate linked conjugate molecules. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Journal of Chemical and Pharmaceutical Sciences, 6(3), 175-180; 2013) with the aminomethyl cephem to give the aminal linked intermediate. Removal of the t-butyl ester protecting group gives the product.

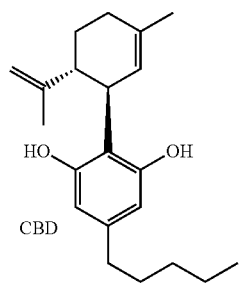

CBD

Bioorg. & Med. Chem., 26(2), 386-393; 2018
J. Amer. Chem. Soc., 136(26), 9260-9263; 2014
Faming Zhuanli Shenqing, 105037382, 11 Nov. 2015

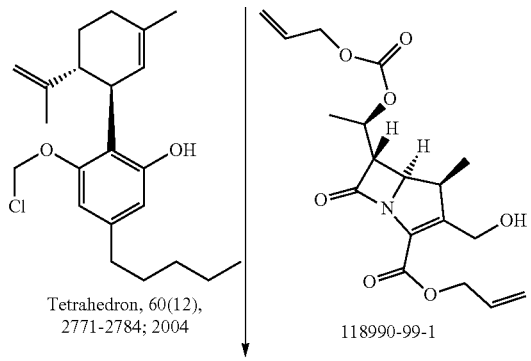

Tetrahedron, 60(12), 2771-2784; 2004

118990-99-1

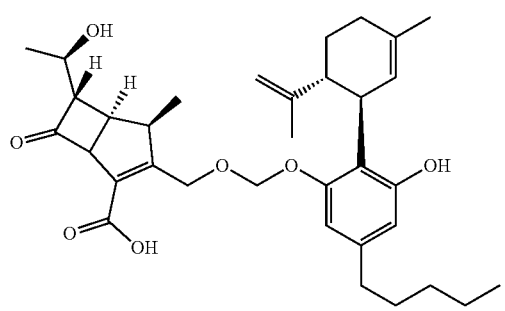

deallylation
WO 96/04247

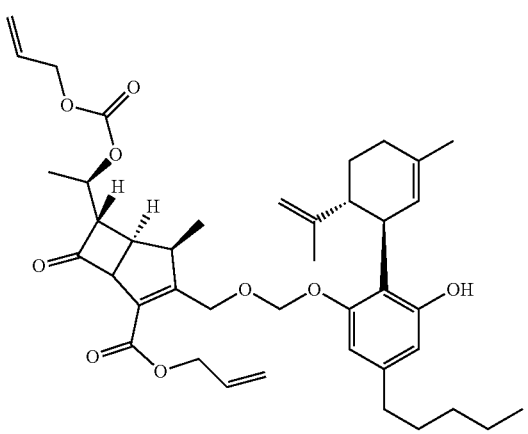

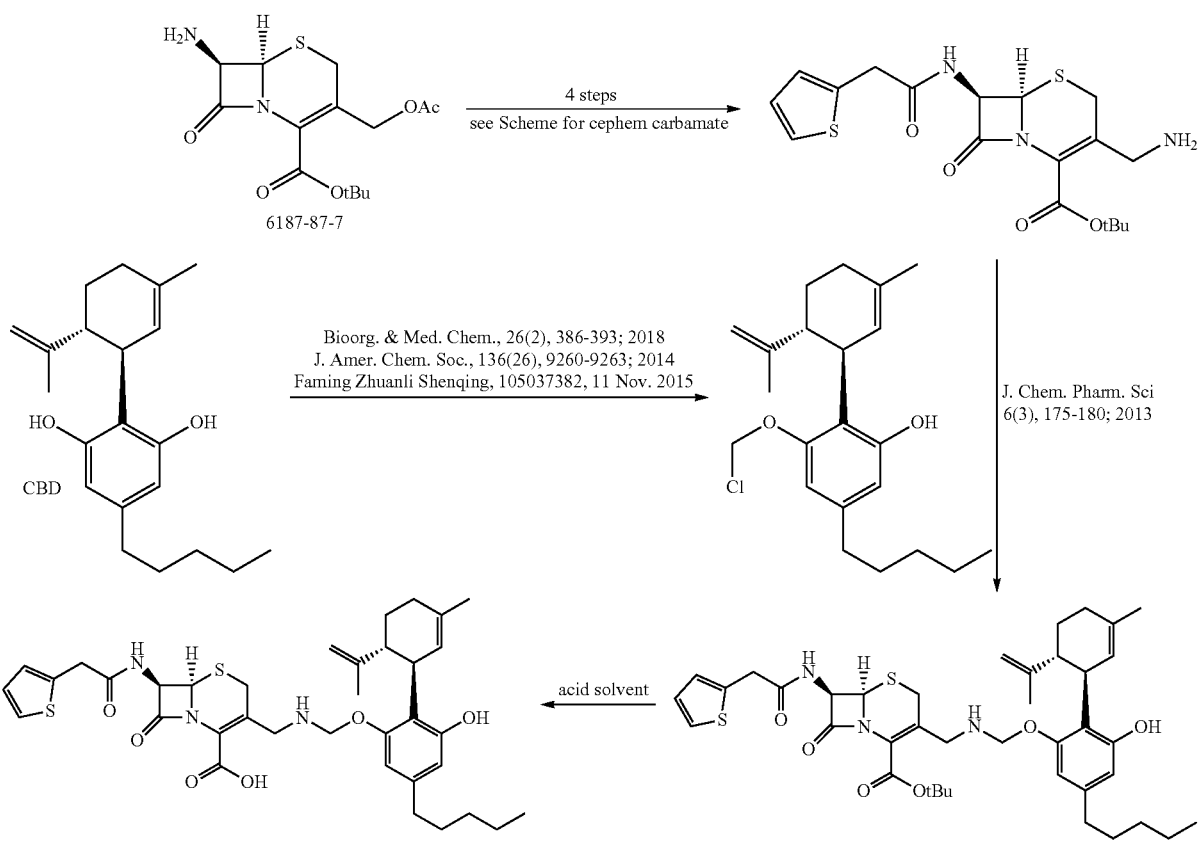

Carbacephem Conjugate Molecules

Carbacephem aminal linked conjugate molecules are synthesized according to the following Scheme. The aminomethyl carbacephem intermediate is synthesized according to the scheme shown above for carbacephem carbamate linked conjugate molecules. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Journal of Chemical and Pharmaceutical Sciences, 6(3), 175-180; 2013) with the aminomethyl carbacephem to give the aminal linked intermediate. Removal of the t-butyl ester protecting group gives the product.

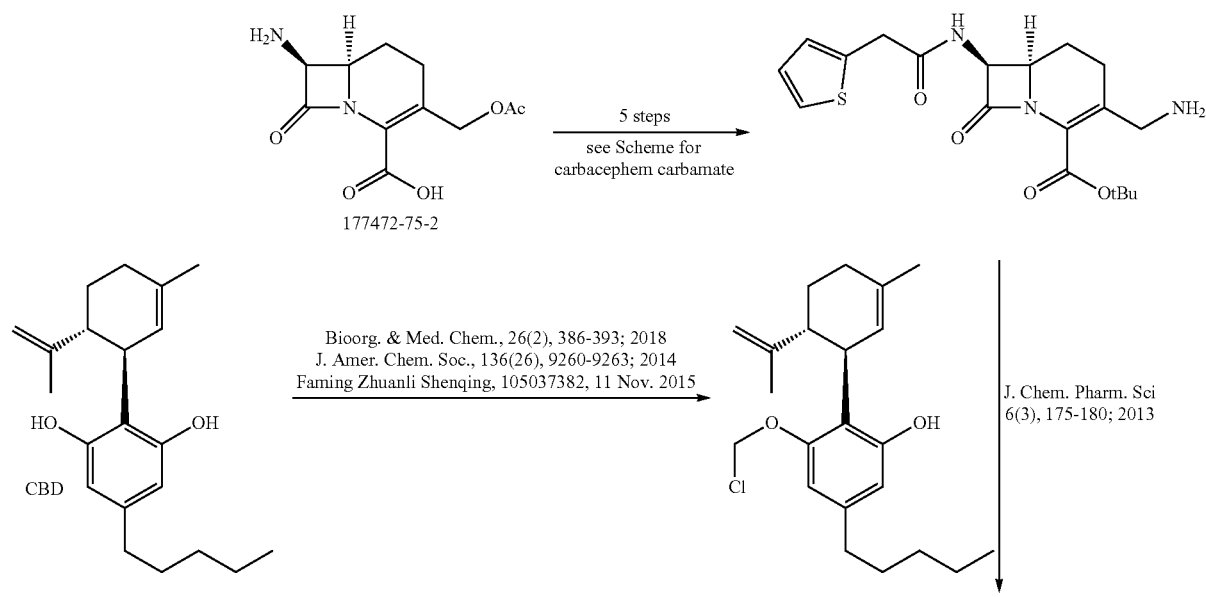

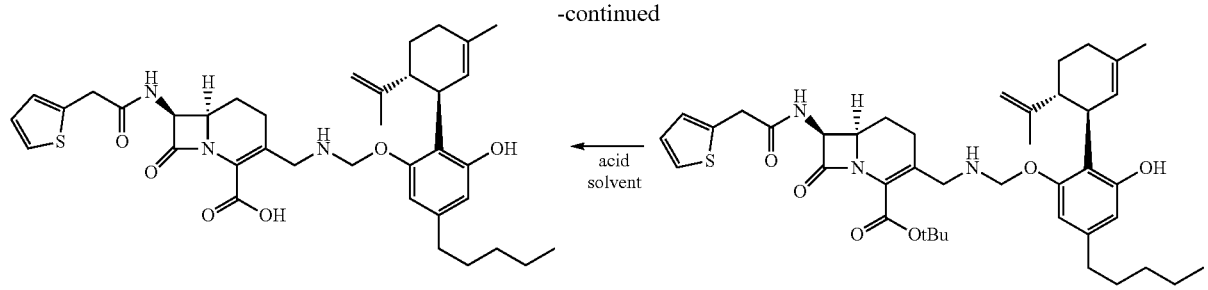

Penem Conjugate Molecules

Penem aminal linked conjugate molecules are synthesized according to the following Scheme. The aminomethyl penem intermediate is synthesized in 5 steps according to the scheme shown above for penem carbamate linked conjugate molecules. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Journal of Chemical and Pharmaceutical Sciences, 6(3), 175-180; 2013) with the aminomethyl penem to give the aminal linked intermediate. Removal of the t-butyl ester protecting group gives the product.

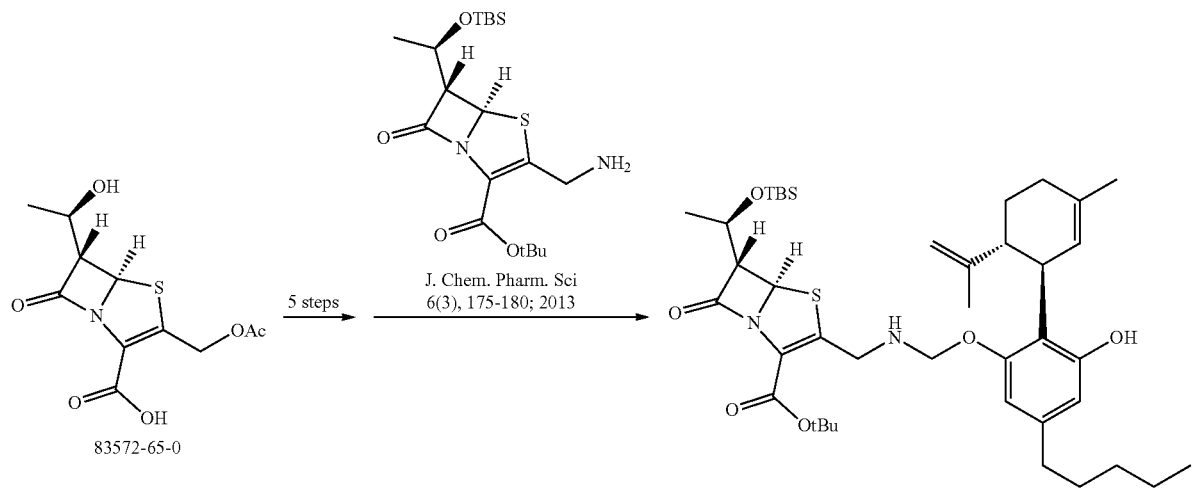

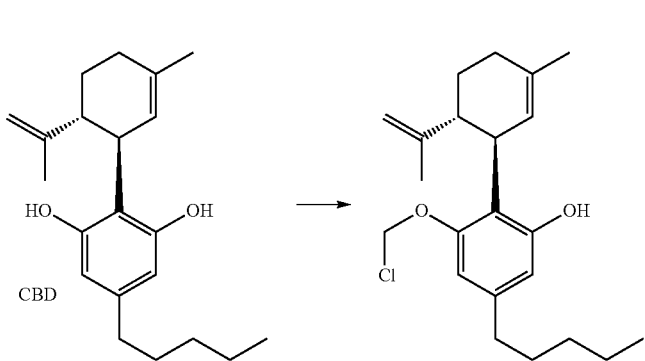

-continued

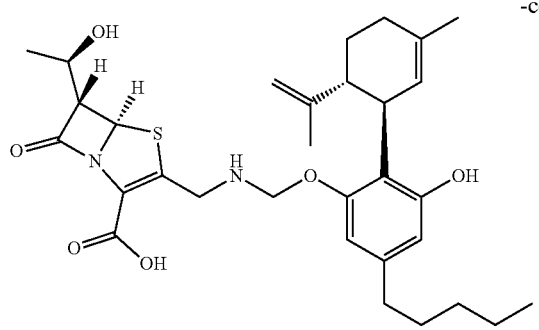
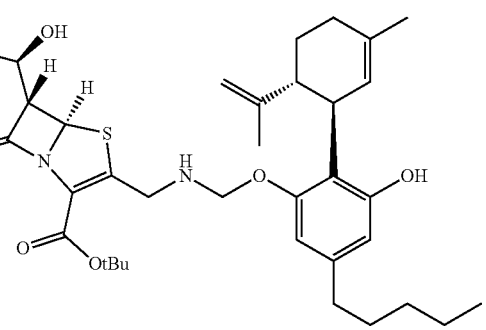

Carbapenem Conjugate Molecules

Carbapenem aminal linked conjugate molecules are synthesized according to the following Scheme. The aminomethyl carbapenem intermediate is synthesized in 5 steps according to the scheme shown above for carbapenem carbamate linked conjugate molecules. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Journal of Chemical and Pharmaceutical Sciences, 6(3), 175-180; 2013) with the aminomethyl carbapenem to give the aminal linked intermediate. Removal of the silyl ether and t-butyl ester protecting groups gives the product.

Example 16. Thioacetal-Linked Conjugate Molecules

Cephem Conjugate Molecules

Cephem thioacetal linked conjugate molecules are synthesized according to the following Scheme. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Bioorganic & Medicinal Chemistry, 18(4), 1441-1448; 2010) with the thiomethyl cephem [61781-78-0] to give the thioacetal linked intermediate. Removal of the diphenylmethyl ester protecting group gives the product.

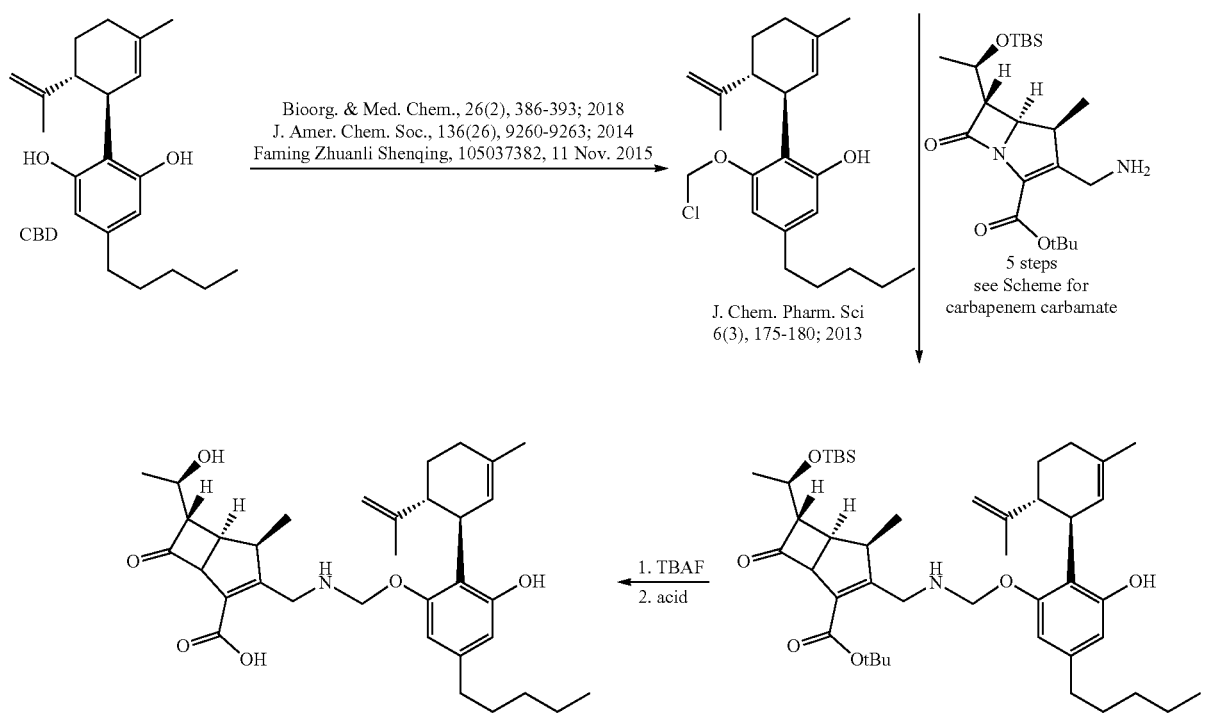

135  136

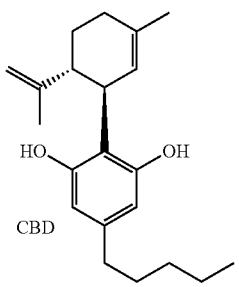
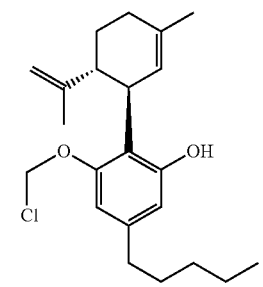
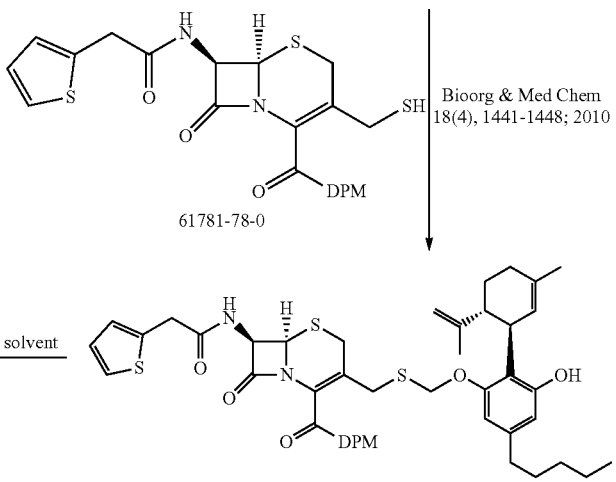

Carbacephem Conjugate Molecules

Carbacephem thioacetal linked conjugate molecules are synthesized according to the following Scheme. The starting material [177325-29-0] is converted to the thiol intermediate using previously described (Faming Zhuanli Shenqing, 108623617, 9 Oct. 2018) conditions for a related system. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Bioorganic & Medicinal Chemistry, 18(4), 1441-1448; 2010) with the thiol carbacephem intermediate to give the thioacetal linked intermediate. Removal of the diphenylmethyl ester protecting group gives the product.

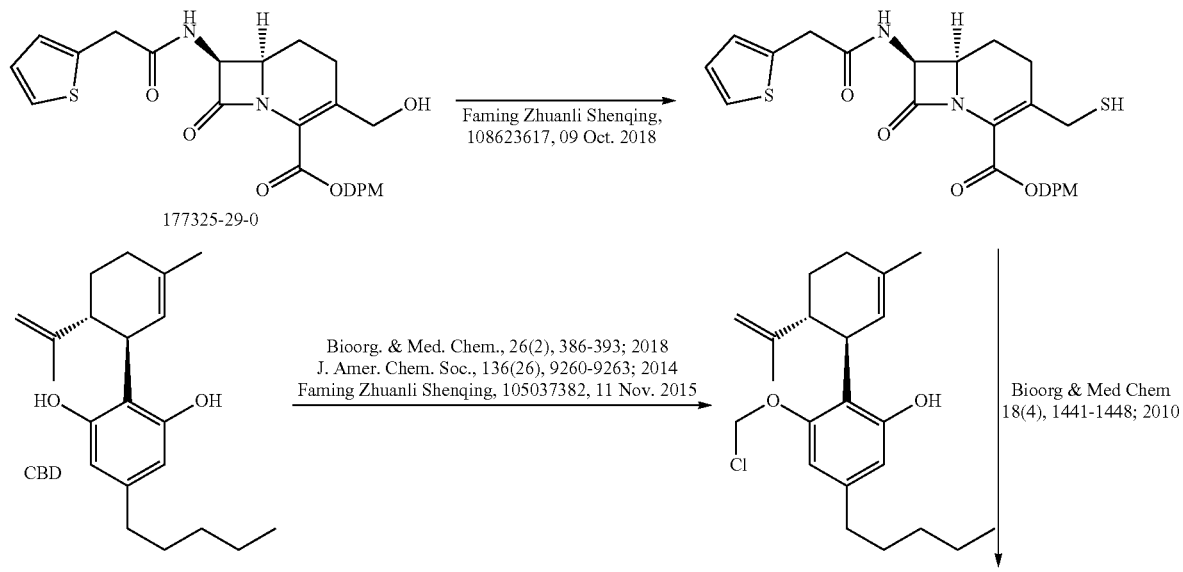

-continued

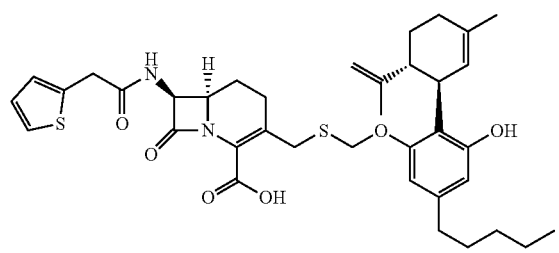
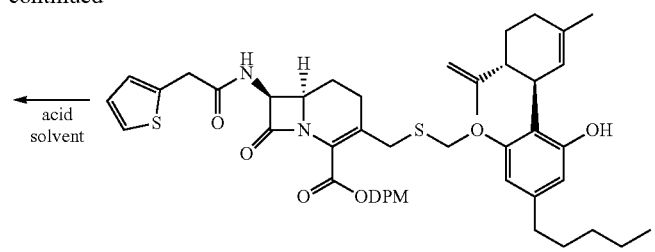

Penem Conjugate Molecules

Penem thioacetal linked conjugate molecules are synthesized according to the following Scheme. The starting material [88585-78-8] is converted to the thiol intermediate [1027391-97-4] using previously described (Faming Zhuanli Shenqing, 108623617, 9 Oct. 2018) conditions for a related system. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Bioorganic & Medicinal Chemistry, 18(4), 1441-1448; 2010) with the thiol penem intermediate to give the thioacetal linked intermediate. Removal of the silyl ether and allyl ester protecting groups gives the product.

Carbapenem Conjugate Molecules

Carbapenem thioacetal linked conjugate molecules are synthesized according to the following Scheme. The starting material [118990-99-1] is converted to the thiol intermediate using previously described (Faming Zhuanli Shenqing, 108623617, 9 Oct. 2018) conditions for a related system. A cannabinoid (CBD) is converted to its O-chloromethyl intermediate via reported conditions (Bioorg. & Med. Chem., 26(2), 386-393; 2018; J. Amer. Chem. Soc., 136(26), 9260-9263; 2014; Faming Zhuanli Shenqing, 105037382, 11 Nov. 2015). This intermediate is reacted (for conditions and related examples, see Bioorganic & Medicinal Chemistry, 18(4), 1441-1448; 2010) with the thiol carbapenem intermediate to give the thioacetal linked intermediate. Removal of the allyl protecting groups gives the product.

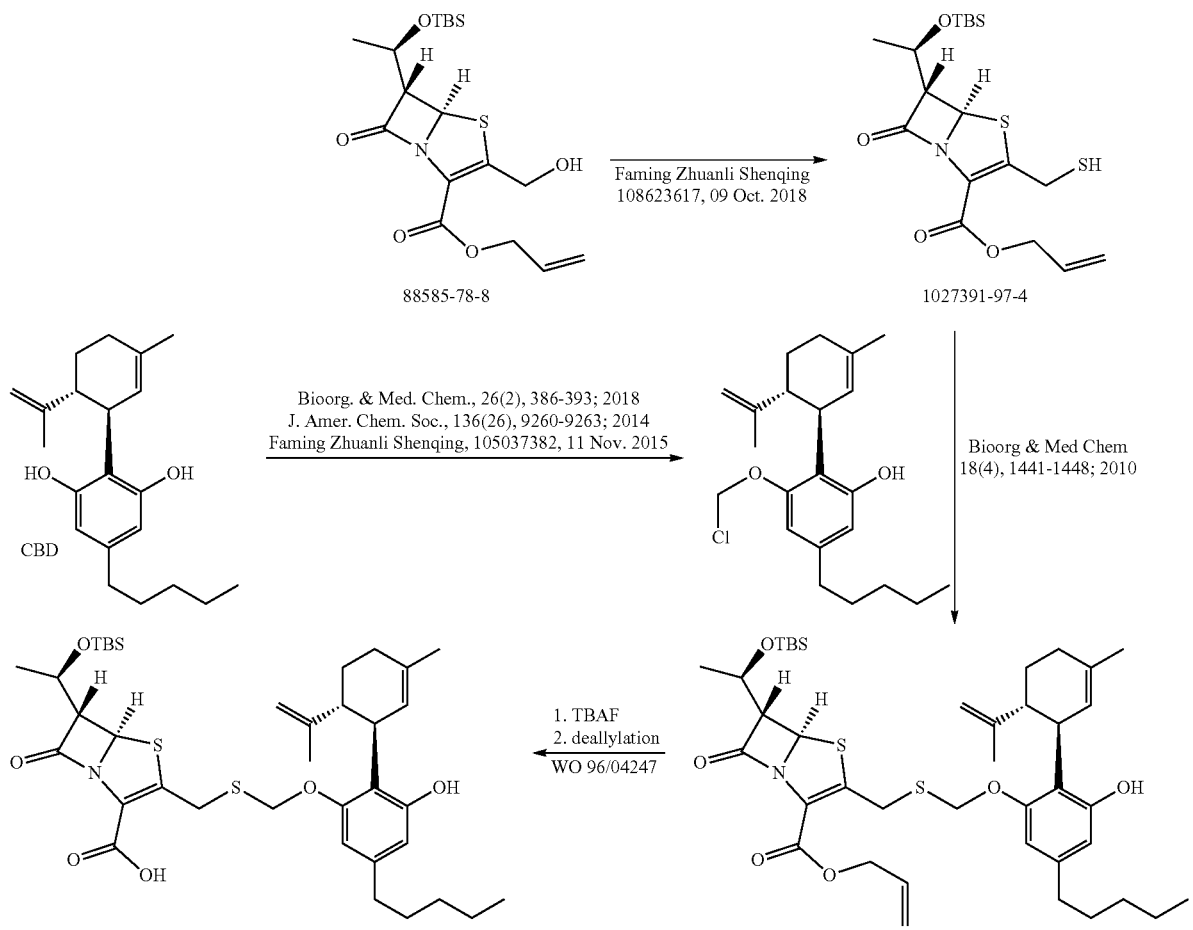

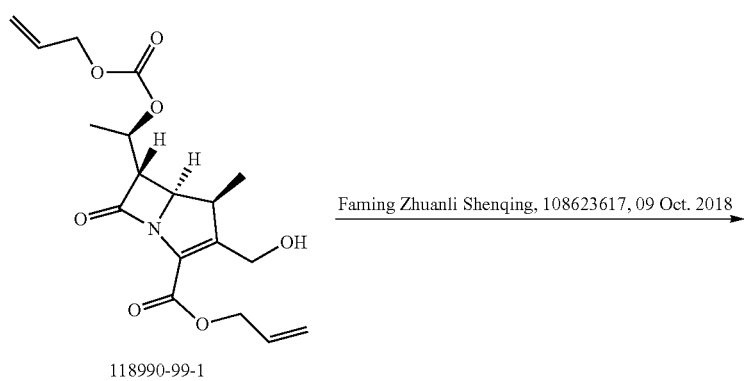

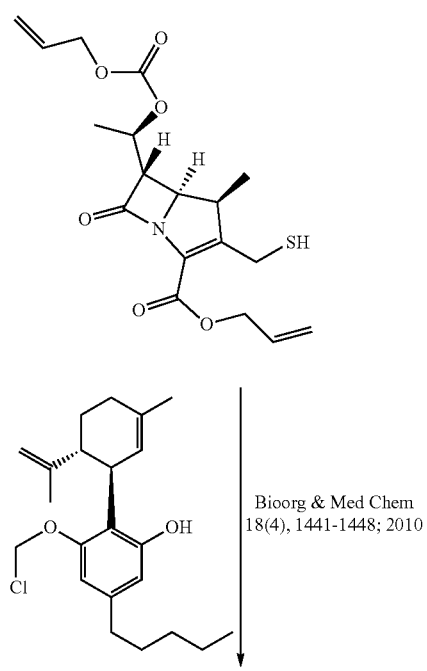

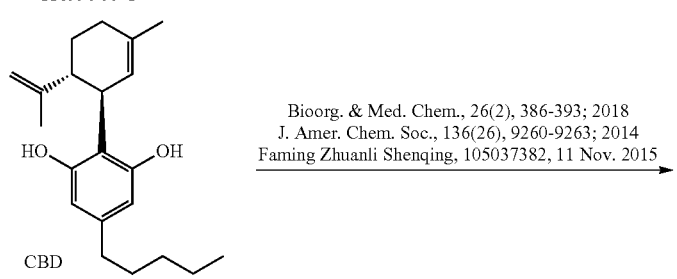

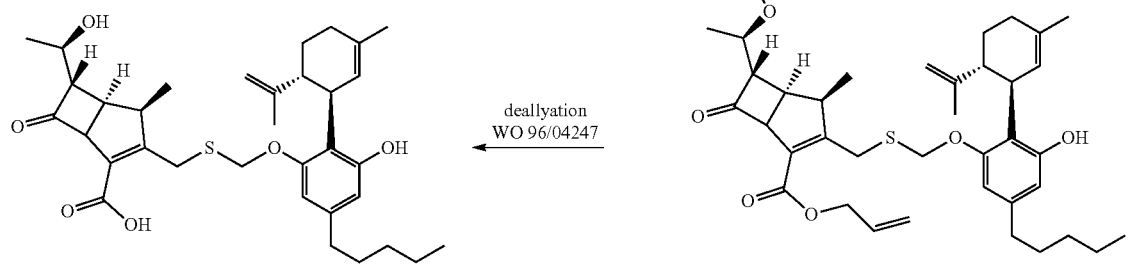

Example 17. Monobactam Ether-Linked Conjugate Molecules

Monobactam ether linked conjugate molecules are synthesized according to the following Scheme. The starting material [76855-69-1] is reacted under reported conditions (Journal of Organic Chemistry, 55(2), 434-7; 1990) for phenolic compounds to form the ether link. Removal of the silyl ether protecting group under standard conditions followed by sulfonation using established conditions gives the product.

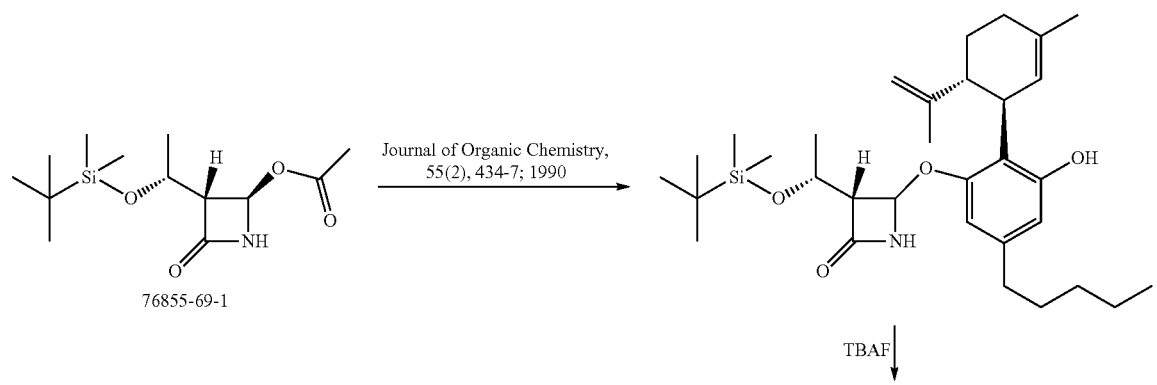

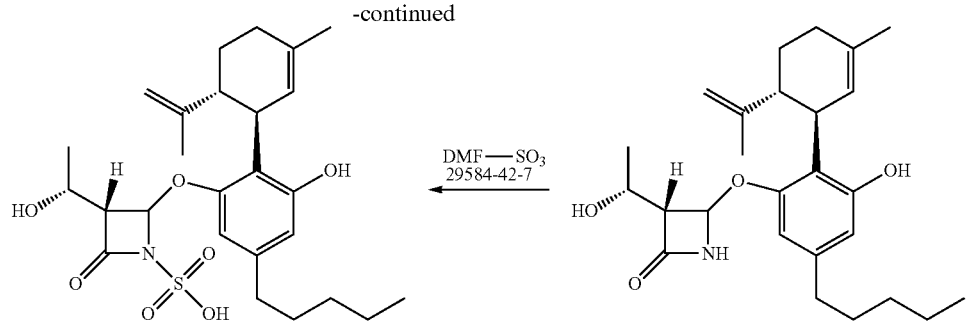

Example 18. Monobactam Acetal-Linked Conjugate Molecules

Monobactam acetal linked conjugate molecules are synthesized according to the following Scheme. The starting material [76855-69-1] is deacetylated under reported conditions (Journal of Fluorine Chemistry, 72(2), 255-9; 1995) to give the 2-hydroxy intermediate. This hydroxy group is then alkylated with the O-chloromethyl cannabinoid which is prepared as described in the cephem acetal example in this Application to form the acetal link. Removal of the silyl ether protecting group followed by sulfonation using established conditions gives the product.

Example 19. Monobactam Carbonate-Linked Conjugate Molecules

Monobactam carbonate linked conjugate molecules are synthesized according to the following Scheme. The starting material [76855-69-1] is deacetylated under reported conditions (Journal of Fluorine Chemistry, 72(2), 255-9; 1995) to give the 2-hydroxy intermediate. This hydroxy group is then reacted with phosgene and a cannabinoid (CBD) under standard basic conditions to form the carbonate link. Removal of the silyl ether protecting group followed by sulfonation using established conditions gives the product.

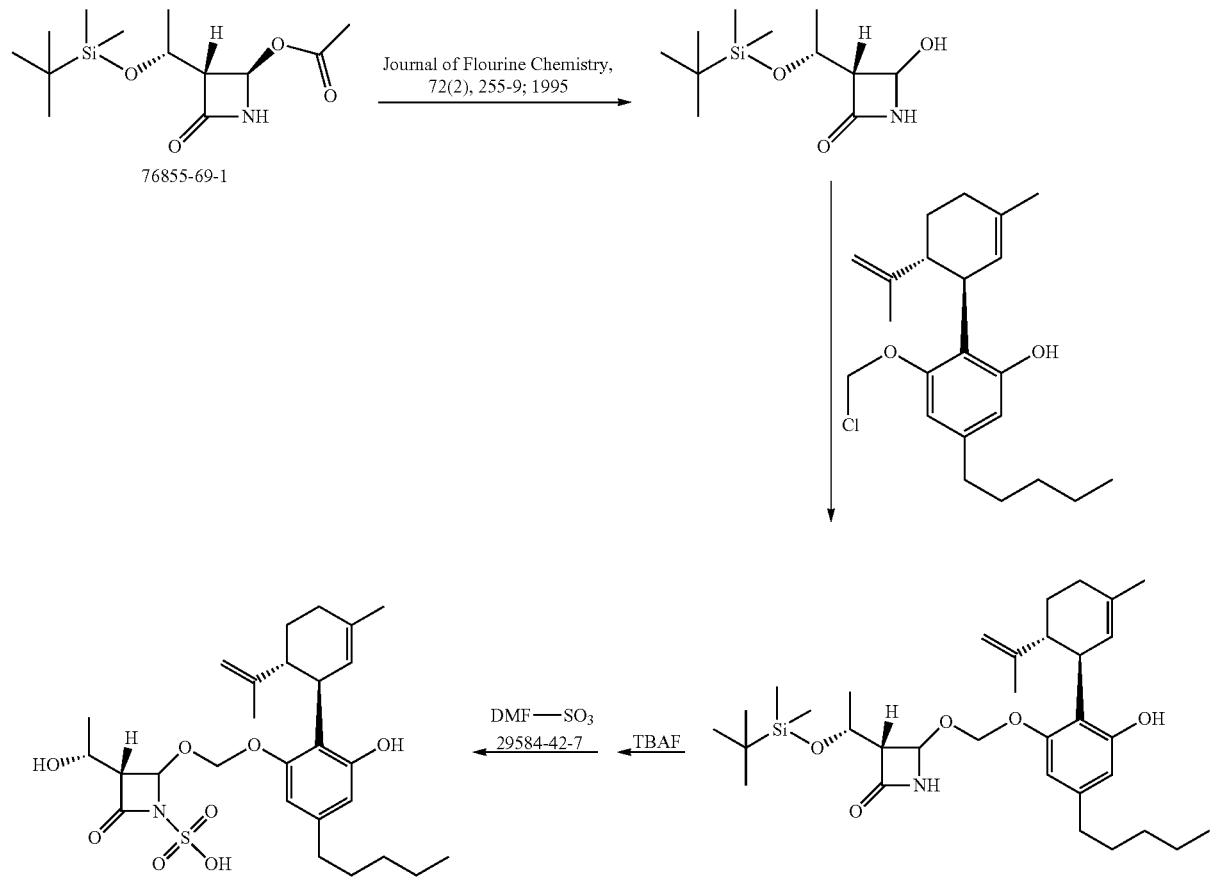

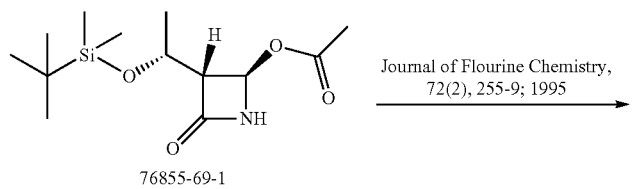
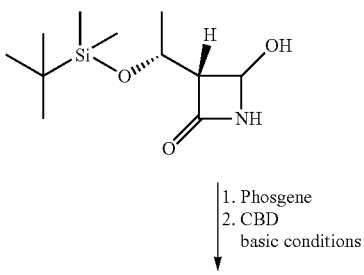
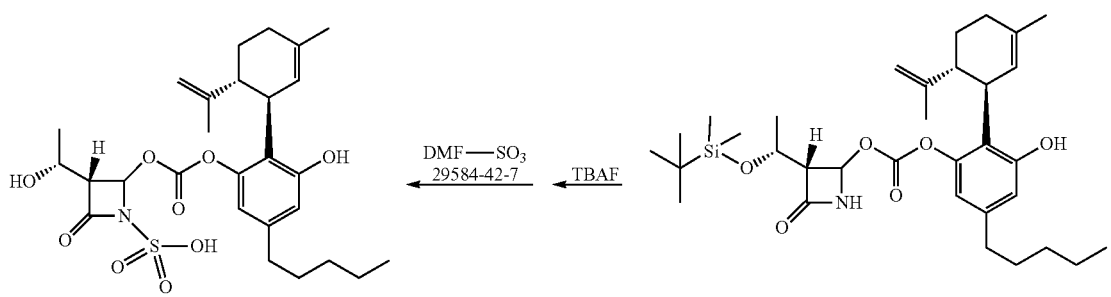

Example 20. Monobactam Thiocarbonate-Linked Conjugate Molecules

Monobactam thiocarbonate linked conjugate molecules are synthesized according to the following Scheme. The starting material [76855-69-1] is deacetylated under reported conditions (Journal of Fluorine Chemistry, 72(2), 255-9; 1995) to give the 2-hydroxy intermediate. This hydroxy group is then reacted with thiophosgene and a cannabinoid (CBD) under standard basic conditions to form the carbonate link. Removal of the silyl ether protecting group followed by sulfonation using established conditions gives the product.

Example 21. Monobactam Imidate-Linked Conjugate Molecules

Monobactam imidate linked conjugate molecules are synthesized according to the following Scheme. The starting material [76855-69-1] is deacetylated under reported conditions (Journal of Fluorine Chemistry, 72(2), 255-9; 1995) to give the 2-hydroxy intermediate. This hydroxy group is then reacted with methyl imidocarbonyl chloride [5652-90-4] and a cannabinoid (CBD) under reported conditions (Tetrahedron Letters, 23(35), 3539-42; 1982) to form the imidate link. Removal of the silyl ether protecting group followed by sulfonation using established conditions gives the product.

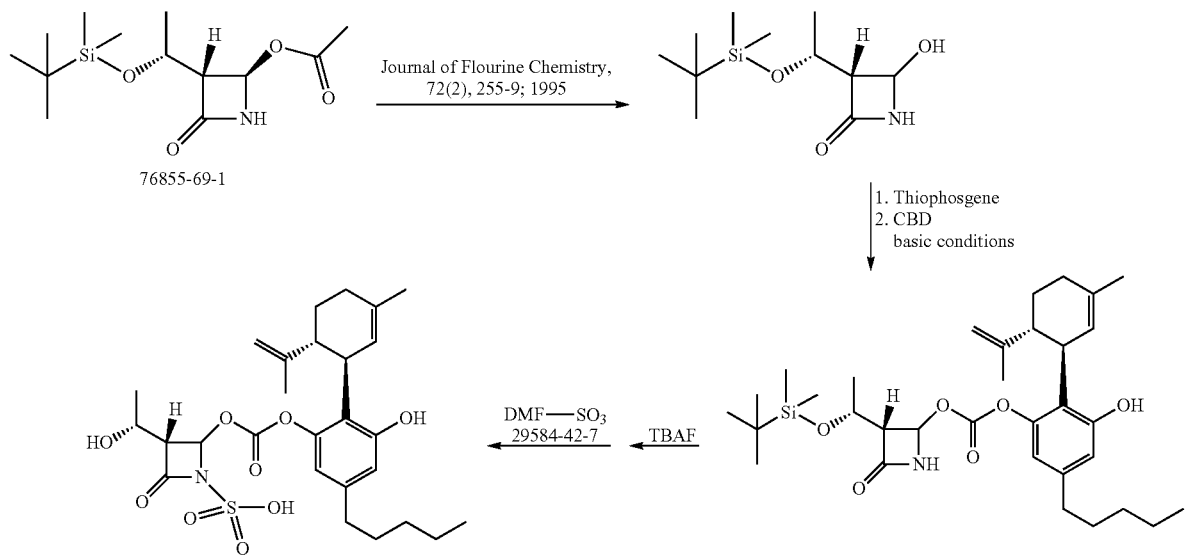

Example 22. Monobactam Aminal-Linked Conjugate Molecules

Monobactam aminal linked conjugate molecules are synthesized according to the following Scheme. The starting material [76855-69-1] is converted to the corresponding amine under reported conditions (Organic Chemistry: An Indian Journal, 9(6), 229-235; 2013) to give the 2-amino intermediate. This amino group is then alkylated with the O-chloromethyl cannabinoid which is prepared as described in the cephem acetal example in this Application to form the acetal link. Removal of the silyl ether protecting group followed by sulfonation using established conditions gives the product.

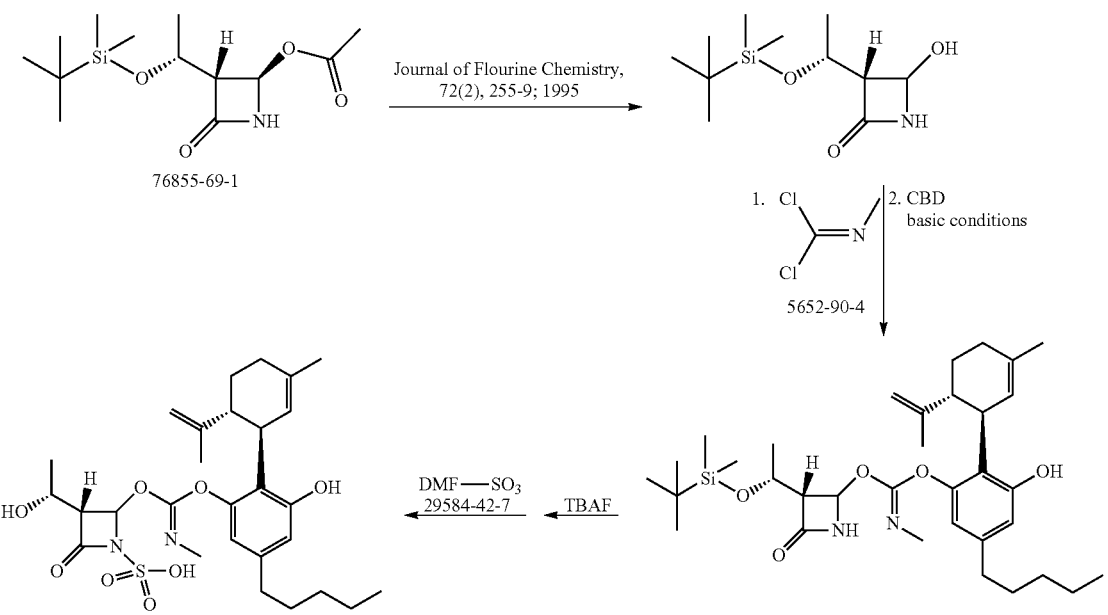

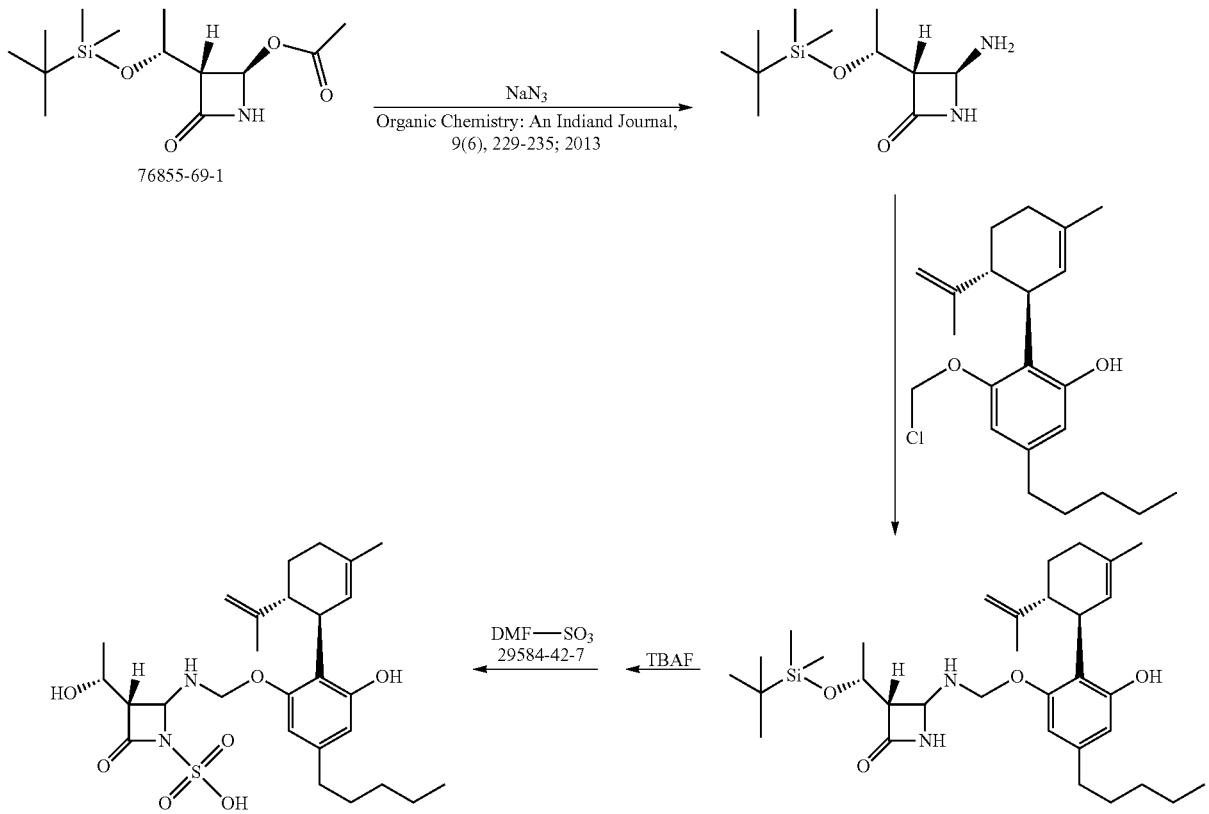

Example 23. Monobactam Carbamate-Linked Conjugate Molecules

Monobactam carbamate linked conjugate molecules are synthesized according to the following Scheme. The starting material [76855-69-1] is converted to the corresponding amine under reported conditions (Organic Chemistry: An Indian Journal, 9(6), 229-235; 2013) to give the 2-amino intermediate. This amino group is then reacted with phosgene and a cannabinoid (CBD) under standard basic conditions to form the carbamate link. Removal of the silyl ether protecting group followed by sulfonation using established conditions gives the product.

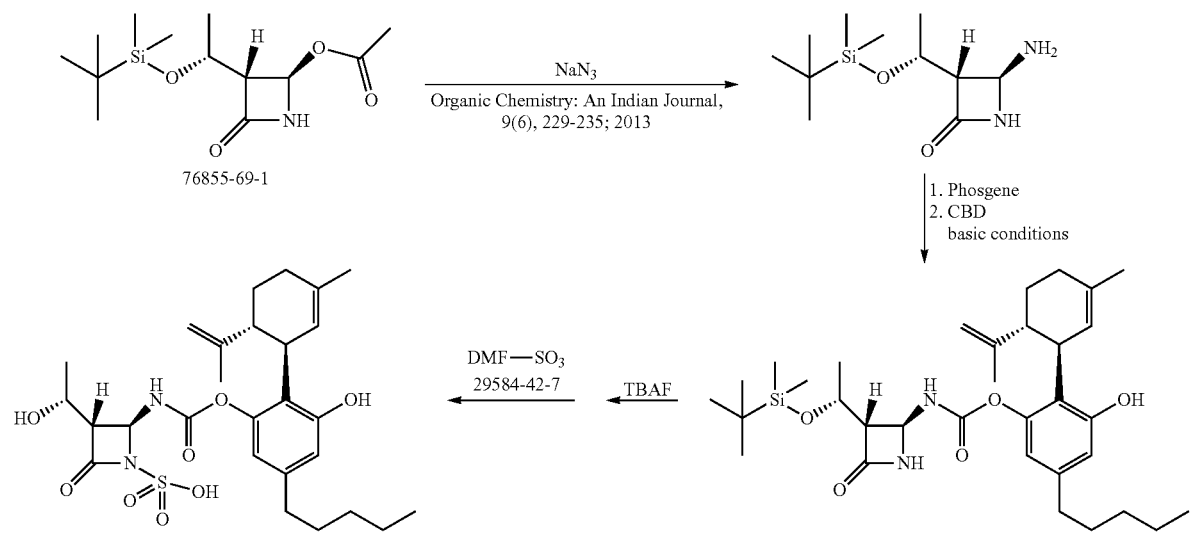

Example 24. Monobactam Thiocarbamate-Linked Conjugate Molecules

Monobactam thiocarbamate linked conjugate molecules are synthesized according to the following Scheme. The starting material [76855-69-1] is converted to the corresponding amine under reported conditions (Organic Chemistry: An Indian Journal, 9(6), 229-235; 2013) to give the 2-amino intermediate. This amino group is then reacted with thiophosgene and a cannabinoid (CBD) under standard basic conditions to form the thiocarbamate link. Removal of the silyl ether protecting group followed by sulfonation using established conditions gives the product.

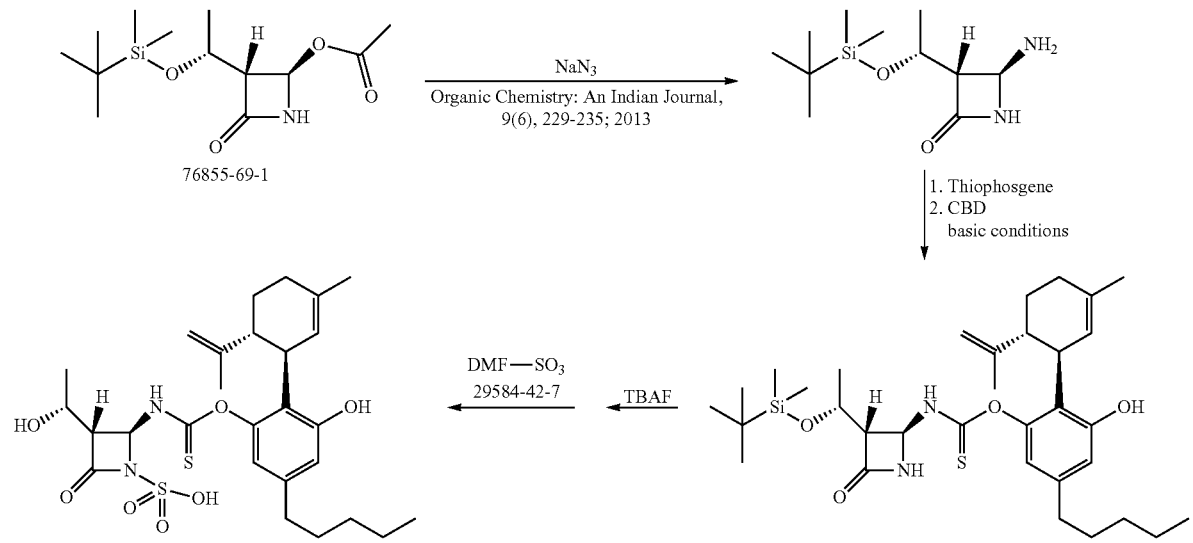

Example 25. Monobactam Isourea-Linked Conjugate Molecules

Monobactam isourea linked conjugate molecules are synthesized according to the following Scheme. The starting material [76855-69-1] is converted to the corresponding amine under reported conditions (Organic Chemistry: An Indian Journal, 9(6), 229-235; 2013) to give the 4-amino intermediate. This amino group is then reacted with methyl imidocarbonyl chloride [5652-90-4] and a cannabinoid (CBD) under reported conditions (Tetrahedron Letters, 23(35), 3539-42; 1982) to form the isourea link. Removal of the silyl ether protecting group followed by sulfonation using established conditions gives the product.

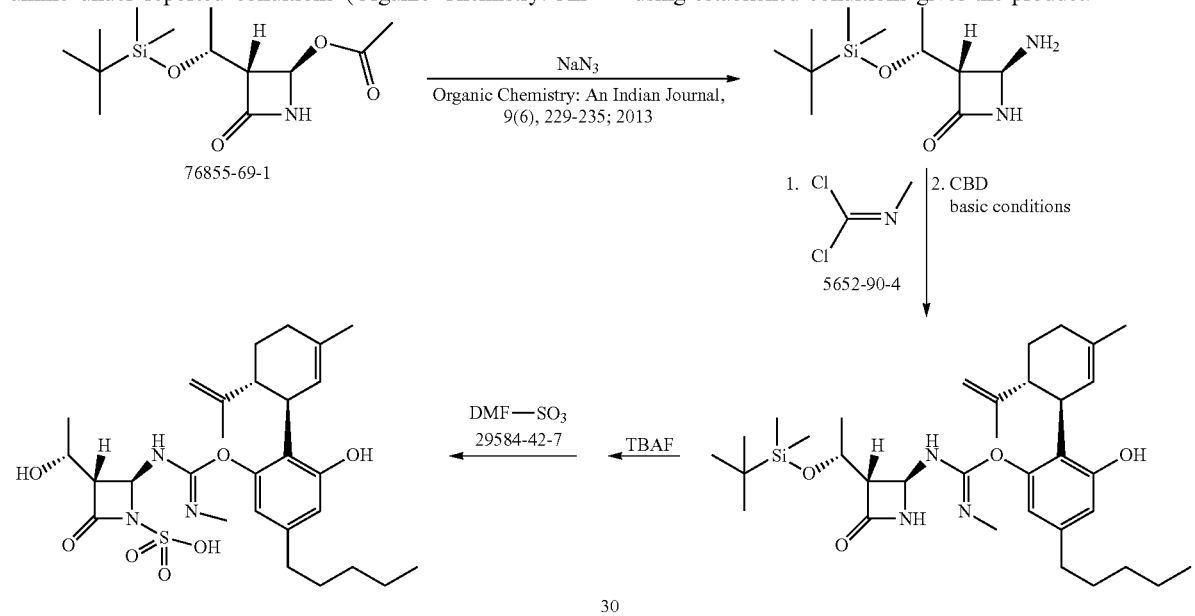

Example 26. Monobactam Thioacetal-Linked Conjugate Molecules

Monobactam thioacetal linked conjugate molecules are synthesized according to the following Scheme. The starting material [76855-69-1] is converted to the thiol silver salt using reported conditions (Shenyang Yaoke Daxue Xuebao, 18(1), 20-22; 2001) to give the 2-SH intermediate. This thiol group is then alkylated with the O-chloromethyl cannabinoid which is prepared as described in the cephem acetal example in this Application to form the thioacetal link. Removal of the silyl ether protecting group followed by sulfonation using established conditions gives the product.

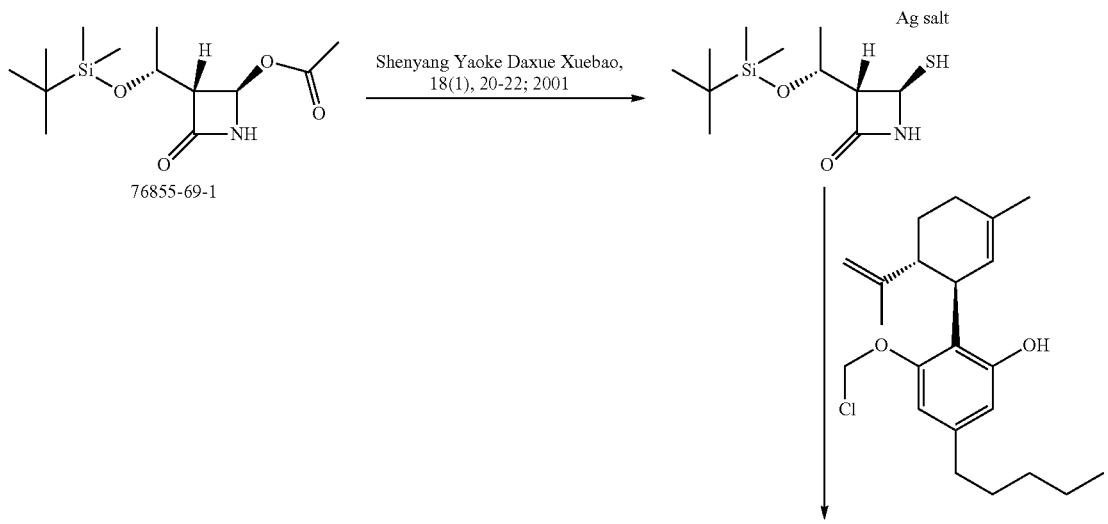

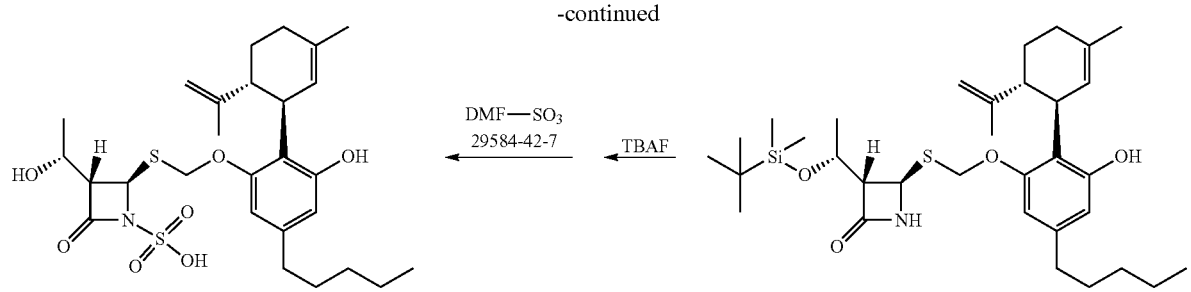

Example 27. Monobactam S-Alkyl Thiocarbonate-Linked Conjugate Molecules

Monobactam S-alkyl thiocarbonate linked conjugate molecules are synthesized according to the following Scheme. The starting material [76855-69-1] is converted to the thiol silver salt using reported conditions (Shenyang Yaoke Daxue Xuebao, 18(1), 20-22; 2001) to give the 2-SH intermediate. This thiol group is then reacted with phosgene and a cannabinoid (CBD) under standard basic conditions to form the S-alkyl thiocarbonate link. Removal of the silyl ether protecting group followed by sulfonation using established conditions gives the product.

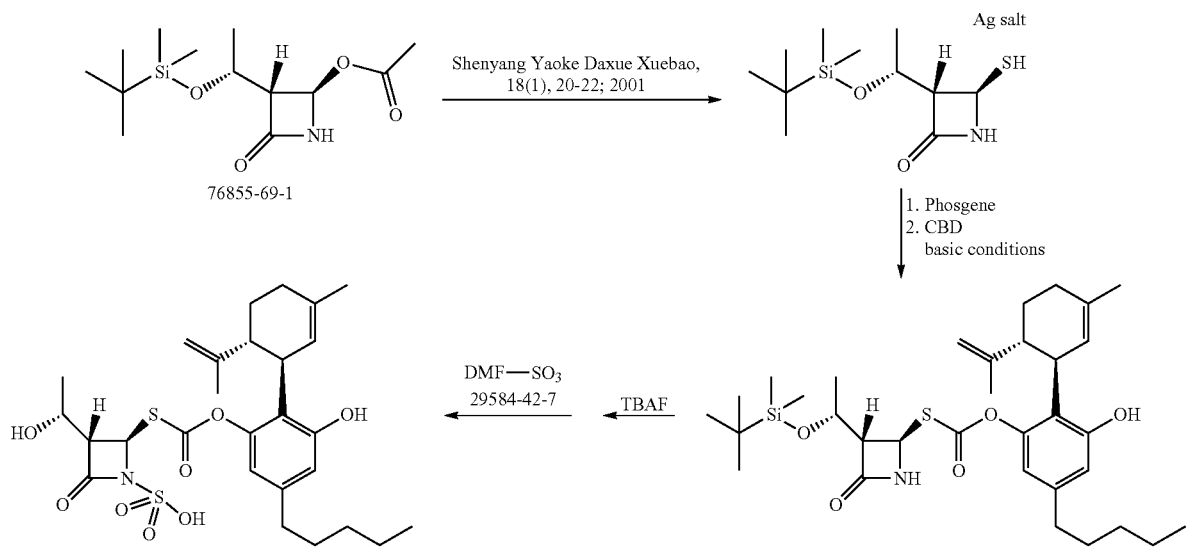

Example 28. Monobactam Xanthate-Linked Conjugate Molecules

Monobactam xanthate linked conjugate molecules are synthesized according to the following Scheme. The starting material [76855-69-1] is converted to the thiol silver salt using reported conditions (Shenyang Yaoke Daxue Xuebao, 18(1), 20-22; 2001) to give the 2-SH intermediate. This thiol group is then reacted with thiophosgene and a cannabinoid (CBD) under standard basic conditions to form the xanthate link. Removal of the silyl ether protecting group followed by sulfonation using established conditions gives the product.

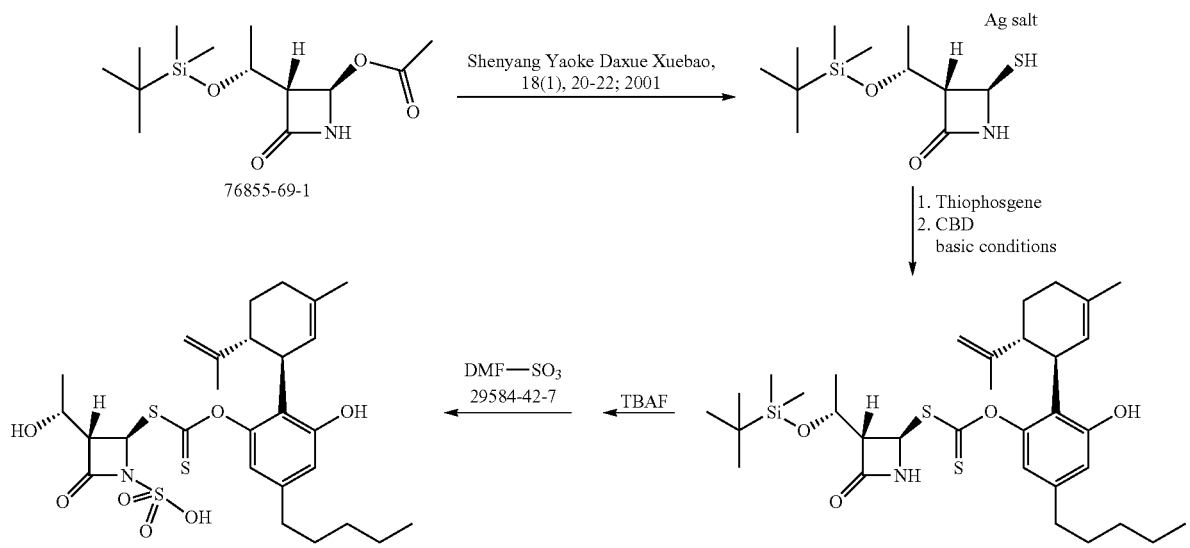

Example 29. Monobactam Thioimidate-Linked Conjugate Molecules

Monobactam thioimidate linked conjugate molecules are synthesized according to the following Scheme. The starting material [76855-69-1] is converted to the thiol silver salt using reported conditions (Shenyang Yaoke Daxue Xuebao, 18(1), 20-22; 2001) to give the 2-SH intermediate. This thiol group is then reacted with methyl imidocarbonyl chloride [5652-90-4] and a cannabinoid (CBD) under reported conditions (Tetrahedron Letters, 23(35), 3539-42; 1982) to form the thioimidate link. Removal of the silyl ether protecting group followed by sulfonation using established conditions gives the product.

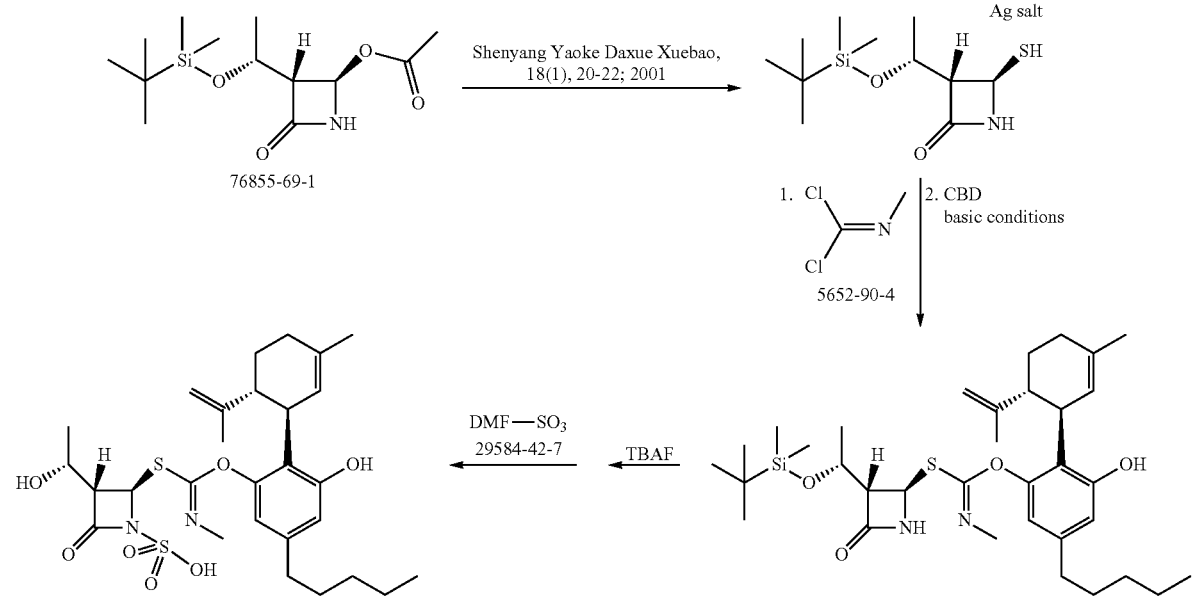

Example 30. Monobactam Alkenyl Ester-Linked Conjugate Molecules

Monobactam alkenyl ester linked conjugate molecules are synthesized according to the following Scheme. The starting material [592528-28-4] is esterified with a cannabinoid (CBD) under standard conditions. Removal of the silyl ether protecting group followed by sulfonation using established conditions gives the product.

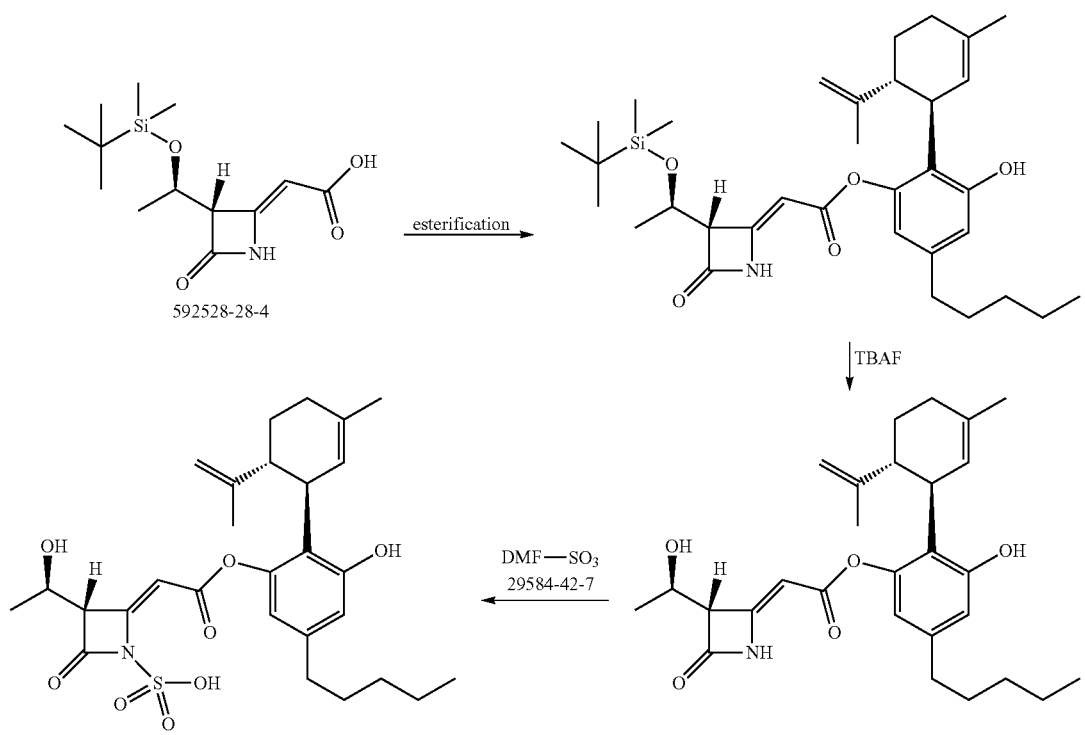

Example 31. Monobactam Alkenyl Ether-, Alkenyl Acetal-, Alkenyl Carbonate-, Alkenyl Thiocarbonate-, and Alkenyl Imidate-Linked Conjugate Molecules Monobactam alkenyl ether, alkenyl acetal, alkenyl carbonate, alkenyl thiocarbonate, and alkenyl imidate linked conjugate molecules are synthesized as shown in the Scheme below. The starting material [410524-32-2] is reduced to the alcohol intermediate using previously reported conditions (Organic Letters, 15(16), 4142-4145; 2013). This alcohol is reacted and connected to a cannabinoid by any of the aforementioned links, using the previously described chemistry and conditions associated with the non-alkenyl variant.

Example 32. Monobactam Alkenyl Aminal-, Alkenyl Carbamate-, Alkenyl Thiocarbamate-, and Alkenyl Isourea-Linked Conjugate Molecules Monobactam alkenyl aminal, alkenyl carbamate, alkenyl thiocarbamate, and alkenyl isourea linked conjugate molecules are synthesized as shown in the Scheme below. The starting material [410524-32-2] is reduced to the alcohol intermediate. This alcohol is then converted to the iodide using known (Tetrahedron, 73(29), 4150-4159; 2017) conditions. The iodide intermediate is converted to the primary amine using the two step azide addition/reduction protocol described above for synthesis of propenylamine cephem conjugate molecules. This amine is then reacted and connected to a cannabinoid by any of the aforementioned links, using the previously described chemistry and conditions associated with the non-alkenyl variant.

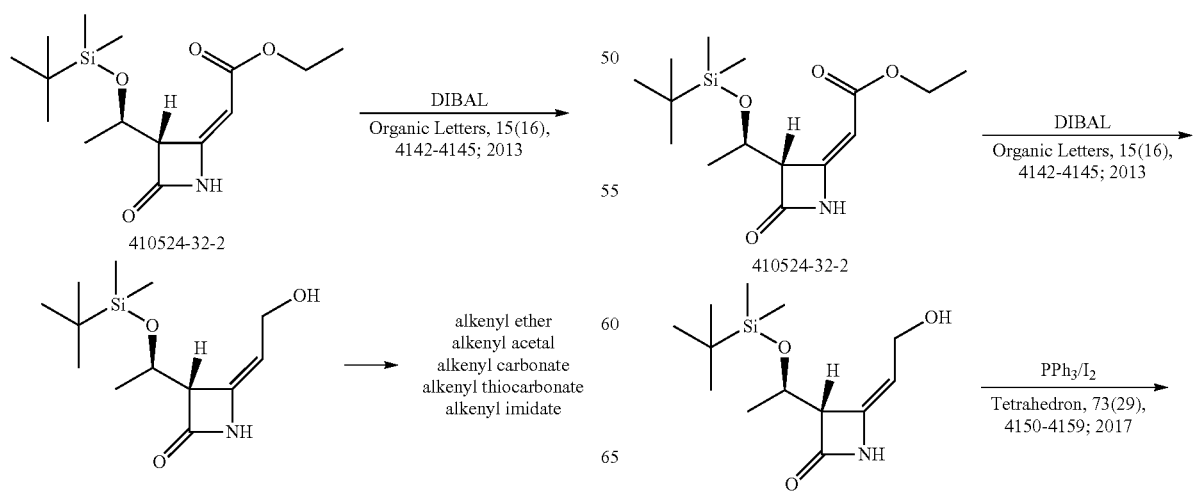

157
-continued

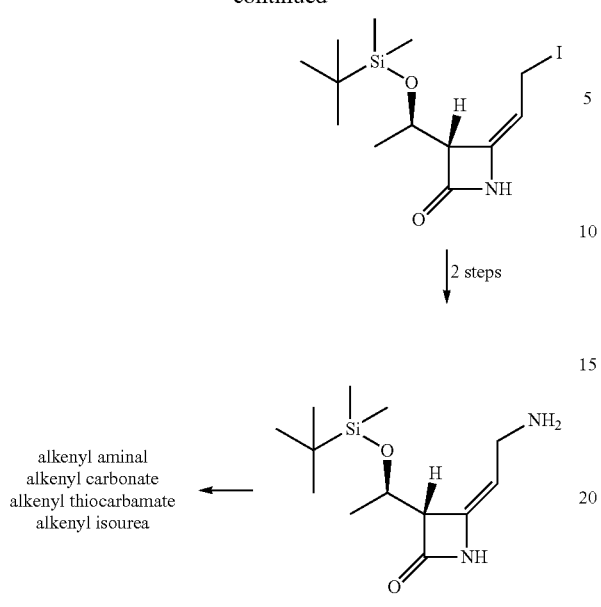

Example 33. Monobactam Alkenyl Thioacetal-, Alkenyl S-Alkyl Thiocarbonate-, Alkenyl Dithiocarbonate-, and Alkenyl Thioimidate-Linked Conjugate Molecules Monobactam alkenyl thioacetal, alkenyl S-alkyl thiocarbonate, alkenyl dithiocarbonate, and alkenyl thioimidate linked conjugate molecules are synthesized as shown in the Scheme below. The starting material [410524-32-2] is reduced to the alcohol intermediate using previously reported conditions (Organic Letters, 15(16), 4142-4145; 2013). This alcohol is reacted with Lawesson's reagent under reported conditions (Journal of the American Chemical Society, 130(15), 5052-5053; 2008) to give the corresponding thiol intermediate. This thiol is then reacted and connected to a cannabinoid by any of the aforementioned links, using the previously described chemistry and conditions associated with the non-alkenyl variant.

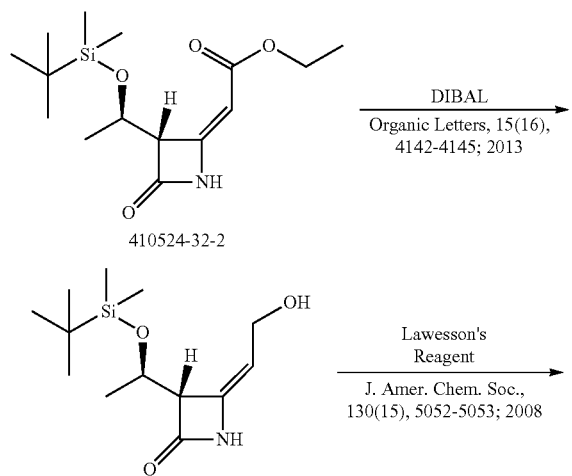

158
-continued

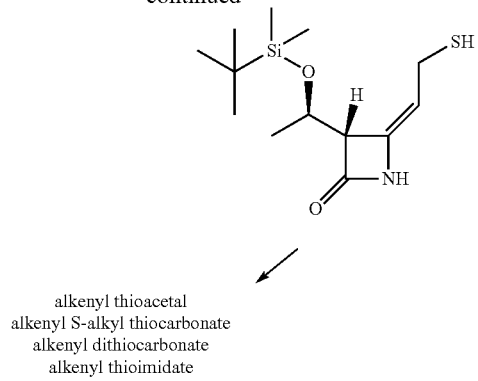

alkenyl thioacetal
alkenyl S-alkyl thiocarbonate
alkenyl dithiocarbonate
alkenyl thioimidate

The invention claimed is:

1. A conjugate molecule, or a pharmaceutically acceptable salt thereof, comprising a first β-lactam antibiotic component, a first linker, and a cannabinoid component, wherein the first linker is covalently attached to a first hydroxy group of the cannabinoid component, wherein:
   (a) the first β-lactam antibiotic component is selected from the group consisting of a first cephem component, a first carbacephem component, a first penem component, and a first carbapenem component covalently attached at its 3 position to the first linker; or
   (b) the first β-lactam antibiotic component is a first monobactam component covalently attached at its 2 position to the first linker.

2. The conjugate molecule of claim 1, or the pharmaceutically acceptable salt thereof, wherein the cannabinoid component further comprises a second hydroxy group.

3. The conjugate molecule of claim 2, or the pharmaceutically acceptable salt thereof, further comprising a second B-lactam antibiotic component covalently attached to a second linker, wherein the second linker is covalently attached to the second hydroxy group of the cannabinoid component.

4. The conjugate molecule of claim 1, or the pharmaceutically acceptable salt thereof, wherein the first β-lactam antibiotic component falls within structural Formula (A):

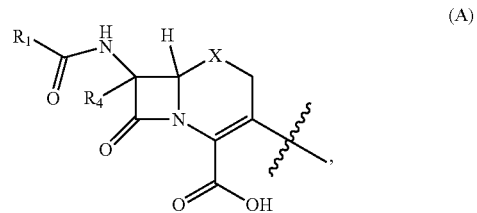

(A)

wherein X is S, C, or O; $R_1$ is a side chain of a first cephem or a side chain of a first carbacephem; and $R_4$ is H or —$OCH_3$.

5. The conjugate molecule of claim 1, or the pharmaceutically acceptable salt thereof, wherein the first β-lactam antibiotic component falls within structural Formula (B):

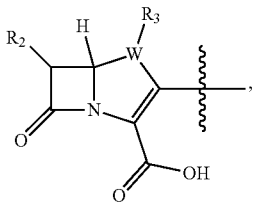

wherein W is S or C; and R₂ is a side chain of a first penem or a side chain of a first carbapenem;

and when W is C, R₃ is H, —CH₃, or phenyl, wherein the phenyl is optionally substituted with 1, 2, 3, or 4 groups independently selected from the group consisting of halide, trifluoromethyl, C1-C6 linear or branched alkyl optionally substituted with up to nine fluorine atoms, and C1-C6 linear or branched heteroalkyl containing 1, 2, or 3 atoms independently selected from O, N, and S and optionally substituted with 1, 2, 3, 4, 5, 6, 7, 8, or 9 fluorine atoms.

6. The conjugate molecule of claim 1, or the pharmaceutically acceptable salt thereof, wherein the first linker is selected from the group consisting of Group AB linkers:

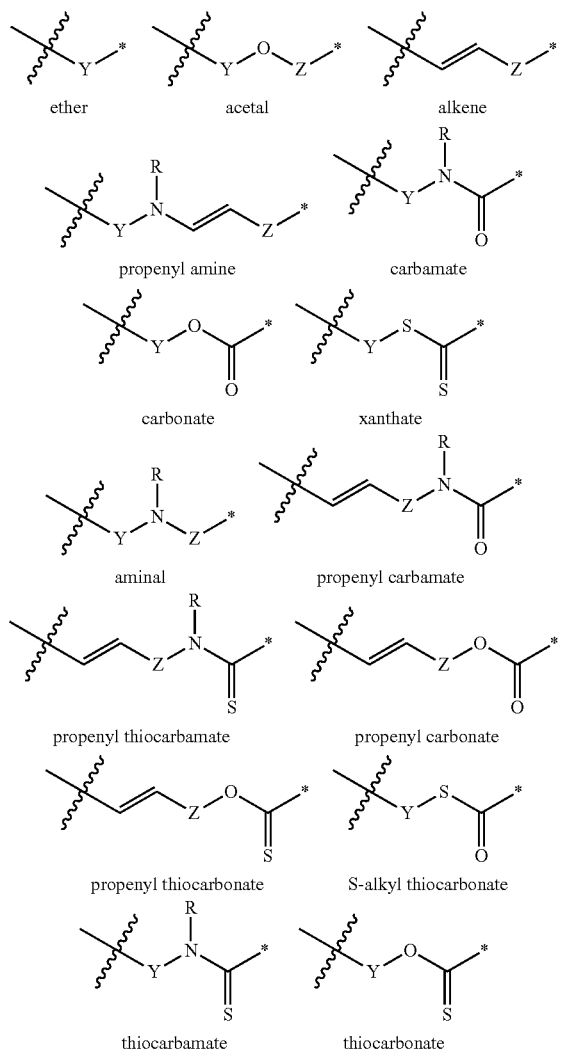

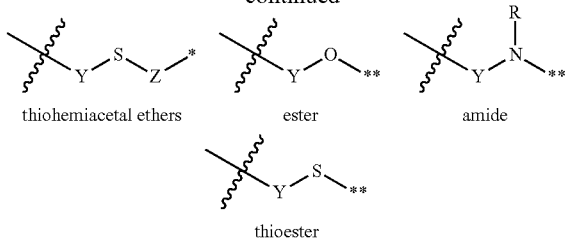

wherein * indicates a site of covalent attachment to the oxygen atom from the OH of a cannabinoid component, ** in cases such as ester, amide, and thioester indicates the site of covalent attachment to the carbon atom of a carbonyl component of a carboxylic acid-bearing cannabinoid component, and ⸺ marks a bond by which the linker is covalently attached to the β-lactam antibiotic component, and wherein Y is absent or is —CH₂, —CHCH₃, or —CH-phenyl;

Z is CR₁R₂; and

R, R₁ and R₂ independently are selected from the group consisting of:
(a) H;
(b) C1-C8 linear or branched alkyl, optionally substituted with
  (1) 1, 2, 3, 4, 5, 6, 7, 8, or 9 fluorine atoms; and/or
  (2) 1, 2, or 3 substituents independently selected from the Group One Substituents;
(c) C1-C8 linear or branched heteroalkyl containing 1, 2, or 3 heteroatoms independently selected from O, N, and S and optionally substituted with
  (1) 1, 2, 3, 4, 5, 6, 7, 8, or 9 fluorine atoms; and/or
  (2) 1, 2, or 3 substituents independently selected from the Group One Substituents;
(d) phenyl, optionally substituted with 1, 2, or 3 substituents independently selected from the group consisting of:
  (1) C1-C6 linear or branched alkyl, optionally substituted with
    (i) 1, 2, 3, 4, 5, or 6 fluorine atoms; and/or
    (ii) 1 or 2 substituents independently selected from the Group Two Substituents; and
  (2) C1-C6 linear or branched heteroalkyl containing 1 or 2 heteroatoms independently selected from O, N, and S and optionally substituted with
    (i) 1, 2, 3, 4, 5, or 6 fluorine atoms; and/or
    (ii) 1 or 2 substituents independently selected from the Group One Substituents;
(e) a 6- to 10-membered aromatic, optionally substituted with 1, 2, 3, or 4 substituents independently selected from the group consisting of:
  (1) phenyl;
  (2) halide;
  (3) cyano;
  (4) C1-C6 linear or branched alkyl, optionally substituted with
    (i) 1, 2, 3, 4, 5, 6, 7, 8, or 9 fluorine atoms; and/or
    (ii) 1, 2, or 3 substituents independently selected from the Group Two Substituents, and
  (5) C1-C6 linear or branched heteroalkyl containing 1, 2, or 3 atoms independently selected from O, N, and S and optionally substituted with
    (i) 1, 2, 3, 4, 5, 6, 7, 8, or 9 fluorine atoms; and/or (ii) 1, 2, or 3 substituents independently selected from the Group Two Substituents;
(f) 5- to 10-membered heteroaromatic comprising 1, 2, 3, 4, 5, or 6 heteroatoms independently selected from O, N, and S and optionally substituted with 1, 2, 3, or 4 substituents independently selected from
(1) phenyl;
(2) halide;
(3) cyano;
(4) trifluoromethyl;
(5) C1-C6 linear or branched alkyl optionally substituted with
(i) 1, 2, 3, 4, 5, 6, 7, 8, or 9 fluorine atoms; and/or
(ii) 1, 2, or 3 substituents independently selected from the Group Two Substituents; and
(6) C1-C6 linear or branched heteroalkyl containing 1, 2, or 3 atoms independently selected from O, N, and S and optionally substituted with
(i) 1, 2, 3, 4, 5, 6, 7, 8, or 9 fluorine atoms; and/or
(ii) 1, 2, or 3 substituents independently selected from the Group Two Substituents;
(g)

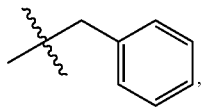 [SMILES: *Cc1ccccc1]

optionally substituted with 1, 2, or 3 substituents independently selected from the group consisting of:
(1) C1-C6 linear or branched alkyl, optionally substituted with
(i) 1, 2, 3, 4, 5, or 6 fluorine atoms; and/or
(ii) 1, 2, or 3 substituents independently selected from the Group Two Substituents;
(h) 3- to 9-membered cycloheteroalkyl having 1, 2, or 3 heteroatoms independently selected from O, N, and S and optionally substituted with 1, 2, or 3 substituents independently selected from the group consisting of:
(1) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents,
(2) C1-C6 linear or branched heteroalkyl, optionally substituted with
(i) 1, 2, 3, 4, 5, 6, 7, 8, or 9 fluorine atoms and/or
(ii) 1, 2, or 3 substituents independently selected from the Group Two Substituents,
(3) phenyl, optionally substituted with 1, 2, or 3 substituents independently selected from the Group Two Substituents, and
(4) 5- to 10-membered heteroaromatic, optionally substituted with 1, 2, or 3 substituents independently selected from the Group Two Substituents; and
(i) C3-C6 cycloalkyl, optionally substituted with 1, 2, or 3 substituents independently selected from:
(1) C1-C6 linear or branched alkyl, optionally substituted with
(i) 1, 2, 3, 4, 5, 6, 7, 8, or 9 fluorine atoms; and/or
(ii) 1, 2, or 3 substituents independently selected from the Group Two Substituents,
(2) C1-C6 linear or branched heteroalkyl, optionally substituted with
(i) 1, 2, 3, 4, 5, 6, 7, 8, or 9 fluorine atoms; and/or
(ii) 1, 2, or 3 substituents independently selected from the Group Two Substituents,
(3) phenyl, optionally substituted with 1, 2, or 3 substituents independently selected from Group Two Substituents; and
(4) 5- to 10-membered heteroaromatic, optionally substituted with 1, 2, or 3 substituents independently selected from the Group Two Substituents;
OR
$R_1$ and $R_2$, together with the atom to which they are attached, form a 3- to 9-membered cycloheteroalkyl having 1, 2, 3, or 4 heteroatoms independently selected from O, S, and N, wherein the cycloheteroalkyl optionally is substituted with 1, 2, or 3 substituents independently selected from, C1-C6 linear or branched alkyl optionally substituted with 1, 2, 3, 4, 5, 6, 7, 8, or 9 fluorine atoms, C1-C6 linear or branched heteroalkyl optionally substituted with 1, 2, 3, 4, 5, 6, 7, 8, or 9 fluorine atoms, phenyl optionally substituted with 1, 2, or 3 substituents independently selected from Group Two Substituents, or 5- to 10-membered heteroaromatic optionally substituted with 1, 2, or 3 independently selected from Group Two Substituents,
Group One Substituents is a group of substituents consisting of:
(a) —OH;
(b) —$NH_2$;
(c) =O;
(d) =S;
(e) =$NR_7$, where $R_7$ is H or is C1-C3 linear or branched alkyl or C1-C3 linear or branched heteroalkyl comprising an O, N, or S atom;
(f) —C(O)$OR_4$, wherein $R_4$ is H or C1-C3 linear or branched alkyl;
(g) —C(O)$NR_5R_6$, wherein $R_5$ and $R_6$ independently are H or C1-C6 linear or branched alkyl;
(h) halide;
(i) C1-C6 linear or branched alkoxyl;
(j) C1-C6 linear or branched alkylamino;
(k) C1-C6 linear or branched dialkylamino;
(l) 6- to 10-membered aromatic, optionally substituted with 1, 2, 3, or 4 substituents independently selected from
(i) phenyl;
(ii) halide;
(iii) cyano;
(iv) C1-C6 linear or branched alkyl, optionally substituted with
(1) 1, 2, 3, 4, 5, 6, 7, 8, or 9 fluorine atoms; and/or
(2) 1, 2, or 3 substituents independently selected from the Group Two Substituents; and
(v) C1-C6 linear or branched heteroalkyl containing 1, 2, or 3 atoms independently selected from O, N, and S and optionally substituted with
(1) 1, 2, 3, 4, 5, 6, 7, 8, or 9 fluorine atoms; and/or
(2) 1, 2, or 3 substituents independently selected from the Group Two Substituents;
(m) 5- to 10-membered heteroaromatic, optionally substituted with 1, 2, 3, or 4 substituents independently selected from
(i) phenyl;
(ii) halide;
(iii) cyano;

(iv) C1-C6 linear or branched alkyl, optionally substituted with
  (1) 1, 2, 3, 4, 5, 6, 7, 8, or 9 fluorine atoms; and/or
  (2) 1, 2, or 3 substituents independently selected from the Group Two Substituents; and
(v) C1-C6 linear or branched heteroalkyl containing 1, 2, or 3 atoms independently selected from O, N, and S and optionally substituted with
  (1) 1, 2, 3, 4, 5, 6, 7, 8, or 9 fluorine atoms; and/or
  (2) 1, 2, or 3 substituents independently selected from the Group Two Substituents;
(n) 3- to 9-membered cycloheteroalkyl having 1, 2, or 3 heteroatoms independently selected from O, N, and S, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and
  (v) C1-C6 linear or branched heteroalkyl containing 1, 2, or 3 atoms independently selected from O, N, and S and optionally substituted with
    (1) 1, 2, 3, 4, 5, 6, 7, 8, or 9 fluorine atoms; and/or
    (2) 1, 2, or 3 substituents independently selected from the Group Two Substituents; and
(o) C3-C6 cycloalkyl, optionally substituted with 1, 2, 3, or 4 substituents independently selected from
  (i) phenyl;
  (ii) halide;
  (iii) cyano;
  (iv) C1-C6 linear or branched alkyl, optionally substituted with
    (1) 1, 2, 3, 4, 5, 6, 7, 8, or 9 fluorine atoms; and/or
    (2) 1, 2, or 3 substituents independently selected from the Group Two Substituents; and
  (v) C1-C6 linear or branched heteroalkyl containing 1, 2, or 3 atoms independently selected from O, N, and S and optionally substituted with
    (1) 1, 2, 3, 4, 5, 6, 7, 8, or 9 fluorine atoms; and/or
    (2) 1, 2, or 3 substituents independently selected from the Group Two Substituents;
Group Two Substituents is a group of substituents consisting of:
(a) —OH;
(b) —NH$_2$;
(c) =O;
(d) =S;
(e) =NR$_7$, where R$_7$ is H or is C1-C3 linear or branched alkyl or C1-C3 linear or branched heteroalkyl comprising an O, N, or S atom;
(f) —C(O)OR$_4$, wherein R$_4$ is H or C1-C3 linear or branched alkyl;
(g) —C(O)NR$_5$R$_6$, wherein R$_5$ and R$_6$ independently are H or C1-C6 linear or branched alkyl;
(h) halide;
(i) cyano;
(j) trifluoromethyl;
(k) C1-C6 linear or branched alkoxyl;
(l) C1-C6 linear or branched alkylamino;
(m) C1-C6 linear or branched dialkylamino;
(n) 6- to 10-membered aromatic; and
(o) 5- to 10-membered heteroaromatic comprising 1, 2, 3, 4, 5, or 6 heteroatoms independently selected from O, N, and S.

7. The conjugate molecule of claim 1, or the pharmaceutically acceptable salt thereof, wherein the first B-lactam antibiotic component falls within structural Formula (C):

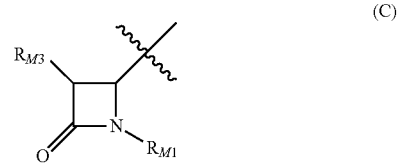

wherein R$_{M3}$ is a first position 3 monobactam substituent, and R$_{M1}$ is a first position 1 monobactam substituent.

8. The conjugate molecule of any claim 1 pharmaceutically acceptable salt thereof, wherein the first linker is selected from the group consisting of Group C linkers:

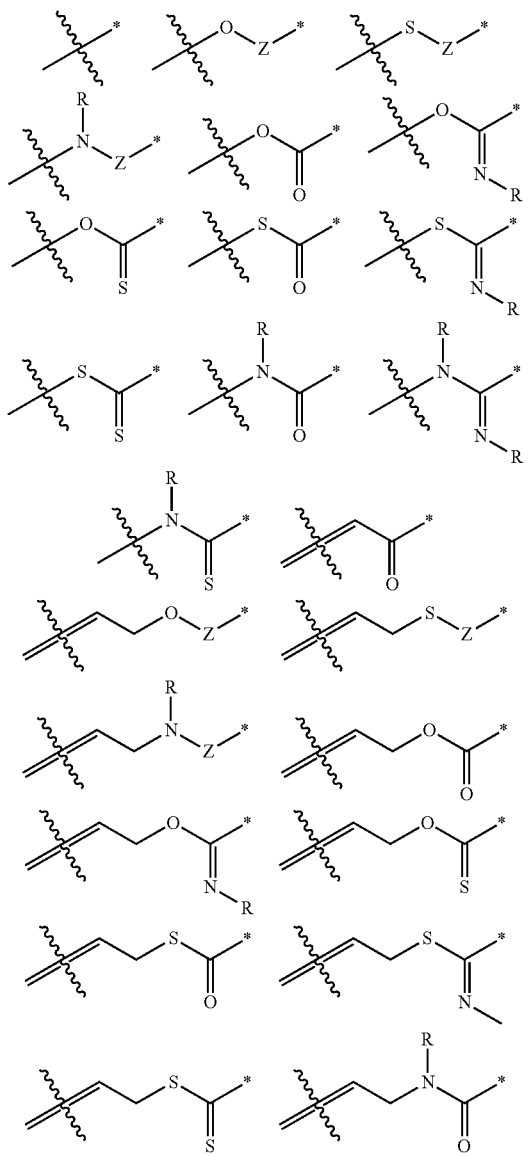

-continued

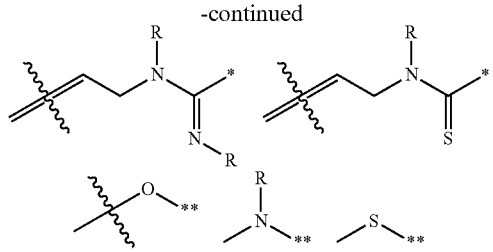

in which *, **, Z, and R are as defined in claim 6.

9. The conjugate molecule of claim 2, or the pharmaceutically acceptable salt thereof, wherein the second β-lactam antibiotic component falls within structural Formula (A):

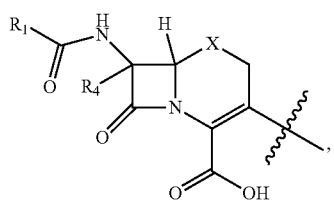
(A)

wherein X is S, C, or O; $R_1$ is a side chain of a second cephem or a side chain of a second carbacephem; and $R_4$ is H or —OCH$_3$.

10. The conjugate molecule of claim 2, or the pharmaceutically acceptable salt thereof, wherein the second B-lactam antibiotic component falls within structural Formula (B):

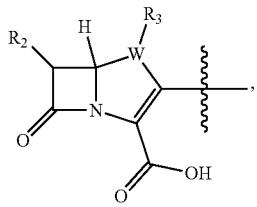
(B)

wherein W is S or C; and $R_2$ is a side chain of a second penem or a side chain of a second carbapenem;

and when W is C, $R_3$ is H, CH$_3$, or phenyl, wherein the phenyl is optionally substituted with 1-4 groups selected from the group consisting of halide, trifluoromethyl, C1-C6 linear or branched alkyl optionally substituted with up to nine fluorine atoms, and C1-C6 linear or branched heteroalkyl containing 1 to 3 atoms independently selected from O, N, and S and optionally substituted with up to 9 fluorine atoms.

11. The conjugate molecule of claim 2, or the pharmaceutically acceptable salt thereof, wherein the second linker is selected from the group consisting of Group AB linkers:

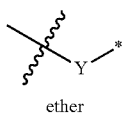 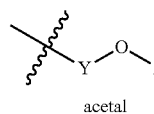 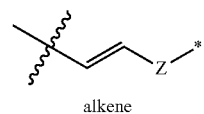
ether       acetal        alkene

-continued

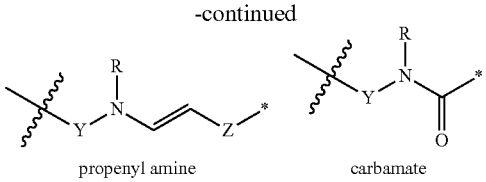
propenyl amine                carbamate carbonate                     xanthate

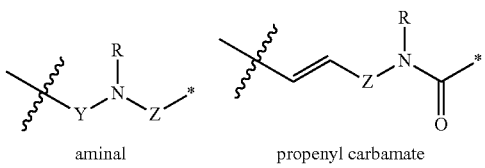
aminal                        propenyl carbamate

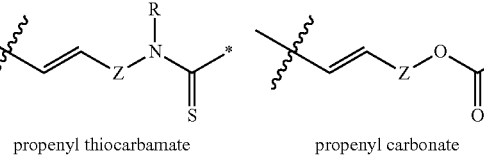
propenyl thiocarbamate        propenyl carbonate

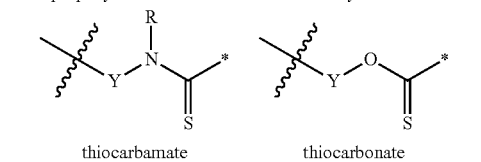
propenyl thiocarbonate        S-alkyl thiocarbonate

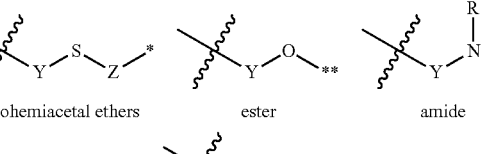
thiocarbamate                 thiocarbonate thiohemiacetal ethers    ester    amide thioester wherein *, **, ⁓, Y, Z, R, $R_1$, and $R_2$ are as defined in claim 6.

12. The conjugate molecule of claim 2, or the pharmaceutically acceptable salt thereof, wherein the second β-lactam antibiotic component falls within structural Formula (C):

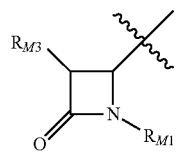
(C)

wherein $R_{M3}$ is a second position 3 monobactam substituent, and $R_{M1}$ is a second position 1 monobactam substituent.

13. The conjugate molecule of claim 2, or the pharmaceutically acceptable salt thereof, wherein the second linker is selected from the group consisting of Group C linkers:

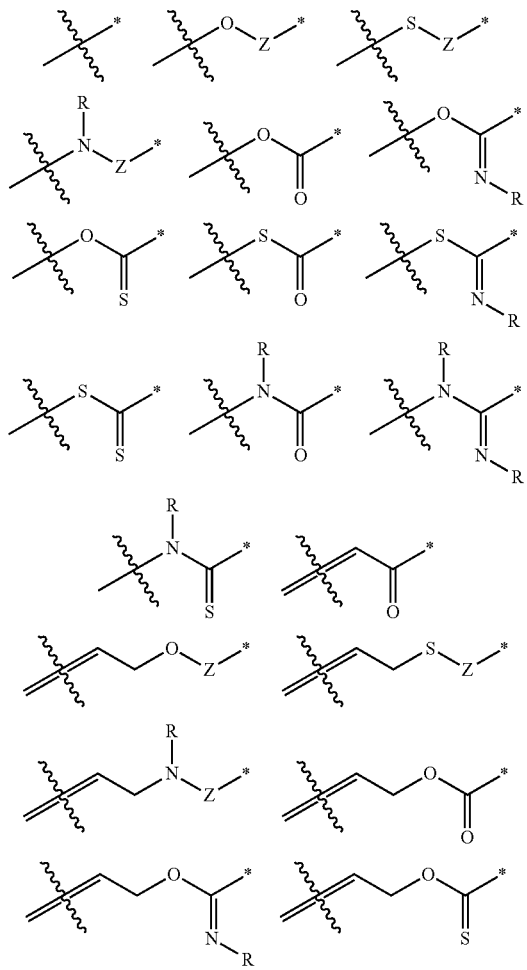

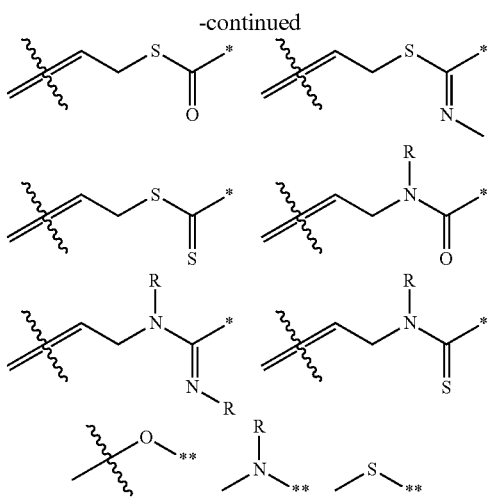

wherein *, **, ⁓, Z, and R are as defined in claim 6.

14. A pharmaceutical composition comprising a conjugate molecule of claim 1, or a pharmaceutically acceptable salt thereof, and a pharmaceutically acceptable vehicle.

15. A method of treating (a) a bacterial infection or (b) inflammation, comprising administering to a patient in need there of a conjugate molecule of claim 1 or a pharmaceutically acceptable salt thereof.

16. The method of claim 15, wherein the patient has cystic fibrosis and wherein at least the first B-lactam antibiotic component is a first monobactam component.

17. The method of claim 15, wherein the inflammation is associated with a disorder selected from the group consisting of type I diabetes, cancer, Alzheimer's disease, cachexia, muscle-wasting diseases, allergies, rheumatoid arthritis, scleroderma, rheumatic fever, inflammatory bowel disease, myasthenia gravis, multiple sclerosis, Guillain-Barre syndrome, conjunctiva of the eye, systemic lupus erythematosus, encephalitis, Adult Respiratory Distress Syndrome, psoriasis, emphysema, and muscular dystrophy.

18. The method of claim 15, further comprising co-administering to the patient a β-lactamase inhibitor.

* * * * *